United States Patent
Holmes et al.

(10) Patent No.: US 9,421,205 B2
(45) Date of Patent: *Aug. 23, 2016

(54) FAK INHIBITORS

(71) Applicant: Cancer Therapeutics CRC PTY LTD., Bundoora (AU)

(72) Inventors: Ian Peter Holmes, Bundoora (AU); Yiva Bergman, Parkville (AU); Gillian Elizabeth Lunnis, Parkville (AU); Marica Nikac, Parkville (AU); Neil Choi, Parkville (AU); Catherine Fae Hemley, Parkville (AU); Scott Raymond Walker, Parkville (AU); Richard Charles Foitzik, Parkville (AU); Danny Ganame, Bundoora (AU); Romina Lessene, Bundoora (AU)

(73) Assignee: Cancer Therapeutics CRC PTY LTD., Bundoora (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/619,674

(22) Filed: Feb. 11, 2015

(65) Prior Publication Data
US 2015/0231135 A1 Aug. 20, 2015

Related U.S. Application Data

(60) Division of application No. 13/543,276, filed on Jul. 6, 2012, now Pat. No. 9,012,461, which is a continuation-in-part of application No. PCT/GB2012/000175, filed on Feb. 17, 2012.

(60) Provisional application No. 61/443,773, filed on Feb. 17, 2011, provisional application No. 61/523,503, filed on Aug. 15, 2011, provisional application No. 61/579,719, filed on Dec. 23, 2011.

(51) Int. Cl.
*A61K 31/506* (2006.01)
*A61K 39/395* (2006.01)

(52) U.S. Cl.
CPC ............ *A61K 31/506* (2013.01); *A61K 39/3955* (2013.01); *A61K 39/395* (2013.01)

(58) Field of Classification Search
CPC ..................... A61K 31/506; A61K 39/395
See application file for complete search history.

(56) References Cited

U.S. PATENT DOCUMENTS

| 2005/0256125 | A1 | 11/2005 | Kath et al. |
| 2005/0256144 | A1 | 11/2005 | Kath et al. |
| 2005/0256145 | A1 | 11/2005 | Kath et al. |
| 2010/0113475 | A1 | 5/2010 | Adams et al. |
| 2013/0022594 | A1 | 1/2013 | Holmes et al. |

FOREIGN PATENT DOCUMENTS

| WO | 9722596 A1 | 6/1997 |
| WO | 9730035 A1 | 8/1997 |
| WO | 9732856 A1 | 9/1997 |
| WO | 9813354 A1 | 4/1998 |
| WO | 9835985 A1 | 8/1998 |
| WO | 9902166 A1 | 1/1999 |
| WO | 0012485 A1 | 3/2000 |
| WO | 0039101 A1 | 7/2000 |
| WO | 0040529 A1 | 7/2000 |
| WO | 0041669 A2 | 7/2000 |
| WO | 0047212 A1 | 8/2000 |
| WO | 0053595 A1 | 9/2000 |
| WO | 0132651 A1 | 5/2001 |
| WO | 0160814 A2 | 8/2001 |
| WO | 0164653 A2 | 9/2001 |
| WO | 0164655 A1 | 9/2001 |
| WO | 0164656 A1 | 9/2001 |
| WO | 0192224 A1 | 12/2001 |
| WO | 0194341 A1 | 12/2001 |
| WO | 0204434 A1 | 1/2002 |
| WO | 0208213 A1 | 1/2002 |
| WO | 03078404 A1 | 9/2003 |
| WO | 2004056786 A1 | 7/2004 |
| WO | 2004056807 A1 | 7/2004 |
| WO | 2004080980 A1 | 9/2004 |
| WO | 2005016894 A1 | 2/2005 |
| WO | 2005023780 A1 | 3/2005 |
| WO | 2006021454 A2 | 3/2006 |

(Continued)

OTHER PUBLICATIONS

Bagi. C.M. et al., "Dual Focal Adhesion Kinase/Pyk2 Inhibitor Has Positive Effects on Bone Tumors", Cancer May 15, 2008, vol. 112, No. 10, pp. 2313-2321.
Abstracts/Bone 48, 2011 S54.
Bali, C.M. et al., "Sunitinib and PF-562,271 (FAK/Pyk2 inhibitor) effectively block growth and recovery of human hepatocellular carcinoma in a rat xenograft model", Cancer Biology & Therapy, vol. 8, No. 9, pp. 856-865, May 1, 2009.
Ebos, J.M et al., "Tumor and Host Mediated Pathways of Resistance and Disease Progression in Response to Antiangiogenic Therapy", Clinical Cancer Research, 2009, vol. 15m pp. 5020-5025.
Halder, J et al., "Identification of 4-benzylamino-2-[(4-morpholin-4-ylphenyl) amino] pyrimidine-5-carboxamide derivatives as potent and orally bioavailable STAT6 inhibitors", Bioorganic & Medicinial Chemistry, vol. 16, 2008, pp. 6509-6521.

(Continued)

*Primary Examiner* — Samira Jean-Louis
(74) *Attorney, Agent, or Firm* — W. David Wallace; Holland & Knight LLP

(57) ABSTRACT

A compound of the formula (I):

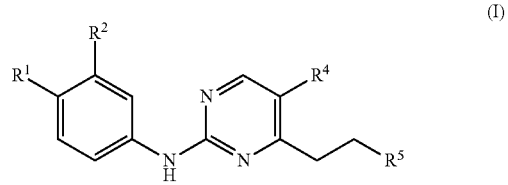

where $R^1$ or $R^2$ is a cyclic amine group and $R^5$ is an aromatic group with a carbonyl containing substituent for use as a FAK inhibitor.

4 Claims, 1 Drawing Sheet

(56) References Cited

FOREIGN PATENT DOCUMENTS

| WO | 2006021457 A2 | 3/2006 |
|---|---|---|
| WO | 2006076442 A1 | 7/2006 |
| WO | 2007063384 A2 | 6/2007 |
| WO | 2007140222 A2 | 12/2007 |
| WO | 2008115369 A2 | 9/2008 |
| WO | 2008115443 A1 | 9/2008 |
| WO | 2008129380 A1 | 10/2008 |
| WO | 2009024332 A1 | 2/2009 |
| WO | 2009071535 A1 | 6/2009 |
| WO | 2009105498 A1 | 8/2009 |
| WO | 2009143389 A1 | 11/2009 |
| WO | 2009153589 A1 | 12/2009 |
| WO | 2010-055117 A1 | 5/2010 |
| WO | 2010058030 A1 | 5/2010 |
| WO | 2010058032 A2 | 5/2010 |
| WO | 2010106097 A1 | 9/2010 |
| WO | 2010126922 A1 | 11/2010 |
| WO | 2010136559 A1 | 12/2010 |
| WO | 2010141406 A2 | 12/2010 |
| WO | 2010141796 A2 | 12/2010 |
| WO | 2011019943 A1 | 2/2011 |
| WO | 2011039344 A1 | 4/2011 |
| WO | 2011049332 A2 | 4/2011 |
| WO | 2012006081 A1 | 1/2012 |
| WO | 2012012139 A1 | 1/2012 |
| WO | 2012022408 A1 | 2/2012 |
| WO | 2012041796 A1 | 4/2012 |
| WO | 2012045194 A1 | 4/2012 |
| WO | 2012045195 A1 | 4/2012 |

OTHER PUBLICATIONS

Angelucci, A. et al., "Targeting Vascular Cell Migration as a Strategy for Blocking Angiogenesis: The Central Role of Focal Ashesion Protein Tyrosine Kinase Family", Current Pharmaceutical Design, 2007, vol. 13, pp. 2129-2145.

Benlimane, N. et al., "FAK signaling is critical for ErbB-2/ErbB-3 receptor cooperation for oncogenic transformation and invasion", The Journal of Cell Biology, Nov. 7, 2005, vol. 171, No. 3, pp. 505-516.

Bolos, V. et al., "The dual kinase complex FAK-Src as a promising therapeutic target in cancer", Onco Targets and Therapy, 2010, vol. 3, pp. 83-97.

Bouchard, V. et al., "B1 integrin/Fak/Src signaling in intestinal epthelial crypt cell survival: integration of complex regulatory mechanism", Apoptosis, 2008, vol. 13, pp. 531-542.

Brunton, V.G. et al., "Identification of Src-Specific Phosphorylation Site on Docal Adhesion Kinase: Dissection of the role of Src SH2 and Catalystic Functions and Their Consequences for Tumor Cell Behavior", Cancer Research, Feb. 15, 2005, vol. 65, No. 4, pp. 1335-1342.

Chatzizacharias, N.A. et al., "Focal adhesion kinase: a promising target for anticancer therapy", Expert Opinion on Therapeutic Targets, 2007, vol. 11, No. 10, pp. 1315-1328.

Choi, H. et al., Design and synthesis of 7H-pyrrolo [2,3-d] pyrimidines as focal adhesion kinase inhibitors. Part 1, Bioorganic & Medicinal Chemistry Letters, vol. 16, 2006, pp. 2173-2176.

Choi, H. et al., Design and synthesis of 7H-pyrrolo [2,3-d] pyrimidines as focal adhesion kinase inhibitors. Part 2, Bioorganic & Medicinal Chemistry Letters, vol. 16, 2006, pp. 2689-2692.

Cohen, L.A. et al., "Mechanisms of Focal Adhesion Kinase Regulation", Current Cancer Drug Targets, 2005, vol. 5, pp. 629-643.

Contestabile, A. et al., "Localization of focal adhesion kinase isoforms in cells of the central nervous system", International Journal of Development Neuroscience, vol. 21, 2003. pp. 89-93.

Frisch, S.M. et al., "Control of Adhesion-dependent Cell Survival by Focal Adhesion Kinase", The Journal of cell biology, vol. 134, No. 3, Aug. 1995, pp. 793-799.

Gan, H.K. et al., "Focal Adhesion Kinase as a Therapeutic Target in Cancer", American Society of Clinical Oncology, pp. 130-136.

Golubovskaya, V.M. et al., "A Small Molecule Inhibitor, 1,2,3,5-Benzenetetraamine Tetrahydrochloride, Targeting the Y397 Site of Focal Adhesion Kinase Decreases Tumor", The Journal of Medicinal Chemistry, 2008, vol. 51, pp. 7405-7416.

Brunton, V.G. et al., "Src and focal adhesion kinase as thereaputic targets in cancer", Current Opinion in Pharmacology, 2008, vol. 8, pp. 427-432.

Burgaya, F. et al., "Alternatively Spliced Focal Adhesion Kinase in Rat Brain with Increased Autophosphorylation Activity", the Journal of Biological Chemistry, vol. 272, No. 45, Nov. 7, 1997, pp. 28720-28725.

Chan, K.T. et al., "FAK alters invadopodia and focal adhesion composition and dynamics to regulate breast cancer invasion", The Journal of Cell Biology, vol. 185, No. 2, pp. 357-370.

Hirt, U. et al., AACR Poster, 2011, #A249.

Hu, X. et al., "Apigenin inhibited migration and invasion of human ovarian cancer A2780 cells through focal adhesion kinase", Carcinogenesis, vol. 29, No. 12, 2008, pp. 2369-2376.

Huanwen, W. et al., "Intrinsic chemoresistance to gemcitabine is associated with constitutive and laminin-induced phosphorylation of FAK in pancreatic cancer cell lines", Molecular Cancer, 2009, vol. 8, No. 125, pp. 1-16.

Lilic, D. et al., "Reduced cell motility and enhanced focal adhesion contact formation in cells from FAK-deficient mice", Nature, vol. 377, Oct. 1995, pp. 539-544.

Lagares, D. et al., "Inhibition of Focal Adhesion Kinase Prevents Experimental Lung Fibrosis and Myofibroblast Information", Arthritis & Rheumatism, vol. 64, No. 5, May 2012, pp. 1653-1664.

Lahlou, H. et al., "Mammary epithelial-specific disruption of the focal adhesion kinase blocks mammary tumor progression", PNAS, vol. 104, No. 51, Dec. 18, 2007, pp. 20302-20307.

Liao, C. et al., "CSE I L/CAS, the cellular apoptosis susceptibility protein, enhances invasion and metastasis but not proliferation of cancer cells", Journal of Experimental & Clinical Cancer Research, 2008, vol. 27, No. 15, pp. 1-12.

Lietha, D. et al., "Structural Basis for the Autoinhibition of Focal Adhesion Kinase", Cell, vol. 129, Jun. 15, 2007, pp. 1177-1187.

Lietha, D. et al., "Crystal Structures of the FAK Kinase in Complex with TAE226 and Related Bis-Anilino Pyrmidine Inhibitors Reveal a Helical DFG Conformation", Plos One, vol. 3, No. 11, Nov. 2008, pp. 1-7.

Long, W. et al., "SRC-3-4 Mediates the Interaction of EGFR with FAK to Promote Cell Migration", Molecular Cell, vol. 37, Feb. 12, 2010, pp. 321-332.

McLean, G.W. eet al., "Decreased Focal Adhesion Kinase Suppresses Papilloma Formation during Experimental Mouse Skin Carcinogens", Cancer Research, vol. 61, Dec. 1, 2001, pp. 8385-8389.

Messina, S. et al., "Specific Interactions of neuronal focal adhesion kinase isoforms with Src kinases and amphiphysin", Journal of Neurochemistry, vol. 84, 2003, pp. 253-265.

Mitra, S.K. et al., "Focal Adhesion Kinase: in Command and Control of Cell Motility", Nature Reviews Molecular Cell Biology, Jan. 2005, vol. 6, pp. 56-68.

Mitra, S.K. et al., "Intrinsic FAK activity and Y925 phosphorylation facilitate an angiogenic switch in tumors", Oncogene, vol. 25, 2006, pp. 5969-5984.

Richardson, A. et al., "A mechanism for regulation of the adhesion-associated protein tyrosine kinase pp125", Nature, vol. 380, Apr. 1996, pp. 538-540.

Yamamoto, D. et al., "FAK overexpression upregulates cyclin D3 and enhances cell proliferation via the PKC and PI3-kinase-Akt pathways", Cellular Signalling, vol. 15, 2003, pp. 575-583.

Zhao, X. et al., "Focal adhesion kinase and its signaling pathways in cell migration and angiogenesis", Advanced Drug Delivery Reviews, vol. 63, 2011, pp. 610-615.

Zificsak, C.A. et al., "Optimization of a novel kinase inhibitor scaffold for the dual inhibition of JAK2 and FAK kinases", Bioorganic & Medicinal Chemistry Letters, vol. 22, 2012, pp. 133-137.

Zouq, N.K. et al. "FAK engages multiple pathways to maintain survival of fibroblasts and epithelia-differential roles of paxillin and p130Cas", Journal of Cell Science, 2009, vol. 122, pp. 357-367.

Roberts, W.G. et al., "Antitumor Activity and Pharmacology of a Selective Focal Adhesion Kinase Inhibitor, PF-562,271", Cancer Research, Mar. 15, 2008, vol. 68, No. 6, pp. 1935-1944.

(56) References Cited

OTHER PUBLICATIONS

Schultze, A. et al., Clinical Importance and Potential Use of Small Molecule Inhibitors of Focal Adhesion Kinase•, Anti-Cancer Agents in Medicinal Chemistry, 2011, vol. 11, pp. 593-599.
Schultze, A. et al., "TAE226-mediated inhibition of focal adhesion kinase interferes with tumor angiogenesis and vasculogenesis", Invest New Drugs, 2010, vol. 28, pp. 825-833.
Schwock, J. et al., Targeting focal adhesion kinase signaling in tumor growth and metastasis•, Expert Opinion Therapy Targets, 2010, vol. 14, No. 1, pp. 77-94.
Shibue, T. et al., Integrin 131-focal adhesion kinase signaling directs the proliferation of metastatic cancer cells disseminated in the lungs•, PNAS Early Edition, 2009, pp. 1-6.
Sieg, D.J. et al., FAK integrates growth-factor and integrin signals to promote cell migration•, Nature Cell Biology, vol. 2,.May 2000, pp. 249-257.
Siesser, P. et al., "The Signaling and Biological Implications of FAK Overexpression in Cancer", Clinical Cancer Research,.Jun. 1, 2006, vol. 12, No. 11, pp. 3233-3237.
Slack-Davis, J.K. et al., •Cellular Characterization of a Novel Focal Adhesion Kinase Inhibitor, The Journal of Biological Chemistry vol. 282, No. 20, May 18, 2007, pp. 14845-14852.
Sood, AK. et al., Biological Significance of Focal Adhesion Kinase in Ovarian Cancer•, American Journal of Pathology, vol. 165, No. 4, Oct. 2004, pp. 1087-1095.
Sood, A.K. et al., Adrenergic modulation of focal adhesion kinase protects human ovarian cancer cells from anoikis•, The Journal of Clinicall investiqation, pp. 1-9.
Sun, H. et al., "Differences in CYP3A4 catalyzed bioactivation of 5-aminooxindole and 5-aminobenzsultam scaffolds in proline-rich tyrosine kinase 2 (PYK2) inhibitors: Retrospective analysis by CYP3A4 molecular docking, quantum chemical calculations and glutathione adduct detection using linear ion traplorbitrap mass spectrometry", Bioorganic & Medicinal Letters, 2009, vol. 19, pp. 3177-3182.
"Tanjoni, I. et al., ""PND-1186 FAK inhibitor selectively promotes tumor cell apoptosis in three dimensionalenvironments""", Cancer Biology & Therapy, May 15, 2010,vol. 9, No. 10, pp. 1-14".
Tomar, A. et al., "Focal adhesion kinase: switching between GAPs and GEFs in the regulation of cell mobility", Current Opinion in Cell Biology, 2009, vol. 21, pp. 676-683.
Hess, A.R. et al., "Focal Adhesion Kinase Promotes the Aggressive Melanoma Phenotype", Cancer Research, Nov. 1, 2005, vol. 65, No. 21, pp. 9851-9860.
Toutant, M. et al., Autophosphorylation of Tyr 397 and its phosphorylation by Src-family kinases are altered in focal-adhesion-kinase neuronal isoforms, Biochem J., 2000, vol. 348, pp. 119-128.
Van Nimwegen, M.J. et al., "Focal adhesion kinase: A potential target in cancer therapy", Biochemical Pharmacology, 2007, vol. 73, pp. 597-6093.
Van Nimwegen, M.J. et al. "Requirement for Focal Adhesion Kinase in the Early Phase of Mammary Adenocarcinoma Lung Metastasis Formation", Cancer Research, Jun. 1, 2005, vol. 65, No. 11, pp. 4698-4706.
Villedieu, M. et al., "Acquisition of chemoresistance following discontinuous exposures to cisplatin is associated in ovarian carcinoma cells with progressive alteration of FAK, ERK and p38 activation in response to treatment", Gynecologic Oncology, 2006, vol. 101 , pp. 507-519.
Walker, D.P. et al., Trifluoromethylpyrimidine-based inhibitors of proline-rich tyrosine kinase 2 (PYK2): Structure-activity relationships and strategies for the elimination of reactive metabolite formation•, Bioorganic & Medicinal Chemistry Letters, 2008, vol. 18, pp, 6071-6077.
Walsh, C. et al., •Oral delivery of PND-1186 FAK inhibitor decreases tumor growth and spontaneous breast to lung metastasis in preclinical models•, Cancer Biology Therapy, May 15, 2010, vol. 9, No. 10, pp. 1-13.
Berge, S.M. et al., •Pharmaceutical Salts•, Journal of Pharmaceutical Sciences, Jan. 1977, vol. 66, No. 1, pp. 1-10.

Cary, L.A. et al., "Stimulation of cell migration by overexpression of focal adhesion kinase and its association with Src and Fyn", Journal of Cell Science, 1996, vol. 109, pp. 1787-1794.
De Heer, Pet al., "Combined expression of the non-receptor protein tyrosine kinases FAK and Src in primary colorectal '?lncer is associated with tumor recurrence and metastasis formation", EJSO, 2008, vol. 34, pp. 1253-1261.
Gilmore, A.P. et al., Inhibition of Focal Adhesion Kinase (FAK) Signaling in Focal Adhesions Decreases Cell Motility•, Molecular Biology of the Cell, Aug. 1996, vol. 7, pp. 1209-1224.
Golas, J.M. et al., "SKI-606, a 4-Anilino-3-quinolinecarbonitrile Dual Inhibitor of Src and Abl Kinases, Is a Potent Antiproliferative Agent against Chronic Myelogenous Luekemia Cells in Culture and Causes Regression of K562 Xenografts in Nude Mice", Cancer Research, 2003, vol. 63, pp. 375-381.
Lombardo, L.J. et al., Discovery of N-(2-Chloro-6-methyl•phenyl)-2-(6-(4-(2-hydroxyethyl)-piperazin-l-yl)-2-methylpyrimidin-4-ylamino)thiazole-5-carboxamide(BMS-354825), a Dual SrclAbl Kinase Inhibitor with Potent Antitumor Activity in Preclinical Assays•, Joumal of Medicinal Chemistry, 2004, vol. 47, No. 27, pp. 6658-6661.
Mouawad, R. et al., "Tumoural expression and circulating level of VEGFR-3 (Flt-4) in metastatic melanoma patients: Correlation with clinical parameters and outcome", European Journal of Cancer, 2009, vol. 45, pp. 1407-1414.
Peng, C. et al., "Sequential Copper(I)-Catalyzed Reaction of Amines with o-Acetylenyl-Substituted Phenyldiazoacetates", Adv. Synth. Catal, 2008, vol. 350, pp. 2359-2364.
Stern, M. et al., •Overview of monoclonal antibodies in cancer therapy: present and promise, Critical Reviews in Oncology/Hematology, 2005, vol. 54, pp. 11-29.
Tremblay, L. et al., "Focal Adhesion Kinase (pp125FAK) ExpreSSion, Activation and Association with Paxillin and p5OCSK in Human Metastatic Prostate Carcinoma", Int. J. Cancer, 1996, vol. 68, !pp. 164-171.
Tsutsumi, K. et al., "Tumor growth inhibition by synthetic and expressed siRNA targeting focal adhesion kinase", International Journal of Oncology, 2008, vol. 33, pp. 215-224.
Xu, L. et al., "Attenuation of the Expression of the Focal Adhesion Kinase Induces Apoptosis in Tumor Cells", Cell Growth & Differentiation, Apr. 1996, vol. 7, pp. 413-418.
Halder, J. et al., "Focal Adhesion Kinase Silencing Augments Docetaxel•Mediated Apoptosis in Ovarian Cancer Cells", Clinical Cancer Research, 2005, vol. 11, pp. 8829-8883.
Hong, K. et al., "Inhibition of Akt activity induces the mesenchymal-to-epithelial reverting transition with restoring E-cardherin expression in KB and KOSCC-25B oral squamous cell carcinoma cells", Journal of Experimental & Clinical Cancer Research, 2009, vol. 28, pp. 1-11.
Halder, J. et al., "Focal Adhesion Kinase Targeting Using in vivo Short Interfering RNA Delivery in Neural Liposomes for Ovarian Carcinoma Therapy", Clinical Cancer Research, Aug. 2006, vol. 12, No. 16, pp. 4916-4924.
Toutant, M. et al., "Altemative Splicing Controls fro the Mechanisms of FAK Autophosphorylation", Molecular and Cellular Biology, Nov. 2002, vol. 22, No. 22, pp. 7731-7743.
Fincham, VJ. et al., v-Src-induced degradation of focal adhesion kinase during morphological transformation of chicken embryo fibroblasts•, Oncogene, 1995, vol. 10, pp. 2247-2252.
Bottsford-Miller, J.N. et al., "Enhancing anti-angiogenic therapy by blocking focal adhesion kinase", Gynecol Oncol, vol. 123, No. 2, p. 432.
Street, I. et al., "Inhibition of Focal Adhesion Kinase in Combination With Bevacizumab Reduces the Rate of Tumor Revascularization and Increases Survival in a Pre-clinical Model of Basal Breast Cancer", Cancer Therapeutics CRC, Abstract 846.
Mitra, S.K. et al., "Intrinsic focal adhesion kinase activity controls orthoptic breast carcinoma metastasis via the regulation of urokinase plasminogen activator expression in a syngeneic tumor model", Oncogene, vol. 25, 2006, pp. 4429-4440.
Nagashima, S. et al., "Identification of 4-benzylamino-2-[(4-morpholin-4-ylphenyl) amino] pyrimidine-5-carboxamide deriva-

(56) References Cited

OTHER PUBLICATIONS tives as potent and orally bioavailable STAT6 inhibitors", Bioorganic & Medicinal Chemistry, vol. 16, 2008, pp. 6509-6521.

Search Report and Written Opinion issued in International Patent Application No. GB/2012000176, mailed Mar. 23, 2012, 11 pages.

Search Report and Written Opinion issued in International Patent Application No. GB2012/000175, mailed Mar. 23, 2012, 13 pages.

Watermann, D. et al., "Specific induction of pp 125 focal adhesion kinase in human breast cancer", British Journal of Cancer, 2005, vol. 93, No. 6, pp. 694-698.

Halder, Jyotsnabaran, et al., "Therapeutic Efficacy of a Novel Focal Adhesion Kinase Inhibitor TAE226 in Ovarian Carcinoma", Cancer Res 2007; 67: (22). Nov. 15, 2007.

FAK INHIBITORS

CROSS-REFERENCE TO RELATED APPLICATIONS

This application is a divisional application of U.S. Non-Provisional application Ser. No. 13/543,276, filed Jul. 6, 2012, which is a continuation-in-part of International Application No. PCT/GB2012/000175, filed Feb. 17, 2012, which claims the benefit of U.S. Provisional Appl. Nos. 61/443,773, filed Feb. 17, 2011; 61/523,503, filed Aug. 15, 2011; and 61/579,719, filed Dec. 23, 2011. All applications are incorporated herein by reference in their entirety.

INTRODUCTION

This invention relates to 2,4,5-substituted pyrimidines that inhibit Focal Adhesion Kinase (FAK), also known as protein tyrosine kinase 2 (PTK2), and VEGFR3, and to pharmaceutical compositions containing such compounds. This invention also relates to a method of using such compounds for the prevention and/or treatment of proliferative diseases, such as cancer.

BACKGROUND

Directional cell migration is important in many physiological and pathological processes including embryonic development, wound healing, angiogenesis, tumour invasion and metastasis. Transduction of extracellular signals, that stimulate cells to move directionally, may be induced by a number of processes including trans-membrane integrins binding to extra cellular matrix proteins and the action of growth factors (for example EGF, IGF and VEGF) on the extracellular domains of their cognate receptors.

FAK is a non receptor tyrosine kinase that mediates signals from both trans-membrane integrins and growth factor receptors. FAK has been reported to play a central role in coordinating these diverse extra cellular signals, integrating them in a fashion that results in directional movement of cells through their external environment (Tomar and Schlaepfer. Current Opinion in Cell Biology: 2009, 21, 676-683).

Integrin clustering or the activation of a growth factor receptor (for example EGFR, IGF-1R, Her2 and VEGFR) promotes FAK autophosphorylation at Y397. Phosphorylated Y397 FAK then binds to c-Src (referred to as Src herein) and Src mediated phosphorylation of FAK at Y576 and Y577 occurs to give rise to an active FAK-Src complex. Active FAK-Src then facilitates signaling via a number of biochemical pathways which influence processes such as cell adhesion, migration, invasion, cell survival, proliferation, acquisition of chemotherapy resistance and metastasis (Brunton and Frame. Current Opinion in Pharmacology: 2008, 8, 437-432 and Chatzizacharias et al. Expert Opinion in Therapeutic Targets: 2007, 11(10), 1315-1328).

Cell Adhesion

Functional studies addressing the role of FAK in cell adhesion suggest that it contributes to both focal adhesion assembly (Richardson and Parsons. Nature: 1996, 380, 538-540) and focal adhesion turnover (Fincham et al. Oncogene: 1995, 10(11), 2247-2252). Inhibition of FAK by RNAi in both human and mouse cell lines, resulting in decreased FAK protein levels, has been shown to reduce cell adhesion to a fibronectin/laminin-coated plate in vitro (Tsutsumi et al. International Journal of Oncology: 2008, 33(1), 215-224).

Cell Migration

There is strong evidence that FAK is a key regulator of cell migration (Angelucci and Bologna. Current Pharmaceutical Design: 2007, 13, 2129-2145 and Mitra et al. Nature Reviews Molecular Cell Biology: 2005, 6, 56-68). Cells derived from FAK −/− mouse embryos exhibit reduced migration as a result of impaired adhesion turnover (Ilić et al. Nature: 1995, 377, 539-544). Moreover, displacement of FAK from focal adhesions reduces cell migration (Gilmore and Romer. Molecular Biology of the Cell: 1996, 7(8), 1209-1224), whilst over-expression in CHO cells stimulates migration (Cary et al. Journal of Cell Science: 1996, 7, 1787-1794). In addition, inhibition of FAK by RNAi in both human and mouse cell lines, resulting in decreased FAK protein levels, has been shown to reduce cell migration in an in vitro haptotactic migration assay (Tsutsumi et al. International Journal of Oncology: 2008, 33(1), 215-224).

Cell Invasion

FAK activation has been shown to enhance matrix degrading invasive behaviour. FAK-Src signaling through cellular apoptosis susceptibility protein (CAS) (Liao et al. Journal of Experimental and Clinical Cancer Research: 2008, 27:15) leads to the expression of matrix metalloproteases (MMPs) including MMP2 and MMP9. FAK-Src activation also promotes cell surface expression of MMP14 via phosphorylation of endophilin A2. MMP14 then activates MMP2 by cleavage of pro-MMP2 to its active form (Siesser and Hanks. Clinical Cancer Research: 2006, 12(11), 3233-3237). Highly invasive cancer cells form specialized actin-rich extra cellular matrix degrading membrane protrusions known as invadopodia which are rich in matrix-degrading proteases such as MMPs. Both FAK and Src have been shown to be instrumental in the formation of invadopodia (Chan et al. Journal of Chemical Biology: 2009, 185(2), 357-370).

Cell Survival

FAK has been shown to play an important role in cell survival. Activation of FAK has been shown to result in suppression of anoikis (apoptosis in response to an inappropriate extra cellular matrix environment) (Frisch et al Journal of Cell Biology. 1996, 134(3), 793-799 and Xu et al Cell Growth and Differentiation. 1996, 7(4), 413-418). Studies have demonstrated that FAK activates multiple downstream pathways to suppress anoikis in both fibroblasts and epithelial cells (Zouq et al. Journal of Cell Science: 2008, 122, 357-367). In human intestinal crypt cells signalling via the association of FAK with β1 integrin and subsequent binding with Src up regulates expression of the anti-apoptotic proteins Bcl-XL and Mcl-1 via PI3-K/Akt-1 signalling. PI3-K/Akt-1 signalling also down regulates expression of the pro-apoptotic activators Bax and Bak, causes phosphorylation of the pro-apoptotic sensitizer Bad and antagonizes p38β activation. Dissociation of FAK/Src results in a sustained/enhanced activation of p38β which is an apoptosis/anoikis driver (Bouchard et al. Apoptosis: 2008, 13, 531-542).

Cell Proliferation

Reduction in the expression of either FAK or β1 integrin and hence disruption of the β1-FAK signalling axis results in decreased initial proliferation of micro-metastatic cells distributed in the lung. Using 3D cultured D2 cells a strong correlation was observed between FAK Y397 and Y861 phosphorylation and proliferative ability (Shibue and Weinberg. PNAS 2009, 106(25), 10290-10295). HL-60 Cells, transfected to over express FAK, have been shown to double at a rate 1.5 times faster than control HL-60 cells. Studies revealed a marked induction of cyclin D3 expression and CDK activity in the cells over expressing FAK. Activation of PI3-K/Akt-1 signalling, a process associated with FAK activation in a number of studies, was identified as a probable cause of the cyclin expression/activation (Yamamoto et al. Cellular Signaling: 2003, 15. 575-583).

Acquisition of Chemotherapy Resistance

Exposure of the cisplatin sensitive ovarian cancer cell line OAW42 to repeated cycles of cisplatin treatment and subsequent recovery resulted in the formation of chemo-resistant OAW42-R cells. Studies aimed at identifying the cause of this chemo-resistance revealed that FAK was constituently active in both the sensitive and chemo-resistant cells. However, inhibition of phosphorylation of Y397 FAK was induced by treatment with cisplatin in OAW42 cells but not in OAW42-R cells (Poulain and co-workers. Gynaecologic oncology: 2006, 101, 507-519). The effects of FAK inhibition on chemo-resistance has also been studied in vitro and in vivo using the FAK inhibitor TAE226, alone and in combination with docetaxel, in taxane-sensitive (SKOV3ip1 and HeyA8) and taxane-resistant (HeyA8-MDR) ovarian cancer cell lines. TAE226 has the structure:

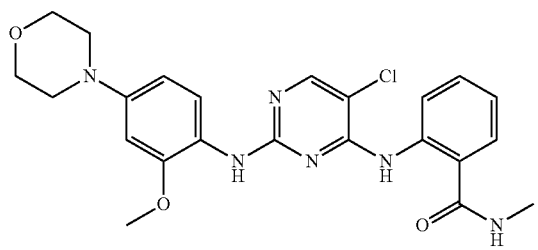 [SMILES: CNC(=O)c1ccccc1Nc1nc(Nc2ccc(N3CCOCC3)cc2OC)ncc1Cl]

and is described in WO 2004/080980 and WO 2005/016894. In vitro, TAE226 inhibited the phosphorylation of FAK at both Y397 and Y861 sites, inhibited cell growth in a time- and dose-dependent manner, and enhanced docetaxel-mediated growth inhibition by 10- and 20-fold in the taxane-sensitive and taxane-resistant cell lines, respectively. In vivo, FAK inhibition by TAE226 significantly reduced tumour burden in the HeyA8, SKOV3ip1, and HeyA8-MDR models (46-64%) compared with vehicle-treated controls. However, the greatest efficacy was observed with concomitant administration of TAE226 and docetaxel in all three models (85-97% reduction). In addition, TAE226 in combination with docetaxel significantly prolonged survival in tumour-bearing mice (Halder et al. Cancer Res: 2007, 67(22), 10976-10983).

Metastatic Potential

Several studies have examined the role of FAK protein levels and it's relation to tumor progression in animal models. In a mouse skin carcinogenesis model using FAK +/− mice, reduced FAK protein expression correlated with decreased papilloma formation (46%), compared with FAK +/+ wild-type control mice (McLean et al. Cancer Research: 2001, 61, 8385-8389). Using human breast carcinoma cells, researchers showed that FAK siRNA treated cells were inhibited from metastasizing to the lung after orthotopic implantation in nude mice (Benlimame et al. Journal of Cell Biology: 2005, 171, 505-516). Similar experiments using short hairpin RNA (shRNA) against FAK in 4T1 mouse breast carcinoma cells resulted in an inhibition of metastasis to the lungs after orthotopic implantation in mammary pads (Mitra et al. Oncogene: 2006, 25, 4429-4440). Inhibition of FAK by dominant negative expression in 4T1 mouse breast carcinoma cells reduced tumour growth and angiogenesis in mice (Mitra et al. Oncogene: 2006, 25, 5969-5984). Use of a Cre/loxP recombination system to disrupt FAK function in the mammary epithelium of a transgenic model of breast cancer has demonstrated that FAK expression is required for the transition of premalignant hyperplasias to carcinomas and their subsequent metastases. The observed decrease in tumor progression was further correlated with impaired mammary epithelial proliferation suggesting that FAK plays a critical role in mammary tumor progression (Lahlou et al. PNAS USA: 2007, 104(51), 20302-20307).

In accordance with the above observations over expression of FAK mRNA and/or protein has been reported in numerous human cancers including colorectal cancer (de Heer. European Journal of Surgical Oncology: 2008, 34(11), 1253-1261), prostate cancer (Tremblay, L., W. Hauck, et al. International Journal of Cancer: 1996, 68(2), 164-171), breast cancer (Watermann et al. British Journal of Cancer 2005, 93(6), 694-698) and melanomas (Hess et al. Cancer Research: 2005, 65(21), 9851-60). Furthermore FAK over expression is frequently correlated with more aggressive phenotypes of these cancers.

Thus, there is strong evidence to suggest that a FAK inhibitor would have application for the reduction of cell adhesion, cell migration, cell invasion, cell proliferation and chemo-resistance. Furthermore, a FAK inhibitor would have applicability to induce apoptosis for cells in inappropriate extra cellular matrix environments and reduce angiogenesis.

It will be appreciated that activity at other tyrosine kinases and serine/threonine kinase in combination with FAK activity may be beneficial for the treatment of proliferative diseases, such as cancer.

For example, the vascular endothelial growth factor receptor VEGFR3 (Flt4) is over expressed in melanoma patients with metastases in regional lymph nodes (Mouawad et al. European Journal of Cancer: 2009, 45, 1407-1414). Abnormal expression levels of endogenous receptor tyrosine kinase ligands are also observed in many human cancers. For example, the expression levels of vascular endothelial growth factors C and D (VEGF-C and VEGF-D), ligands of VEGFR3, are significantly correlated with lymphatic metastasis and lymphatic vessel invasion in early-stage invasive cervical carcinoma (Journal of Experimental & Clinical Cancer Research 2009, 28).

Accordingly, compounds that selectively inhibit FAK and VEGFR3 would be useful for the treatment of proliferative diseases, such as cancer.

Two compounds reported to inhibit FAK are PF-562,271 and PF-573,228.

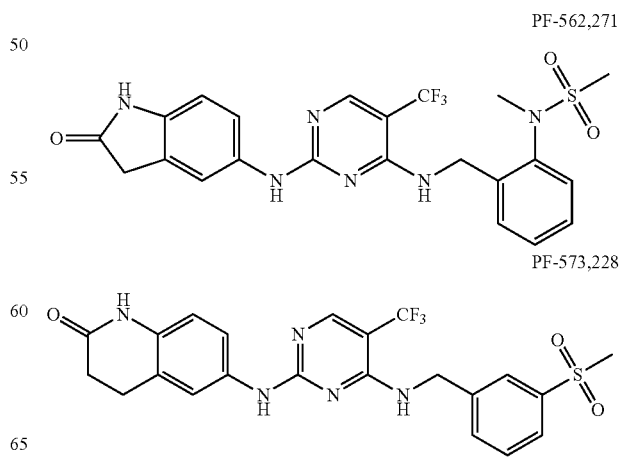

PF-562,271 is described in WO2004/056786, WO2004/056807, WO2005/023780, WO2007/063384 and Roberts et al. Cancer Res 2008, 68(6), 1935-1944.

PF-573,228 is described in Slack-Davis et al. J. Biol. Chem. 2007, 282(20), 14845-14852.

In addition to these specifically described compounds, further classes of FAK inhibitors are disclosed in WO2008/129380, WO2008/115369, WO2009/105498, US2010/113475, WO2009/143389, WO2009/071535, WO2010/055117, WO2010/058030, WO2010/058032, WO2007/140222, and WO2009/024332.

SUMMARY OF THE INVENTION

The present inventors have discovered a particular class of compounds which are effective as FAK inhibitors, and also inhibit VEGFR3. These compounds may exhibit selectivity for FAK over kinases such as VEGFR1, IGF-1R (Insulin-like growth factor 1 receptor), IR (insulin receptor) and CDKs (cyclin-dependent kinases). Additionally, the compounds of the invention may have enhanced selectivity for the inhibition of cytochrome p450 enzymes, specifically the 2C9 and 3A4 isoforms. Furthermore, the compounds of the invention may be less prone to the formation of adducts with glutathione.

In a first aspect, the present invention provides compounds of the following formula (I):

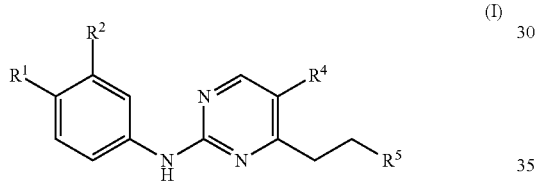

wherein:
$R^1$ is selected from: H and

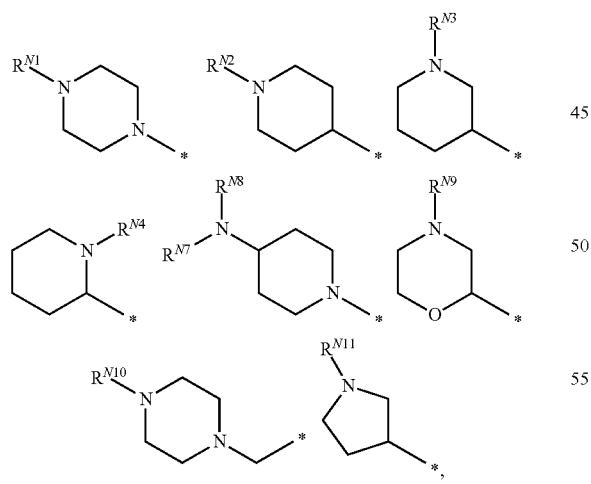

wherein:
$R^{N1}$ is selected from H, $C_{1-3}$ alkyl and C(=O)Me;
$R^{N2}$ is selected from H, $C_{1-3}$ alkyl and C(=O)Me;
$R^{N3}$ is selected from H, $C_{1-3}$ alkyl and C(=O)Me;
$R^{N4}$ is selected from H and $CH_3$;
$R^{N7}$ and $R^{N8}$ are independently selected from H and $CH_3$;
$R^{N9}$ is selected from H, $C_{1-3}$ alkyl and C(=O)Me;
$R^{N10}$ is selected from H, $C_{1-3}$ alkyl and C(=O)Me;
$R^{N11}$ is selected from H, $C_{1-3}$ alkyl and C(=O)Me;
$R^2$ is selected from H and

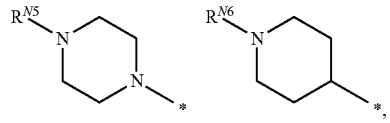

wherein:
$R^{N5}$ is selected from H, $C_{1-3}$ alkyl and C(=O)Me;
$R^{N6}$ is selected from H, $C_{1-3}$ alkyl and C(=O)Me;
and wherein only one of $R^1$ and $R^2$ is H;
or $R^1$ and $R^2$ together form the group —$CH_2$—N($R^{N12}$)—$C_2H_4$—, where $R^{N12}$ is selected from H, $C_{1-3}$ alkyl and C(=O)Me;
$R^4$ is selected from $CF_3$, halo, $CF_2H$ and CN; and
$R^5$ is selected from groups of the following formulae:

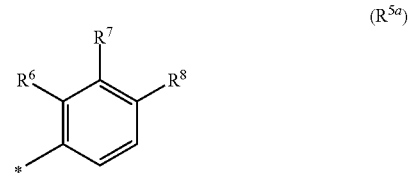
($R^{5a}$)

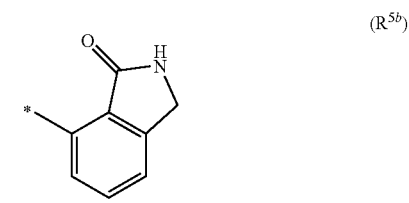
($R^{5b}$)

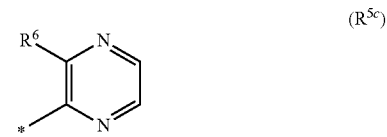
($R^{5c}$)

($R^{5d}$)

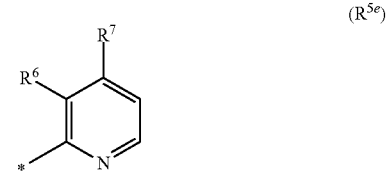
($R^{5e}$)

wherein:
$R^6$ is selected from H, $(CHR^{c1})_{n1}C(O)N(R^{N13})Z^1$ and $(CH_2)_{n2}C(O)OZ^2$; wherein:
n1 is 1;
$R^{C1}$ is H or Me;
$R^{N13}$ is H or $CH_3$;
$Z^1$ is H, $CH_3$ or $OCH_3$;
n2 is 1; and
$Z^2$ is $CH_3$;
and where only one of $R^{N13}$ and $Z^1$ can be $CH_3$, $R^7$, if present, is selected from H, and $(CH_2)_{m1}C(O)N(R^{M1})Y^1$, wherein:

m1 is 0 or 1;

$R^{M1}$ is H; and $Y^1$ is H, Me or $OCH_3$;

wherein when both $R^6$ and $R^7$ are present, one is H and the other is not H, and wherein only $R^6$ is present, it is not H; and $R^8$, if present, is H or, when $R^7$ is $C(=O)NH_2$, $R^8$, if present, is selected from H and $C_{1-2}$ alkyl.

A second aspect of the present invention provides a composition comprising a compound of the first aspect and a pharmaceutically acceptable carrier or diluent.

A third aspect of the invention provides a compound of the first aspect for use in a method of therapy.

A fourth aspect of the invention provides for the use of a compound of the first aspect in the preparation of a medicament for treating a disease ameliorated by the inhibition of FAK and VEGFR3. The fourth aspect of the invention also provides a compound of the first aspect for use in the method of treatment of a disease ameliorated by the inhibition of FAK VEGFR3.

A further aspect of the invention provides an active compound as described herein for use in a method of treatment of the human or animal body, preferably in the form of a pharmaceutical composition.

Another aspect of the invention provides a method of inhibiting FAK and VEGFR3 in vitro or in vivo, comprising contacting a cell with an effective amount of an active compound as described herein.

Each of the groups $R^1$ to $R^8$ will be discussed in more detail below.

$R^1$ $R^1$ may have one of the following structures:

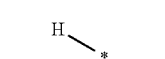 ($R^{1a}$)

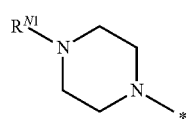 ($R^{1b}$)

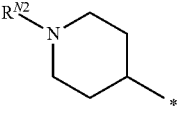 ($R^{1c}$)

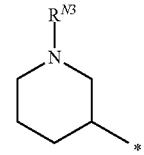 ($R^{1d}$)

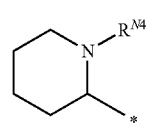 ($R^{1e}$)

-continued

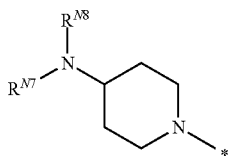 ($R^{1f}$)

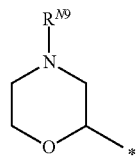 ($R^{1g}$)

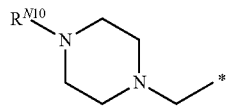 ($R^{1h}$)

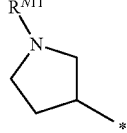 ($R^{1i}$)

When $R^1$ is H, $R^2$ (discussed below) is not H.

Each of $R^{N1}$, $R^{N2}$ and $R^{N3}$ is independently selected from H, $C_{1-3}$ alkyl (i.e. methyl, ethyl, prop-1-yl and prop-2-yl) and $C(=O)Me$ and $R^{N4}$ is selected from either H or methyl. $R^{N7}$ is either H or methyl. $R^{N7}$ and $R^{N8}$ are independently selected from H and $CH_3$. Each of $R^{N9}$, $R^{N10}$ and $R^{N11}$ are also independently selected from H, $C_{1-3}$ alkyl (i.e. methyl, ethyl, prop-1-yl and prop-2-yl) and $C(=O)Me$.

$R^2$ $R^2$ may have one of the following structures:

 ($R^{2A}$)

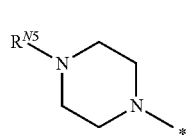 ($R^{2B}$)

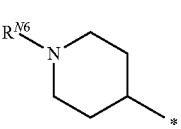 ($R^{2C}$)

When $R^2$ is H, $R^1$ (discussed above) is not H.

$R^{N5}$ and $R^{N6}$ are independently selected from H, $C_{1-3}$ alkyl (i.e. methyl, ethyl, prop-1-yl and prop-2-yl) and $C(=O)Me$.

$R^1$ and $R^2$

When $R^1$ and $R^2$ together form the group —$CH_2$—N($R^{N12}$)—$C_2H_4$—,

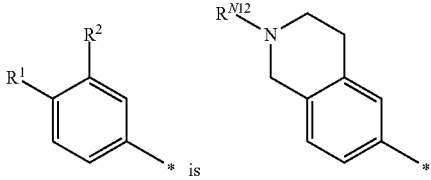 is $R^{N12}$ is selected from H, $C_{1-3}$ alkyl (i.e. methyl, ethyl, prop-1-yl and prop-2-yl) and C(=O)Me.

$R^4$ $R^4$ is selected from $CF_3$, halo (i.e. F, Cl, Br, I), $CF_2H$ and CN.

In some embodiments, the halo group is either Cl or Br.

$R^5$ $R^5$ is selected from groups of the following formulae:

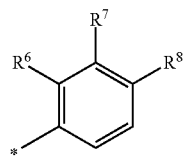 ($R^{5a}$)

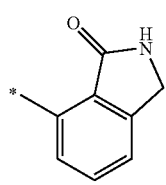 ($R^{5b}$)

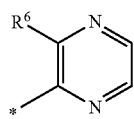 ($R^{5c}$)

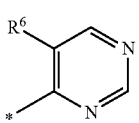 ($R^{5d}$)

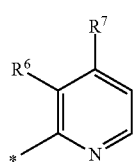 ($R^{5e}$)

$R^6$ $R^6$ is selected from H, $(CHR^{C1})_{n1}C(O)N(R^{N13})Z^1$ and $(CH_2)_{n2}C(O)OZ^2$; wherein:

n1 is 1;
$R^{C1}$ is H or Me;
$R^{N13}$ is H or $CH_3$;
$Z^1$ is H, $CH_3$ or $OCH_3$;
n2 is 1; and
$Z^2$ is $CH_3$;
wherein only one of $R^{N13}$ and $Z^1$ may be $CH_3$.

When $R^6$ is H, $R^7$ (discussed below) is not H.

If $R^6$ is $(CHR^{C1})_{n1}C(O)N(R^{N6})Z^1$, it may be selected from: $CH_2C(O)NH_2$, $CH_2C(O)NHCH_3$, $CH_2C(O)NHOCH_3$, $CH_2C(O)NCH_3OCH_3$, $CHCH_3C(O)NH_2$, $CHCH_3C(O)NHCH_3$, $CHCH_3C(O)NHOCH_3$, and $CHCH_3C(O)NCH_3OCH_3$.

If $R^6$ is $(CH_2)_{n2}C(O)OZ^2$, it is $CH_2C(O)OCH_3$.

$R^7$ $R^7$ is selected from H, and $(CH_2)_{m1}C(O)N(R^{M1})Y^1$, wherein:

m1 is 0 or 1;
$R^{M1}$ is H; and
$Y^1$ is H, Me or $OCH_3$;

When $R^7$ is H, $R^6$ (discussed above) is not H. In addition, when $R^7$ is not present, $R^6$ (discussed above) is not H.

When $R^7$ is $(CH_2)_{m1}C(O)N(R^{M1})Y^1$, it may be selected from $C(O)NH_2$, $C(O)NHCH_3$, $C(O)NHOCH_3$, $CH_2C(O)NH_2$, $CH_2C(O)NHCH_3$ and $CH_2C(O)NHOCH_3$.

$R^8$ $R^8$ is H, except for when $R^7$ is $C(=O)NH_2$, it may alternatively be $C_{1-2}$ alkyl, i.e. methyl or ethyl.

Includes Other Forms

Included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

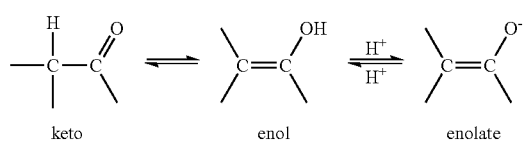

keto     enol     enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$ and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al. J. Pharm. Sci., 66, 1-19 (1977).

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R^{2+}$, $NHR^{3+}$, $NR^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc. It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(=O)R), for example, as: a t-butyl ether; a benzyl, benzhydryl(diphenylmethyl), or trityl(triphenylmethyl) ether; a trimethylsilyl or t-butyldimethylsilyl ether; or an acetyl ester (—OC(=O)$CH_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—$CH_3$); a benzyloxy amide (—NHCO—$OCH_2C_6H_5$, —NH-Cbz); as a t-butoxy amide (—NHCO—$OC(CH_3)_3$, —NH-Boc); a 2-biphenyl-2-propoxy amide (—NHCO—$OC(CH_3)_2C_6H_4C_6H_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases, as an N-oxide (>NO*).

For example, a carboxylic acid group may be protected as an ester for example, as: an $C_{1-7}$ alkyl ester (e.g. a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—$CH_2NHC$(=O)$CH_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties. For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C1-7 alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxyl)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Selectivity

The selectivity of the compounds for inhibiting FAK and VEGFR3 over other kinases, such as IGF-1R, IR and CDKs can be demonstrated by biochemical assay results (see, for example, the FAK kinase assay and VEGFR3 assays described below). The compounds of the invention may also be selective over VEGFR1 and/or VEGFR2.

The selectivity of the compounds for FAK over the inhibition of cytochrome p450 enzymes, specifically the 2C9 and 3A4 isoforms may be determined using standard inhibition assays.

How prone the compounds of the invention may be to the formation of adducts with glutathione may be determined by the protocol described in Walker, et al. Biorg. Med. Chem. Letts. 2008, 18, 6071-6077.

FURTHER EMBODIMENTS

Figure 1:
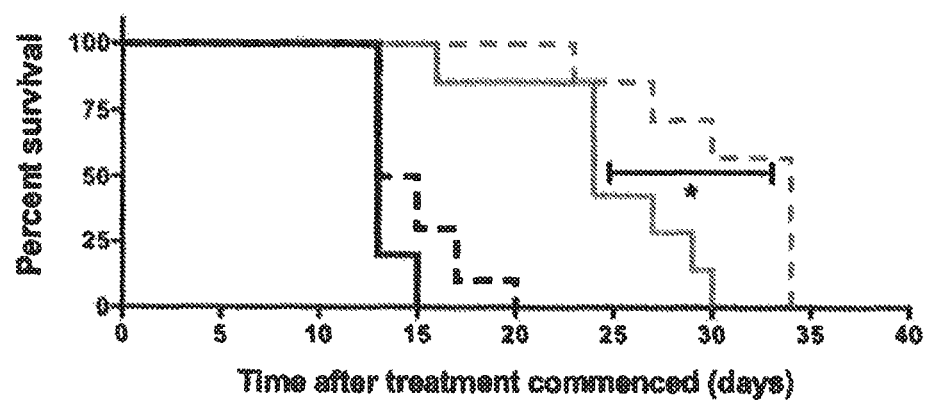
FIG. 1 shows Kaplan-Meier survival curves of tumour bearing mice treated with a compound of the invention and/or Avastin.

The following embodiments and preferences may be combined with one another as appropriate.

In some embodiments, $R^2$ is H and $R^1$ is:

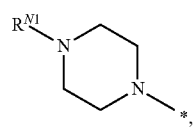

wherein $R^{N1}$ is selected from H, $C_{1-3}$ alkyl (i.e. methyl, ethyl, prop-1-yl and prop-2-yl) and C(=O)Me. In some of these embodiments, it may be preferred that $R^{N1}$ is C(=O)Me. In others of these embodiments, it may be preferred that $R^{N1}$ is H, methyl or ethyl.

In other embodiments, $R^2$ is H and $R^1$ is:

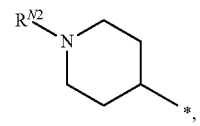

wherein $R^{N2}$ is selected from H and $C_{1-3}$ alkyl (i.e. methyl, ethyl, prop-1-yl and prop-2-yl). In these embodiments, it may be preferred that $R^{N2}$ is selected from H and methyl. In other of these embodiments, it may be preferred that $R^{N2}$ is ethyl.

In other embodiments, $R^2$ is H and $R^1$ is:

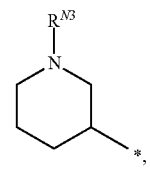

wherein $R^{N3}$ is selected from H and $C_{1-3}$ alkyl (i.e. methyl, ethyl, prop-1-yl and prop-2-yl). In these embodiments, it may be preferred that $R^{N3}$ is selected from H and methyl. In other of these embodiments, it may be preferred that $R^{N3}$ is ethyl.

In other embodiments, $R^2$ is H and $R^1$ is:

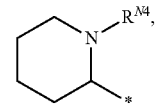

wherein $R^{N4}$ is selected from H and methyl. In these embodiments, it may be preferred that $R^{N4}$ is H.

In other embodiments, $R^2$ is H and $R^1$ is:

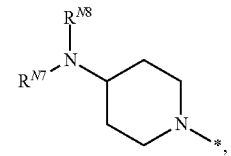

wherein $R^{N7}$ and $R^{N8}$ are both H or both methyl. In some of these embodiments, it may be preferred that $R^{N7}$ and $R^{N8}$ are both H.

In other embodiments, $R^2$ is H and $R^1$ is:

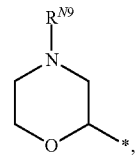

wherein $R^{N9}$ is selected from H and $C_{1-3}$ alkyl (i.e. methyl, ethyl, prop-1-yl and prop-2-yl). In these embodiments, it may be preferred that $R^{N9}$ is H.

In other embodiments, $R^2$ is H and $R^1$ is:

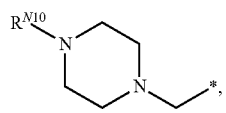

wherein $R^{N10}$ is selected from H and $C_{1-3}$ alkyl (i.e. methyl, ethyl, prop-1-yl and prop-2-yl). In these embodiments, it may be preferred that $R^{N10}$ is selected from H and methyl.

In other embodiments, $R^2$ is H and $R^1$ is:

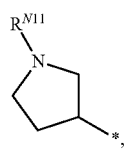

wherein $R^{N11}$ is selected from H and $C_{1-3}$ alkyl (i.e. methyl, ethyl, prop-1-yl and prop-2-yl). In these embodiments, it may be preferred that $R^{N11}$ is H.

In some embodiments, $R^1$ is H and $R^2$ is:

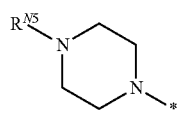

where $R^{N5}$ is selected from H and $C_{1-3}$ alkyl (i.e. methyl, ethyl, prop-1-yl and prop-2-yl). In these embodiments, it may be preferred that $R^{N5}$ is selected from H and methyl.

In some embodiments, $R^1$ is H and $R^2$ is:

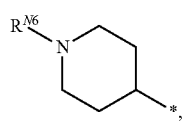

where $R^{N6}$ is selected from H and $C_{1-3}$ alkyl (i.e. methyl, ethyl, prop-1-yl and prop-2-yl). In these embodiments, it may be preferred that $R^{N6}$ is selected from H and methyl.

It may be further preferred that $R^1$ is H and $R^2$ is:

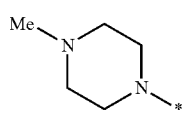

In some embodiments, when $R^1$ and $R^2$ together form the group —$CH_2$—N($R^{N12}$)—$C_2H_4$—, $R^{N12}$ is selected from H and $C_{1-3}$ alkyl (i.e. methyl, ethyl, prop-1-yl and prop-2-yl). In these embodiments, it may be preferred that $R^{N12}$ is selected from H and methyl, and it may be more preferred that $R^{N12}$ is methyl.

In some embodiments, $R^4$ is selected from $CF_3$, Cl, Br, $CF_2H$, and CN.

In further embodiments, $R^4$ is selected from $CF_3$, Cl and $CF_2H$. In further embodiments, $R^4$ is selected from $CF_3$ and Cl. It may be preferred that $R^4$ is $CF_3$.

In some embodiments, it may be preferred that $R^5$ is a group of the following formulae:

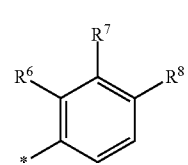

In some embodiments, $R^5$ is a group selected from:

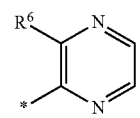

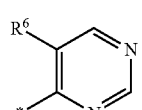

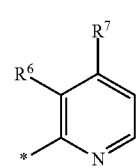

In these embodiments, $R^5$ may be preferably selected from $R^{5e}$ and $R^{5c}$, and may more preferably be $R^{5e}$.

In some embodiments, $R^7$ is H and $R^6$ is $(CHR^{C1})_{m1}C(O)N(R^{N6})Z^1$.

In further embodiments, $R^7$ is H and $R^6$ is selected from $CH_2C(O)NH_2$, $CH_2C(O)NHCH_3$, $CHCH_3C(O)NH_2$ and $CHCH_3C(O)NHCH_3$.

It may be preferred that $R^7$ is H and $R^6$ is selected from $CH_2C(O)NH_2$, $CHCH_3C(O)NH_2$ and $CH_2C(O)NHCH_3$, and more preferably from $CH_2C(O)NH_2$, and $CHCH_3C(O)NH_2$.

In some embodiments, $R^6$ is H and $R^7$ is $(CH_2)_{m1}C(O)N(R^{M1})Y^1$.

In further embodiments, $R^6$ is H and $R^7$ is selected from $C(O)NH_2$, $C(O)NHCH_3$, $CH_2C(O)NH_2$ and $CH_2C(O)NHCH_3$.

It may be preferred that $R^6$ is H and $R^7$ is $C(O)NH_2$.

In some embodiments where $R^6$ is H and $R^7$ is $C(O)NH_2$, $R^8$ is methyl.

In some embodiments, it may be preferred that $R^5$ is a group of the following formula:

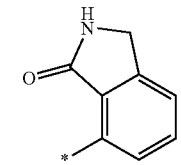

In selected embodiments of the invention, the compounds may of formula Ia:

(Ia)

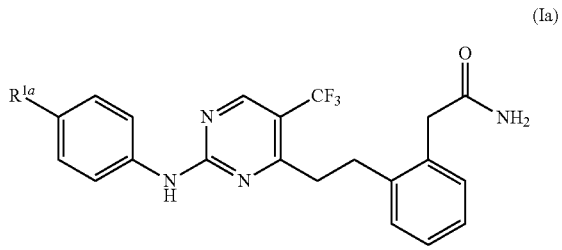

wherein $R^{1a}$ is selected from:

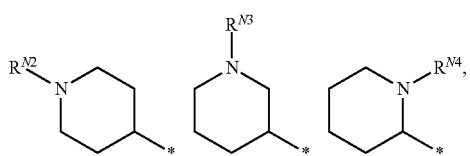

wherein:
$R^{N2}$ is selected from H, $C_{1-3}$ alkyl and C(=O)Me;
$R^{N3}$ is selected from H, $C_{1-3}$ alkyl and C(=O)Me; and
$R^{N4}$ is selected from H and $CH_3$.

The preferences expressed above for $R^{N2}$, $R^{N3}$ and $R^{N4}$ apply here as well.

In selected embodiments of the invention, the compounds may of formula Ib:

(Ib)

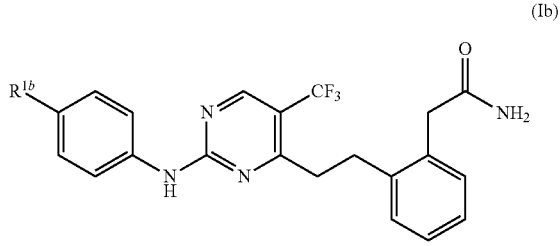

wherein $R^{1b}$ is selected from:

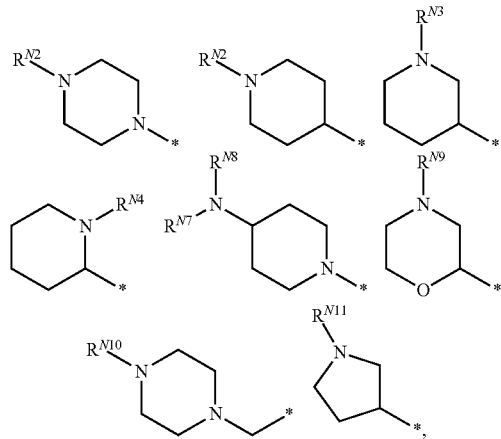

wherein
$R^{N1}$ is selected from H, $C_{1-3}$ alkyl and C(=O)Me;
$R^{N2}$ is selected from H, $C_{1-3}$ alkyl and C(=O)Me;
$R^{N3}$ is selected from H, $C_{1-3}$ alkyl and C(=O)Me;
$R^{N4}$ is selected from H and $CH_3$;
$R^{N7}$ and $R^{N8}$ are independently selected from H and $CH_3$;
$R^{N9}$ is selected from H, $C_{1-3}$ alkyl and C(=O)Me;
$R^{N10}$ is selected from H, $C_{1-3}$ alkyl and C(=O)Me; and
$R^{N11}$ is selected from H, $C_{1-3}$ alkyl and C(=O)Me.

The preferences expressed above for $R^{N1}$, $R^{N2}$, $R^{N3}$, $R^{N4}$, $R^{N7}$, $R^{N8}$, $R^{N9}$, $R^{N10}$ and $R^{N11}$ apply here as well.

In particular, compounds of formula Ib where $R^{1b}$ is selected from:

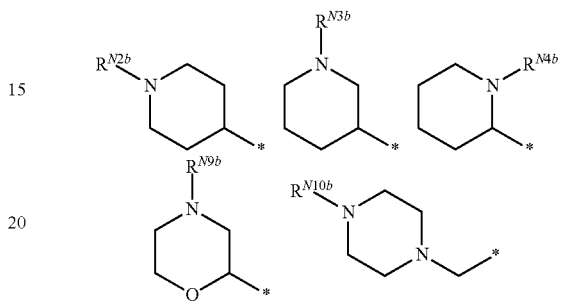

and wherein:
$R^{N2b}$ is selected from H, methyl and ethyl;
$R^{N3b}$ is selected from H and methyl;
$R^{N4b}$ is H;
$R^{N9b}$ is H; and
$R^{N10}$ is selected from H and methyl.

Embodiments of the inventions are compounds of the examples, including compounds 1 to 40. Embodiments of particular interest include compounds 4, 5, 8, 11 and 16. Further embodiments of particular interest include compounds 21, 22, 25, 31 and 36.

General Synthesis Methods

The compounds of the invention can be prepared employing the following general methods and using procedures described in detail in the experimental section. The reaction conditions referred to are illustrative and non-limiting.

Compounds of formula I, as described above, can be prepared by synthetic strategies outlined below, wherein the definitions above apply:

Scheme A

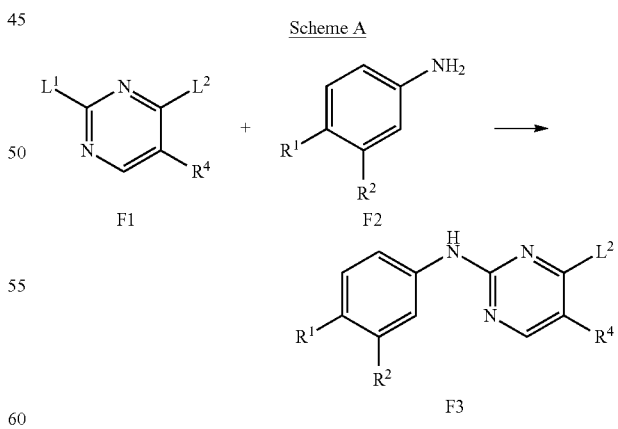

Compounds of formula F1 may be reacted with substituted commercial or synthetic anilines of formula F2 (as prepared in scheme C, D, E, F, G, H, I, J, K and L) to form intermediates of formula F3 where $L^1$ and $L^2$ may be the same or different and include Cl, Br, I, SMe, $SO_2Me$ and $R^4$=$CF_3$, halogen, $CF_2H$ or CN.

An example of a commercial aniline is:

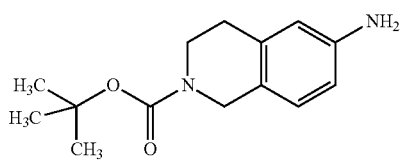 [SMILES: CC(C)(C)OC(=O)N1CCc2cc(N)ccc2C1]

which is useful for preparing compounds where $R^1$ and $R^2$ together form the group —CH$_2$—N(R$^{N12}$)—C$_2$H$_4$—.

Compounds of the formula F1 may be prepared where $L^1$ and $L^2$ are different (see scheme B) to allow regioselective substitution or when $L^1$=$L^2$ suitable reaction conditions can be employed (choice of solvent, reaction temperature, addition of a Lewis acid, for example ZnCl$_2$ in diethyl ether) to allow $L^1$ to be selectively displaced over $L^2$. Where regiochemical mixtures and di-substitution are obtained the regioisomers may be separated by chromatography.

Compounds of the formula F1 where $L^1$=$L^2$ are either commercially available, for example 2,4-dichloro-5-(trifluoromethyl)pyrimidine, 2,4-dichloro-5-fluoropyrimidine, 2,4,5-trichloropyrimidine, 2,4-dichloro-5-bromopyrimidine, 2,4-dichloro-5-iodopyrimidine, 2,4-dichloro-5-cyanopyrimidine or may be prepared readily from commercial starting materials. Where $R^4$=CF$_3$ and differentiation of $L^1$ and $L^2$ is desirable, the method outlined in scheme B may be employed.

Scheme B

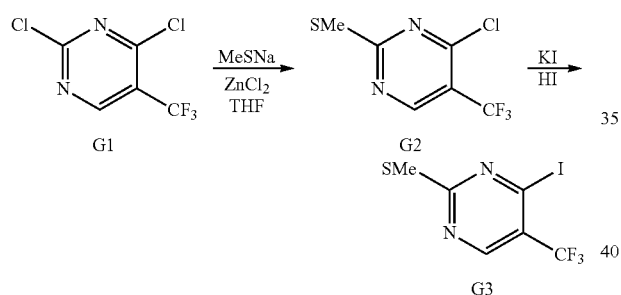

Commercially available 2,4-dichloro-5-(trifluoromethyl)pyrimidine (G1) can be selectively reacted with sodium thiomethoxide in the presence of zinc(II) chloride to give 2-thiomethyl-4-chloro-5-(trifluoromethyl)pyrimidine (G2). 2-Thiomethyl-4-chloro-5-(trifluoromethyl)pyrimidine (G2) can be further reacted, for example by conversion to 2-thiomethyl-4-iodo-5-(trifluoromethyl)pyrimidine (G3) under Finkelstein conditions and/or by oxidation with mCPBA to give the corresponding sulfone if further differentiation of the 2 and 4-position is required or if additional activation is desirable.

Scheme C

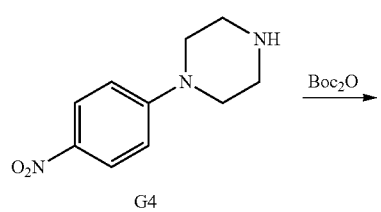

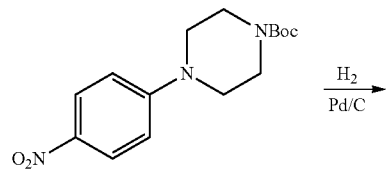

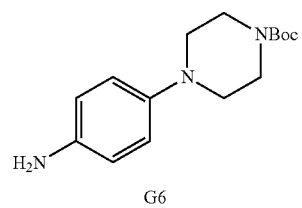

Commercially available 1-(4-nitrophenyl)piperazine (G4), or a salt thereof, can be reacted with Boc anhydride to give tert-butyl 4-(4-nitrophenyl)piperazine-1-carboxylate (G5). Subsequent reduction via hydrogenation in the presence of a catalyst, for example palladium on charcoal, gives the corresponding aniline, tert-butyl 4-(4-aminophenyl)piperazine-1-carboxylate (G6).

Scheme D

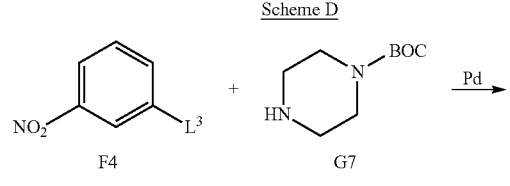

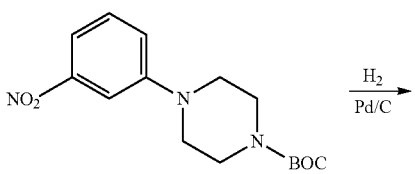

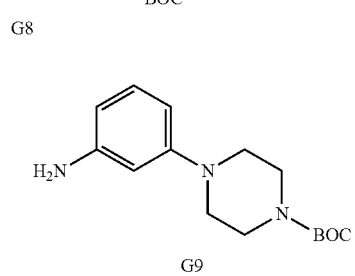

tert-Butyl 4-(3-aminophenyl)piperazine-1-carboxylate (G9) can be prepared by coupling of commercially available tert-butyl piperazine-1-carboxylate (G7) and compounds of the formula F4, where $L^{3=I}$ or Br, in a Buchwald type reaction to give tert-butyl 4-(3-nitrophenyl)piperazine-1-carboxylate (G8). Reduction with hydrogen in the presence of a catalyst, for example palladium on charcoal, gives tert-butyl 4-(3-aminophenyl)piperazine-1-carboxylate (G9).

Scheme E

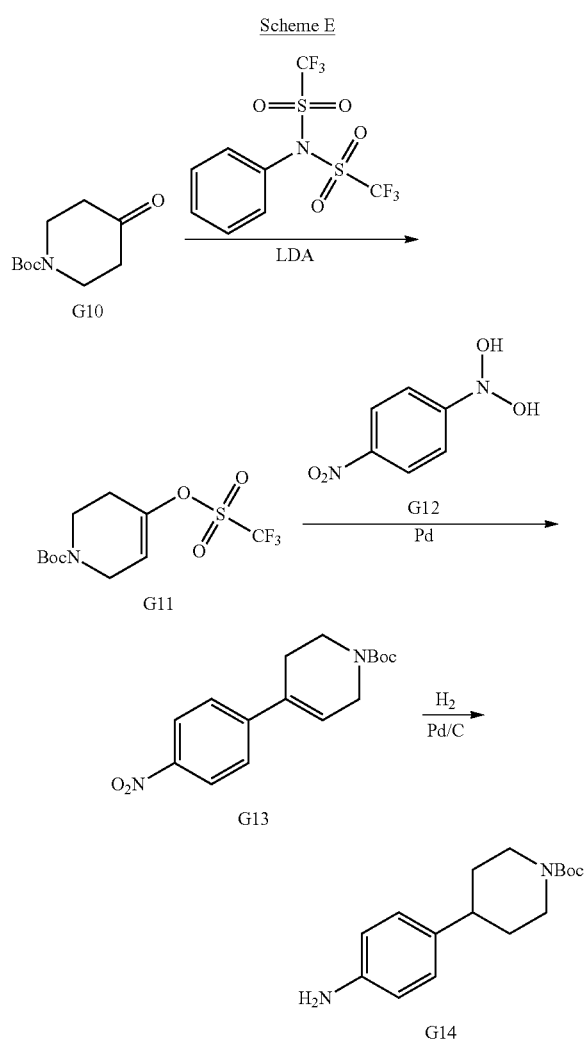

The corresponding 4-piperidine analogues of G6 can be prepared by a sequence of reactions starting with the conversion of commercially available tert-butyl 4-oxopiperidine-1-carboxylate (G10) to vinyl triflate G11. Coupling of G11 in a Suzuki type reaction with (4-nitrophenyl)boronic acid (G12) gives tetrahydropyridine (G13). Subsequent reduction via hydrogenation in the presence of a catalyst, for example palladium on charcoal, gives gives tert-butyl 4-(4-aminophenyl)piperidine-1-carboxylate (G14).

Scheme F

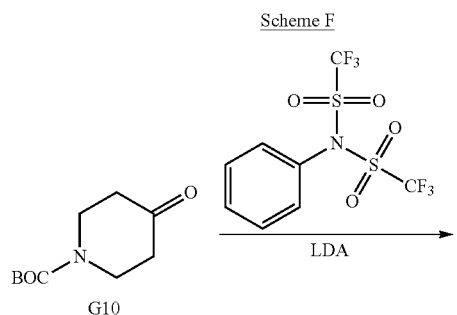

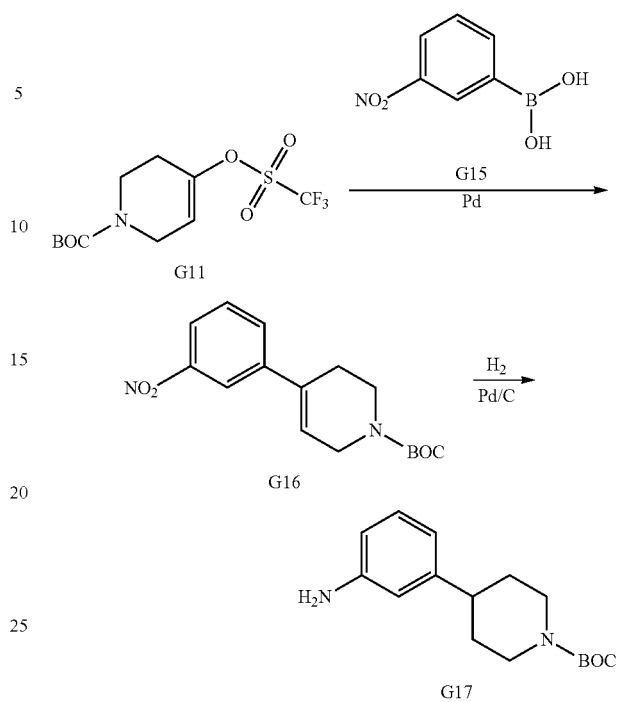

The corresponding 4-(3-aminophenyl)piperidine analogue of G9 can be prepared by a sequence of reactions starting with the conversion of commercially available tert-butyl 4-oxopiperidine-1-carboxylate (G10) to vinyl triflate G11. Coupling of G11 in a Suzuki type reaction with (3-nitrophenyl)boronic acid (G15) gives tetrahydropyridine (G16). Subsequent reduction via hydrogenation in the presence of a catalyst, for example palladium on charcoal, gives tert-butyl 4-(3-aminophenyl)piperidine-1-carboxylate (G17).

Scheme G

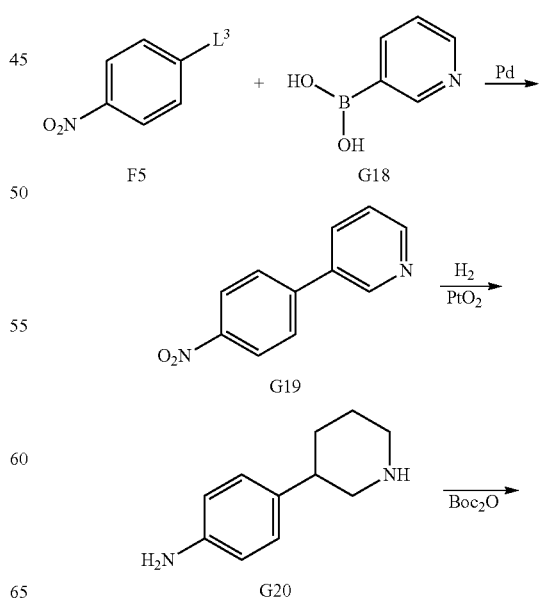

Scheme I

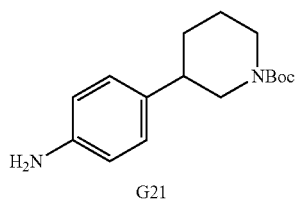

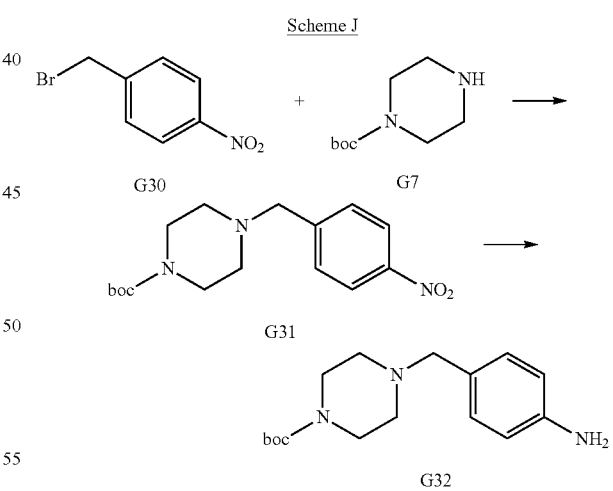

The 3-(4-aminophenyl)piperidine regioisomers of G14 can be prepared by reaction of commercially available compounds of the formula F5, where $L^3$=I or Br, with pyridin-3-ylboronic acid (G18) in a Suzuki type reaction to form 3-(4-nitrophenyl)pyridine (G19). Reduction of G19 with hydrogen in the presence of a catalyst, for example platinum oxide, gives 4-(piperidin-3-yl)aniline (G20) which may be protected using Boc anhydride to give tert-butyl 3-(4-aminophenyl)piperidine-1-carboxylate (G21).

Scheme H

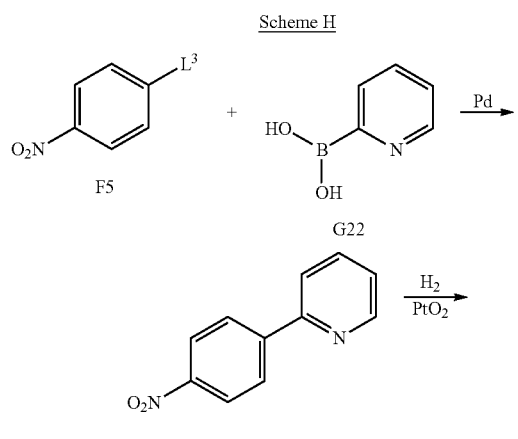

tert-Butyl(1-(4-aminophenyl)piperidin-4-yl)carbamate (G29) can be prepared by nucleophilic aromatic substitution of commercially available tert-butyl piperidin-4-ylcarbamate (G26) and 1-fluoro-4-nitrobenzene (G27) under thermal conditions to give tert-butyl(1-(4-nitrophenyl)piperidin-4-yl)carbamate (G28). Reduction of G28 with hydrogen in the presence of a catalyst, for example 10% palladium on charcoal gives tert-butyl(1-(4-aminophenyl)piperidin-4-yl)carbamate (G29).

The 2-(4-aminophenyl)piperidine regioisomer of G14 can be prepared by reaction of commercially available compounds of the formula F5, where $L^3$=I or Br, with pyridin-2-ylboronic acid (G22) in a Suzuki type reaction to form 2-(4-nitrophenyl)pyridine (G23). Reduction of G23 with hydrogen in the presence of a catalyst, for example platinum oxide, gives 4-(piperidin-2-yl)aniline (G24) which may be protected using Boc anhydride to give tert-butyl 2-(4-aminophenyl)piperidine-1-carboxylate (G25).

tert-Butyl 4-(4-aminobenzyl)piperazine-1-carboxylate (G32) can be prepared by the nucleophilic displacement of commercially available 1-(bromomethyl)-4-nitrobenzene (G30) with tert-butyl piperazine-1-carboxylate (G7) to give tert-butyl 4-(4-nitrobenzyl)piperazine-1-carboxylate (G31). Subsequent reduction with hydrogen in the presence of a catalyst, for example 10% % palladium on charcoal, gives tert-butyl 4-(4-aminobenzyl)piperazine-1-carboxylate (G32).

Scheme K

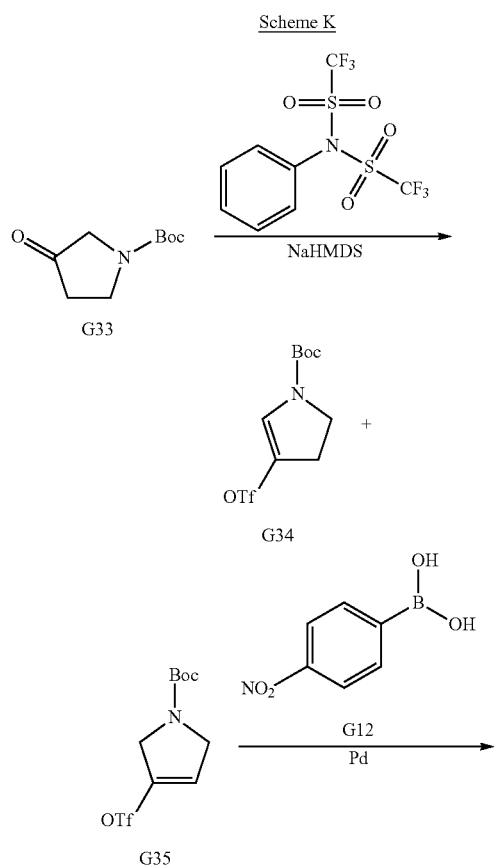

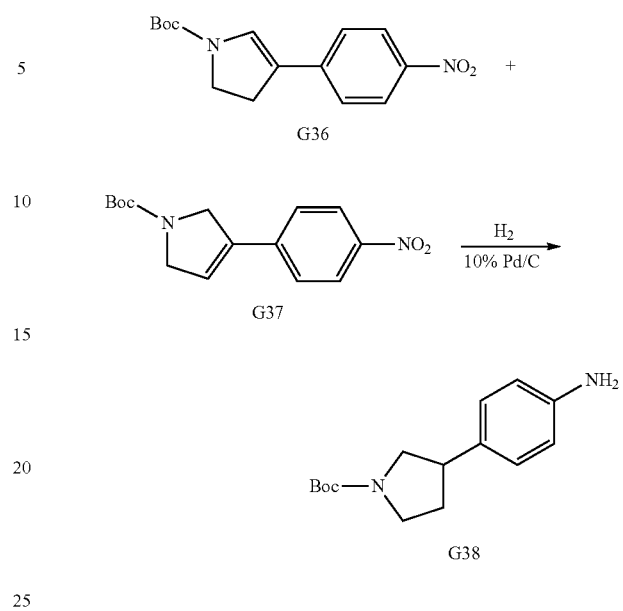

Commercially available tert-butyl 3-oxopyrrolidine-1-carboxylate (G33) can be converted to a mixture of vinyl triflates (G34) and (G35) in the presence of a triflamide and a suitable base, for example NaHMDS. Coupling of the mixture with (4-nitrophenyl)boronic acid (G12) under Suzuki conditions gives dihydropyrroles (G36) and (G37). Reduction of this mixture using hydrogen in the presence of a catalyst, for example 10% palladium on charcoal, gives tert-butyl 3-(4-aminophenyl)pyrrolidine-1-carboxylate (G38).

Scheme L

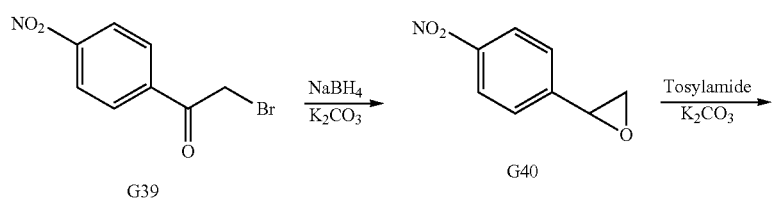

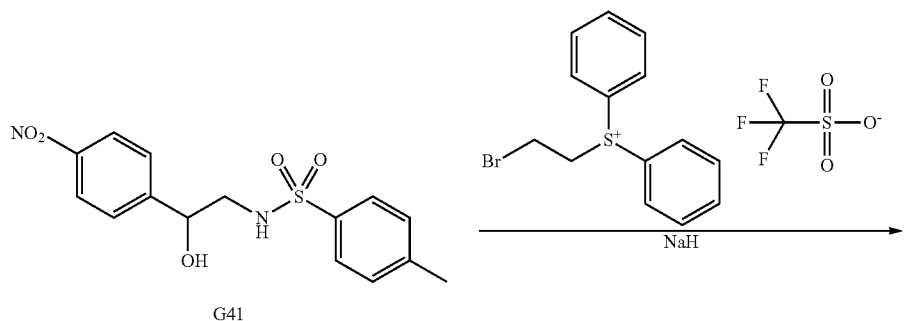

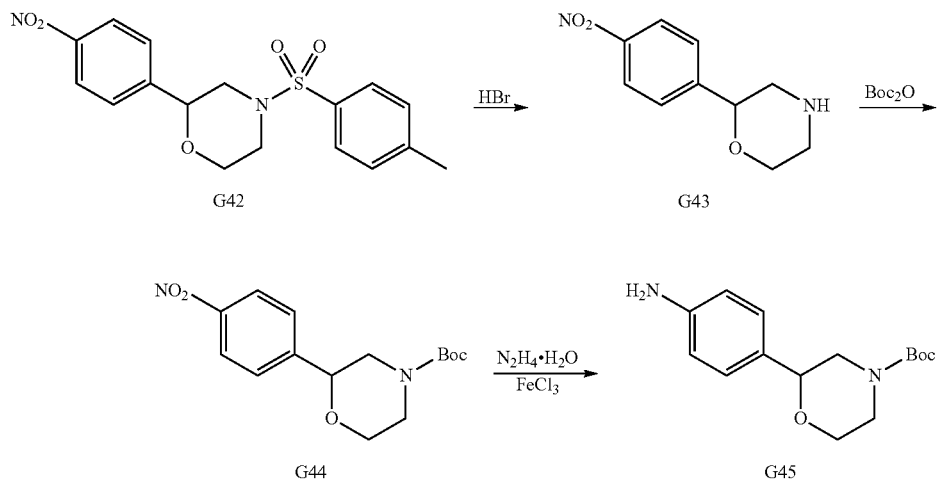

Commercially available 2-bromo-1-(4-nitrophenyl)ethanone (G39) can be reduced and cyclised to give epoxide (G40). Opening of the epoxide with tosylamide followed by cyclisation with (2-bromoethyl)diphenylsulfonium trifluoromethanesulfonate gives morpholine (G42). Cleavage of the sulphonamide and subsequent re-protection with Boc anhydride gives carbamate (G44). Reduction using hydrazine in the presence of iron(III) chloride gives tert-butyl 2-(4-aminophenyl)morpholine-4-carboxylate (G45).

Scheme M

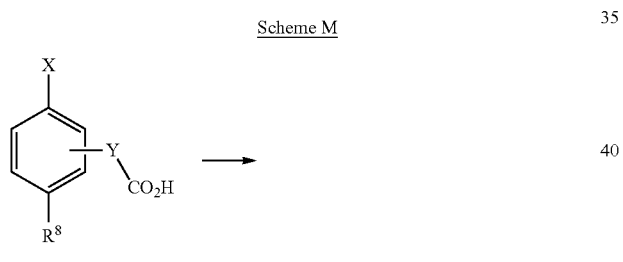

-continued

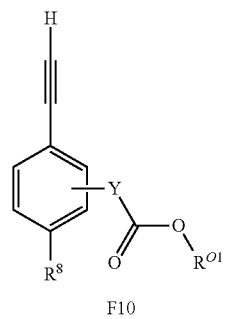

Compounds of the formula F6 may be reacted to form esters of the formula F7 where X=Br or I, $R^8$=H or Me and Y is selected from a single bond, —$CH_2$— and —$CHCH_3$—. When $R^{O1}$=t-Bu, Boc anhydride may be employed or where $R^{O1}$=Me methanol in the presence of an acid, for example sulfuric acid, may be used to form the desired ester. Esters of the formula F7 can be reacted with terminal acetylenes of the formula F8 in a Sonagashira type coupling to give acetylenes of the formula F9 where $R^9$=TMS, TES or $(CH_3)_2COH$. $R^9$ may then be removed to generate compounds of the formula F10. When $R^9$=TMS or TES potassium carbonate or tetra-n-butyl ammonium fluoride may be employed to induce this transformation. When $R^9$=$(CH_3)_2C^*OH$, sodium hydride in refluxed toluene may be used.

Scheme N

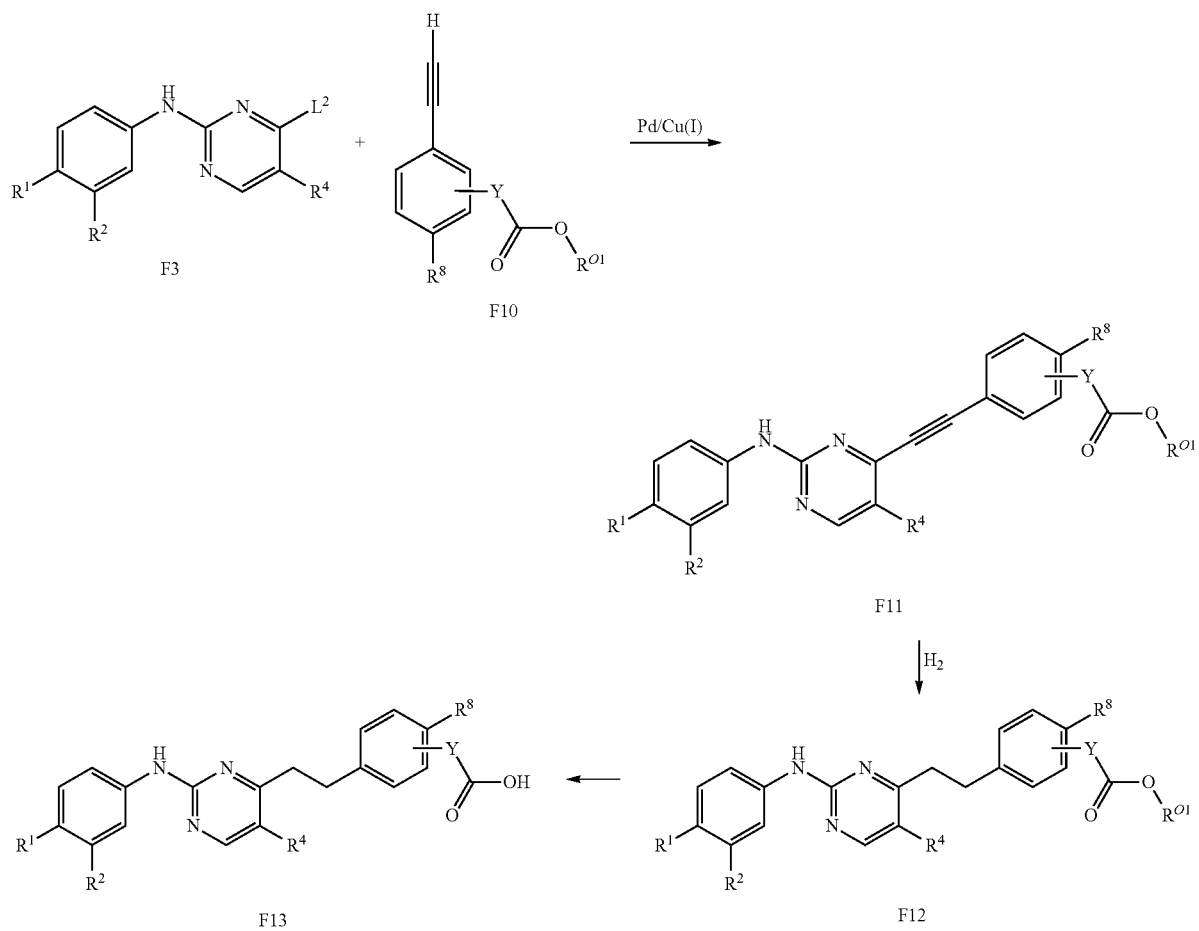

Pyrimidines of the formula F3 may be reacted with terminal acetylenes of the formula F10 to give acetylenes of the formula F11 in a Sonagashira type coupling. The acetylene in compounds of the formula F11 may be reduced to an alkane of the formula F26 using hydrogen gas in the presence of a transition metal catalyst. The exact choice of catalyst and conditions employed is dependant on the nature of $R^4$. For example, where $R^4$=$CF_3$, 10% Pd/C may be used, where $R^4$=Cl, platinum oxide is employed. Esters of the formula F12 may then be deprotected to give carboxylic acids of the formula F13. Where $R^{O1}$=Me, lithium hydroxide solutions may be employed. Where $R^{O1}$=t-Bu, acidic solutions, for example trifluoroacetic acid in dichloromethane may be used. It will be appreciated that under acidic conditions Boc protecting groups in $R^1$ and $R^2$ will also be cleaved.

-continued

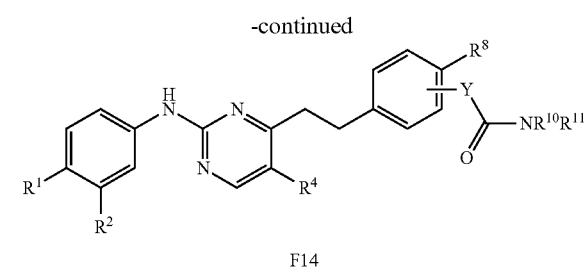

Carboxylic acids of the formula F13 can be converted to amides of the formula F14 using a suitable amine or ammonia salt in the presence of a peptide coupling agent, for example HATU.

Scheme O

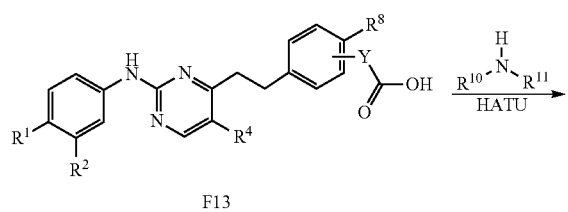

Scheme P

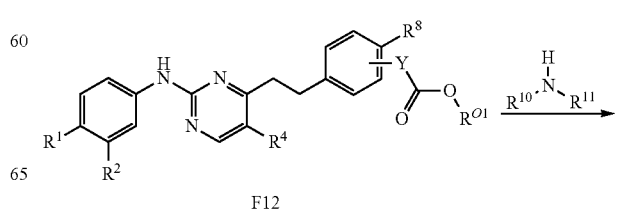

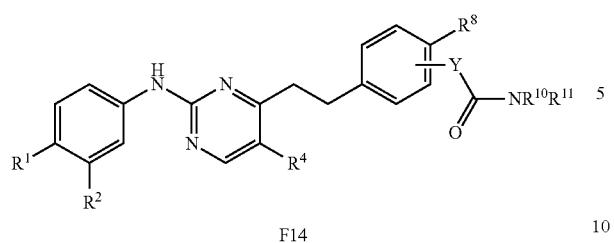

F14

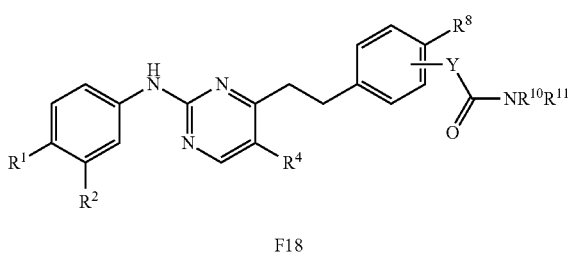

F18

Alternatively, when $R^{O1}$=Me, esters of the formula F12 may be directly converted to amides of the formula F14 by reaction with an amine at elevated temperatures.

Compounds of the formula F14, or analogues containing lactams, with Boc protecting groups present in $R^1$ or $R^2$ (in the place of $R^{N1}$ to $R^{N12}$) may then be deprotected under acidic conditions, for example using trifluoroacetic acid in dichloromethane solutions, to give the corresponding parent compounds of the formula F18.

Scheme Q

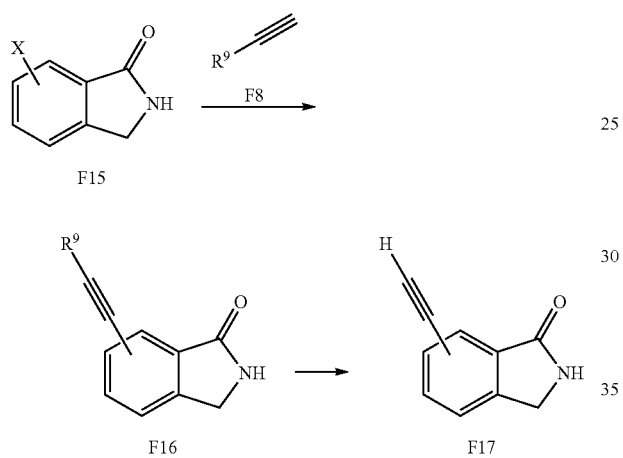

Scheme S

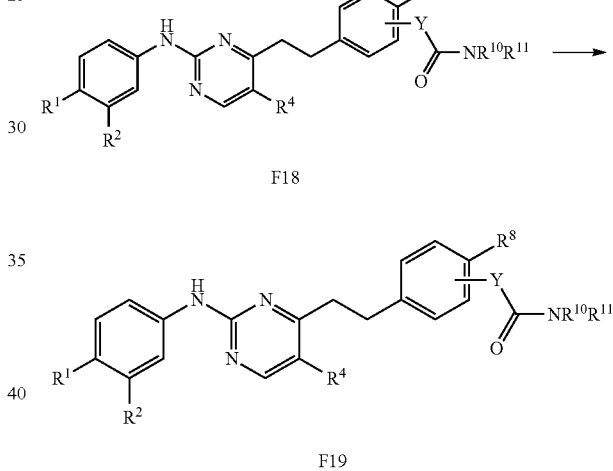

Where molecules with lactams fused to the right hand side aromatic ring are required compounds of the formula F15 can be reacted with terminal acetylenes of the formula F8 in a Sonagashira type coupling to give acetylenes of the formula F16 where $R^9$=TMS, TES or $(CH_3)_2C^*OH$. $R^9$ may then be removed to generate compounds of the formula F17. When $R^9$=TMS or TES, potassium carbonate or tetra-n-butyl ammonium fluoride may be employed to induce this transformation. When $R^9$=$(CH_3)_2C^*OH$, sodium hydride in refluxed toluene may be used.

Compounds of the formula F17 can then be coupled to compounds of the formula F3 (as in Scheme N) and further elaborated as described above.

Compounds of the formula F18 may then be further modified by derivitisation of the amine functionality. For example, compounds of the formula F19 where $R^{N1}$, $R^{N2}$, $R^{N3}$, $R^{N4}$, $R^{N5}$, $R^{N6}$, $R^{N7}$, $R^{N8}$, $R^{N9}$, $R^{N10}$, $R^{N11}$ or $R^{N12}$=Me may be prepared by reductive alkylation with formaldehyde in the presence of sodium triacetoxyborohydride. Derivatives were $R^{N1}$, $R^{N2}$, $R^{N3}$, $R^{N5}$, $R^{N6}$, $R^{N7}$, $R^{N8}$, $R^{N9}$, $R^{N10}$, $R^{N11}$ or $R^{N12}$=Et may be prepared by reductive alkylation with acetaldehyde in the presence of sodium triacetoxyborohydride. Compounds of the formula F19 where $R^{N1}$, $R^{N2}$, $R^{N3}$, $R^{N5}$, $R^{N6}$, $R^{N7}$, $R^{N8}$, $R^{N9}$, $R^{N10}$, $R^{N11}$ or $R^{N12}$=acetyl may be prepared by reaction of compounds of the formula F18 with a suitable acylating agent, for example acetic anhydride.

Alternatively, when compounds in which $R^5$=heteroaryl are desired heteroaryl analogues of F10 may be prepared as outlined in Schemes T, U and V. These heteroaryl acetylenes can be coupled to compounds of the formula F3, and then further elaborated in an analogous manner to that described above in schemes N, O, P, R and S.

Scheme R

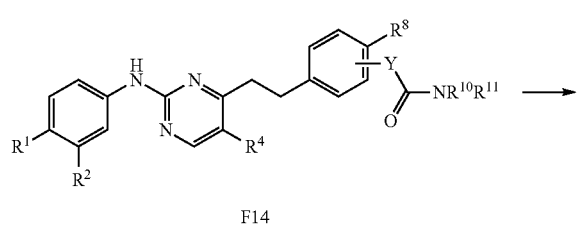

F14

Scheme T

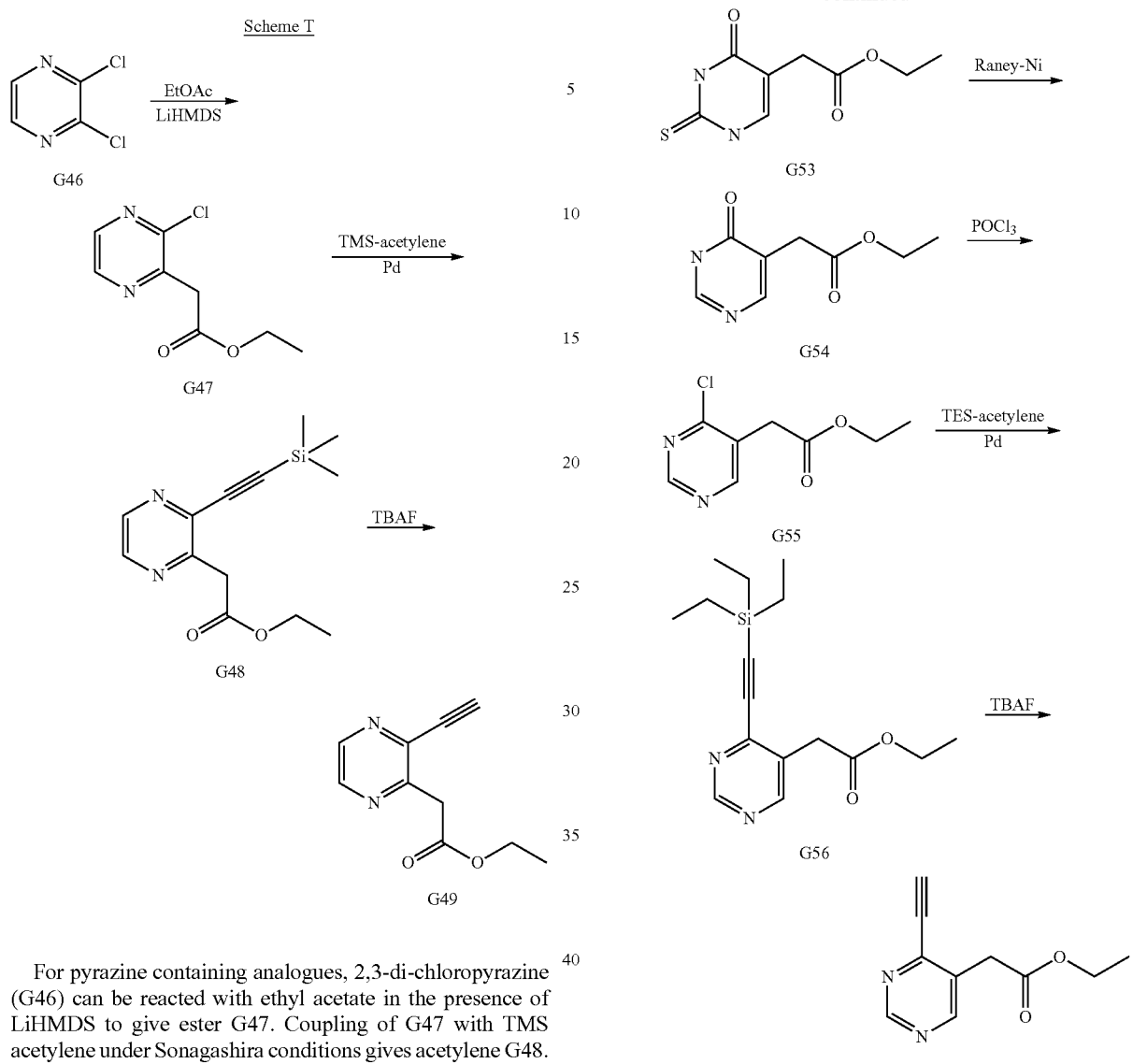

For pyrazine containing analogues, 2,3-di-chloropyrazine (G46) can be reacted with ethyl acetate in the presence of LiHMDS to give ester G47. Coupling of G47 with TMS acetylene under Sonagashira conditions gives acetylene G48. Removal of the trimethylsilyl group using TBAF gives ethyl 2-(3-ethynylpyrazin-2-yl)acetate (G49).

Scheme U

For pyrimidine analogues, diethyl succinate (G50) and ethyl formate (G51) can be condensed to give aldehyde G52 in the presence of sodium metal. Cyclisation using thiourea gives 4-oxo-2-thioxo-1,2,3,4-tetrahydropyrimidine (G53). Desulfurisation using Raney-nickel gives pyrimidone G54, which can be converted to 4-chloro pyrimidine G55 using phosphorous oxychloride. Coupling of TES-acetylene under Sonagashira conditions, followed by removal of the triethylsilyl group using TBAF gives ethyl 2-(4-ethynylpyrimidin-5-yl)acetate (G57).

Scheme V

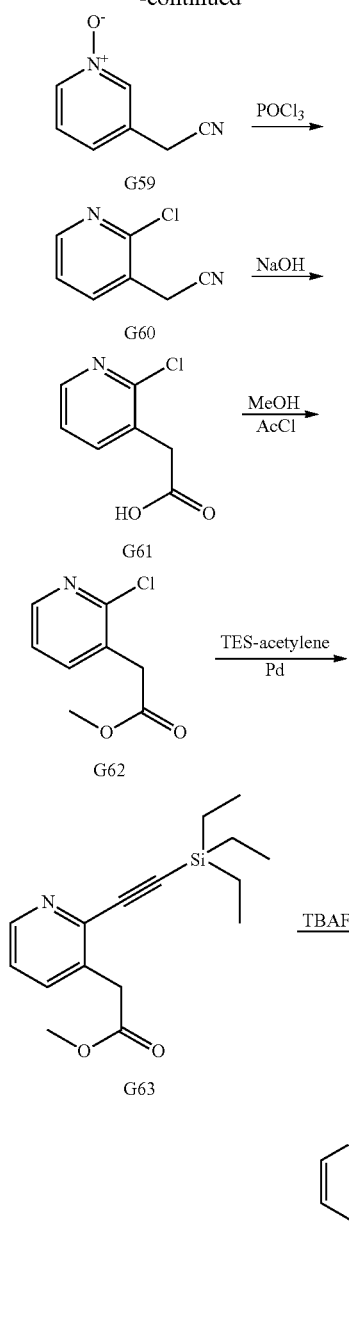

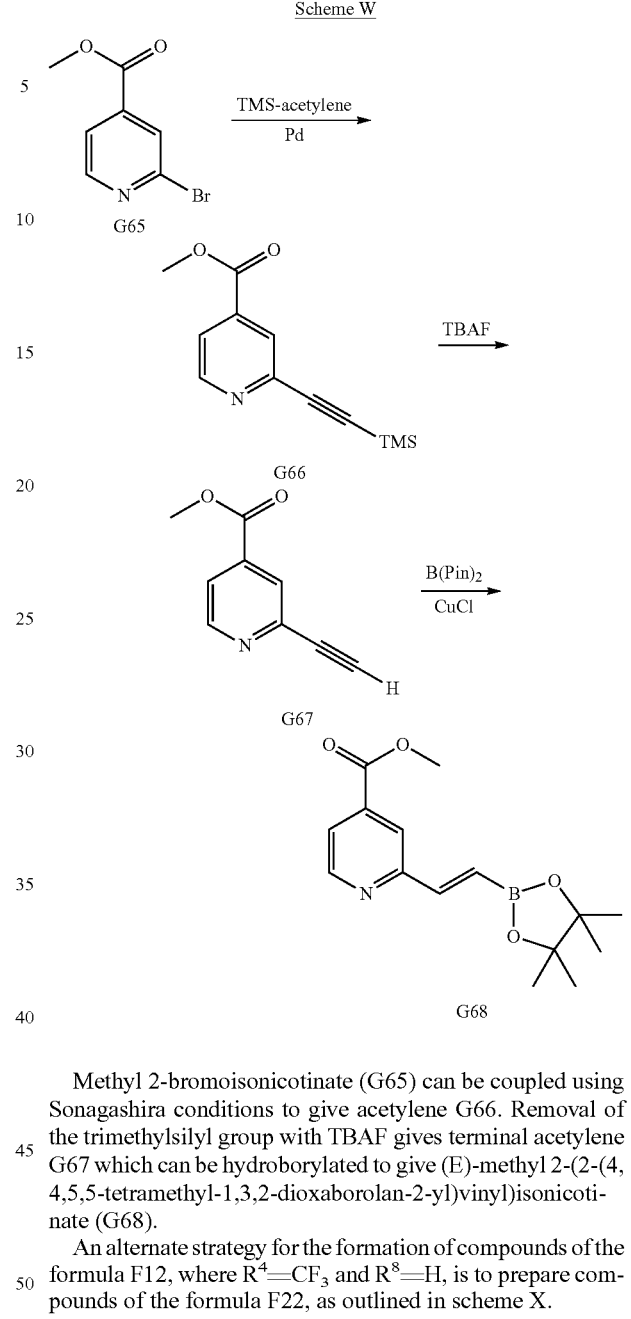

Methyl 2-bromoisonicotinate (G65) can be coupled using Sonagashira conditions to give acetylene G66. Removal of the trimethylsilyl group with TBAF gives terminal acetylene G67 which can be hydroborylated to give (E)-methyl 2-(2-(4,4,5,5-tetramethyl-1,3,2-dioxaborolan-2-yl)vinyl)isonicotinate (G68).

An alternate strategy for the formation of compounds of the formula F12, where $R^4$=$CF_3$ and $R^8$=H, is to prepare compounds of the formula F22, as outlined in scheme X.

For 3-pyridyl acetates, 2-(pyridin-3-yl)acetonitrile (G58) can be oxidised to N-oxide G59. Chlorination with phosphorous oxychloride gives 2-chloropyridine G60 which can be hydrolysed with sodium hydroxide to acetic acid G61. Ester formation using methanol gives 2-chloropyridine ester G62. Coupling of TES-acetylene under Sonagashira conditions, followed by removal of the triethylsilyl group using TBAF gives methyl 2-(2-ethynylpyridin-3-yl)acetate (G64).

Alternatively, heteroaryl acetylenes analagous to F10 can be hydroborylated to give vinyl boranes as in scheme W. These can be coupled using Suzuki chemistry to compounds of the formula F3, then further elaborated in an analogous manner to that described above in schemes N, O, P, R and S.

Scheme X

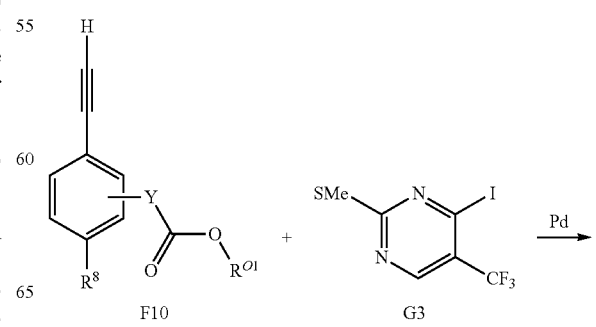

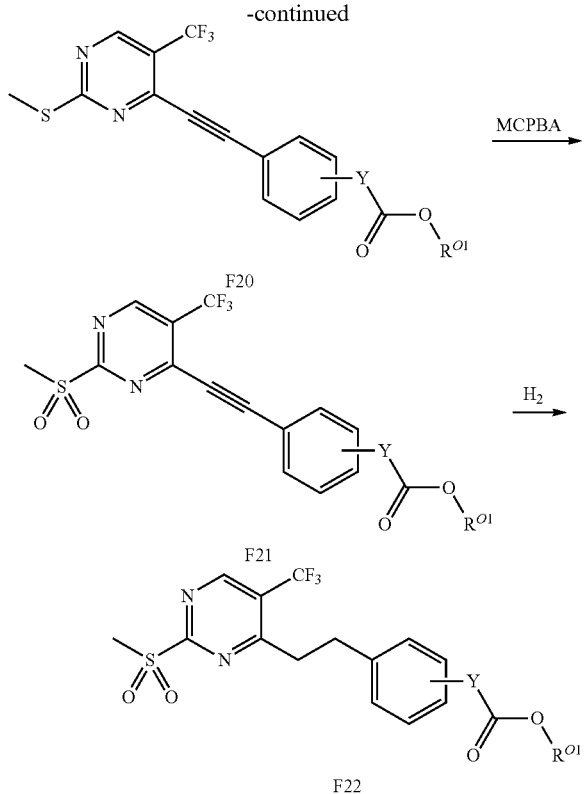

Coupling of esters of the formula F10, where $R^8$=H, with 4-iodo-2-(methylthio)-5-(trifluoromethyl)pyrimidine (G3) under Sonagashira conditions gives acetylenes of the formula F20. Oxidation, using MCPBA, gives sulfones of the formula F21. Reduction of the acetylene using hydrogen, in the presence of a catalyst, for example 10% palladium on charcoal, gives compounds of the formula F22.

Compounds of the formula F22 can be reacted with anilines of the formula F2 under acidic conditions, for example in the presence of trifluoro acetic acid to give compounds of the formula F12 which can then be further elaborated as described above.

Use of Compounds of the Invention

The present invention provides active compounds, specifically, active 2,4,5-substituted pyrimidines.

The term "active", as used herein, pertains to compounds which are capable of inhibiting FAK activity as well as the activity of VEGFR3, and specifically includes both compounds with intrinsic activity (drugs) as well as prodrugs of such compounds, which prodrugs may themselves exhibit little or no intrinsic activity.

Assays which may be used in order to assess the FAK and VEGFR3 inhibition offered by a particular compound are described in the examples below.

The present invention further provides a method of inhibiting FAK inhibition, as well as the activity of VEGFR3, in a cell, comprising contacting said cell with an effective amount of an active compound, preferably in the form of a pharmaceutically acceptable composition. Such a method may be practised in vitro or in vivo.

The present invention further provides active compounds which inhibit FAK activity, as well as the activity of VEGFR3, as well as methods of methods of inhibiting FAK activity, as well as the activity of VEGFR3, comprising contacting a cell with an effective amount of an active compound, whether in vitro or in vivo.

Active compounds may also be used as part of an in vitro assay, for example, in order to determine whether a candidate host is likely to benefit from treatment with the compound in question.

The invention further provides active compounds for use in a method of treatment of the human or animal body. Such a method may comprise administering to such a subject a therapeutically-effective amount of an active compound, preferably in the form of a pharmaceutical composition.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio.

Cancer

The present invention provides active compounds which are anticancer agents. One of ordinary skill in the art is readily able to determine whether or not a candidate compound treats a cancerous condition for any particular cell type, either alone or in combination.

Examples of cancers include, but are not limited to, bone cancer, brain stem glioma, breast Cancer, cancer of the adrenal gland, cancer of the anal region, cancer of the bladder. cancer of the endocrine system, cancer of the oesophagus, cancer of the head or neck, cancer of the kidney or ureter, cancer of the liver, cancer of the parathyroid gland, cancer of the penis, cancer of the small intestine, cancer of the thyroid gland, cancer of the urethra, carcinoma of the cervix, carcinoma of the endometrium, carcinoma of the fallopian tubes, carcinoma of the renal pelvis, carcinoma of the vagina, carcinoma of the vulva, chronic or acute leukemia, colon cancer, cutaneous or intraocular melanoma, haemetological malignancies, Hodgkin's disease, lung cancer, lymphocytic lymphomas, neoplasms of the central nervous system (CNS), ovarian cancer, pancreatic cancer, pituitary adenoma, primary CNS lymphoma, prostate cancer, rectal cancer, renal cell carcinoma, sarcoma of soft tissue, skin cancer, spinal axis tumors, stomach cancer and uterine cancer.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

The anti cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibody bevacizumab (AvastinT) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies A combination of particular interest is with docetaxel. Other possible combinations of interest include with gemcitabine, cisplatin and the camptothecin prodrug irinotecan.

Further combinations of interest include compounds of the invention, in particular, compound 16, with antiangiogenic agents, such as VEGF receptor tyrosine kinase inhibitors or therapeutic antibodies against vascular endothelial growth factors (VEGFs), for example VEGFA, VEGFC or VEGFD. Of these inhibitors and antibodies, combination with bevacizumab may be preferred. These combinations may be of particular use in treating breast cancer, prostate cancer, ovarian cancer, renal cancer, glioblastoma, neuroblastoma, medulloblastoma, colon carcinoma, non-small cell lung cancer, mesothelioma and other cancers in which over-expression of VEGFA or over-activation of VEGFR2 or over-expression of VEGFC/D or over-activation of VEGFR3 has been implicated in maintenance and progression of the malignant phenotype.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et2O), acetic acid (AcOH), dichloromethane(methylene chloride, DCM), trifluoroacetic acid (TFA), dimethylformamide (DMF), tetrahydrofuran (THF), dimethylsulfoxide (DMSO), meta-chloroperoxybenzoic acid (mCPBA), tert-butyloxycarbonyl (Boc), trimethylsilyl (TMS), triethylsilyl (TES), 2-(1H-7-azabenzotriazol-1-yl)-1,1,3,3-tetramethyluronium hexafluorophosphate (HATU), diphenylphosphoryl azide (DPPA), 1,8-diazabicyclo[5.4.0]undec-7-ene (DBU), 1-ethyl-3-(3-dimethylaminopropyl) carbodiimide (EDCl), 4-dimethylaminopyridine (DMAP), tetra-n-butylammonium fluoride (TBAF), N,N-Diisopropylethylamine (DIPEA), 1-hydroxybenzotriazole (HOBt), and 1,2-dichloroethene (DCE).

General Experimental Details

Unless otherwise stated the following generalisations apply.

[1]NMR spectra were recorded on either a Bruker Avance DRX300 (300 MHz), a Bruker Ultrasheild plus (400 MHz) or a Varian Unity Inova 600 (600 MHz) spectrometer. The multiplicity of a signal is designated by the following abbreviations: s, singlet; d, doublet; t, triplet; q, quartet; br, broad; m, multiplet. All observed coupling constants, J, are reported in Hertz. $^{13}$C NMR were recorded on a Bruker Avance DRX300

(75 MHz), a Bruker Ultrasheild plus (100 MHz) or a Varian Unity Inova 600 (150 MHz) spectrometer in a broad band decoupled mode.

LC/MS data was generated using either a Finnigan LCQ Advantage Max (LCMS-A), a Waters ZQ 3100 system (LCMS-B) or an Agilent 6100 Series Single Quad LC/MS (LCMS-C).

LCMS Method A (LCMS-A)
Instrument: Finnigan LCQ Advantage Max
Pump: Finnigan Surveyor LC Pump
Finnigan Surveyor Autosampler
Finnigan Surveyor PDA Detector
LC conditions:
Reverse Phase HPLC analysis
Column: Gemini 3μ C18 20×4.0 mm 110 A
Injection Volume 10 μL
Solvent A: Water 0.1% Formic Acid
Solvent B: Acetonitrile 0.1% Formic Acid
Gradient: 10-100% B over 10 min
Detection: 100-600 nm
MS conditions:
Ion Source: Ion trap
Ion Mode: ES positive
Temp: 300° C.
Capillary V-25
Detection: Ion counting
Scan Range: 80-1000 A mu
Scan Time: 0.2 sec
Acquisition time: 10 min
LCMS Method B (LCMS-B)
Instrument: Waters ZQ 3100-Mass Detector
Waters 2545-Pump
Waters SFO System Fluidics Organizer
Waters 2996 Diode Array Detector
Waters 2767 Sample Manager
LC conditions:
Reverse Phase HPLC analysis
Column: XBridge™ C18 5 μm 4.6×100 mm
Injection Volume 10 μL
Solvent A: Water 0.1% Formic Acid
Solvent B: Acetonitrile 0.1% Formic Acid
Gradient: 10-100% B over 10 min
Flow rate: 1.5 mL/min
Detection: 100-600 nm
MS conditions:
Ion Source: Single-quadrupole
Ion Mode: ES positive
Source Temp: 150° C.
Desolvation Temp: 350° C.
Detection: Ion counting
Cpillary (KV)-3.00
Cone (V): 30
Extractor (V):3
RF Lens (V): 0.1
Scan Range: 100-1000 Amu
Scan Time: 0.5 sec
Acquisition time: 10 min
Gas Flow
Desolvation L/hr-650
LCMS Method C (LCMS-C)
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC conditions:
Reverse Phase HPLC analysis
Column: Luna C8(2) 5μ 50×4.6 mm 100 A
Column temperature: 30° C.
Injection Volume: 5 μL
Solvent A: Water 0.1% Formic Acid
Solvent B: Acetonitrile 0.1% Formic Acid
Gradient: 5-100% B over 10 min
Detection: 254 nm or 214 nm
MS conditions:
Ion Source: Quadrupole
Ion Mode: Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min Analytical thin-layer chromatography was performed on Merck silica gel 60F254 aluminium-backed plates which were visualised using fluorescence quenching under UV light or acidic anisaldehyde or a basic potassium permanganate dip. Flash chromatography was performed using either a Teledyne Isco CombiFlash Rf purification system using standard RediSep® cartridges or a Biotage Isolera purification system using either Grace or Biotage silica cartridges.

Where necessary, anhydrous solvents were prepared using a Braun purification system or purchased from Sigma-Aldrich.

Example 1

2-(2-(2-(2-((4-(Piperazin-1-yl)phenyl)amino)-5-(trifluoromethyl)pyrimidin-4-yl)ethyl)phenyl)acetamide (1)

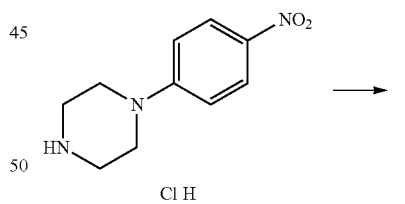

Cl H

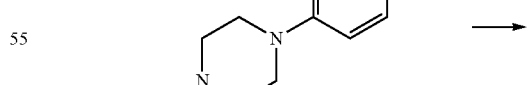

I1

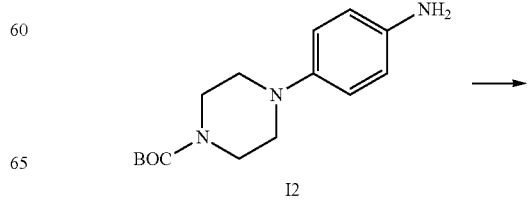

I2

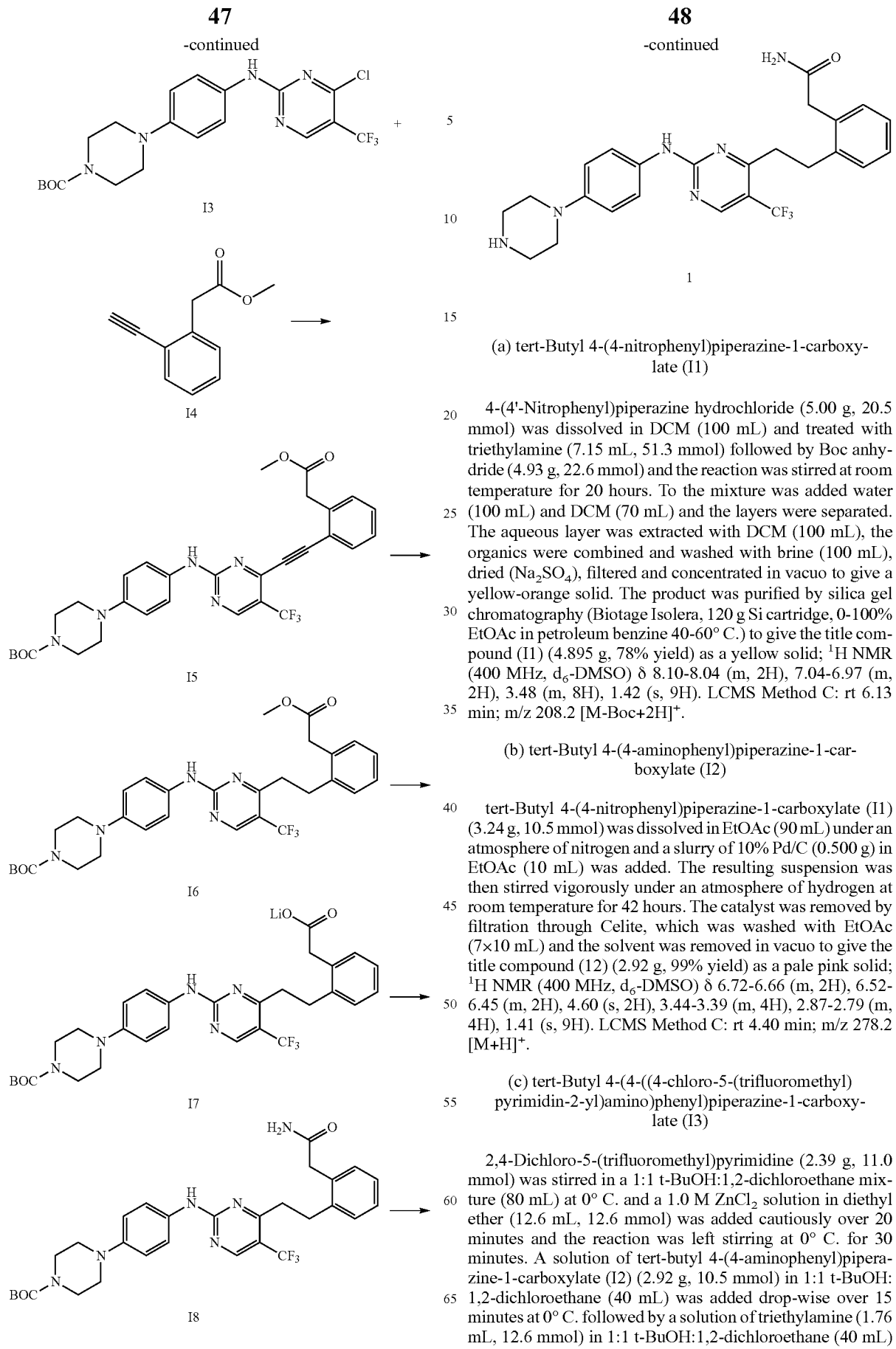

(a) tert-Butyl 4-(4-nitrophenyl)piperazine-1-carboxylate (I1)

4-(4'-Nitrophenyl)piperazine hydrochloride (5.00 g, 20.5 mmol) was dissolved in DCM (100 mL) and treated with triethylamine (7.15 mL, 51.3 mmol) followed by Boc anhydride (4.93 g, 22.6 mmol) and the reaction was stirred at room temperature for 20 hours. To the mixture was added water (100 mL) and DCM (70 mL) and the layers were separated. The aqueous layer was extracted with DCM (100 mL), the organics were combined and washed with brine (100 mL), dried ($Na_2SO_4$), filtered and concentrated in vacuo to give a yellow-orange solid. The product was purified by silica gel chromatography (Biotage Isolera, 120 g Si cartridge, 0-100% EtOAc in petroleum benzine 40-60° C.) to give the title compound (I1) (4.895 g, 78% yield) as a yellow solid; $^1$H NMR (400 MHz, $d_6$-DMSO) δ 8.10-8.04 (m, 2H), 7.04-6.97 (m, 2H), 3.48 (m, 8H), 1.42 (s, 9H). LCMS Method C: rt 6.13 min; m/z 208.2 [M-Boc+2H]$^+$.

(b) tert-Butyl 4-(4-aminophenyl)piperazine-1-carboxylate (I2)

tert-Butyl 4-(4-nitrophenyl)piperazine-1-carboxylate (I1) (3.24 g, 10.5 mmol) was dissolved in EtOAc (90 mL) under an atmosphere of nitrogen and a slurry of 10% Pd/C (0.500 g) in EtOAc (10 mL) was added. The resulting suspension was then stirred vigorously under an atmosphere of hydrogen at room temperature for 42 hours. The catalyst was removed by filtration through Celite, which was washed with EtOAc (7×10 mL) and the solvent was removed in vacuo to give the title compound (I2) (2.92 g, 99% yield) as a pale pink solid; $^1$H NMR (400 MHz, $d_6$-DMSO) δ 6.72-6.66 (m, 2H), 6.52-6.45 (m, 2H), 4.60 (s, 2H), 3.44-3.39 (m, 4H), 2.87-2.79 (m, 4H), 1.41 (s, 9H). LCMS Method C: rt 4.40 min; m/z 278.2 [M+H]$^+$.

(c) tert-Butyl 4-(4-((4-chloro-5-(trifluoromethyl)pyrimidin-2-yl)amino)phenyl)piperazine-1-carboxylate (I3)

2,4-Dichloro-5-(trifluoromethyl)pyrimidine (2.39 g, 11.0 mmol) was stirred in a 1:1 t-BuOH:1,2-dichloroethane mixture (80 mL) at 0° C. and a 1.0 M $ZnCl_2$ solution in diethyl ether (12.6 mL, 12.6 mmol) was added cautiously over 20 minutes and the reaction was left stirring at 0° C. for 30 minutes. A solution of tert-butyl 4-(4-aminophenyl)piperazine-1-carboxylate (I2) (2.92 g, 10.5 mmol) in 1:1 t-BuOH: 1,2-dichloroethane (40 mL) was added drop-wise over 15 minutes at 0° C. followed by a solution of triethylamine (1.76 mL, 12.6 mmol) in 1:1 t-BuOH:1,2-dichloroethane (40 mL)

and the reaction was allowed to warm to room temperature and was stirred for 18 hours. The organic solvents were evaporated in vacuo and the crude yellow oily solid was suspended in water (400 mL), the suspension was sonicated for 30 minutes and the product was collected by filtration, the solid was washed with water (10×20 mL) and dried under a high vacuum to give the title compound (I3) (4.75 g, 98% yield) as a beige solid; $^1$H NMR (400 MHz, d$_6$-DMSO) δ 10.45 (s, 1H), 8.72 (s, 1H), 7.50 (d, J=8.5 Hz, 2H), 6.96 (d, J=9.0 Hz, 2H), 3.50-3.42 (m, 4H), 3.09-3.02 (m, 4H), 1.42 (s, 9H). LCMS Method C: rt 6.56 min; m/z 456.2, 458.1 [M−H]$^−$.

(d) tert-Butyl 4-(4-((4-((2-(2-methoxy-2-oxoethyl)phenyl)ethynyl)-5-(trifluoromethyl)pyrimidin-2-yl)amino)phenyl)piperazine-1-carboxylate (I5)

To a nitrogen de-gassed solution of methyl 2-(2-ethynylphenyl)acetate (14: prepared according to the procedure of Peng, C. et al; *Adv. Synth. Catal.* 2008, 350, 2359-2364 or as detailed below) (0.114 g, 0.653 mmol) in dry DMF (6 mL) were added triethylamine (0.280 mL, 2.01 mmol) followed by tert-butyl 4-(4-((4-chloro-5-(trifluoromethyl)pyrimidin-2-yl)amino)phenyl)piperazine-1-carboxylate (I3) (0.230 g, 0.502 mmol), triphenylphosphine (0.020 g, 0.075 mmol), trans-dichlorobis(triphenylphosphine) palladium(II) (0.035 g, 0.050 mmol) and CuI (0.014 g, 0.075 mmol). The reaction mixture was heated under microwave irradiation at 120° C. for 20 minutes and then concentrated to dryness in vacuo and purified by silica gel chromatography (Biotage Isolera, 40 g Si cartridge, 0-80% EtOAc in cyclohexane) to give the title compound (I5) (0.267 g, 89% yield) as an orange glassy solid; $^1$H NMR (400 MHz, d$_6$-DMSO) δ 10.27 (br s, 1H), 8.76 (s, 1H), 7.65-7.49 (m, 4H), 7.49-7.38 (m, 2H), 6.95 (d, J=9.1 Hz, 2H), 3.94 (s, 2H), 3.61 (s, 3H), 3.51-3.42 (m, 4H), 3.09-3.00 (m, 4H), 1.42 (s, 9H). LCMS Method C: rt 6.67 min; m/z 596.3 [M+H]$^+$.

(e) tert-Butyl 4-(4-((4-(2-(2-methoxy-2-oxoethyl)phenethyl)-5-(trifluoromethyl)pyrimidin-2-yl)amino)phenyl)piperazine-1-carboxylate (I6)

tert-Butyl 4-(4-((4-((2-(2-methoxy-2-oxoethyl)phenyl)ethynyl)-5-(trifluoromethyl)pyrimidin-2-yl)amino)phenyl)piperazine-1-carboxylate (I5) (0.250 g, 0.420 mmol) was dissolved in EtOAc (8 mL) and absolute ethanol (10 mL) under an atmosphere of nitrogen. 10% Pd/C (0.200 g) in EtOAc (4 mL) was added to the solution and the atmosphere was changed to hydrogen gas (balloon). The reaction was sealed with a balloon and stirred at room temperature for 18 hours. The catalyst was removed by filtration through Celite, which was washed with EtOAc (7×10 mL). The solvent was removed in vacuo to give the title compound (I6) (0.211 g, 84% yield) as a yellow solid. LCMS Method C: rt 6.78 min; m/z 600.3 [M+H]$^+$.

(f) Lithium 2-(2-(2-(2-((4-(4-(tert-butoxycarbonyl)piperazin-1-yl)phenyl)amino)-5-(trifluoromethyl)pyrimidin-4-yl)ethyl)phenyl)acetate (I7)

LiOH.H$_2$O (0.044 g, 1.06 mmol) was added to tert-butyl 4-(4-((4-(2-(2-methoxy-2-oxoethyl)phenethyl)-5-(trifluoromethyl)pyrimidin-2-yl)amino)phenyl)piperazine-1-carboxylate (I6) (0.211 g, 0.352 mmol) in THF (10 mL), water (2.5 mL) and methanol (1 mL). The resulting mixture was allowed to stir for 3 hours at 40° C. The volatiles were removed in vacuo and the residue was diluted with EtOAc (100 mL) and 2 M aq. NaOH (100 mL). The layers were separated and the aqueous layer was extracted with EtOAc (70 mL), the organic layers were combined, washed with brine (100 mL), dried (MgSO$_4$), filtered and concentrated under reduced pressure to give the title compound (I7) (0.195 g, 96% yield) as a yellow solid; $^1$H NMR (400 MHz, d$_6$-DMSO) δ 10.02 (s, 1H), 8.61 (s, 1H), 7.64-7.55 (m, 2H), 7.26-7.14 (m, 4H), 6.97-6.91 (m, 2H), 3.65 (s, 2H), 3.50-3.41 (m, 4H), 3.10-2.93 (m, 8H), 1.42 (s, 9H). LCMS Method C: rt 6.32 min; m/z 586.3 [M+H]$^+$.

(g) tert-Butyl 4-(4-((4-(2-(2-amino-2-oxoethyl)phenethyl)-5-(trifluoromethyl)pyrimidin-2-yl)amino)phenyl)piperazine-1-carboxylate (I8)

Lithium 2-(2-(2-(2-((4-(4-(tert-butoxycarbonyl)piperazin-1-yl)phenyl)amino)-5-(trifluoromethyl)pyrimidin-4-yl)ethyl)phenyl)acetate (I7) (0.195 g, 0.333 mmol) was dissolved in dry THF (10 mL) and dry DMF (2 mL) under an atmosphere of nitrogen. To the solution were added 1-hydroxybenzotriazole (0.049 g, 0.37 mmol) and EDCl (0.070 g, 0.37 mmol) and N,N-diisopropylethylamine (0.232 mL, 1.33 mmol) and the reaction mixture was stirred at room temperature for 10 minutes. Ammonium carbonate (0.128 g, 1.332 mmol) was added in one portion, and the reaction was stirred room temperature for 20 hours. The volatiles were removed in vacuo and the residual solution was diluted with EtOAc (70 mL) and sat. aq. NaHCO$_3$ (70 mL). The layers were separated and the organic layer was washed with water (70 mL), brine (70 mL), dried (MgSO$_4$), filtered and concentrated in vacuo to give the crude product which was purified by silica gel chromatography (Biotage Isolera, 12 g Si Cartridge, 0-100% EtOAc in petroleum benzine 40-60° C., then 0-10% methanol in EtOAc) to give the title compound (I8) (0.133 g, 68% yield) as a pale yellow solid; $^1$H NMR (400 MHz, d$_6$-DMSO) δ 10.01 (s, 1H), 8.61 (s, 1H), 7.65-7.56 (m, 2H), 7.44 (s, 1H), 7.26-7.13 (m, 4H), 6.98-6.89 (m, 3H), 3.52-3.41 (m, 6H), 3.13-2.95 (m, 8H), 1.42 (s, 9H). LCMS Method C: rt 6.18 min; m/z 585.3 [M+H]$^+$.

(h) 2-(2-(2-(2-((4-(Piperazin-1-yl)phenyl)amino)-5-(trifluoromethyl)pyrimidin-4-yl)ethyl)phenyl)acetamide (1)

tert-Butyl 4-(4-((4-(2-(2-amino-2-oxoethyl)phenethyl)-5-(trifluoromethyl)pyrimidin-2-yl)amino)phenyl)piperazine-1-carboxylate (I8) (0.131 g, 0.224 mmol) was dissolved in DCM (7 mL) under an atmosphere of nitrogen. Trifluoroacetic acid (0.857 mL, 11.2 mmol) was added to the solution and the reaction was stirred at room temperature for 24 hours. Volatiles were removed in vacuo, EtOAc (70 mL) and 2 M aq. NaOH (70 mL) were added to the oil and the layers were separated. The aqueous layer was extracted with EtOAc (50 mL), the combined organics were washed with brine (50 mL), dried (Na$_2$SO$_4$), filtered and concentrated in vacuo. The resulting solid was taken up in DCM (~5 mL) and methanol (~1 mL) and concentrated in vacuo. The process was repeated with only DCM twice to give the title compound (1) (0.104 g, 96% yield) as a pale yellow solid; $^1$H NMR (400 MHz, d$_6$-DMSO) δ 9.96 (s, 1H), 8.60 (s, 1H), 7.61-7.53 (m, 2H), 7.43 (br s, 1H), 7.25-7.13 (m, 4H), 6.98-6.86 (m, 3H), 3.50 (s, 2H), 3.12-3.05 (m, 2H), 3.04-2.94 (m, 6H), 2.86-2.78 (m, 4H). LCMS Method C: rt 4.774 min; m/z 485.2 [M+H]+.

Synthesis of intermediate 14: Methyl 2-(2-ethynylphenyl)acetate (I4)

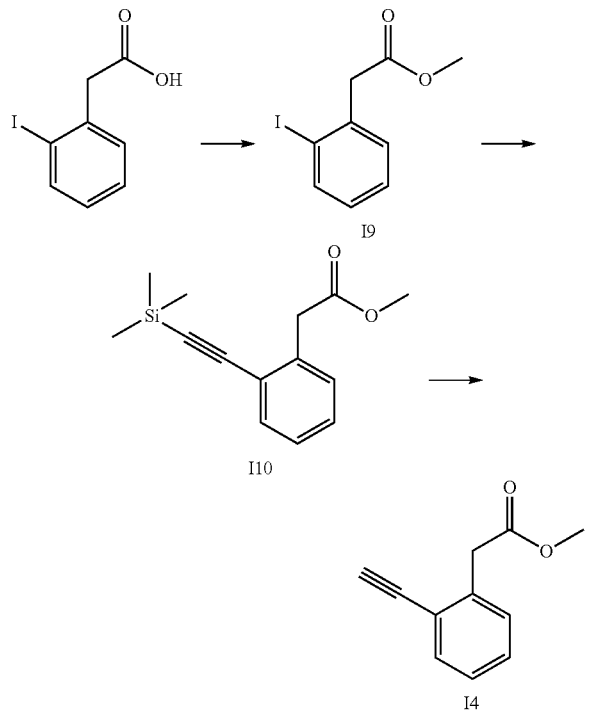

(a) Methyl 2-(2-iodophenyl)acetate (I9)

2-(2-Iodophenyl)acetic acid (5.00 g, 19.1 mmol) was placed into a reaction flask and dissolved in MeOH (150 mL). Sulfuric acid (250 μL) was added and reaction mixture was stirred and heated at 80° C. under nitrogen for 16 hours. The resulting mixture was cooled to room temperature and the volatiles removed by evaporation under reduced pressure. The residue was taken up in ethyl acetate (100 mL), washed with 10% NaHCO$_3$ (100 mL), dried (MgSO$_4$) and evaporated under reduced pressure to give the title compound (I9) (5.20 g, 99%) as a clear liquid; $^1$H NMR (400 MHz, CDCl$_3$) δ 7.85 (dd, J=7.9, 1.0 Hz, 1H), 7.35-7.27 (m, 2H), 6.97 (ddd, J=7.9, 7.0, 2.1 Hz, 1H), 3.81 (s, 2H), 3.72 (s, 3H).

(b) Methyl 2-(2-((trimethylsilyl)ethynyl)phenyl)acetate (I10)

Methyl 2-(2-iodophenyl)acetate (I9) (4.65 g, 16.8 mmol), PdCl$_2$(PPh$_3$)$_2$ (295 mg, 421 μmol) and Cu(I)I (80.0 mg, 421 μmol) were placed into an oven dried reaction flask under nitrogen. (Trimethylsilyl)acetylene (2.80 mL, 20.2 mmol), dry degassed THF (20 mL) and triethylamine (20 mL) were added and the reaction mixture was stirred at room temperature for 16 hours. The volatiles were removed under reduced pressure to give a black residue which was adsorbed onto silica then chromatographed on silica gel (0-5% ethyl acetate/petroleum benzine 40-60° C.) to give the title compound (I10) (4.63 g, 99%) as a light brown liquid; $^1$H NMR (400 MHz, CDCl$_3$) δ 7.48 (dd, J=7.5, 0.8 Hz, 1H), 7.32-7.14 (m, 3H), 3.84 (s, 2H), 3.71 (s, 3H), 0.26 (s, 9H). LCMS Method C: rt 6.64 min.

(c) Methyl 2-(2-ethynylphenyl)acetate (I4)

Methyl 2-(2-((trimethylsilyl)ethynyl)phenyl)acetate (I10) (4.63 g, 19.0 mmol) was dissolved in DCM (200 mL) and TBAF (1.0 M in THF) (28.5 mL, 28.5 mmol, 1.5 eq) was added at 0° C. The resulting solution was stirred at room temperature for 1 hour before washing with 10% NaHCO$_3$ (100 mL). The organic layer was dried (MgSO$_4$) then evaporated under reduced pressure to give a dark brown/black residue. The residue was adsorbed onto silica and then chromatographed on silica gel (0-10% ethyl acetate/petroleum benzine 40-60° C.) to give the title compound (I4) (2.76 g, 83%) as a red liquid; $^1$H NMR (400 MHz, CDCl$_3$) δ 7.52 (dd, J=7.6, 1.1 Hz, 1H), 7.43-7.16 (m, 3H), 3.88 (d, J=9.6 Hz, 2H), 3.77-3.52 (m, 3H), 3.28 (s, 1H).

Example 2

3-(2-(2-((4-(4-Methylpiperazin-1-yl)phenyl)amino)-5-(trifluoromethyl)pyrimidin-4-yl)ethyl)benzamide (2)

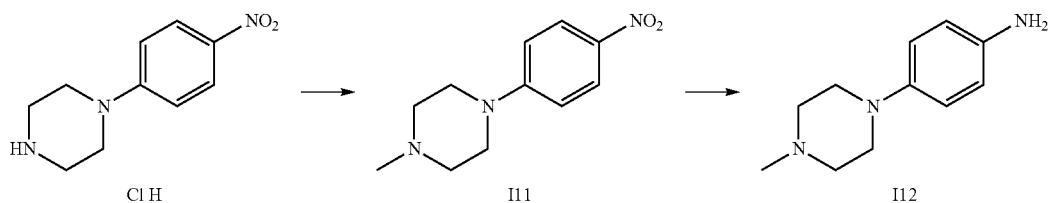

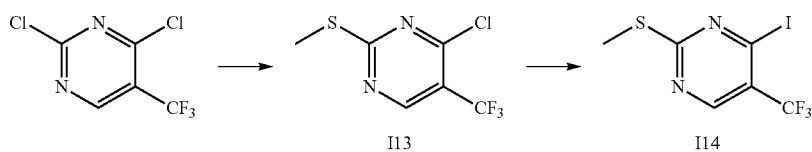

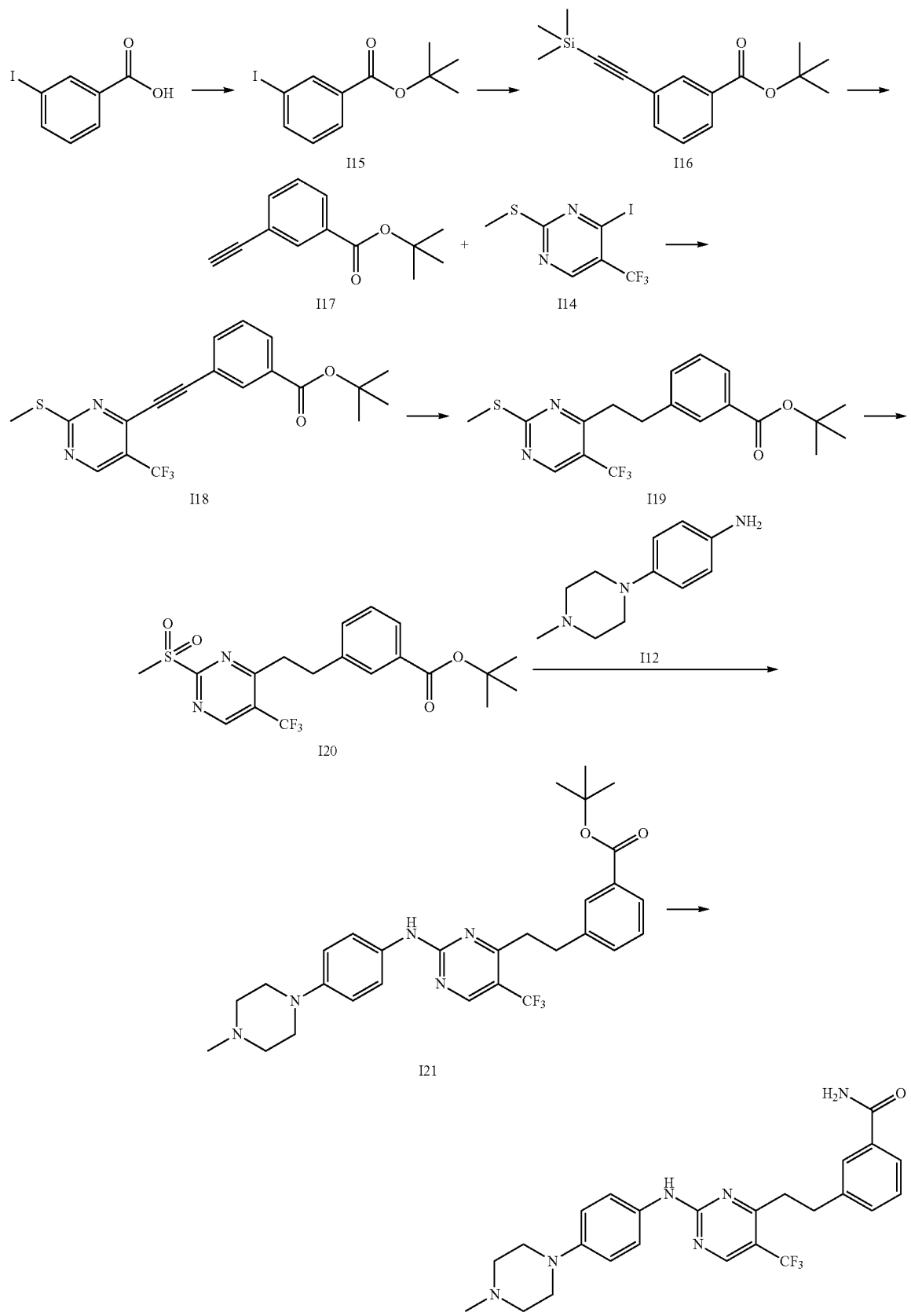
-continued

(a) 1-Methyl-4-(4-nitrophenyl)piperazine (I11)

To 4-(4'-nitrophenyl)piperazine hydrochloride (1.00 g, 4.10 mmol) was added formic acid (1.55 mL, 41.0 mmol) and 37% aq. formaldehyde (3.06 mL, 41.0 mmol) in a microwave vessel and the reaction was heated at 120° C. for 3 minutes. To the cooled reaction mixture was added EtOAc (100 mL) and 2 M aq. NaOH (70 mL). The layers were separated and the organic layer was washed with brine (50 mL), the layers were separated and the aqueous brine layer was extracted with EtOAc (50 mL), the organic layers were combined and dried ($Na_2SO_4$), filtered and concentrated in vacuo to give the crude product which was purified by silica gel chromatography (Biotage Isolera, 40 g Si cartridge, 0-60% methanol (containing 1% ammonia solution) in EtOAc) to give the title compound (I11) (0.636 g, 70% yield) as a yellow solid; $^1$H NMR (400 MHz, $d_6$-DMSO) δ 8.07-8.01 (m, 2H), 7.05-6.99 (m, 2H), 3.48-3.40 (m, 4H), 2.46-2.39 (m, 4H), 2.21 (s, 3H). LCMS Method C: rt 1.45 min; m/z 222.2 $[M+H]^+$.

(b) 1-4-(4-Methylpiperazin-1-yl)aniline (I12)

1-Methyl-4-(4-nitrophenyl)piperazine (I11) (0.632 g, 2.86 mmol) was dissolved in EtOAc (45 mL) under an atmosphere of nitrogen and a slurry of 10% Pd/C (0.200 g) in EtOAc (5 mL) was added. The resulting suspension was then stirred vigorously under an atmosphere of hydrogen at room temperature for 18 hours. The catalyst was removed by filtration through Celite, which was washed with EtOAc (7×10 mL) and the solvent was removed in vacuo to give the title compound (I12) (0.537 g, 98% yield) as a pink solid; $^1$H NMR (400 MHz, $d_6$-DMSO) δ 6.70-6.64 (m, 2H), 6.51-6.45 (m, 2H), 4.54 (s, 2H), 2.94-2.84 (m, 4H), 2.46-2.36 (m, 4H), 2.19 (s, 3H). LCMS Method C: rt 0.98 min; m/z 192.3 $[M+H]^+$.

(c) 4-Chloro-2-(methylthio)-5-(trifluoromethyl)pyrimidine (I13)

To a solution of the 2,4-dichloro-5-(trifluoromethyl)pyrimidine (2.50 g, 11.5 mmol) in THF (50 mL) in an ice bath under nitrogen was added zinc(II) chloride (1.0 M in ether, 13.8 mL, 13.8 mmol) dropwise. The mixture was stirred in the ice bath for two hours, then sodium methanethiolate (0.888 g, 12.7 mmol) was added. The mixture was stirred overnight, allowing the reaction to slowly come to room temperature. After 18 hours the reaction was quenched with 2 M HCl (15 mL), and the organics removed by evaporation under reduced pressure. The aqueous residue was diluted with brine (15 mL), and extracted with DCM (3×30 mL). The combined organic phases were dried (phase separator) and carefully evaporated to give a pale yellow oil. Chromatography (Biotage Isolera, 2×40 g silica cartridge, 0-20% DCM/n-hexane) followed by carefully evaporation of solvent (40° C.@400 mmHg then room temperature@200 mmHg) gave the title compound (I13) (2.149 g, 82% yield) as a colourless oil; $^1$H NMR (600 MHz, $CDCl_3$) δ 8.66 (s, 1H), 2.61 (s, 3H). LCMS Method C: rt: 7.95 min; m/z 229.1$[M+H]^+$. Note: I13 is volatile.

(d) 4-Iodo-2-(methylthio)-5-(trifluoromethyl)pyrimidine (I14)

4-Chloro-2-(methylthio)-5-(trifluoromethyl)pyrimidine (I13) (5.00 g, 21.9 mmol) was placed into a reaction flask then sodium iodide (9.80 g, 65.6 mmol) and hydroiodic acid (58%; 70 mL) were added. The reaction mixture was stirred for 48 hours in darkness then diluted with water (200 mL) where upon a colourless solid precipitated. The precipitate was collected by filtration and was washed with 10% $NaHCO_3$ solution until neutral. The resulting solid was washed with water (100 mL) then suction dried for 2 hours to give the title compound (I14) (3.956 g, 57%) as a pale yellow solid; $^1$H NMR (400 MHz, $CDCl_3$) δ 8.42 (s, 1H), 2.58 (s, 3H). LCMS Method C: rt 6.30 min, m/z 321.0 $[M+H]^+$.

(e) tert-Butyl 3-iodobenzoate (I15)

To a solution of 3-iodobenzoic acid (5.06 g, 20.4 mmol) in DCM (25 mL) was added a solution of $Boc_2O$ (4.90 g, 22.5 mmol) in dichloromethane (10 mL) and 4-DMAP (0.624 g, 5.11 mmol) in dichloromethane (5 mL). The resulting solution was stirred at room temperature under a nitrogen atmosphere for 64 hours. The resulting mixture was partitioned between water (100 mL) and dichloromethane (50 mL) and the layers separated. The organic layer was washed with water (2×100 mL) before being concentrated under reduced pressure. The resulting residue was purified using silica gel column chromatography (0-50% dichloromethane/petroleum benzene 40-60° C.) to give the title compound (I15) (65% 4.02 g) as a colourless oil; $^1$H NMR (400 MHz, $CDCl_3$) δ 8.30 (dd, J=1.6, 1.6 Hz, 1H), 7.95 (ddd, J=7.8, 1.5, 1.1 Hz, 1H), 7.85 (ddd, J=7.9, 1.8, 1.1 Hz, 1H), 7.16 (ddd, J=7.8, 7.8, 0.2 Hz, 1H), 1.59 (s, 9H). LCMS Method C: rt 6.88 min.

(f) tert-Butyl 3-((trimethylsilyl)ethynyl)benzoate (I16)

A mixture of tert-butyl 3-iodobenzoate (I15) (4.02 g, 13.2 mmol), $Pd(PPh_3)_4$ (0.38 g, 0.33 mmol) and copper(I) iodide (0.13 g, 0.68 mmol) was dissolved in anhydrous THF (50 mL) under a nitrogen atmosphere and the resulting solution degassed by bubbling nitrogen through it. Triethylamine (9.2 mL, 66 mmol) was added and the mixture was then stirred for 10 minutes before addition of TMS-acetylene (3.8 mL, 27 mmol). The resulting mixture was then stirred for 18 hours. The mixture was concentrated under reduced pressure and purified using silica gel column chromatography (0-10% ethyl acetate/petroleum benzine 40-60° C.) to give the title compound (I16) (3.57 g, 99%) as a cream crystalline solid; $^1$H NMR (400 MHz, $CDCl_3$) δ 8.06 (ddd, J=1.7, 1.7, 0.5 Hz, 1H), 7.92 (ddd, J=7.9, 1.3, 1.3 Hz, 1H), 7.60 (ddd, J=7.7, 1.4, 1.4 Hz, 1H), 7.35 (ddd, J=7.8, 7.8, 0.5 Hz, 1H), 1.59 (s, 9H), 0.26 (s, 9H). LCMS Method C: rt 7.46 min.

(g) tert-Butyl 3-ethynylbenzoate (I17)

To a solution of tert-butyl 3-((trimethylsilyl)ethynyl)benzoate (I16) (4.40 g, 16.0 mmol) in THF (100 mL) at 0° C. under nitrogen was added 1.0 M TBAF in THF (20.0 mL, 20.0 mmol). The mixture was then stirred at 0° C. for 1 hour then 16 hours at room temperature. The mixture was then concentrated under reduced pressure, diluted with ethyl acetate (100 mL) and washed with water (3×100 mL). The organic extract was then purified using silica gel column chromatogaphy (0-5% EtOAc/petroleum benzine 40-60° C.) to give the title compound (I17) (2.72 g, 84%) as a pale yellow oil; $^1$H NMR (400 MHz, $CDCl_3$) δ 8.09 (dd, J=1.5, 1.5 Hz, 1H), 7.97 (ddd, J=7.9, 1.5, 1.5 Hz, 1H), 7.63 (ddd, J=7.7, 1.4, 1.4 Hz, 1H), 7.38 (ddd, J=7.8, 7.8, 0.5 Hz, 1H), 3.11 (s, 1H), 1.59 (s, 9H).

(h) tert-Butyl 3-((2-(methylthio)-5-(trifluoromethyl)pyrimidin-4-yl)ethynyl)benzoate (I18)

t-Butyl 3-ethynylbenzoate (I17) (1.603 g, 7.93 mmol), 4-iodo-2-(methylthio)-5-(trifluoromethyl)pyrimidine (I14)

(1.647 g, 5.15 mmol), PdCl$_2$(PPh$_3$)$_2$ (0.316 g, 0.45 mmol), PPh$_3$ (0.355 g, 1.35 mmol), Cu(I)I (0.232 g, 1.22 mmol) and trethylamine (4.00 mL, 28.7 mmol) were combined in DMF (20 mL) and the resulting mixture heated at 120° C. under microwave irradiation for 25 minutes. The mixture was then concentrated under reduced pressure and purified twice using silica gel column chromatography (10-20% EtOAc/petroleum benzine 40-60° C. then 50-100% DCM/petroleum benzine 40-60° C.) to give the title compound (I18) (0.624 g, 31%) as a yellow solid; $^1$H NMR (400 MHz, CDCl$_3$) δ 8.73 (d, J=0.8 Hz, 1H), 8.25 (m, 1H), 8.08 (m, 1H), 7.78 (m, 1H), 7.48 (m, 1H), 2.63 (s, 3H), 1.61 (s, 9H).

(i) tert-Butyl 3-(2-(2-(methylthio)-5-(trifluoromethyl)pyrimidin-4-yl)ethyl)benzoate (I19)

tert-Butyl 3-((2-(methylthio)-5-(trifluoromethyl)pyrimidin-4-yl)ethynyl)benzoate (I18) (0.624 g, 1.58 mmol) and 10% Pd/C (0.206 g) was taken up in THF (20 mL) and H$_2$ bubbled through the mixture for 5 minutes before stirring at room temperature for 20 hours under a hydrogen atmosphere. The mixture was filtered through celite and concentrated under reduced pressure. This procedure was repeated twice with 10% Pd/C (0.212 g) and 20% Pearlman's catalyst (0.316 g) respectively to give the title compound (I19) as a yellow oil that was reacted without further purification. LCMS Method C: rt 7.14 min.

(j) tert-Butyl 3-(2-(2-(methylsulfonyl)-5-(trifluoromethyl)pyrimidin-4-yl)ethyl)benzoate (I20)

A mixture of tert-butyl 3-(2-(2-(methylthio)-5-(trifluoromethyl)pyrimidin-4-yl)ethyl)benzoate (I19) (0.630 g, 1.58 mmol) and MCPBA (0.975 g, 3.96 mmol) were dissolved in DCM (20 mL) at 0° C. The resulting solution was allowed to warm to room temperature, at which stirring was continued for 16 hours. The volatiles were evaporated under reduced pressure and the residue triturated with DCM. The resulting suspension was filtered and the filtrate was evaporated to dryness. The residue was triturated a second time with DCM and the precipitate removed via filtration. The filtrate was evaporated to dryness and the residue purified using silica gel column chromatography (20-100% DCM/petroleum benzine 40-60° C., 0-50% EtOAc/petroleum benzine 40-60° C.) to give the title compound (I20) (0.360 g, 53%) as a yellow semi solid in 70% purity by NMR; $^1$H NMR (400 MHz, CDCl$_3$) δ 9.06 (s, 1H), 7.85 (m, 2H), 7.38 (m, 2H), 3.42 (m, 2H), 3.36 (s, 3H), 3.24 (m, 2H), 1.60 (s, 10H). LCMS Method C: rt 6.40 min; m/z 357.1 [M−t-BuO]+, 453.1 [M+Na]$^+$.

(k) tert-Butyl 3-(2-(2-((4-(4-methylpiperazin-1-yl)phenyl)amino)-5-(trifluoromethyl)pyrimidin-4-yl)ethyl)benzoate (I21)

1-4-(4-Methylpiperazin-1-yl)aniline (I12) (0.071 g, 0.372 mmol), tert-butyl 3-(2-(2-(methylsulfonyl)-5-(trifluoromethyl)pyrimidin-4-yl)ethyl)benzoate (I20) (0.100 g, 0.232 mmol) and tosic acid monohydrate (0.088 g, 0.465 mmol) were combined in a microwave vessel and dry dioxane (3 mL) was added. The reaction was heated under microwave irradiation at 150° C. for 30 minutes then concentrated in vacuo and purified by silica gel chromatography (Biotage Isolera, 12 g Si Cartridge, 0-100% EtOAc in petroleum benzine 40-60° C., then 0-100% MeOH in EtOAc) to give a pale yellow solid. The solid was dissolved in EtOAc (20 mL) and sat. aq. NaHCO$_3$ (10 mL) and the layers were separated. The aqueous layer was extracted with EtOAc (20 mL), the organics were combined and washed with water (20 mL), brine (20 mL), dried (MgSO$_4$), filtered and concentrated in vacuo to give the title compound (I21) (0.025 g, 20% yield) as a pale yellow solid; $^1$H NMR (400 MHz, d$_6$-DMSO) δ 9.98 (s, 1H), 8.59 (s, 1H), 7.76-7.69 (m, 2H), 7.57-7.37 (m, 4H), 6.90 (d, J=9.1 Hz, 2H), 3.19-3.00 (m, 8H), 2.48-2.40 (m, 4H), 2.21 (s, 3H), 1.52 (s, 9H). LCMS Method C: rt 5.41 min; m/z 542.3 [M+H]$^+$.

(I) 3-(2-(2-((4-(4-Methylpiperazin-1-yl)phenyl)amino)-5-(trifluoromethyl)pyrimidin-4-yl)ethyl)benzamide (2)

tert-Butyl 3-(2-(2-((4-(4-methylpiperazin-1-yl)phenyl)amino)-5-(trifluoromethyl)pyrimidin-4-yl)ethyl)benzoate (I21) (0.025 g, 0.046 mmol) was dissolved in dry DCM (3 mL) under an atmosphere of nitrogen. Trifluoroacetic acid (0.177 mL, 2.31 mmol) was added to the solution and the reaction was stirred at 35° C. for 2 hours. The mixture was concentrated to dryness, toluene (~2 mL) was added to the residue and the solvent was removed in vacuo to give a yellow solid. This material was dissolved in dry THF (3 mL) and dry DMF (0.2 mL) under an atmosphere of nitrogen. To the solution were added 1-hydroxybenzotriazole (0.009 g, 0.064 mmol) and EDCl (0.012 g, 0.064 mmol) and N,N-diisopropylethylamine (0.048 mL, 0.276 mmol) and the reaction mixture was stirred at room temperature for 10 minutes. Ammonium carbonate (0.018 g, 0.18 mmol) was added in one portion, and the reaction was stirred room temperature for 20 hours. The volatiles were removed in vacuo and the residual solution was diluted with EtOAc (20 mL) and saturated aq. NaHCO$_3$ (10 mL). The layers were separated and the organic layer was washed with water (10 mL), brine (10 mL), dried (MgSO$_4$), filtered and concentrated in vacuo to give a pale yellow solid. The product was dissolved in DCM (~4 mL) and MeOH (~1 mL) and the solvents were removed in vacuo. The process was repeated 3 times with DCM only and to give the title compound (2) (0.017 g, 76% yield over 2 steps) as a pale yellow solid; $^1$H NMR (400 MHz, d$_6$-DMSO) δ 9.97 (s, 1H), 8.60 (s, 1H), 7.95 (br s, 1H), 7.79 (s, 1H), 7.75-7.66 (m, 1H), 7.57-7.47 (m, 2H), 7.40-7.30 (m, 3H), 6.94-6.86 (m, 2H), 3.14-3.01 (m, 8H), 2.47-2.42 (m, 4H), 2.21 (s, 3H). LCMS Method C: rt 4.75 min; m/z 485.3 [M+H]$^+$.

Example 3

2-(2-(2-(2-((4-(4-Methylpiperazin-1-yl)phenyl)amino)-5-(trifluoromethyl)pyrimidin-4-yl)ethyl)phenyl)acetamide (3)

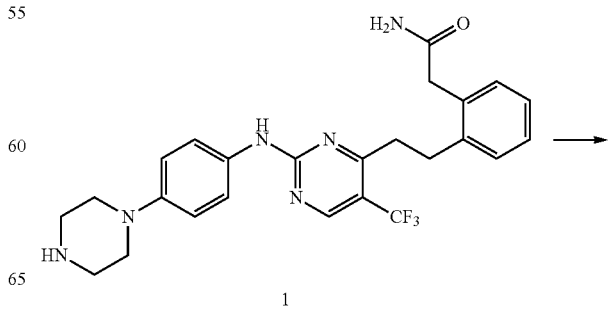

1

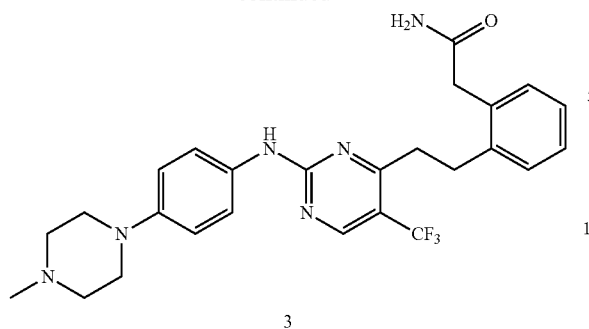

3

To a suspension of 2-(2-(2-(2-((4-(piperazin-1-yl)phenyl) amino)-5-(trifluoromethyl)pyrimidin-4-yl)ethyl)phenyl)acetamide (1) (0.015 g, 0.031 mmol) in anhydrous methanol (1.5 mL) were added a 37% aq. solution of formaldehyde (0.005 mL, 0.062 mmol) followed by sodium triacetoxyborohydride (0.033 g, 0.155 mmol) under an atmosphere of nitrogen. The reaction was stirred at room temperature for 1.5 hours, the volatiles were removed in vacuo and the residue was diluted with EtOAc (15 mL) and sat. aq. NaHCO$_3$ (10 mL). The layers were separated and the aqueous layer was extracted with EtOAc (2×10 mL), the combined organic layers were washed with water (10 mL), brine (10 mL), dried (MgSO$_4$), filtered and concentrated in vacuo to give the title compound (3) (14.5 mg, 97% yield) as a pale yellow solid; $^1$H NMR (400 MHz, d$_6$-DMSO) δ 9.97 (s, 1H), 8.60 (s, 1H), 7.57 (d, J=9.0 Hz, 2H), 7.43 (s, 1H), 7.26-7.13 (m, 4H), 6.96-6.87 (m, 3H), 3.50 (s, 2H), 3.12-3.03 (m, 6H), 3.03-2.94 (m, 2H), 2.47-2.42 (m, 4H), 2.22 (s, 3H). LCMS Method C: rt 4.74 min; m/z 499.3 [M+H]$^+$.

Example 4

2-(2-(2-(2-((4-(Piperidin-3-yl)phenyl)amino)-5-(trifluoromethyl)pyrimidin-4-yl)ethyl)phenyl)acetamide (4)

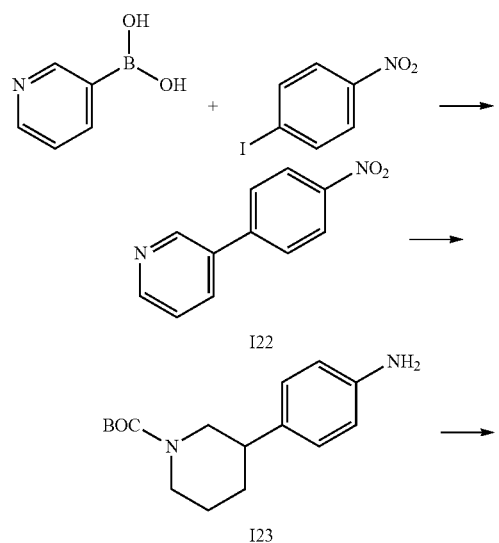

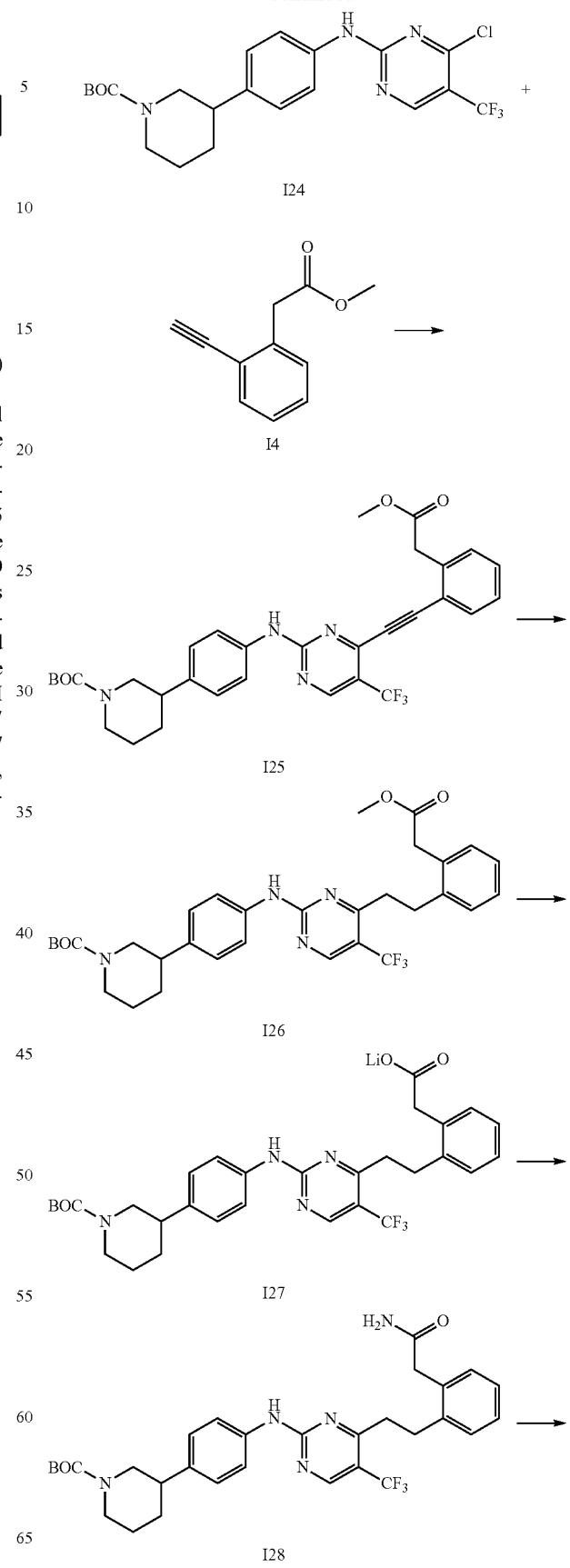

-continued

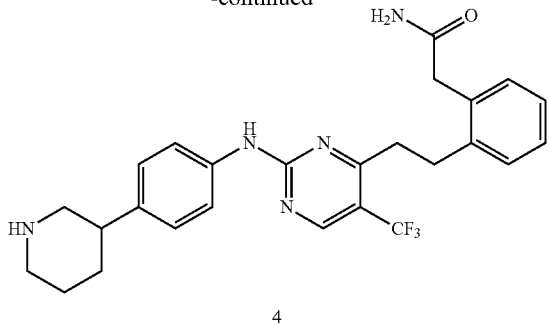

4

(a) 3-(4-Nitrophenyl)pyridine (I22)

To a solution of 1-iodo-4-nitrobenzene (1.00 g, 4.02 mmol) in nitrogen degassed dry DMF (20 mL) was added 3-pyridineboronic acid (0.592 g, 4.82 mmol), Cs$_2$CO$_3$ (5.23 g, 16.1 mmol), triphenylphosphine (0.158 g, 0.602 mmol) and Pd(OAc)$_2$ (0.090 g, 0.40 mmol). The reaction mixture was heated at 80° C. for 18 hours, cooled to room temperature and concentrated to dryness in vacuo. The crude material was purified by silica gel chromatography (Biotage Isolera, 40 g Si cartridge, 20-100% EtOAc in petroleum benzine 40-60° C.) to give the title compound (I22) (0.590 g, 73% yield) as a yellow solid; $^1$H NMR (400 MHz, CDCl$_3$) δ 8.90 (d, J=1.8 Hz, 1H), 8.70 (dd, J=4.8, 1.5 Hz, 1H), 8.39-8.32 (m, 2H), 7.93 (ddd, J=7.9, 2.4, 1.7 Hz, 1H), 7.78-7.72 (m, 2H), 7.44 (ddd, J=7.9, 4.8, 0.8 Hz, 1H). LCMS Method C: rt 4.62 min; m/z 201.1 [M+H]$^+$.

(b) tert-Butyl 3-(4-aminophenyl)piperidine-1-carboxylate (I23)

To a solution of 3-(4-nitrophenyl)pyridine (I22) (0.590 g, 2.947 mmol) in 1 M HCl (3 mL) and methanol (30 mL) was added PtO$_2$ (0.059 g) under an atmosphere of nitrogen. The reaction was then subjected to a 40 psi hydrogen atmosphere in a Parr hydrogenator for 24 hours, the catalyst was removed by filtration, and the solvents were removed in vacuo. The resulting yellow solid was again dissolved in 1 M HCl (3 mL) and methanol (30 mL) and PtO$_2$ (0.059 g) was added under an atmosphere of nitrogen. The reaction was subjected to a 40 psi hydrogen atmosphere in a Parr hydrogenator for 24 hours, the reaction mixture was filtered through celite which was washed with EtOAc (3×10 mL) and water (3×10 mL) and the filtrate was concentrated in vacuo to give the crude material (0.720 g) as a pale brown glassy solid. This material was dissolved in DCM (25 mL), DMF (5 mL) and methanol (20 mL) and treated with triethylamine (1.438 mL, 10.315 mmol) followed by Boc anhydride (0.675 g, 3.094 mmol). The reaction was stirred at room temperature for 20 hours, then concentrated in vacuo and EtOAc (100 mL) and sat. aq. NaHCO$_3$ (50 mL) were added and the layers were separated. The aqueous layer was extracted with EtOAc (70 mL), the organics were combined and washed with water (100 mL), brine (100 mL), water (100 mL), brine (100 mL), dried (Na$_2$SO$_4$), filtered and concentrated in vacuo to give a pink foam. The crude product was purified by silica gel chromatography (Biotage Isolera, 40 g Si cartridge, 0-55% EtOAc in petroleum benzine 40-60° C.) to give the title compound (I23) (0.435 g, 53% yield over 2 steps) as a pink solid; $^1$H NMR (400 MHz, d$_6$-DMSO) δ 6.91-6.86 (m, 2H), 6.52-6.47 (m, 2H), 4.88 (s, 2H), 3.99-3.80 (m, 2H), 2.80-2.54 (m, 2H), 2.37 (tt, J=11.6, 3.7 Hz, 1H), 1.85-1.75 (m, 1H), 1.70-1.62 (m, 1H), 1.53 (ddd, J=24.4, 12.4, 3.3 Hz, 1H), 1.46-1.33 (m, 10H). LCMS Method C: rt 4.86 min; m/z 177.2 [M-Boc+2H]$^+$.

(c) tert-Butyl 3-(4-((4-chloro-5-(trifluoromethyl)pyrimidin-2-yl)amino)phenyl)piperidine-1-carboxylate (I24)

2,4-Dichloro-5-(trifluoromethyl)pyrimidine (0.355 g, 1.64 mmol) was stirred in a 1:1 t-BuOH:1,2-dichloroethane mixture (30 mL) at 0° C. and a 1.0 M ZnCl$_2$ solution in diethyl ether (1.87 mL, 1.87 mmol) was added cautiously over 20 minutes and the reaction was left stirring at 0° C. for 30 minutes. A solution of tert-butyl 3-(4-aminophenyl)piperidine-1-carboxylate (I23) (0.431 g, 1.56 mmol) in 1:1 t-BuOH:1,2-dichloroethane (10 mL) was added drop-wise over 15 minutes at 0° C. followed by a solution of triethylamine (0.261 µL, 1.871 mmol) in 1:1 t-BuOH:1,2-dichloroethane (10 mL). The reaction was allowed to warm to room temperature and was stirred for 60 hours. Volatiles were evaporated in vacuo and the resulting oily residue was suspended in water (200 mL), the suspension was sonicated for 30 minutes and the product was collected by filtration, the solid was washed with water (5×10 mL) and dried under a high vacuum to give the title compound (I24) (0.638 g, 90% yield) as a pale pink solid; $^1$H NMR (400 MHz, d$_6$-DMSO) δ 10.62 (s, 1H), 8.78 (s, 1H), 7.61 (d, J=8.5 Hz, 2H), 7.26 (d, J=8.6 Hz, 2H), 4.05-3.87 (m, 2H), 2.94-2.63 (m, 2H), 2.57 (ddd, J=11.2, 7.7, 3.7 Hz, 1H), 1.87 (d, J=12.8 Hz, 1H), 1.75-1.54 (m, 2H), 1.51-1.35 (m, 10H). LCMS Method C: rt 6.89 min; m/z 455.3 M−H]$^−$.

(d) tert-Butyl 3-(4-((4-((2-(2-methoxy-2-oxoethyl)phenyl)ethynyl)-5-(trifluoromethyl)pyrimidin-2-yl)amino)phenyl)piperidine-1-carboxylate (I25)

To a nitrogen de-gassed solution of methyl 2-(2-ethynylphenyl)acetate (I4) (0.137 g, 0.788 mmol) in dry DMF (7 mL) were added triethylamine (0.366 mL, 2.63 mmol) followed by tert-butyl 3-(4-((4-chloro-5-(trifluoromethyl)pyrimidin-2-yl)amino)phenyl)piperidine-1-carboxylate (I24) (0.300 g, 0.657 mmol), triphenylphosphine (0.026 g, 0.098 mmol), trans-dichlorobis(triphenylphosphine) palladium(II) (0.046 g, 0.066 mmol) and CuI (0.019 g, 0.098 mmol). The reaction mixture was heated under microwave irradiation at 120° C. for 20 minutes and then concentrated to dryness in vacuo and purified by silica gel chromatography (Biotage Isolera, 40 g Si cartridge, 0-70% EtOAc in petroleum benzine 40-60° C.) to give the title compound (I25) (0.310 g, 79% yield) as a yellow sticky oil; $^1$H NMR (400 MHz, d$_6$-DMSO) 10.44 (s, 1H), 8.81 (s, 1H), 7.73-7.60 (m, 3H), 7.54 (td, J=7.6, 1.3 Hz, 1H), 7.50-7.34 (m, 2H), 7.24 (d, J=8.6 Hz, 2H), 4.02-3.87 (m, 4H), 3.61 (s, 3H), 2.90-2.51 (m, 4H), 1.88 (d, J=12.0 Hz, 1H), 1.76-1.55 (m, 2H), 1.51-1.34 (m, 10H). LCMS Method C: rt 6.98 min; m/z 539.2 [M-C$_4$H$_9$ (t-Bu)+H]$^+$.

(e) tert-Butyl 3-(4-((4-(2-(2-methoxy-2-oxoethyl)phenethyl)-5-(trifluoromethyl)pyrimidin-2-yl)amino)phenyl)piperidine-1-carboxylate (I26)

tert-Butyl 3-(4-((4-((2-(2-methoxy-2-oxoethyl)phenyl)ethynyl)-5-(trifluoromethyl)pyrimidin-2-yl)amino)phenyl)piperidine-1-carboxylate (I25) (0.302 g, 0.508 mmol) was dissolved in EtOAc (12 mL) and absolute ethanol (8 mL) under an atmosphere of nitrogen. 10% Pd/C (0.250 g) in EtOAc (4 mL) was added to the solution and the atmosphere was changed to hydrogen gas (balloon). The reaction was sealed with a balloon and stirred at room temperature for 18 hours after which the catalyst was removed by filtration through Celite and the solvent was removed in vacuo. The resulting solid was again dissolved in EtOAc (12 mL) and absolute ethanol (8 mL) under an atmosphere of nitrogen and 10% Pd/C (0.250 g) in EtOAc (4 mL) was added to the solution and the atmosphere was changed to hydrogen gas (balloon). The reaction was sealed with a balloon and stirred at room temperature for 24 hours. The catalyst was removed by filtration through Celite, which was washed with EtOAc (7×10 mL) and the solvent was removed in vacuo to give a pale yellow viscous oil. The crude product was purified by silica gel chromatography (Biotage Isolera, 40 g Si Cartridge, 0-50% EtOAc in petroleum benzine 40-60° C.) to give the title compound (I26) (0.249 g, 82% yield) as a pale yellow viscous oil; $^1$H NMR (400 MHz, $d_6$-DMSO) δ 10.18 (s, 1H), 8.67 (s, 1H), 7.72-7.64 (m, 2H), 7.26-7.16 (m, 6H), 4.02-3.89 (m, 2H), 3.76 (s, 2H), 3.57 (s, 3H), 3.10-2.95 (m, 4H), 2.91-2.66 (m, 2H), 2.61-2.51 (m, 1H), 1.88 (d, J=11.8 Hz, 1H), 1.75-1.54 (m, 2H), 1.43 (m, 10H). LCMS Method C: rt 7.11 min; m/z 599.3 [M+H]$^+$.

(f) Lithium 2-(2-(2-(2-((4-(1-(tert-butoxycarbonyl) piperidin-3-yl)phenyl)amino)-5-(trifluoromethyl) pyrimidin-4-yl)ethyl)phenyl)acetate (I27)

LiOH.H$_2$O (0.052 g, 1.25 mmol) was added to tert-butyl 3-(4-((4-(2-(2-methoxy-2-oxoethyl)phenethyl)-5-(trifluoromethyl)pyrimidin-2-yl)amino)phenyl)piperidine-1-carboxylate (I26) (0.249 g, 0.416 mmol) in THF (10 mL), water (2.5 mL) and methanol (1 mL). The resulting mixture was allowed to stir for 2 hours at 40° C. and then 20 hours at room temperature. The volatiles were removed in vacuo and the residue was diluted with EtOAc (70 mL) and 2 M aq. NaOH (50 mL). The layers were separated and the aqueous layer was extracted with EtOAc (70 mL), the organic layers were combined, washed with brine (70 mL), dried (MgSO$_4$), filtered and concentrated under reduced pressure to give the title compound (I27) (0.250 g, 100% yield) as an off-white oily solid; $^1$H NMR (400 MHz, $d_6$-DMSO) δ 10.23 (s, 1H), 8.64 (s, 1H), 7.72-7.60 (m, 2H), 7.25-7.00 (m, 6H), 4.01-3.88 (m, 2H), 3.48 (s, 2H), 3.13-2.92 (m, 4H), 2.86-2.63 (m, 2H), 1.91-1.81 (m, 1H), 1.72-1.54 (m, 2H), 1.48-1.34 (m, 10H). LCMS Method C: rt 6.71 min; m/z 585.3 [M+H]$^+$.

(g) tert-Butyl 3-(4-((4-(2-(2-amino-2-oxoethyl)phenethyl)-5-(trifluoromethyl)pyrimidin-2-yl)amino)phenyl)piperidine-1-carboxylate (I28)

Lithium 2-(2-(2-(2-((4-(1-(tert-butoxycarbonyl)piperidin-3-yl)phenyl)amino)-5-(trifluoromethyl)pyrimidin-4-yl) ethyl)phenyl)acetate (I27) (0.246 g, 0.416 mmol) was dissolved in dry THF (10 mL) and dry DMF (2 mL) under an atmosphere of nitrogen. To the solution were added 1-hydroxybenzotriazole (0.067 g, 0.50 mmol) and EDCl (0.096 g, 0.50 mmol) and N,N-diisopropylethylamine (0.290 mL, 1.66 mmol) and the reaction mixture was stirred at room temperature for 10 minutes. Ammonium carbonate (0.160 g, 1.66 mmol) was added in one portion, and the reaction was stirred at room temperature for 45 hours. The volatiles were removed in vacuo and the residual solution was diluted with EtOAc (70 mL) and sat. aq. NaHCO$_3$ (70 mL). The layers were separated and the aqueous layer was extracted with EtOAc (70 mL), the combined organic layers were washed with water (70 mL), brine (70 mL), dried (MgSO$_4$), filtered and concentrated in vacuo to give an off-white solid. The crude product was purified by silica gel chromatography (Biotage Isolera, 40 g Si Cartridge, 0-100% EtOAc in petroleum benzine 40-60° C., then 0-10% methanol in EtOAc) to give the title compound (I28) (0.186 g, 77% yield) as a white solid; $^1$H NMR (400 MHz, $d_6$-DMSO) δ 10.17 (s, 1H), 8.67 (s, 1H), 7.69 (d, J=8.6 Hz, 2H), 7.44 (brs, 1H), 7.28-7.11 (m, 6H), 6.93 (br s, 1H), 4.02-3.89 (m, 2H), 3.50 (s, 2H), 3.15-3.07 (m, 2H), 3.06-2.98 (m, 2H), 2.89-2.67 (m, 2H), 2.61-2.51 (m, 1H), 1.88 (d, J=11.1 Hz, 1H), 1.74-1.55 (m, 2H), 1.50-1.35 (m, 10H). LCMS Method C: rt 6.57 min; m/z 584.3 [M+H]$^+$.

(h) 2-(2-(2-(2-((4-(Piperidin-3-yl)phenyl)amino)-5-(trifluoromethyl)pyrimidin-4-yl)ethyl)phenyl)acetamide (4)

tert-Butyl 3-(4-((4-(2-(2-amino-2-oxoethyl)phenethyl)-5-(trifluoromethyl)pyrimidin-2-yl)amino)phenyl)piperidine-1-carboxylate (I28) (0.184 g, 0.315 mmol) was dissolved in DCM (10 mL) under an atmosphere of nitrogen. Trifluoroacetic acid (1.21 mL, 15.8 mmol) was added to the solution and the reaction was stirred at room temperature for 1 hour. Volatiles were removed in vacuo, EtOAc (100 mL) and 2 M aq. NaOH (70 mL) were added to the residue and the layers were separated. The aqueous layer was extracted with EtOAc (70 mL), the combined organics were washed with water (50 mL), brine (50 mL), dried (MgSO$_4$), filtered and concentrated in vacuo to give a white solid. The solid was taken up in DCM (~7 mL) and methanol (~1 mL) and concentrated in vacuo. The process was repeated with only DCM twice to give the title compound (4) (0.110 g, 72% yield) as a white solid; $^1$H NMR (400 MHz, $d_6$-DMSO) δ 10.13 (s, 1H), 8.65 (s, 1H), 7.69-7.62 (m, 2H), 7.44 (s, 1H), 7.26-7.12 (m, 6H), 6.93 (s, 1H), 3.50 (s, 2H), 3.15-3.06 (m, 2H), 3.06-2.90 (m, 4H), 2.60-2.43 (m, 3H), 1.85 (d, J=11.1 Hz, 1H), 1.69-1.61 (m, 1H), 1.61-1.41 (m, 2H). 3 Aliphatic protons obscured by residual DMSO. LCMS Method C: rt 4.81 min; m/z 484.3 [M+H]$^+$.

Example 5

2-(2-(2-(2-((4-(1-Methylpiperidin-3-yl)phenyl) amino)-5-(trifluoromethyl)pyrimidin-4-yl)ethyl)phenyl)acetamide (5)

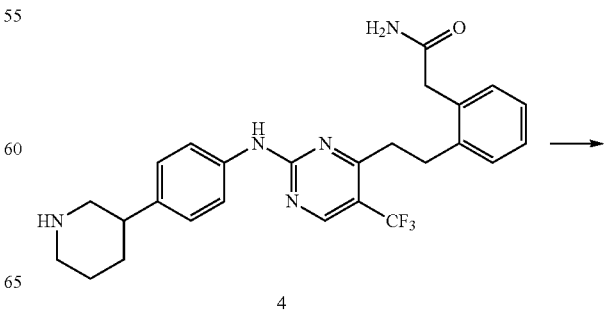

-continued

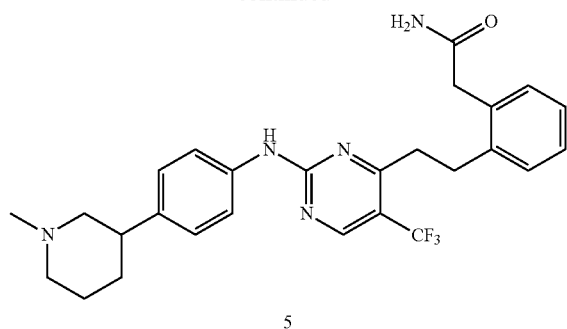

5

To a suspension of 2-(2-(2-(2-((4-(piperidin-3-yl)phenyl)amino)-5-(trifluoromethyl)pyrimidin-4-yl)ethyl)phenyl)acetamide (4) (0.021 g, 0.043 mmol) in anhydrous methanol (2 mL) were added a 37% aq. solution of formaldehyde (0.006 g, 0.195 mmol) followed by sodium triacetoxyborohydride (0.046 g, 0.217 mmol) under an atmosphere of nitrogen. The reaction was stirred at room temperature for 1 hour, the volatiles were removed in vacuo and the residue was diluted with EtOAc (15 mL) and sat. aq. NaHCO$_3$ (10 mL). The layers were separated and the aqueous layer was extracted with EtOAc (15 mL), the combined organic layers were washed with water (10 mL), brine (10 mL), dried (MgSO$_4$), filtered and concentrated in vacuo to give the title compound (5) (20 mg, 93% yield) as a an off-white solid; $^1$H NMR (400 MHz, d$_4$-MeOD) δ 8.54 (s, 1H), 7.62 (d, J=8.5 Hz, 2H), 7.30-7.15 (m, 6H), 3.67 (s, 2H), 3.19-3.12 (m, 2H), 3.12-3.02 (m, 2H), 2.96 (d, J=11.1 Hz, 2H), 2.85-2.74 (m, 1H), 2.34 (s, 3H), 2.13-2.03 (m, 2H), 1.96-1.67 (m, 3H), 1.49 (ddd, J=24.8, 12.5, 3.9 Hz, 1H). LCMS Method C: rt 4.86 min; m/z 498.3 [M+H]$^+$.

Example 6

3-(2-(2-((3-(4-Methylpiperazin-1-yl)phenyl)amino)-5-(trifluoromethyl)pyrimidin-4-yl)ethyl)benzamide (6)

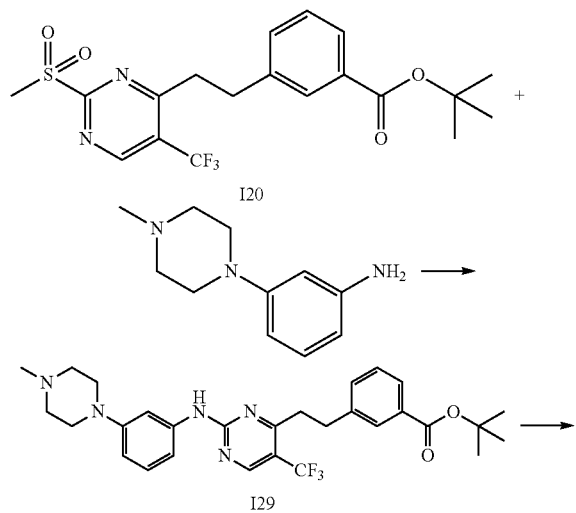

-continued

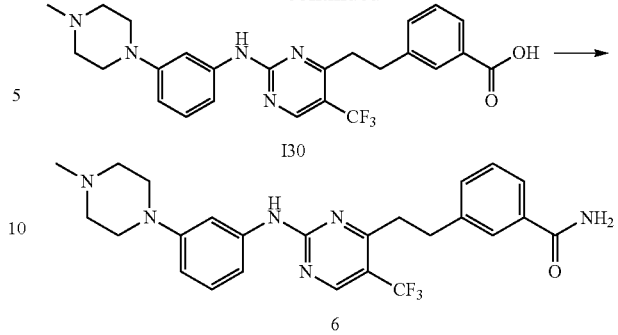

(a) tert-Butyl 3-(2-(2-((3-(4-methylpiperazin-1-yl)phenyl)amino)-5-(trifluoromethyl)pyrimidin-4-yl)ethyl)benzoate (I29)

A mixture of tert-butyl 3-(2-(2-(methylsulfonyl)-5-(trifluoromethyl)pyrimidin-4-yl)ethyl)benzoate (I20) (0.072 g, 0.17 mmol), Tosic acid monohydrate (0.044 g, 0.231 mmol), and 3-(4-methylpiperazinyl-1-yl)aniline (0.055 g, 0.29 mmol) in dioxane (3.0 mL) was heated to 140-150° C. under microwave irradiation for 30 minutes. The mixture was then concentrated under reduced pressure and purified using silica gel column chromatography (0-10% MeOH/EtOAc with 1% NH$_3$ aq.) to give the title compound (I29) (0.048 g, 52%); $^1$H NMR (400 MHz, CDCl$_3$) δ 8.54 (s, 1H), 7.88 (s, 1H), 7.84 (ddd, J=7.4, 1.6, 1.6 Hz, 1H), 7.37 (m, 4H), 7.23 (m, 1H), 7.04 (dd, J=7.9, 1.4 Hz, 1H), 6.69 (dd, J=8.2, 1.8 Hz, 1H), 3.27 (m, 4H), 3.14 (m, 4H), 2.58 (m, 4H), 2.35 (s, 3H), 1.59 (s, 9H). LCMS Method C: rt 5.45 min; m/z 542.3 [M+H]$^+$.

(b) 3-(2-(2-((3-(4-Methylpiperazin-1-yl)phenyl)amino)-5-(trifluoromethyl)pyrimidin-4-yl)ethyl)benzoic acid (I30)

To a solution of tert-butyl 3-(2-(2-((3-(4-methylpiperazin-1-yl)phenyl)amino)-5-(trifluoromethyl)pyrimidin-4-yl)ethyl)benzoate (I29) (0.048 g, 0.088 mmol) in DCM (3 mL) was added TFA (0.5 mL); the reaction was then stirred for 35 minutes at room temperature before concentrating under reduced pressure. The residue was taken up in toluene (2×10 mL) and concentrated under reduced pressure. The resulting residue was taken up in DCM (3 mL) and TFA (0.5 mL) was added. The resulting solution was stirred at room temperature for 1 hour then the volatiles removed by evaporation under reduced pressure. The residue was taken up in toluene (2×20 mL) and concentrated under reduced pressure to give the title compound (I30) in quantative yield; $^1$H NMR (400 MHz, d$_6$-Acetone) b 9.14 (s, 1H), 8.62 (s, 1H), 7.96 (s, 1H), 7.89 (d, J=7.7 Hz, 1H), 7.74 (bs, 1H), 7.54 (d, J=7.7 Hz, 1H), 7.44 (dd, J=7.6, 7.6 Hz, 1H), 7.34 (bd, J=8.0 Hz, 1H), 7.25 (dd, J=8.1, 8.1 Hz, 1H), 6.77 (dd, J=8.1, 1.8 Hz, 1H), 3.60 (m, 4H), 3.47 (m, 4H), 3.20 (m, 4H), 2.94 (s, 3H). LCMS Method C: rt 4.93 min; m/z 486.2 [M+H]$^+$.

(c) 3-(2-(2-((3-(4-Methylpiperazin-1-yl)phenyl)amino)-5-(trifluoromethyl)pyrimidin-4-yl)ethyl)benzamide (6)

To a solution of 3-(2-(2-((3-(4-methylpiperazin-1-yl)phenyl)amino)-5-(trifluoromethyl)pyrimidin-4-yl)ethyl)benzoic acid (I30) (0.048 g, 0.10 mmol) and HATU (0.051 g, 0.13 mmol) in DMF (2 mL) was added DIPEA (0.068 mL, 0.39 mmol), the resulting solution was then stirred for 10 minutes before addition of NH$_4$OH (0.2 mL). The resulting mixture was then stirred overnight (16 hours) at room temperature. The mixture was diluted with water and extracted with EtOAc (2×20 mL). The combined organic extracts were dried using a phase separation cartridge before concentrating under reduced pressure. The organic residues were then purified using silica gel column chromatography (0-30% MeOH/EtOAc with 1% NH$_4$OH in the MeOH) to give the title compound (6)(0.028 mg, 58%) as a white solid; $^1$H NMR (400 MHz, d$_6$-DMSO) δ 10.07 (s, 1H), 8.67 (s, 1H), 7.95 (s, 1H), 7.78 (s, 1H), 7.72 (m, 1H), 7.54 (s, 1H), 7.38 (m, 2H), 7.34 (m, 1H), 7.14 (d, J=5.2 Hz, 2H), 6.64 (m, 1H), 3.10 (m, 8H), 2.42 (m, 4H), 2.19 (s, 3H). LCMS Method C: rt 4.80 min; m/z 485.3 [M+H]$^+$.

Example 7

2-(2-(2-(2-((4-(1-Methylpiperidin-3-yl)phenyl)amino)-5-(trifluoromethyl)pyrimidin-4-yl)ethyl)phenyl)acetamide (7)

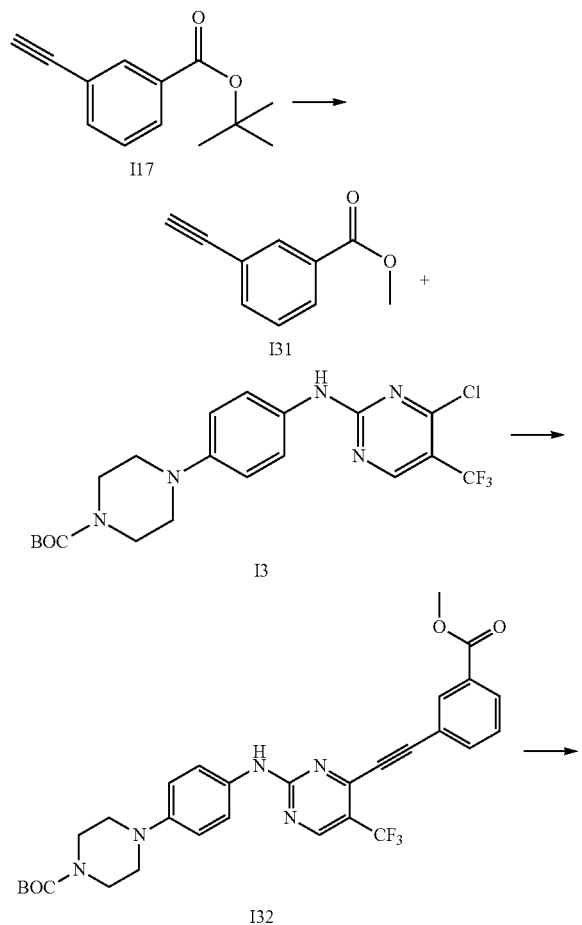

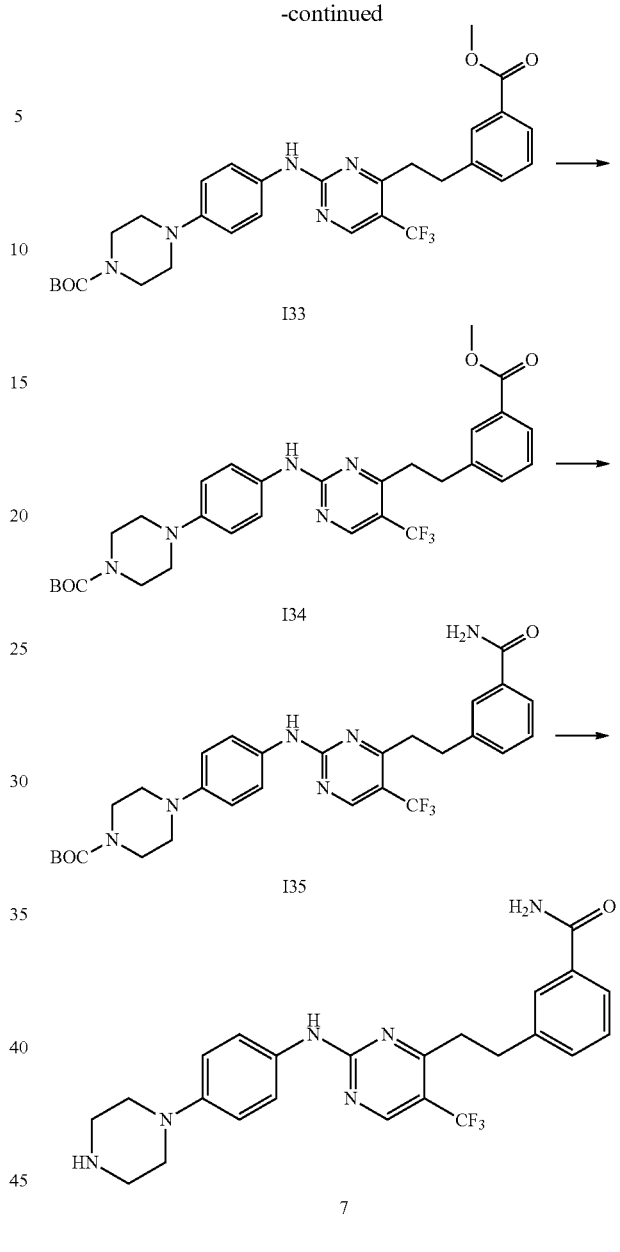

(a) Methyl 3-ethynylbenzoate (I31)

tert-Butyl 3-ethynylbenzoate (I17) (1.50 g, 9.37 mmol) was dissolved in dry DCM (70 mL) and TFA (35.9 mL, 468 mmol) was added carefully. The reaction was stirred at room temperature for 3 hours, concentrated in vacuo and toluene was added and then removed in vacuo to give a pale yellow solid. This material was dissolved in methanol (50 mL) and conc. H$_2$SO$_4$ (~1 mL) was added and the resulting solution was stirred at 65° C. for 20 hours. Upon cooling to room temperature, the volatiles were removed in vacuo and the residue was diluted with EtOAc (200 mL) and sat. aq. NaHCO$_3$ (100 mL) was added slowly. The layers were separated and the aqueous layer was extracted with EtOAc (200 mL), the organic layers were combined and washed with water (100 mL), brine (100 mL), dried (MgSO$_4$), filtered and concentrated in vacuo to give the title compound (I31) (1.136 g, 96% yield over 2 steps) as a pale yellow solid; $^1$H NMR (400 MHz, CDCl$_3$) δ 8.17 (t, J=1.5 Hz, 1H), 8.03-8.00 (m, 1H), 7.66 (dt, J=7.7, 1.4 Hz, 1H), 7.41 (td, J=7.8, 0.4 Hz, 1H), 3.93 (s, 3H), 3.12 (s, 1H). LCMS Method C: rt 5.84 min.

(b) tert-Butyl 4-(4-((4-((3-(methoxycarbonyl)phenyl) ethynyl)-5-(trifluoromethyl)pyrimidin-2-yl)amino) phenyl)piperazine-1-carboxylate (I32)

To a nitrogen de-gassed solution of methyl 3-ethynylbenzoate (I31) (0.105 g, 0.655 mmol) in dry DMF (6 mL) were added triethylamine (0.308 mL, 2.18 mmol) followed by tert-butyl 4-(4-((4-chloro-5-(trifluoromethyl)pyrimidin-2-yl)amino)phenyl)piperazine-1-carboxylate (I3) (0.250 g, 0.546 mmol), triphenylphosphine (0.021 g, 0.082 mmol), trans-dichlorobis(triphenylphosphine)palladium(II) (0.038 g, 0.055 mmol) and Cu(I)I (0.016 g, 0.082 mmol). The reaction mixture was heated under microwave irradiation at 120° C. for 20 minutes, concentrated to dryness in vacuo and purified by silica gel chromatography (Biotage Isolera, 40 g Si cartridge, 0-50% EtOAc in petroleum benzine 40-60° C.) to give the title compound (I32) (0.182 g, 57% yield) as an orange solid; $^1$H NMR (400 MHz, d$_6$-DMSO) δ 10.28 (brs, 1H), 8.78 (s, 1H), 8.16-8.03 (m, 2H), 7.90 (d, J=7.8 Hz, 1H), 7.69 (t, J=7.9 Hz, 1H), 7.55 (d, J=9.0 Hz, 2H), 6.96 (d, J=9.0 Hz, 2H), 3.90 (s, 3H), 3.50-3.41 (m, 4H), 3.11-2.99 (m, 4H), 1.42 (s, 9H). LCMS Method C: rt 6.82 min; m/z 582.2 [M+H]$^+$.

(c) tert-Butyl 4-(4-((4-(3-(methoxycarbonyl)phenethyl)-5-(trifluoromethyl)pyrimidin-2-yl)amino)phenyl)piperazine-1-carboxylate (I33)

tert-Butyl 4-(4-((4-((3-(methoxycarbonyl)phenyl)ethynyl)-5-(trifluoromethyl)pyrimidin-2-yl)amino)phenyl)piperazine-1-carboxylate (I32) (0.180 g, 0.309 mmol) was dissolved in dry DMF (10 mL) under an atmosphere of nitrogen. 10% Pd/C (0.100 g) in EtOAc (10 mL) was added to the solution and the atmosphere was changed to hydrogen gas (balloon). The reaction was sealed with a balloon and stirred at room temperature for 18 hours after which the reaction was flushed with nitrogen gas and Pearlman's catalyst (0.150 g) in EtOAc (5 mL) was added. The atmosphere was again changed to hydrogen gas (balloon) and the reaction was sealed with balloon and stirred for 20 hours at room temperature. The catalyst was removed by filtration through Celite, which was washed with EtOAc (5×10 mL). The solvent was removed in vacuo to give a yellow oil which was purified by silica gel chromatography (Biotage Isolera, 40 g Si Cartridge, 0-40% EtOAc in petroleum benzine 40-60° C.) to give the title compound (I33) (0.120 g, 66% yield) as a yellow foam; $^1$H NMR (400 MHz, d$_6$-DMSO) δ 10.01 (s, 1H), 8.60 (s, 1H), 7.88-7.77 (m, 2H), 7.61-7.39 (m, 4H), 6.93 (d, J=9.1 Hz, 2H), 3.85 (s, 3H), 3.52-3.42 (m, 4H), 3.21-2.99 (m, 8H), 1.42 (s, 9H). LCMS Method C: rt 6.86 min; m/z 586.3 [M+H]$^+$.

(d) Lithium 3-(2-(2-((4-(4-(tert-butoxycarbonyl)piperazin-1-yl)phenyl)amino)-5-(trifluoromethyl)pyrimidin-4-yl)ethyl)benzoate (I34)

LiOH.H$_2$O (0.025 g, 0.60 mmol) was added to tert-butyl 4-(4-((4-(3-(methoxycarbonyl)phenethyl)-5-(trifluoromethyl)pyrimidin-2-yl)amino)phenyl)piperazine-1-carboxylate (I33) (0.117 g, 0.200 mmol) in THF (7 mL), water (1.5 mL) and methanol (1 mL). The resulting mixture was allowed to stir at room temperature for 17 hours, the volatiles were removed in vacuo and the residue was diluted with EtOAc (100 mL) and sat. aq. NaHCO$_3$ (80 mL). The layers were separated and the aqueous layer was extracted with EtOAc (2×80 mL), the organic layers were combined, washed with brine (70 mL), dried (MgSO$_4$), filtered and concentrated under reduced pressure to give the title compound (I34) (0.105 g, 91% yield) as a pale yellow solid; $^1$H NMR (400 MHz, d$_6$-DMSO) δ 10.00 (s, 1H), 8.60 (s, 1H), 7.85-7.74 (m, 2H), 7.56-7.48 (m, 2H), 7.47-7.35 (m, 2H), 6.93 (d, J=9.1 Hz, 2H), 3.50-3.41 (m, 4H), 3.17-2.98 (m, 8H), 1.42 (s, 9H). LCMS Method C: rt 6.30 min; m/z 572.3 [M+H]$^+$.

(e) tert-Butyl 4-(4-((4-(3-carbamoylphenethyl)-5-(trifluoromethyl)pyrimidin-2-yl)amino)phenyl)piperazine-1-carboxylate (I35)

Lithium 3-(2-(2-((4-(4-(tert-butoxycarbonyl)piperazin-1-yl)phenyl)amino)-5-(trifluoromethyl)pyrimidin-4-yl)ethyl)benzoate (I34) (0.100 g, 0.173 mmol) was dissolved in dry THF (7 mL) and dry DMF (1 mL) under an atmosphere of nitrogen. To the solution were added 1-hydroxybenzotriazole (0.028 g, 0.21 mmol) and EDCl (0.040 g, 0.21 mmol) and N,N-diisopropylethylamine (0.121 mL, 0.693 mmol) and the reaction mixture was stirred at room temperature for 10 minutes. Ammonium carbonate (0.067 g, 0.69 mmol) was added in one portion, and the reaction was stirred room temperature for 60 hours. The volatiles were removed in vacuo and the residual solution was diluted with EtOAc (70 mL) and sat. aq. NaHCO$_3$ (70 mL). The layers were separated and the aqueous layer was extracted with EtOAc (70 mL), the combined organic layers were washed with water (70 mL), brine (70 mL), dried (MgSO$_4$), filtered and concentrated in vacuo to give an off-white solid. The crude product was purified by silica gel chromatography (Biotage Isolera, 12 g Si Cartridge, 0-100% EtOAc in petroleum benzine 40-60° C.) to give the title compound (I35) (0.073 g, 74% yield) as an off-white solid; $^1$H NMR (400 MHz, d$_6$-DMSO) δ 10.00 (s, 1H), 8.61 (s, 1H), 7.95 (s, 1H), 7.79 (s, 1H), 7.75-7.68 (m, 1H), 7.54 (d, J=8.6 Hz, 2H), 7.40-7.29 (m, 3H), 6.93 (d, J=9.1 Hz, 2H), 3.50-3.41 (m, 4H), 3.14-3.00 (m, 8H), 1.42 (s, 9H).

(f) 2-(2-(2-(2-((4-(1-Methylpiperidin-3-yl)phenyl)amino)-5-(trifluoromethyl)pyrimidin-4-yl)ethyl)phenyl)acetamide (7)

tert-Butyl 4-(4-((4-(3-carbamoylphenethyl)-5-(trifluoromethyl)pyrimidin-2-yl)amino)phenyl)piperazine-1-carboxylate (I35) (0.070 g, 0.12 mmol) was dissolved in DCM (5 mL) under an atmosphere of nitrogen. Trifluoroacetic acid (0.282 mL, 3.68 mmol) was added to the solution and the reaction was stirred at room temperature for 18 hours. Volatiles were removed in vacuo, EtOAc (50 mL) and 2 M aq. NaOH (50 mL) were added to the residue and the layers were separated. The aqueous layer was extracted with EtOAc (50 mL), the combined organics were washed with water (50 mL), brine (50 mL), dried (MgSO$_4$), filtered and concentrated in vacuo to give a pale yellow solid. The solid was taken up in DCM (~10 mL) and methanol (~1 mL) and concentrated in vacuo. The process was repeated with only DCM twice to give the title compound (7) (0.043 g, 75% yield) as a pale yellow solid; $^1$H NMR (400 MHz, d$_6$-DMSO) δ 9.96 (s, 1H), 8.60 (s, 1H), 7.95 (s, 1H), 7.79 (s, 1H), 7.74-7.66 (m, 1H), 7.56-7.47 (m, 2H), 7.40-7.29 (m, 3H), 6.94-6.82 (m, 2H), 3.15-2.96 (m, 8H), 2.86-2.79 (m, 4H). LCMS Method C: rt 4.71 min; m/z 471.2 [M+H]+.

Example 8

2-(2-(2-(2-((4-(Piperidin-2-yl)phenyl)amino)-5-(trifluoromethyl)pyrimidin-4-yl)ethyl)phenyl)acetamide (8)

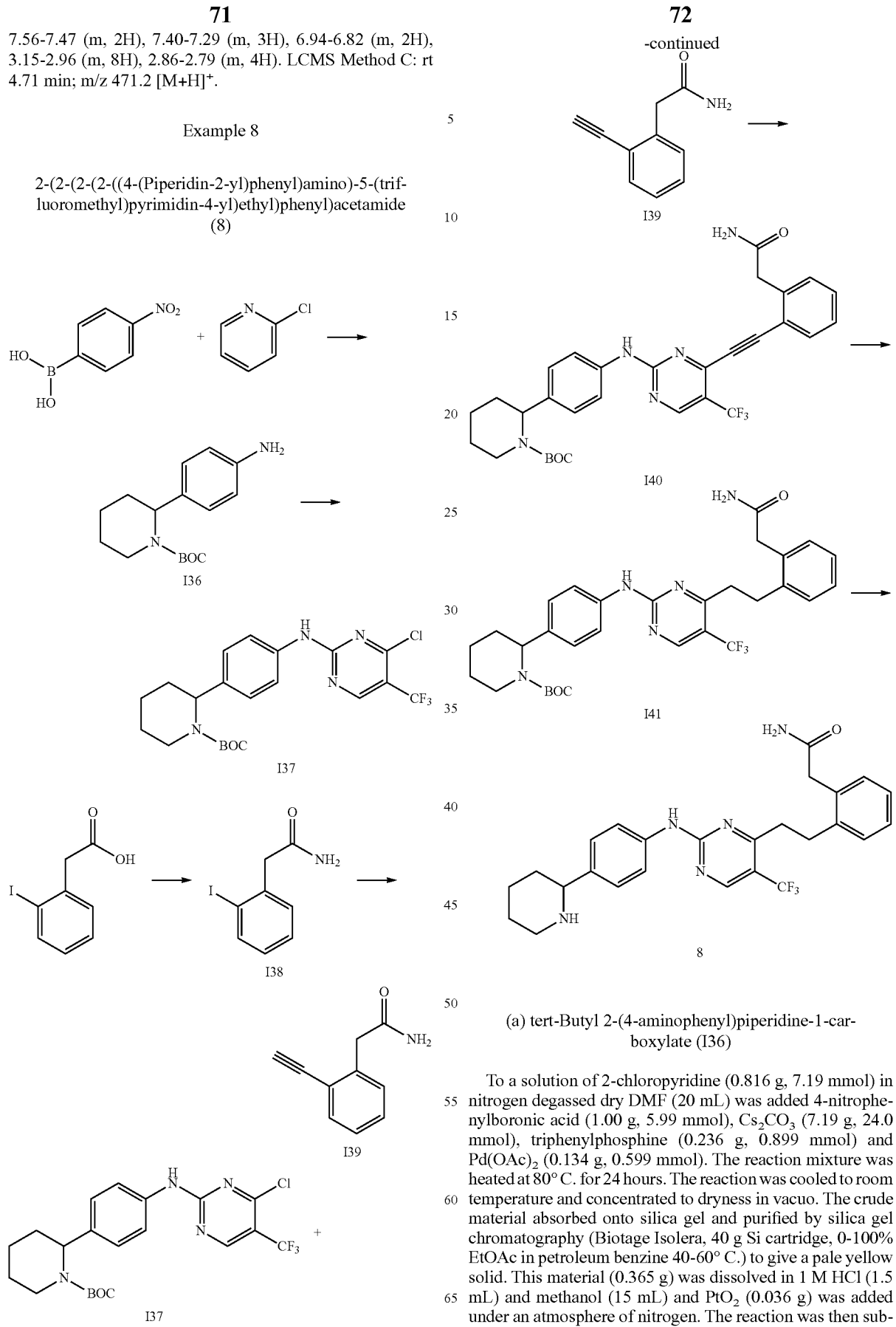

(a) tert-Butyl 2-(4-aminophenyl)piperidine-1-carboxylate (I36)

To a solution of 2-chloropyridine (0.816 g, 7.19 mmol) in nitrogen degassed dry DMF (20 mL) was added 4-nitrophenylboronic acid (1.00 g, 5.99 mmol), Cs$_2$CO$_3$ (7.19 g, 24.0 mmol), triphenylphosphine (0.236 g, 0.899 mmol) and Pd(OAc)$_2$ (0.134 g, 0.599 mmol). The reaction mixture was heated at 80° C. for 24 hours. The reaction was cooled to room temperature and concentrated to dryness in vacuo. The crude material absorbed onto silica gel and purified by silica gel chromatography (Biotage Isolera, 40 g Si cartridge, 0-100% EtOAc in petroleum benzine 40-60° C.) to give a pale yellow solid. This material (0.365 g) was dissolved in 1 M HCl (1.5 mL) and methanol (15 mL) and PtO$_2$ (0.036 g) was added under an atmosphere of nitrogen. The reaction was then subjected to a 40 psi hydrogen atmosphere in a Parr hydrogenator for 24 hours, and then filtered through celite which was washed with EtOAc (3×10 mL) and water (3×10 mL). The combined filtrate was concentrated in vacuo to give the crude material (0.460 g) as a pale brown-pink oily solid. This material was dissolved in anhydrous methanol (20 mL) and treated with triethylamine (0.889 mL, 6.38 mmol) followed by Boc anhydride (0.418 g, 1.91 mmol). The reaction was stirred at room temperature for 20 hours, concentrated in vacuo and EtOAc (100 mL) and sat. aq. NaHCO$_3$ (50 mL) were added and the layers were separated. The aqueous layer was extracted with EtOAc (70 mL), the organics were combined and washed with water (50 mL), brine (50 mL), dried (MgSO$_4$), filtered and concentrated in vacuo to give a yellow solid. The crude product was purified by silica gel chromatography (Biotage Isolera, 12 g Si cartridge, 0-100% EtOAc in petroleum benzine 40-60° C.), to give the title compound (I36) (0.122 g, 8% yield over 3 steps) as a white solid; $^1$H NMR (400 MHz, d$_6$-DMSO) δ 6.85-6.78 (m, 2H), 6.57-6.51 (m, 2H), 5.14 (d, J=3.7 Hz, 1H), 4.98-4.89 (m, 2H), 3.85 (d, J=13.0 Hz, 1H), 2.70-2.57 (m, 1H), 2.19 (d, J=13.9 Hz, 1H), 1.73-1.61 (m, 1H), 1.57-1.44 (m, 2H), 1.44-1.27 (m, 11H). LCMS Method C: rt 4.94 min; m/z 177.3 [M-Boc+2H]$^+$.

(b) tert-Butyl 2-(4-((4-chloro-5-(trifluoromethyl) pyrimidin-2-yl)amino)phenyl)piperidine-1-carboxylate (I37)

2,4-Dichloro-5-(trifluoromethyl)pyrimidine (0.101 g, 0.464 mmol) was stirred in a 1:1 t-BuOH:1,2-dichloroethane mixture (10 mL) at 0° C. and a 1.0 M ZnCl$_2$ solution in diethyl ether (0.530 mL, 0.530 mmol) was added cautiously over 20 minutes. After addition, the reaction was left stirring at 0° C. for 30 minutes and a solution of tert-butyl 2-(4-aminophenyl) piperidine-1-carboxylate (I36) (0.122 g, 0.441 mmol) in 1:1 t-BuOH:1,2-dichloroethane (4 mL) was added drop-wise over 15 minutes at 0° C. followed by a solution of triethylamine (0.074 μL, 0.530 mmol) in 1:1 t-BuOH:1,2-dichloroethane (4 mL) and the reaction was allowed to warm to room temperature and was stirred for 60 hours. Volatiles were evaporated in vacuo and the resulting residue was suspended in water (40 mL), the suspension was sonicated for 40 minutes and the product was collected by filtration, the solid was washed with water (5×10 mL) and dried under a high vacuum to give the title compound (I37) (0.135 g, 67% yield) as a pale pink solid. LCMS Method C: rt 6.96 min; m/z 455.2, 457.2 M−H]$^-$.

(c) 2-(2-Iodophenyl)acetamide (I38)

2-Iodophenylacetic acid (2.00 g, 7.63 mmol) was dissolved in dry THF (70 mL) and dry DMF (10 mL) under an atmosphere of nitrogen. To the solution were added 1-hydroxybenzotriazole (1.134 g, 8.396 mmol) and EDCI (1.609 g, 8.396 mmol) and N,N-diisopropylethylamine (5.318 mL, 30.53 mmol) and the reaction mixture was stirred at room temperature for 10 minutes. Ammonium carbonate (2.933 g, 30.53 mmol) was added in one portion, and the reaction was stirred room temperature for 17 hours. The volatiles were removed in vacuo and the residual solution was diluted with EtOAc (150 mL) and sat. aq. NaHCO$_3$ (100 mL). The layers were separated and the organic layer were washed with water (100 mL), brine (100 mL), dried (MgSO$_4$), filtered and concentrated in vacuo to give the title compound (I38) (1.755 g, 88% yield) as a beige solid; $^1$H NMR (400 MHz, d$_6$-DMSO) δ 7.82 (dd, J=7.9, 0.9 Hz, 1H), 7.42 (s, 1H), 7.36-7.28 (m, 2H), 7.02-6.94 (m, 3H), 3.55 (s, 2H). LCMS Method C: rt 4.77 min; m/z 262.0 [M+H]$^+$.

(d) 2-(2-Ethynylphenyl)acetamide (I39)

To a nitrogen de-gassed solution of 2-(2-iodophenyl)acetamide (I38) (1.75 g, 6.70 mmol) in dry THF (50 mL) and dry DMF (10 mL) was added Pd(PPh$_3$)$_4$ (0.194 g, 0.168 mmol) and Cu(I)I (0.064 g, 0.34 mmol), triethylamine (3.27 mL, 23.5 mmol). The mixture was stirred for 10 minutes and TMS-acetylene (1.52 mL, 10.7 mmol) was added. The reaction mixture was then stirred at room temperature for 18 hours, concentrated in vacuo and purified by silica gel chromatography (Biotage Isolera, 40 g Si cartridge, 0-100% EtOAc in petroleum benzine 40-60° C.) to give a beige solid. This material was dissolved in dry THF (25 mL) under an atmosphere of nitrogen and TBAF (1.0 M in THF, 2.805 mL, 2.805 mmol) was added dropwise at 0° C. The solution was stirred at this temperature for 1 hour and 15 minutes after which water (5 mL) was added. The reaction mixture was concentrated in vacuo and diluted with EtOAc (100 mL) and sat. aq. NaHCO$_3$ (100 mL). The layers were separated and aqueous layer was extracted with EtOAc (100 mL), the organic layers were combined and washed with water (100 mL), brine (100 mL), dried (MgSO$_4$), filtered and concentrated in vacuo to give the crude product. The material was purified by silica gel chromatography (Biotage Isolera, 40 g Si cartridge, 0-100% EtOAc in petroleum benzine 40-60° C., then 0-20% methanol in EtOAc) to give the title compound (I39) (0.239 g, 22% yield over 2 steps) as a beige solid; $^1$H NMR (400 MHz, d$_6$-DMSO) δ 7.21 (dd, J=7.6, 1.1 Hz, 1H), 7.18-7.05 (m, 3H), 7.04-6.98 (m, 1H), 6.70 (s, 1H), 4.08 (s, 1H), 3.36 (s, 2H). LCMS Method C: rt 4.71 min; m/z 160.2 [M+H]$^+$.

(e) tert-Butyl 2-(4-((4-((2-(2-amino-2-oxoethyl)phenyl)ethynyl)-5-(trifluoromethyl)pyrimidin-2-yl) amino)phenyl)piperidine-1-carboxylate (I40)

To a nitrogen de-gassed solution of 2-(2-ethynylphenyl) acetamide (I39) (0.054 g, 0.788 mmol) and tert-butyl 2-(4-((4-chloro-5-(trifluoromethyl)pyrimidin-2-yl)amino)phenyl)piperidine-1-carboxylate (I37) in dry DMF (4 mL) were added triethylamine (0.159 mL, 1.138 mmol), triphenylphosphine (0.011 g, 0.043 mmol), trans-dichlorobis(triphenylphosphine)palladium(II) (0.020 g, 0.028 mmol) and CuI (0.008 g, 0.04 mmol). The reaction mixture was heated under microwave irradiation at 120° C. for 20 minutes. The reaction was concentrated to dryness in vacuo and purified by silica gel chromatography (Biotage Isolera, 40 g Si cartridge, 0-100% EtOAc in petroleum benzine 40-60° C., then 0-5% methanol in EtOAc) to give the title compound (I40) (0.122 g, 74% yield) as a yellow glassy solid; $^1$H NMR (400 MHz, d$_6$-DMSO) δ 10.48 (s, 1H), 8.82 (s, 1H), 7.73 (d, J=8.7 Hz, 2H), 7.65-7.55 (m, 1H), 7.55-7.47 (m, 1H), 7.47-7.33 (m, 3H), 7.16 (d, J=8.5 Hz, 2H), 7.01 (s, 1H), 5.29-5.22 (m, 1H), 3.92 (d, J=13.1 Hz, 1H), 3.70 (s, 2H), 2.71 (t, J=13.3 Hz, 1H), 2.34-2.24 (m, 1H), 1.82-1.68 (m, 1H), 1.54 (d, J=11.3 Hz, 2H), 1.45-1.22 (m, 11H). LCMS Method C: rt 6.52 min; m/z 578.3 [M−H]$^-$.

(f) tert-Butyl 2-(4-((4-(2-(2-amino-2-oxoethyl)phenethyl)-5-(trifluoromethyl)pyrimidin-2-yl)amino)phenyl)piperidine-1-carboxylate (I41)

tert-Butyl 2-(4-((4-((2-(2-amino-2-oxoethyl)phenyl)ethynyl)-5-(trifluoromethyl)pyrimidin-2-yl)amino)phenyl)piperidine-1-carboxylate (I40) (0.120 g, 0.207 mmol) was dissolved in dry DMF (5 mL) under an atmosphere of nitrogen. 20% Pearlman's catalyst (0.060 g) in EtOAc (5 mL) was added to the solution and the atmosphere was changed to hydrogen gas (balloon). The reaction was sealed with a balloon and stirred at room temperature for 20 hours at room temperature. The catalyst was removed by filtration through Celite, which was washed with EtOAc (5×10 mL). The solvent was removed in vacuo to give a pale yellow gum which was purified by silica gel chromatography (Biotage, Isolera 12 g Si Cartridge, 0-100% EtOAc in petroleum benzine 40-60° C.) to give the title compound (I41) (0.090 g, 74% yield) as a pale yellow solid; $^1$H NMR (400 MHz, d$_6$-DMSO) δ 10.20 (s, 1H), 8.67 (s, 1H), 7.73 (d, J=8.7 Hz, 2H), 7.43 (s, 1H), 7.26-7.21 (m, 1H), 7.20-7.09 (m, 5H), 6.89 (s, 1H), 5.31-5.19 (m, 1H), 3.92 (d, J=13.2 Hz, 1H), 3.49 (s, 2H), 3.16-2.98 (m, 4H), 2.71 (t, J=11.8 Hz, 1H), 2.29 (d, J=13.2 Hz, 1H), 1.75 (t, J=11.0 Hz, 1H), 1.58-1.50 (m, 2H), 1.46-1.23 (m, 11H). LCMS Method C: rt 6.59 min; m/z 584.3 [M+H]$^+$.

(g) 2-(2-(2-(2-((4-(Piperidin-2-yl)phenyl)amino)-5-(trifluoromethyl)pyrimidin-4-yl)ethyl)phenyl)acetamide (8)

tert-Butyl 2-(4-((4-(2-(2-amino-2-oxoethyl)phenethyl)-5-(trifluoromethyl)pyrimidin-2-yl)amino)phenyl)piperidine-1-carboxylate (I41) (0.087 g, 0.15 mmol) was dissolved in dry DCM (5 mL) under an atmosphere of nitrogen. Trifluoroacetic acid (0.351 mL, 4.58 mmol) was added to the solution and the reaction was stirred at room temperature for 22 hours. Volatiles were removed in vacuo, EtOAc (20 mL) and sat. aq. NaHCO$_3$ (15 mL) were added to the residue and the layers were separated. The aqueous layer was extracted with EtOAc (15 mL), the combined organics were washed with water (50 mL), brine (50 mL), dried (MgSO$_4$), filtered and concentrated in vacuo to give a pale yellow solid which was taken up in DCM (~10 mL) and methanol (~1 mL) and concentrated in vacuo. The process was repeated with only DCM twice to give the title compound (8) (0.064 g, 89% yield) as a pale yellow solid; $^1$H NMR (400 MHz, d$_6$-DMSO) δ 10.15 (s, 1H), 8.66 (s, 1H), 7.70-7.62 (m, 2H), 7.44 (s, 1H), 7.30 (d, J=8.6 Hz, 2H), 7.26-7.12 (m, 4H), 6.92 (s, 1H), 3.54-3.47 (m, 3H), 3.15-2.97 (m, 5H), 2.71-2.59 (m, 1H), 1.84-1.76 (m, 1H), 1.67 (d, J=12.4 Hz, 1H), 1.61-1.50 (m, 1H), 1.46-1.27 (m, 3H). LCMS Method C: rt 4.84 min; m/z 484.3 [M+H]$^+$.

Example 9

2-(2-(2-(2-((4-(1-methylpiperidin-2-yl)phenyl)amino)-5-(trifluoromethyl)pyrimidin-4-yl)ethyl)phenyl)acetamide (9)

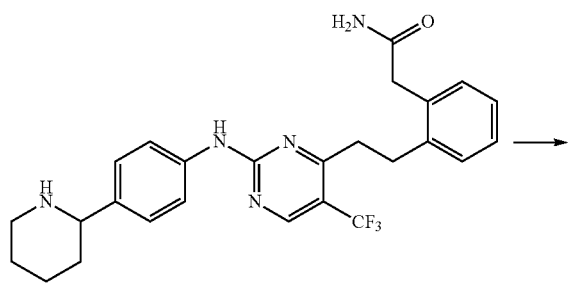

8

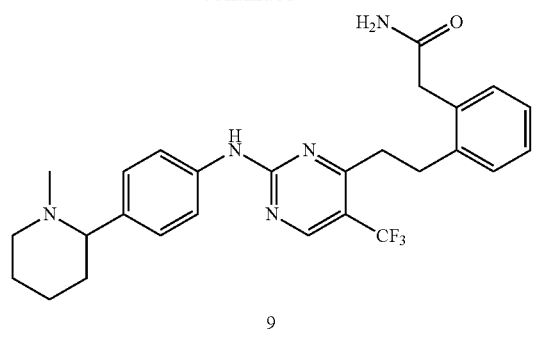

9

To a suspension of 2-(2-(2-(2-((4-piperidin-2-yl)phenyl)amino)-5-(trifluoromethyl)pyrimidin-4-yl)ethyl)phenyl)acetamide (8) (0.023 g, 0.048 mmol) in anhydrous methanol (1.5 mL) were added a 37% aq. solution of formaldehyde (0.014 mL, 0.19 mmol) and sodium triacetoxyborohydride (0.050 g, 0.24 mmol) under an atmosphere of nitrogen. The reaction was stirred at room temperature for 2.5 hours, the volatiles were removed in vacuo and the residue was diluted with EtOAc (15 mL) and sat. aq. NaHCO$_3$ (10 mL). The layers were separated and the aqueous layer was extracted with EtOAc (10 mL), the combined organic layers were washed with water (10 mL), brine (10 mL), dried (MgSO$_4$), filtered and concentrated in vacuo to give a solid which was taken up in DCM (~10 mL) and methanol (~1 mL) and concentrated in vacuo. The process was repeated with only DCM twice after which the sample was further dried on high-vacuum to give the title compound (9) (0.022 g, 91% yield) as an off-white solid; $^1$H NMR (400 MHz, d$_6$-DMSO) δ 10.17 (s, 1H), 8.66 (s, 1H), 7.68 (d, J=8.6 Hz, 2H), 7.43 (s, 1H), 7.27-7.13 (m, 6H), 6.92 (s, 1H), 3.49 (s, 2H), 3.15-2.98 (m, 4H), 2.97-2.90 (m, 1H), 2.75-2.69 (m, 1H), 2.07-1.97 (m, 1H), 1.90 (s, 3H), 1.73 (d, J=12.8 Hz, 1H), 1.66-1.54 (m, 3H), 1.50-1.38 (m, 1H), 1.36-1.27 (m, 1H). LCMS Method C: rt 4.88 min; m/z 498.3 [M+H]$^+$.

Example 10

2-(2-(2-(2-((4-(4-Ethylpiperazin-1-yl)phenyl)amino)-5-(trifluoromethyl)pyrimidin-4-yl)ethyl)phenyl)acetamide (10)

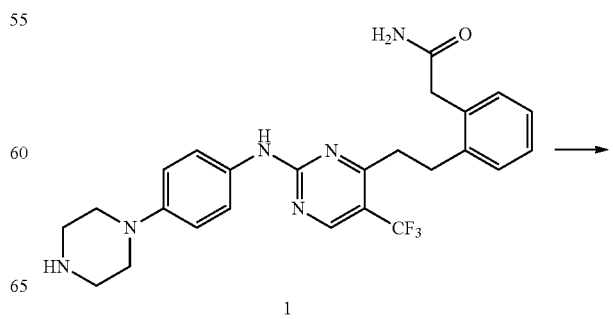

1

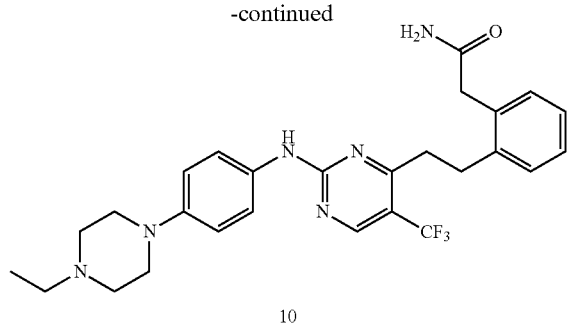

10

To a suspension of 2-(2-(2-(2-((4-(piperazin-1-yl)phenyl) amino)-5-(trifluoromethyl)pyrimidin-4-yl)ethyl)phenyl)acetamide (1) (0.020 g, 0.041 mmol) in anhydrous methanol (1.5 mL) were added acetaldehyde (0.0090 mL, 0.17 mmol) and sodium triacetoxyborohydride (0.044 g, 0.21 mmol) under an atmosphere of nitrogen The reaction was stirred at room temperature for 18 hours, the volatiles were removed in vacuo and the residue was diluted with EtOAc (15 mL) and sat. aq. NaHCO$_3$ (10 mL). The layers were separated and the aqueous layer was extracted with EtOAc (10 mL), the combined organic layers were washed with water (10 mL), brine (10 mL), dried (MgSO$_4$), filtered and concentrated in vacuo to give a solid which was taken up in DCM (~10 mL) and methanol (~1 mL) and concentrated in vacuo. The process was repeated with only DCM twice after which the sample was further dried on high-vacuum to give the title compound (10) (0.016 g, 76% yield) as an off-white solid; $^1$H NMR (400 MHz, d$_6$-DMSO) δ 9.97 (s, 1H), 8.60 (s, 1H), 7.57 (d, J=8.9 Hz, 2H), 7.43 (s, 1H), 7.26-7.13 (m, 4H), 6.97-6.87 (m, 3H), 3.50 (s, 2H), 3.13-2.94 (m, 8H), 2.36 (q, J=7.2 Hz, 2H), 1.03 (t, J=7.2 Hz, 3H). 4 Aliphatic protons obscured by the residual DMSO. LCMS Method C: rt 4.82 min; m/z 513.3 [M+H]$^+$.

Example 11

2-(2-(2-(2-((4-(piperidin-4-yl)phenyl)amino)-5-(trifluoromethyl)pyrimidin-4-yl)ethyl)phenyl)acetamide (11)

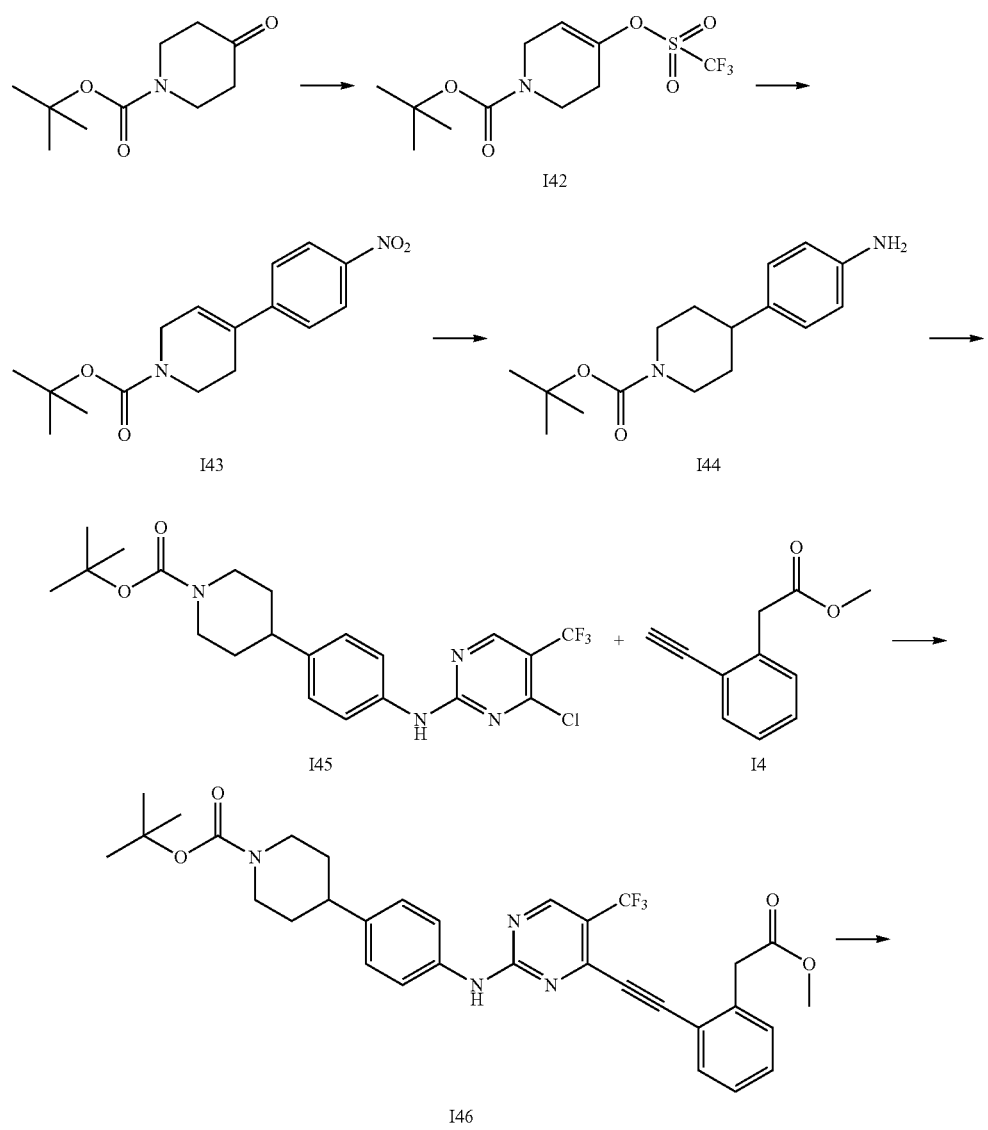

-continued

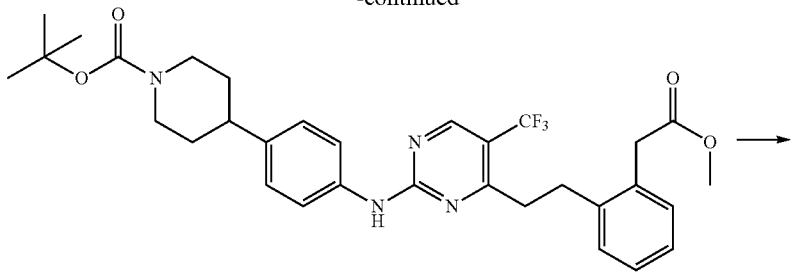

I47

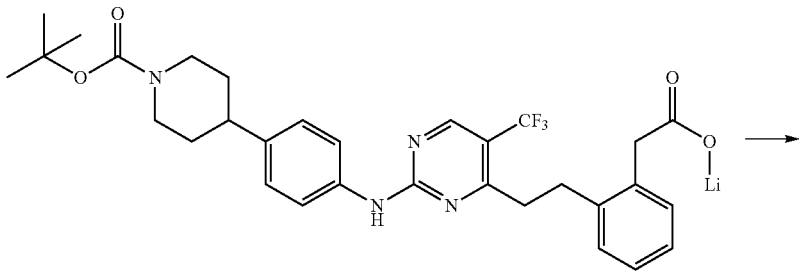

I48

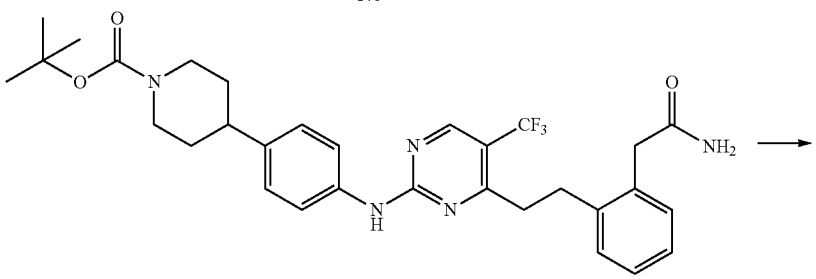

I49

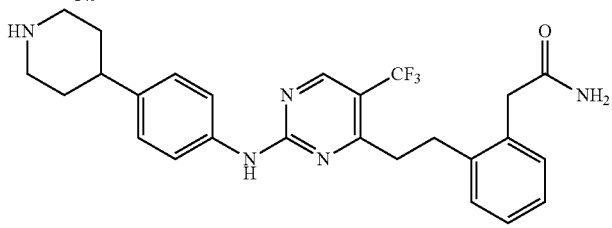

11

(a) tert-Butyl 4-(((trifluoromethyl)sulfonyl)oxy)-5,6-dihydropyridine-1(2H)-carboxylate (I42)

Lithium diisopropylamide (2 M in heptane/THF/ethylbenzene; 15.1 mL, 30.1 mmol) was added dropwise to a solution of tert-butyl 4-oxopiperidine-1-carboxylate (3.00 g, 15.1 mmol) in THF (50 mL) at −78° C. and the mixture left to stir for 30 minutes. A solution of N-phenyl-bis(trifluoromethanesulfonimide) (6.46 g, 18.1 mmol) in THF (60 mL) was then added dropwise over 30 minutes to the reaction and mixture left to stir for 30 minutes-78° C. The resulting mixture was then allowed to warm to room temperature and was stirred for 24 hours. The solvent was partially removed (ca 80 mL) and the reaction mixture quenched with saturated $NaHCO_3$ solution (50 mL).

DCM (50 mL) was added to the solution and the layers separated. The aqueous layer was then extracted with DCM (2×50 mL). The organic layers were combined and washed with 0.2 M citric acid solution (50 mL), 1 M NaOH (50 mL), brine (50 mL) and dried over $Na_2SO_4$. The solvent was removed under reduced pressure to give a brown oil which was purified by column chromatography on silica gel (0-10% diethyl ether in petroleum benzine 40-60° C.) to afford the title compound (I42) (2.48 g, 50%) as an orange oil which crystallized on cooling to −18° C.; $^1$H NMR (400 MHz, $CDCl_3$) δ 5.76 (s, 1H), 4.05-4.04 (m, 2H), 3.63 (t, J=5.6 Hz, 2H), 2.46-2.43 (m, 2H), 1.47 (s, 9H).

(b) tert-Butyl 4-(4-nitrophenyl)-5,6-dihydropyridine-1 (2H)-carboxylate (I43)

A solution of 2 M $Na_2CO_3$ (5.66 mL, 11.3 mmol) was added to a mixture of 4-nitrophenylboronic acid (0.831 g, 4.98 mmol), tert-butyl 4-(((trifluoromethyl)sulfonyl)oxy)-5,6-dihydropyridine-1(2H)-carboxylate (I42) (1.50 g, 4.53 mmol), LiCl (0.384 g, 9.06 mmol) and $Pd(PPh_3)_4$ (1.308 g, 1.132 mmol) in 1,4-dioxane (20 mL). The reaction mixture was stirred at 85-90° C. for 4 hours. The resulting mixture was dissolved in EtOAc (100 mL) and the organic layer was washed with $H_2O$ (50 mL), brine (50 mL) and dried over Na$_2$SO$_4$ to yield a dark red oil. The oil was purified by column chromatography on silica gel (0-20% EtOAc in petroleum benzine 40-60° C.) to yield the title compound (I43) (0.683 g, 50%) as a pale brown solid; $^1$H NMR (400 MHz, CDCl$_3$) δ 8.24-8.16 (m, 2H), 7.55-7.47 (m, 2H), 6.23 (s, 1H), 4.14-4.12 (m, 2H), 3.66 (t, J=5.7 Hz, 2H), 2.55 (bs, 2H), 1.50 (s, 9H). LCMS Method C: rt 6.39 min; m/z 249 [M-Boc+2H]$^+$, 205 [M-$^t$Butyl+2H]$^+$.

(c) tert-Butyl 4-(4-aminophenyl)piperidine-1-carboxylate (I44)

A solution of tert-butyl 4-(4-nitrophenyl)-5,6-dihydropyridine-1(2H)-carboxylate (I43) (0.570 g, 1.87 mmol) in EtOH (5 mL) and DMF (5 mL) was added to a solution of 10% Pd/C (200 mg) in DMF (10 mL). The reaction was stirred at room temperature for 24 hours under an atmosphere of hydrogen. The reaction was filtered through a pad of celite and washed through with EtOAc (130 mL). The solvent was removed in vacuo to yield a brown oil which was purified by column chromatography on silica gel (0-50% EtOAc in petroleum benzine 40-60° C.) to afford the title compound (I44) (0.46 g, 89%) as a crystalline solid; $^1$H NMR (400 MHz, CDCl$_3$) δ 7.02-6.96 (m, 2H), 6.67-6.61 (m, 2H), 4.21 (bs, 2H), 3.57 (s, 2H), 2.77 (t, J=12.2 Hz, 2H), 2.53 (tt, J=12.1, 3.5 Hz, 1H), 1.77 (d, J=13.3 Hz, 2H), 1.64-1.50 (m, peak obscured by solvent), 1.48 (s, 9H). LCMS Method C: rt 4.77 min; m/z 221 [M-$^t$Butyl+2H]$^+$, 177 [M-Boc+2H]$^+$.

(d) tert-Butyl 4-(4-((4-chloro-5-(trifluoromethyl) pyrimidin-2-yl)amino)phenyl)piperidine-1-carboxylate (I45)

Zinc chloride (1.0 M in Et$_2$O) (1.97 mL, 1.97 mmol) was added to a solution of 2,4-dichloro-5-(trifluoromethyl)pyrimidine (0.384 g, 1.77 mmol) in 1:1 DCE/t-BuOH (10 mL) at 0° C. under a stream of N$_2$ gas. The mixture was stirred for 1 hour at 0° C. and then tert-butyl 4-(4-aminophenyl)piperidine-1-carboxylate (I44) (0.453 g, 1.64 mmol) in 1:1 DCE/tBuOH (7 mL) was added. A solution of NEt$_3$ (0.251 mL, 1.80 mmol) in 1:1 DCE/t-BuOH (8 mL) was next added dropwise at 0° C. The reaction mixture was vigorously stirred for a further 30 minutes at 0° C. after the final addition and then at room temperature for 24 hours. The solvent was removed in vacuo to afford a brown oily residue which was purified by column chromatography on silica gel (0-20% EtOAc in petroleum benzine 40-60° C.) to yield a pale yellow solid. The solid was suspended in MeOH (10 mL) and water (10 mL). The resulting precipitate was filtered to afford the title compound (I45) (0.658 g, 88%) as a white solid; $^1$H NMR (400 MHz, d$_6$-DMSO) δ 10.60 (s, 1H), 8.77 (d, J=0.5 Hz, 1H), 7.59 (d, J=8.5 Hz, 2H), 7.23 (d, J=8.6 Hz, 2H), 4.13-3.98 (m, 2H), 2.80 (bs, 2H), 2.69-2.61 (m, 1H), 1.74 (d, J=12.4 Hz, 2H), 1.53-1.39 (m, 11H). LCMS Method C: rt 6.81 min; m/z 401 [M-$^t$Butyl+2H]$^+$, 357 [M-Boc+2H]$^+$.

(e) tert-Butyl 4-(4-((4-((2-(2-methoxy-2-oxoethyl) phenyl)ethynyl)-5-(trifluoromethyl)pyrimidin-2-yl) amino)phenyl)piperidine-1-carboxylate (I46)

A solution of methyl 2-(2-ethynylphenyl)acetate (I4) (0.069 g, 0.394 mmol) in dimethylformamide (2 mL) and triethylamine (0.183 mL, 1.31 mmol) was added to a mixture of tert-butyl 4-(4-((4-chloro-5-(trifluoromethyl)pyrimidin-2-yl)amino)phenyl)piperidine-1-carboxylate (I45) (0.150 g, 0.328 mmol), Pd(PPh$_3$)$_2$Cl$_2$ (0.023 g, 0.033 mmol), Cu(I)I (0.0090 g, 0.049 mmol) and triphenylphosphine (0.013 g, 0.049 mmol) in dimethylformamide (2 mL). The reaction mixture was heated under microwave irradiation at 120° C. for 15 minutes. The reaction was cooled and the mixture diluted with EtOAc and passed through a plug of celite and washed through with ethyl acetate (50 mL). Water (50 mL) was added and the layers separated. The aqueous layer was extracted with EtOAc (2×50 mL). The combined organic extracts were washed with water (50 mL) and brine (50 mL) and dried over Na$_2$SO$_4$. After filtration the solvent was removed under reduced pressure to give a dark brown residue. The residue was purified by column chromatography on silica gel (0-20% EtOAc in cyclohexane) to yield the title compound (I46) (0.157 g, 80%) as a brown viscous oil.

(f) tert-Butyl 4-(4-((4-(2-(2-methoxy-2-oxoethyl) phenethyl)-5-(trifluoromethyl)pyrimidin-2-yl)amino) phenyl)piperidine-1-carboxylate (I47)

A solution of tert-butyl 4-(4-((4-((2-(2-methoxy-2-oxoethyl)phenyl)ethynyl)-5-(trifluoromethyl)pyrimidin-2-yl) amino)phenyl)piperidine-1-carboxylate (I46) (0.157 g, 0.264 mmol) in DMF (15 mL) was added to a solution of 10% Pd/C (95 mg) in DMF (5 mL). The reaction was stirred at room temperature for 24 hours under an atmosphere of hydrogen. The reaction was filtered through a pad of celite and washed through with EtOAc (100 mL). The solvent was removed in vacuo to afford a pale yellow oil which was purified by column chromatography on silica gel (0-20% EtOAc in petroleum benzine 40-60° C.) to yield the title compound (I47) (0.128 g, 81%) as a pale yellow viscous oil; $^1$H NMR (400 MHz, CDCl$_3$) δ 8.53 (d, J=0.4 Hz, 1H), 7.59-7.54 (m, 2H), 7.39 (s, 1H), 7.28-7.17 (m, peaks obscured by CDCl$_3$), 4.25 (bs, 2H), 3.75 (s, 2H), 3.68 (s, 3H), 3.17-3.04 (m, 4H), 2.81 (t, J=12.1 Hz, 2H), 2.64 (tt, J=11.8, 3.4 Hz, 1H), 1.83 (d, J=13.0 Hz, 2H), 1.67-1.59 (m, 2H), 1.49 (s, 9H). LCMS Method C: rt 7.02 min; m/z 621 [M+Na]$^+$, 599 [M+H]$^+$, 543 [M-$^t$Butyl+2H]$^+$, 499 [M-Boc+2H]$^+$.

(g) Lithium 2-(2-(2-(2-((4-(1-(tert-butoxycarbonyl) piperidin-4-yl)phenyl)amino)-5-(trifluoromethyl) pyrimidin-4-yl)ethyl)phenyl)acetate (I48)

LiOH.H$_2$O (0.027 g, 0.647 mmol) was added to a solution of tert-butyl 4-(4-((4-(2-(2-methoxy-2-oxoethyl)phenethyl)-5-(trifluoromethyl)pyrimidin-2-yl)amino)phenyl)piperidine-1-carboxylate (I47) (0.128 g, 0.214 mmol) in THF (7 mL), water (1.5 mL) and methanol (1 mL). The resulting mixture was allowed to stir at room temperature for 20 hours. The volatiles were removed in vacuo and the residue was diluted with EtOAc (50 mL) and sat. aq. NaHCO$_3$ (50 mL). The layers were separated and the aqueous layer was extracted with EtOAc (2×50 mL), the organic layers were combined, washed with brine (50 mL), dried over Na$_2$SO$_4$, filtered and concentrated under reduced pressure to give the title compound (I48) (0.130 g) as a pale yellow viscous oil.

(h) tert-Butyl 4-(4-((4-(2-(2-amino-2-oxoethyl)phenethyl)-5-(trifluoromethyl)pyrimidin-2-yl)amino)phenyl)piperidine-1-carboxylate (I49)

1-Hydroxybenzotriazole (32.8 mg, 0.243 mmol), EDCl (46.6 mg, 0.243 mmol) and N,N-diisopropylethylamine (84.6 μL, 0.486 mmol) were added to a solution of lithium 2-(2-(2-(2-((4-(1-(tert-butoxycarbonyl)piperidin-4-yl)phenyl) amino)-5-(trifluoromethyl)pyrimidin-4-yl)ethyl)phenyl)acetate (I48) (0.130 g, 0.221 mmol) in dry THF (6 mL) and dry DMF (1 mL) under an atmosphere of nitrogen. Ammonium carbonate (84.8 mg, 0.883 mmol) was added in one portion to the stirred reaction mixture after 10 minutes. The reaction was left stirred at room temperature for 18 hours. The volatiles were removed in vacuo and the residual solution was diluted with EtOAc (50 mL), transferred to a separating funnel and washed with saturated NaHCO$_3$ (50 mL). The aqueous layer was extracted with EtOAc (2×50 mL). The combined organic layers were washed with water (50 mL) and brine (2×50 mL) and dried over Na$_2$SO$_4$. After filtration the solvent was removed in vacuo to afford a pale yellow solid. The crude material was purified by column chromatography on silica gel (0-80% EtOAc in petroleum benzine 40-60° C.) to afford the title compound (I49) (90.8 mg, 70%) as a white foamy solid; $^1$H NMR (400 MHz, CDCl$_3$) δ 8.53 (s, 1H), 7.53 (m, 3H), 7.31-7.23 (m, peaks obscured by CDCl$_3$), 7.20 (d, J=8.5 Hz, 2H), 5.37 (s, 1H), 5.29 (s, 1H), 4.25 (b s, 2H), 3.72 (s, 2H), 3.15-3.03 (m, 4H), 2.80 (t, J=12.4 Hz, 2H), 2.69-2.59 (m, 1H), 1.83 (d, J=12.6 Hz, 2H), 1.68-1.55 (m, peaks obscured by water peak), 1.49 (s, 9H). LCMS Method C: rt 6.48 min; m/z 606 [M+Na]$^+$, 584 [M+H]$^+$, 528 [M-$^t$Butyl+2H]$^+$, 484 [M-Boc+2H]$^+$.

(i) 2-(2-(2-(2-((4-(Piperidin-4-yl)phenyl)amino)-5-(trifluoromethyl)pyrimidin-4-yl)ethyl)phenyl)acetamide (I1)

Trifluoroacetic acid (0.595 mL, 7.78 mmol) was added to a solution of tert-butyl 4-(4-((4-(2-(2-amino-2-oxoethyl)phenethyl)-5-(trifluoromethyl)pyrimidin-2-yl)amino)phenyl)piperidine-1-carboxylate (I49) (90.8 mg, 0.156 mmol) in dry DCM (5 mL) under an atmosphere of nitrogen. The reaction was stirred at room temperature for 23 hours. The volatiles were removed in vacuo and the residue partitioned between EtOAc (30 mL) and 2M NaOH (30 mL). The two layers were separated and the aqueous layer was extracted with EtOAc (2×30 mL). The combined organic layers were washed with water (30 mL), brine (30 mL), dried over Na$_2$SO$_4$. After filtration the solvent was removed under reduced pressure to give a white solid which was suspended in DCM (2 mL) and cyclohexane (10 mL). The resulting precipitate was filtered to afford title compound (11) (63 mg, 84%) as an off-white solid; $^1$H NMR (400 MHz, d$_6$-DMSO) δ 10.13 (s, 1H), 8.65 (s, 1H), 7.67-7.64 (m, 2H), 7.44 (s, 1H), 7.27-7.12 (m, 6H), 6.93 (s, 1H), 3.50 (s, 2H), 3.14-3.06 (m, 2H), 3.02-2.99 (m, 4H), 2.62-2.46 (m, peaks obscured by DMSO), 1.67 (d, J=11.4 Hz, 2H), 1.49 (qd, J=12.5, 3.9 Hz, 2H). LCMS Method C: rt 4.84 min; m/z 484 [M+H]$^+$.

Example 12

2-(2-(2-(2-((4-(piperidin-4-yl)phenyl)amino)-5-(trifluoromethyl)pyrimidin-4-yl)ethyl)phenyl)propanamide (12)

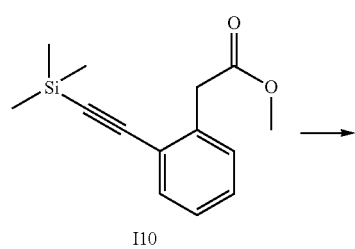

I10

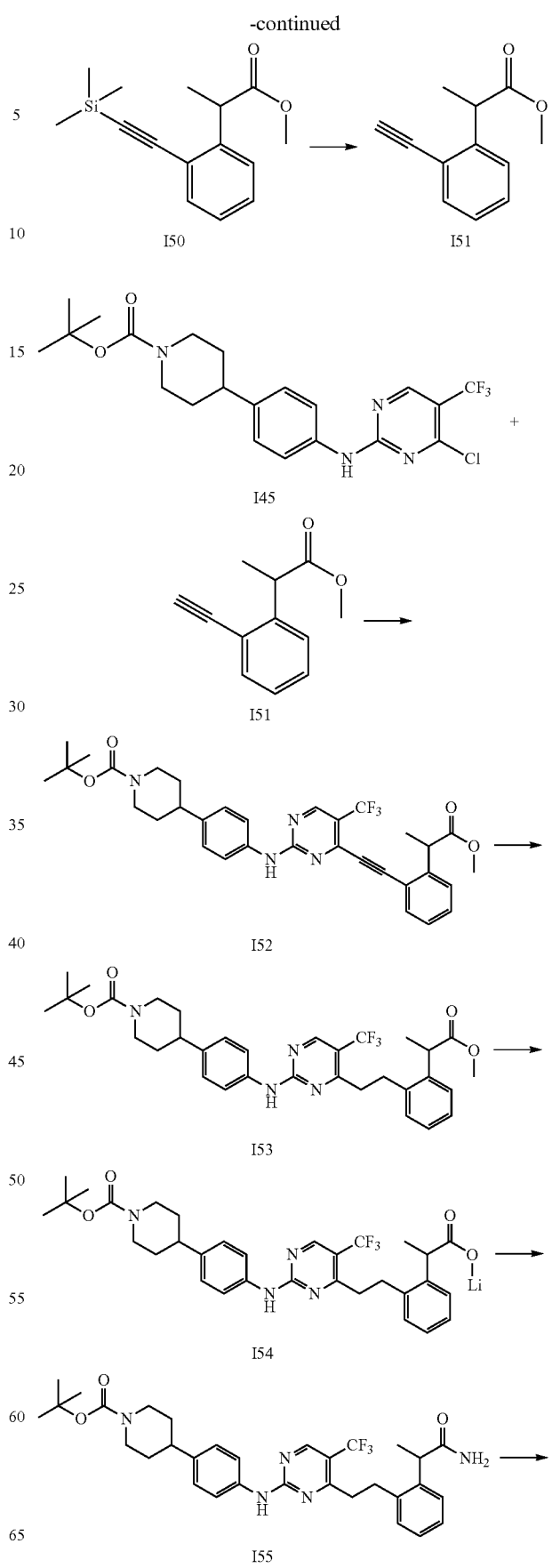

-continued

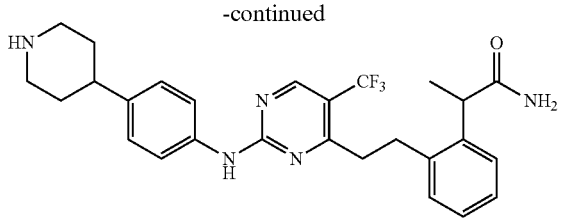

12

(a) Methyl 2-(2-((trimethysiyl)ethynyl)phenyl)propanoate (I50)

2 M LDA solution (1.24 mL, 2.48 mmol) was added to solution of methyl 2-(2-((trimethylsilyl)ethynyl)phenyl)acetate (I10) (0.306 g, 1.24 mmol) in THF (10 mL) at −78° C. and the mixture stirred for 30 minutes. Methyl iodide was then added (0.155 mL, 2.48 mmol) and the reaction mixture slowly warmed to room temperature over 1.5 hours. The reaction mixture was then left to stir at room temperature for 18 hours before quenching with a saturated solution of NH$_4$Cl (20 mL). EtOAc (20 mL) was then added and the layers separated. The aqueous layer was further extracted with EtOAc (2×20 mL). The solvent was removed in vacuo to give a brown oil which was purified by column chromatography on silica gel (0-5% EtOAc in petroleum benzine 40-60° C.) to afford the title compound (I50) (0.297 g, 92%) as a yellow oil; $^1$H NMR (400 MHz, CDCl$_3$) δ 7.49-7.44 (m, 1H), 7.33-7.24 (m, peaks obscured by CDCl$_3$), 7.21-7.17 (m, 1H), 4.25 (q, J=7.2 Hz, 1H), 3.67 (s, 3H), 1.51 (d, J=7.2 Hz, 3H), 0.26 (s, 9H).

(b) Methyl 2-(2-ethynylphenyl)propanoate (I51)

A solution of TBAF (1 M solution in THF; 2.28 mL, 2.28 mmol) was added to a solution of methyl 2-(2-((trimethylsilyl)ethynyl)phenyl)propanoate (I50) (0.297 g, 1.14 mmol) in THF (10 mL) at 0° C. The reaction was stirred for 50 minutes at 0° C. then concentrated under reduced pressure and the residue taken up in EtOAc (20 mL). The organic solution was washed with saturated NaHCO$_3$ (20 mL), water (20 mL) and dried over Na$_2$SO$_4$. The solvent was removed in vacuo to yield a brown oily residue. The oil was purified using column chromatography on silica gel (0-5% EtOAc in cyclohexane) to afford the title compound (I51) (0.192 g, 89%) as a pale yellow oil; $^1$H NMR (400 MHz, CDCl$_3$) δ 7.53-7.48 (m, 1H), 7.36-7.28 (m, 2H), 7.24-7.20 (m, 1H), 4.31 (q, J=7.2 Hz, 1H), 3.67 (s, 3H), 3.28 (s, 1H), 1.50 (d, J=7.2 Hz, 3H). LCMS Method C: rt 5.92 min; m/z 189 [M+H]$^+$.

(c) tert-Butyl 4-(4-((4-((2-(1-methoxy-1-oxopropan-2-yl)phenyl)ethynyl)-5-(trifluoromethyl)pyrimidin-2-yl)amino)phenyl)piperidine-1-carboxylate (I52)

A solution of methyl 2-(2-ethynylphenyl)propanoate (I51) (0.074 g, 0.39 mmol) in dimethylformamide (2 mL) and triethylamine (0.183 mL, 1.31 mmol) was added to a mixture of tert-butyl 4-(4-((4-chloro-5-(trifluoromethyl)pyrimidin-2-yl)amino)phenyl)piperidine-1-carboxylate (I45) (0.150 g, 0.328 mmol), Pd(PPh$_3$)$_2$Cl$_2$ (0.023 g, 0.033 mmol), CuI (0.0090 g, 0.049 mmol) and triphenylphosphine (0.013 g, 0.049 mmol) in dimethylformamide (2 mL). The reaction mixture was heated under microwave irradiation at 120° C. for 15 minutes. The reaction was cooled and the mixture diluted with EtOAc and passed through a plug of Celite washing with ethyl acetate (50 mL). Water (50 mL) was added and the layers separated. The aqueous layer was extracted with EtOAc (2×50 mL). The combined organic extracts were washed with water (50 mL) and brine (50 mL) and dried over Na$_2$SO$_4$. After filtration the solvent was removed under reduced pressure to give a dark brown residue. The residue was purified by column chromatography on silica gel (0-20% EtOAc in cyclohexane) to yield the title compound (I52) (0.108 g, 54%) as a brown viscous oil.

(d) tert-Butyl 4-(4-((4-(2-(1-methoxy-1-oxopropan-2-yl)phenethyl)-5-(trifluoromethyl)pyrimidin-2-yl)amino)phenyl)piperidine-1-carboxylate (I53)

A solution of tert-butyl 4-(4-((4-((2-(1-methoxy-1-oxopropan-2-yl)phenyl)ethynyl)-5-(trifluoromethyl)pyrimidin-2-yl)amino)phenyl)piperidine-1-carboxylate (I52) (0.108 g, 0.177 mmol) in EtOAc (5 mL) and DMF (10 mL) was added to a suspension of 10% Pd/C (80 mg) in EtOAc (5 mL). The reaction was stirred at room temperature for 24 hours under an atmosphere of hydrogen. The reaction was filtered and the solvent removed in vacuo to yield a brown residue. The residue was redissolved in DMF (15 mL) and added to a suspension of 10% Pd/C (55 mg) in DMF (5 mL). The reaction was stirred at room temperature for 24 hours under an atmosphere of hydrogen. The reaction was filtered through a pad of celite washing with EtOAc (100 mL). Removal of the solvent under reduced pressure yielded a brown viscous oil which was purified by column chromatography on silica gel (0-15% EtOAc in petroleum benzine 40-60° C.) to afford the title compound (I53) (84.3 mg, 77%) as a pale yellow viscous oil; $^1$H NMR (400 MHz, CDCl$_3$) δ 8.54 (s, 1H), 7.59-7.54 (m, 2H), 7.38 (s, 1H), 7.33-7.30 (m, 1H), 7.25-7.17 (m, 5H), 4.25 (s, 2H), 4.11 (q, J=7.1 Hz, 1H), 3.64 (s, 3H), 3.23-3.02 (m, 4H), 2.81 (t, J=12.0 Hz, 2H), 2.64 (tt, J=12.0, 3.4 Hz, 1H), 1.83 (d, J=12.9 Hz, 2H), 1.67-1.59 (m, 2H), 1.50-1.48 (d, J=7.0 Hz, 3H; s, 9H). LCMS Method C: rt 7.15 min; m/z 635 [M+Na]$^+$, 613 [M+H]$^+$, 557 [M-$^t$Butyl+2H]$^+$.

(e) Lithium 2-(2-(2-(2-((4-(1-(tert-butoxycarbonyl)piperidin-4-yl)phenyl)amino)-5-(trifluoromethyl)pyrimidin-4-yl)ethyl)phenyl)propanoate (I54)

LiOH.H$_2$O (17.3 mg, 0.413 mmol) was added to a solution of tert-butyl 4-(4-((4-(2-(1-methoxy-1-oxopropan-2-yl)phenethyl)-5-(trifluoromethyl)pyrimidin-2-yl)amino)phenyl)piperidine-1-carboxylate (I53) (0.084 g, 0.137 mmol) in THF (7 mL), water (1.5 mL) and methanol (1 mL). The resulting mixture was allowed to stir at room temperature for 20 hours. The volatiles were removed in vacuo and the residue diluted with EtOAc (50 mL) and sat. aq. NaHCO$_3$ (50 mL). The layers were separated and the aqueous layer was extracted with EtOAc (1×50 mL). The organic layers were combined, washed with brine (50 mL), dried with Na$_2$SO$_4$, filtered and concentrated under reduced pressure to give the title compound (I54) (86 mg) as a pale yellow viscous oil.

(f) tert-Butyl 4-(4-((4-(2-(1-amino-1-oxopropan-2-yl)phenethyl)-5-(trifluoromethyl)pyrimidin-2-yl)amino)phenyl)piperidine-1-carboxylate (I55)

1-Hydroxybenzotriazole (21.1 mg, 0.156 mmol), EDCl (30.0 mg, 0.156 mmol) and N,N-diisopropylethylamine (54.5 µL, 0.313 mmol) were added to a solution of lithium 2-(2-(2-(2-((4-(1-(tert-butoxycarbonyl)piperidin-4-yl)phenyl)amino)-5-(trifluoromethyl)pyrimidin-4-yl)ethyl)phenyl)propanoate (I54) (0.086 g, 0.142 mmol) in dry THF (6 mL) and dry DMF (1 mL) under an atmosphere of nitrogen. Ammonium carbonate (54.6 mg, 0.569 mmol) was added in one portion to the stirred reaction mixture after 10 minutes. The reaction was left stirred at room temperature for 18 hours. The volatiles were removed in vacuo and the residual solution was diluted with EtOAc (50 mL) then washed with saturated NaHCO$_3$ (50 mL). The aqueous layer was extracted with EtOAc (2×50 mL). The combined organic layers were washed with water (50 mL) and brine (50 mL) and dried over Na$_2$SO$_4$. After filtration the solvent was removed in vacuo to afford a pale yellow solid. The crude material was purified by column chromatography on silica gel (0-85% EtOAc in petroleum benzine 40-60° C.) to afford the title compound (I55) (65.2 mg, 77%) as a white foamy solid; $^1$H NMR (400 MHz, CDCl$_3$) δ 8.54 (s, 1H), 7.51 (d, J=8.5 Hz, 2H), 7.47 (s, 1H), 7.40-7.36 (m, 1H), 7.30-7.17 (m, peaks obscured by CDCl$_3$), 5.37 (s, 1H), 5.20 (s, 1H), 4.25 (b s, 2H), 4.01 (q, J=7.1 Hz, 1H), 3.17-3.02 (m, 4H), 2.80 (t, J=12.3 Hz, 2H), 2.64 (tt, J=12.3, 3.6 Hz, 1H), 1.83 (d, J=12.7 Hz, 2H), 1.67-1.59 (m, peaks obscured by water peak), 1.56 (d, J=7.2 Hz, 3H), 1.49 (s, 9H). LCMS Method C: rt 6.60 min; m/z 620 [M+Na]$^+$, 598 [M+H]$^+$, 542 [M-$^t$Butyl+2H]$^+$, 498 [M-Boc+2H]$^+$.

(g) 2-(2-(2-(2-((4-(Piperidin-4-yl)phenyl)amino)-5-(trifluoromethyl)pyrimidin-4-yl)ethyl)phenyl)propanamide (12)

Trifluoroacetic acid (0.417 mL, 5.46 mmol) was added to a solution of tert-butyl 4-(4-((4-(2-(1-amino-1-oxopropan-2-yl)phenethyl)-5-(trifluoromethyl)pyrimidin-2-yl)amino)phenyl)piperidine-1-carboxylate (I55) (65.2 mg, 0.109 mmol) in dry DCM (8 mL) under an atmosphere of nitrogen. The reaction was stirred at room temperature for 23 hours. The volatiles were removed in vacuo and the residue partitioned between EtOAc (20 mL) and 2 M NaOH (20 mL). The layers were separated and the aqueous layer was extracted with EtOAc (2×20 mL). The combined organic layers were washed with water (20 mL), brine (20 mL), dried over Na$_2$SO$_4$. After filtration the solvent was removed under reduced pressure to give a pale yellow solid which was dissolved in EtOAc (2 mL) to which was added cyclohexane (10 mL). The resulting precipitate was collected by filtration to afford the title compound (I2) (25 mg, 47%) as an off-white solid; $^1$H NMR (400 MHz, d$_6$-DMSO) δ 10.14 (s, 1H), 8.67 (s, 1H), 7.68-7.65 (m, 2H), 7.42-7.34 (m, 1H), 7.26-7.12 (m, 6H), 6.87 (s, 1H), 3.86 (q, J=7.0 Hz, 1H), 3.44-3.18 (m, peaks obscured by water peak), 3.14-2.95 (m, 5H), 2.64-2.46 (m, peaks obscured by DMSO), 1.68 (d, J=13.0 Hz, 2H), 1.49 (qd, J=12.1, 2.4 Hz, 2H), 1.31 (d, J=7.0 Hz, 3H). LCMS Method C: rt 4.91 min; m/z 498 [M+H]$^+$.

Example 13

2-(2-(2-(2-((4-(4-Acetylpiperazin-1-yl)phenyl)amino)-5-(trifluoromethyl)pyrimidin-4-yl)ethyl)phenyl)acetamide (13)

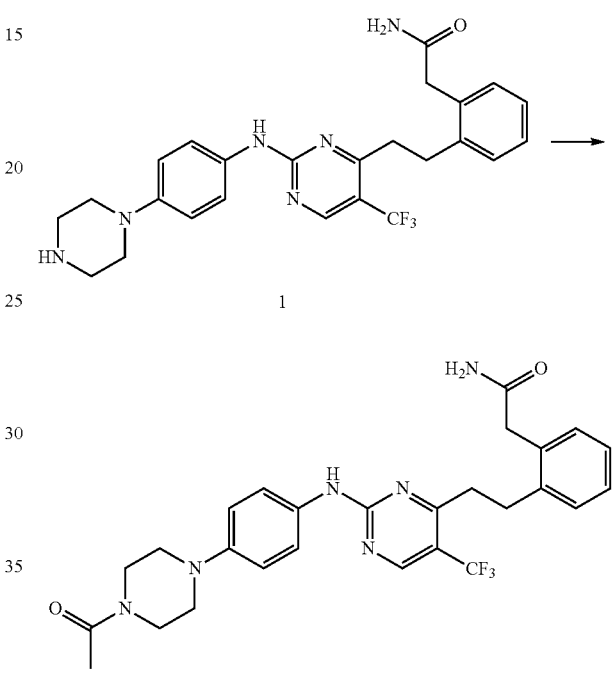

2-(2-(2-(2-((4-(Piperazin-1-yl)phenyl)amino)-5-(trifluoromethyl)pyrimidin-4-yl)ethyl)phenyl)acetamide (1) (0.020 g, 0.041 mmol) was dissolved in dry DCM (2 mL), dry THF (1 mL) and dry DMF (1 mL) then triethylamine (0.012 mL, 0.083 mmol) followed by acetic anhydride (0.008 mL, 0.083 mmol) were added. The reaction was then stirred at room temperature for 5 hours, the volatiles were removed in vacuo and the residue was diluted with EtOAc (15 mL) and sat. aq. NaHCO$_3$ (10 mL). The layers were separated and the aqueous layer was extracted with EtOAc (10 mL), the combined organic layers were washed with water (10 mL), brine (10 mL), water (10 mL), brine (10 mL), dried (MgSO$_4$), filtered and concentrated in vacuo to give a solid which was taken up in DCM (~10 mL) and methanol (~1 mL) and concentrated in vacuo. The process was repeated with only DCM twice after which the sample was further dried on high-vacuum to give the title compound (I3) (0.019 g, 87% yield) as an off-white solid; $^1$H NMR (400 MHz, d$_6$-DMSO) δ 10.01 (s, 1H), 8.61 (s, 1H), 7.63-7.56 (m, 2H), 7.44 (s, 1H), 7.26-7.13 (m, 4H), 6.98-6.90 (m, 3H), 3.61-3.54 (m, 4H), 3.50 (s, 2H), 3.13-2.95 (m, 8H), 2.04 (s, 3H). LCMS Method C: rt 5.62 min; m/z 527.2 [M+H]$^+$.

Example 14

N-Methyl-2-(2-(2-(2-((4-(piperazin-1-yl)phenyl)amino)-5-(trifluoromethyl)pyrimidin-4-yl)ethyl)phenyl)acetamide (14)

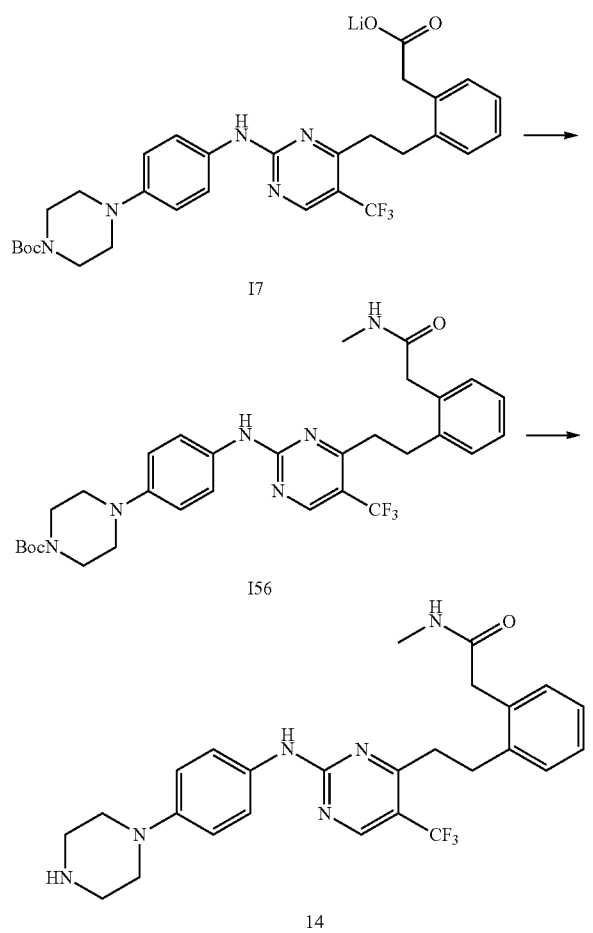

(a) tert-Butyl 4-(4-((4-(2-(2-(methylamino)-2-oxoethyl)phenethyl)-5-(trifluoromethyl)pyrimidin-2-yl)amino)phenyl)piperazine-1-carboxylate (I56)

Lithium 2-(2-(2-(2-((4-(4-(tert-butoxycarbonyl)piperazin-1-yl)phenyl)amino)-5-(trifluoromethyl)pyrimidin-4-yl)ethyl)phenyl)acetate (I7) (0.130 g, 0.220 mmol) was dissolved in dry THF (7 mL) and dry DMF (1 mL) under an atmosphere of nitrogen. To the solution were added 1-hydroxybenzotriazole (0.036 g, 0.26 mmol) and EDCl (0.051 g, 0.26 mmol) and N,N-diisopropylethylamine (0.153 mL, 0.879 mmol) and the reaction mixture was stirred at room temperature for 10 minutes. Methylamine hydrochloride (0.059 g, 0.88 mmol) was added in one portion, and the reaction was stirred at room temperature for 60 hours. The volatiles were removed in vacuo and the residual solution was diluted with EtOAc (100 mL) and sat. aq. NaHCO₃ (80 mL). The layers were separated and the aqueous layer was extracted with EtOAc (70 mL), the organic layers were combined and washed with water (100 mL), brine (100 mL), dried (MgSO₄), filtered and concentrated in vacuo to give a pale yellow solid. The crude product was purified by silica gel chromatography (Biotage Isolera, 40 g Si Cartridge, 0-100% EtOAc in petroleum benzine 40-60° C., then 0-60% methanol in EtOAc) to give the title compound (I56) (0.091 g, 69% yield) as a pale yellow solid; $^1$H NMR (400 MHz, d$_6$-DMSO) δ 10.00 (s, 1H), 8.61 (s, 1H), 7.93-7.86 (m, 1H), 7.63-7.56 (m, 2H), 7.24-7.12 (m, 4H), 6.96-6.89 (m, 2H), 3.54-3.42 (m, 6H), 3.14-2.93 (m, 8H), 2.56 (d, J=4.6 Hz, 3H), 1.42 (s, 9H). LCMS Method C: rt 6.27 min; m/z 599.3 [M+H]$^+$.

(b) N-Methyl-2-(2-(2-(2-((4-(piperazin-1-yl)phenyl)amino)-5-(trifluoromethyl)pyrimidin-4-yl)ethyl)phenyl)acetamide (14)

tert-Butyl 4-(4-((4-(2-(2-(methylamino)-2-oxoethyl)phenethyl)-5-(trifluoromethyl)pyrimidin-2-yl)amino)phenyl)piperazine-1-carboxylate (I56) (0.087 g, 0.15 mmol) was dissolved in DCM (5 mL) under an atmosphere of nitrogen. Trifluoroacetic acid (0.222 mL, 2.906 mmol) was added to the solution and the reaction was stirred at room temperature for 6 hours. Volatiles were removed in vacuo, EtOAc (70 mL) and 2 M aq. NaOH (70 mL) were added to the residue and the layers were separated. The aqueous layer was extracted with EtOAc (2×70 mL), the combined organics were washed with water (50 mL), brine (50 mL), dried (MgSO₄), filtered and concentrated in vacuo to give a solid which was taken up in DCM (~10 mL) and methanol (~1 mL) and concentrated in vacuo. The process was repeated with only DCM twice after which the sample was further dried on high-vacuum to give the title compound (14) (0.068 g, 94% yield) as a pale yellow solid; $^1$H NMR (400 MHz, d$_6$-DMSO) δ 9.97 (s, 1H), 8.60 (s, 1H), 7.93-7.85 (m, 1H), 7.60-7.53 (m, 2H), 7.23-7.12 (m, 4H), 6.91-6.86 (m, 2H), 3.50 (s, 2H), 3.14-3.06 (m, 2H), 3.02-2.93 (m, 6H), 2.87-2.80 (m, 4H), 2.56 (d, J=4.6 Hz, 3H). LCMS Method A: rt 4.37 min; m/z 499.6 [M+H]$^+$.

Example 15

N-Methyl-2-(2-(2-(2-((4-(piperazin-1-yl)phenyl)amino)-5-(trifluoromethyl)pyrimidin-4-yl)ethyl)phenyl)acetamide (15)

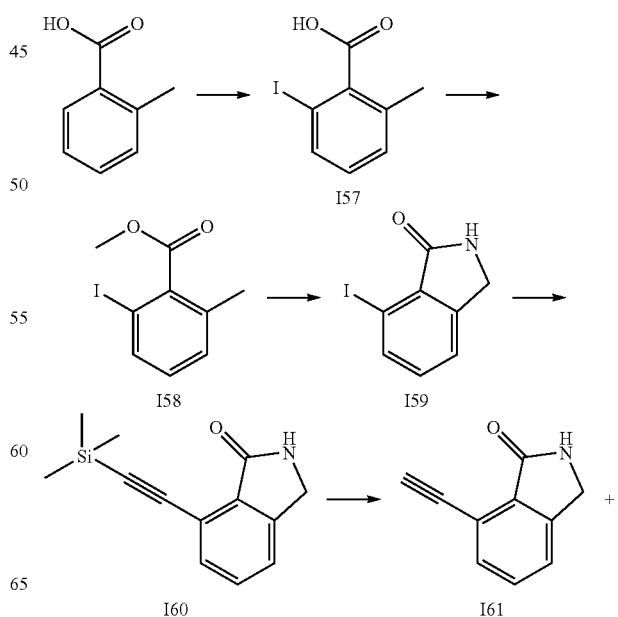

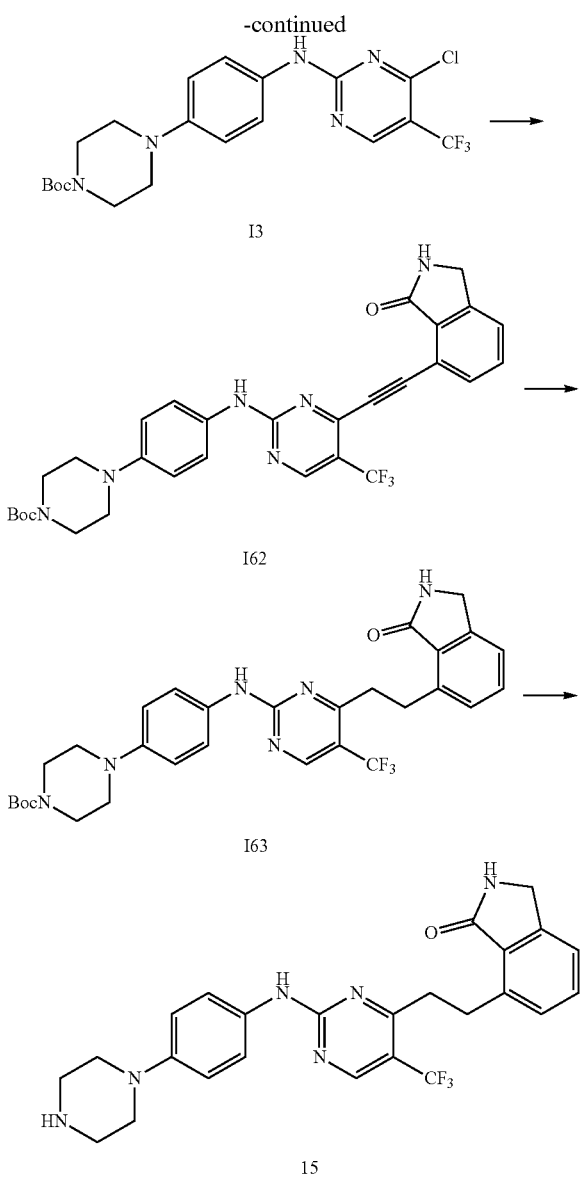

(a) 2-Iodo-6-methylbenzoic acid (I57)

To a solution of o-toluic acid (2.00 g, 14.7 mmol) in dry DMF (60 mL) under an atmosphere of nitrogen was added N-iodosuccinimide (3.64 g, 16.2 mmol) followed by Pd(OAc)$_2$ (0.330 g, 1.47 mmol). The resulting reaction mixture was heated to 100° C. and stirred for 17 hours. Upon cooling to room temperature the reaction was diluted with water (100 mL) and EtOAc (150 mL), the layers were separated and the aqueous layer was extracted with EtOAc (2×100 mL), the combined organics were washed with water (100 mL), brine (100 mL), water (100 mL), brine (100 mL), dried (MgSO$_4$), filtered and concentrated in vacuo to give the title compound (I57) (3.56 g, 92% yield) as a brown oily solid; $^1$H NMR (400 MHz, CDCl$_3$) δ 7.69 (d, J=7.9 Hz, 1H), 7.21 (d, J=7.6 Hz, 1H), 7.02 (t, J=7.8 Hz, 1H), 2.44 (s, 3H). LCMS Method C: rt 5.36 min.

(b) Methyl 2-iodo-6-methylbenzoate (I58)

A solution of 2-iodo-6-methylbenzoic acid (I57) (2.50 g, 9.54 mmol) in DCM (30 mL) and methanol (8 mL) under an atmosphere of nitrogen was cooled to 0° C. and trimethylsilyldiazomethane (2.0 M in diethyl ether, 9.54 mL, 19.1 mmol) was added dropwise. The reaction was stirred at 0° C. for 45 minutes and then quenched with 2 M aq. HCl (50 mL). DCM (150 mL) was added to the quenched reaction and the layers were separated. The aqueous layer was extracted with DCM (100 mL), the organics were combined and washed with sat. aq. NaHCO$_3$ (100 mL), water (100 mL), brine (100 mL), dried (MgSO$_4$), filtered and concentrated in vacuo to give a yellow oil. The crude product was purified by silica gel chromatography (Biotage Isolera, 40 g Si Cartridge, 0-20% EtOAc in petroleum benzine 40-60° C.) to give the title compound (I58) (2.00 g, 76% yield) as a colourless oil; $^1$H NMR (400 MHz, CDCl$_3$) δ 7.65 (ddd, J=7.9, 1.0, 0.5 Hz, 1H), 7.19-7.15 (m, 1H), 6.99 (t, J=7.8 Hz, 1H), 3.95 (s, 3H), 2.33 (s, 3H). LCMS Method C: rt 6.08 min; m/z 277.0 [M+H]$^+$.

(c) 7-Iodoisoindolin-1-one (I59)

Methyl 2-iodo-6-methylbenzoate (I58) (2.00 g, 7.245 mmol) and NBS (1.418 g, 7.969 mmol) were stirred in chlorobenzene (50 mL) and benzoyl peroxide (75% w/w, 0.234 g, 0.724 mmol) was added. The reaction was stirred at 90° C. for 18 hours, cooled to room temperature, filtered and the precipitate was washed with cyclohexane (4×10 mL). The combined filtrates were evaporated, and the resulting brown oil was diluted with THF (50 mL). Aqueous ammonia solution (20 mL) was added, and the mixture was stirred vigorously for 17 hours. The mixture was diluted with water (20 mL) and the THF was removed in vacuo. DCM (150 mL) was added, the layers were separated and the aqueous layer was extracted with DCM (2×100 mL), the combined organics were washed with brine (100 mL), dried (MgSO$_4$) and filtered. Silica gel was added and the volatiles were removed in vacuo to give the crude material absorbed onto silica gel. The material was purified by silica gel chromatography (Biotage Isolera, 40 g Si cartridge, 0-100% EtOAc in petroleum benzine 40-60° C., then 0-20% methanol in EtOAc) to give the title compound (I59) (0.757 g, 40% yield) as a beige solid; $^1$H NMR (400 MHz, CDCl$_3$) δ 7.93 (dd, J=7.8, 0.7 Hz, 1H), 7.46 (dd, J=7.5, 0.8 Hz, 1H), 7.26-7.21 (m, 1H), 7.10 (brs, 1H), 4.37 (d, J=0.6 Hz, 2H). LCMS Method C: rt 5.06 min; m/z 260.0 [M+H]$^+$.

(d) 7-((Trimethylsilyl)ethynyl)isoindolin-1-one (I60)

To a nitrogen de-gassed solution of 7-iodoisoindolin-1-one (I59) (0.233 g, 0.899 mmol) in dry DMF (6 mL) were added triethylamine (0.501 mL, 3.598 mmol) followed by triphenylphosphine (0.035 g, 0.14 mmol), trans-dichlorobis(triphenylphosphine) palladium(II) (0.063 g, 0.090 mmol), CuI (0.026 g, 0.14 mmol) and finally (trimethylsilyl)acetylene (0.292 mL, 1.63 mmol). The reaction mixture was then heated under microwave irradiation at 100° C. for 30 then 10 minutes. The reaction mixture was concentrated in vacuo, then absorbed onto silica gel and purified by silica gel chromatography (Biotage Isolera, 40 g Si cartridge, 0-46% EtOAc in dichloromethane) to give the title compound (I60) (0.120 g, 49% yield) as an off-white solid; $^1$H NMR (400 MHz, d$_6$-DMSO) δ 8.47 (s, 1H), 7.60-7.51 (m, 2H), 7.49 (dd, J=6.7, 2.0 Hz, 1H), 4.32 (s, 2H), 1.03 (t, J=7.9 Hz, 9H), 0.66 (q, J=7.9 Hz, 6H). LCMS Method C: rt 6.44 min; m/z 272.2 [M+H]$^+$.

(e) 7-Ethynylisoindolin-1-one (I61)

To a solution of 7-((trimethylsilyl)ethynyl)isoindolin-1-one (I60) (0.172 g, 0.634 mmol) in dry THF (8 mL) under an atmosphere of nitrogen was added TBAF (1.0 M in THF, 0.697 mL, 0.697 mmol) dropwise at 0° C. The solution was stirred at this temperature for 1.5 hours and then quenched by the addition of water (2 mL). The reaction mixture was concentrated in vacuo and diluted with DCM (100 mL) and sat. aq. NaHCO$_3$ (70 mL). The layers were separated and the aqueous layer was extracted with DCM (70 mL), the combined organic layers were washed with water (100 mL), brine (100 mL), dried (MgSO$_4$), filtered and concentrated in vacuo to give a beige solid. The crude product was purified by silica gel chromatography (Biotage Isolera, 12 g Si Cartridge, 0-80% EtOAc in DCM) to give the title compound (I61) (0.076 g, 76% yield) as an off-white solid; $^1$H NMR (400 MHz, d$_6$-DMSO) δ 8.59 (s, 1H), 7.61-7.50 (m, 3H), 4.39 (s, 1H), 4.33 (s, 2H). LCMS Method C: rt 4.56 min, m/z 158.1 [M+H]$^+$ (f) tert-Butyl 4-(4-((4-((3-oxoisoindolin-4-yl)ethynyl)-5-(trifluoromethyl)pyrimidin-2-yl)amino)phenyl)piperazine-1-carboxylate (I62)

To a nitrogen de-gassed solution of 7-ethynylisoindolin-1-one (I61) (0.074 g, 0.47 mmol) and tert-butyl 4-(4-((4-chloro-5-(trifluoromethyl)pyrimidin-2-yl)amino)phenyl)piperazine-1-carboxylate (I3) (0.180 g, 0.393 mmol), in dry DMF (7 mL) were added triethylamine (0.219 mL, 1.57 mmol) followed by triphenylphosphine (0.015 g, 0.059 mmol), trans-dichlorobis(triphenylphosphine)palladium(II) (0.028 g, 0.039 mmol) and CuI (0.011 g, 0.059 mmol). The reaction mixture was heated under microwave irradiation at 120° C. for 20 minutes and then concentrated to dryness in vacuo and purified by silica gel chromatography (Biotage Isolera, 40 g Si cartridge, 0-100% EtOAc in petroleum benzine 40-60° C., then 0-5% methanol in EtOAc) to give the title compound (I62) (0.151 g, 66% yield) as an orange gum; $^1$H NMR (400 MHz, d$_6$-DMSO) δ 10.32 (s, 1H), 8.77 (s, 1H), 8.72 (s, 1H), 7.75-7.67 (m, 2H), 7.67-7.64 (m, 1H), 7.60-7.56 (m, 2H).), 6.95 (d, J=9.1 Hz, 2H), 4.40 (s, 2H), 3.51-3.42 (m, 4H), 3.11-3.00 (m, 4H), 1.42 (s, 9H). LCMS Method C: rt 6.23 min, m/z 579.2 [M+H]$^+$.

(g) tert-Butyl 4-(4-((4-(2-(3-oxoisoindolin-4-yl)ethyl)-5-(trifluoromethyl)pyrimidin-2-yl)amino)phenyl)piperazine-1-carboxylate (I63)

tert-Butyl 4-(4-((4-((3-oxoisoindolin-4-yl)ethynyl)-5-(trifluoromethyl)pyrimidin-2-yl)amino)phenyl)piperazine-1-carboxylate (I62) (0.149 g, 0.258 mmol) was dissolved in dry DMF (6 mL) under an atmosphere of nitrogen. 20% Pearlman's catalyst (0.090 g) in EtOAc (6 mL) was added to the solution and the atmosphere was changed to hydrogen gas (balloon). The reaction was sealed with a balloon and stirred at room temperature for 18 hours at room temperature. The catalyst was removed by filtration through Celite, which was washed with EtOAc (5×10 mL). The solvent was removed in vacuo to give a yellow solid which was purified by silica gel chromatography (Biotage Isolera, 40 g Si Cartridge, 0-100% EtOAc in petroleum benzine 40-60° C., then 0-5% methanol in EtOAc) to give the title compound (I63) (0.084 g, 56% yield) as an off-white solid; $^1$H NMR (400 MHz, d$_6$-DMSO) δ 9.98 (s, 1H), 8.57 (s, 1H), 8.48 (s, 1H), 7.62-7.55 (m, 2H), 7.44 (t, J=7.4 Hz, 1H), 7.38 (d, J=7.3 Hz, 1H), 7.17 (brd, J=6.0 Hz, 1H), 6.92 (d, J=9.0 Hz, 2H), 4.31 (s, 2H), 3.56 (t, J=7.6 Hz, 2H), 3.51-3.41 (m, 4H), 3.12 (t, J=7.5 Hz, 2H), 3.08-2.98 (m, 4H), 1.42 (s, 9H). LCMS Method A: rt 5.86 min; m/z 583.5 [M+H]$^+$.

(h) 7-(2-(2-((4-(Piperazin-1-yl)phenyl)amino)-5-(trifluoromethyl)pyrimidin-4-yl)ethyl)isoindolin-1-one (15)

tert-Butyl 4-(4-((4-(2-(3-oxoisoindolin-4-yl)ethyl)-5-(trifluoromethyl)pyrimidin-2-yl)amino)phenyl)piperazine-1-carboxylate (I63) (0.080 g, 0.137 mmol) was dissolved in DCM (5 mL) under an atmosphere of nitrogen. Trifluoroacetic acid (0.210 mL, 2.75 mmol) was added to the solution and the reaction was stirred at room temperature for 1 hour and then at 35° C. for another 30 minutes. More trifluoroacetic acid (0.100 mL) was added and the reaction was further stirred at 35° C. for another 30 minutes. Volatiles were removed in vacuo then EtOAc (70 mL) and 2 M aq. NaOH (70 mL) were added to the residue and the layers were separated. The aqueous layer was extracted with EtOAc (2×70 mL), the combined organics were washed with water (50 mL), brine (50 mL), dried (MgSO$_4$), filtered and concentrated in vacuo to give an oily solid which was taken up in DCM (~10 mL) and concentrated in vacuo.

The process was repeated twice after which the sample was further dried on high-vacuum to give the title compound (I5) (0.050 g, 75% yield) as an off-white solid; $^1$H NMR (400 MHz, d$_6$-DMSO) δ 9.94 (s, 1H), 8.56 (s, 1H), 8.48 (s, 1H), 7.59-7.52 (m, 2H), 7.47-7.36 (m, 2H), 7.23-7.11 (m, 1H), 6.87 (d, J=9.0 Hz, 2H), 4.31 (s, 2H), 3.56 (t, J=7.6 Hz, 2H), 3.11 (t, J=7.4 Hz, 2H), 3.01-2.95 (m, 4H), 2.86-2.79 (m, 4H). LCMS Method A: rt 4.40 min; m/z 483.8 [M+H]$^+$.

Example 16

2-(2-(2-(2-((4-(1-methylpiperidin-4-yl)phenyl)amino)-5-(trifluoromethyl)pyrimidin-4-yl)ethyl)phenyl)acetamide (16)

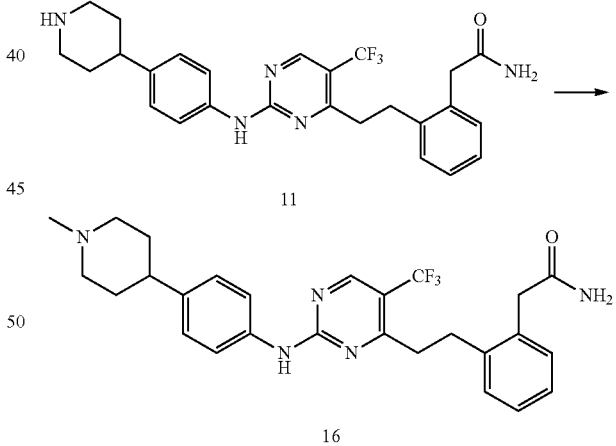

Formaldehyde (37% in H$_2$O; 15.6 μL, 0.210 mmol) was added to a suspension of 2-(2-(2-(2-((4-(piperidin-4-yl)phenyl)amino)-5-(trifluoromethyl)pyrimidin-4-yl)ethyl)phenyl)acetamide (I1) (25 mg, 0.053 mmol) in anhydrous methanol (5 mL) under an atmosphere of nitrogen. Sodium triacetoxyborohydride (0.111 g, 0.525 mmol) was then added in one portion to the reaction mixture. The reaction was stirred at room temperature for 1.5 hours. The volatiles were removed in vacuo and the residue was diluted with EtOAc (25 mL) and saturated aq. NaHCO$_3$ (25 mL). The layers were separated and the aqueous layer was extracted with EtOAc (2×25 mL), the combined organic layers were washed with water (25 mL), brine (25 mL) and dried over $Na_2SO_4$. The solvent was removed under reduced pressure yield a white solid. The solid was suspended in DCM (2 mL) and cyclohexane (10 mL) then filtered to afford the title compound (16) (19 mg, 73%) as a white solid; $^1$H NMR (400 MHz, $d_6$-DMSO) δ 10.14 (s, 1H), 8.65 (s, 1H), 7.70-7.61 (m, 2H), 7.44 (s, 1H), 7.27-7.12 (m, 6H), 6.93 (s, 1H), 3.50 (s, 2H), 3.14-2.97 (m, 4H), 2.88 (d, J=10.6 Hz, 2H), 2.46-2.36 (m, 1H), 2.22 (s, 3H), 2.07-1.93 (m, 2H), 1.78-1.58 (m, 4H). LCMS Method C: rt 4.86 min; m/z 498 [M+H]$^+$.

Example 17

2-(2-(2-(2-((3-(4-methylpiperazin-1-yl)phenyl)amino)-5-(trifluoromethyl)pyrimidin-4-yl)ethyl)phenyl)acetamide (17)

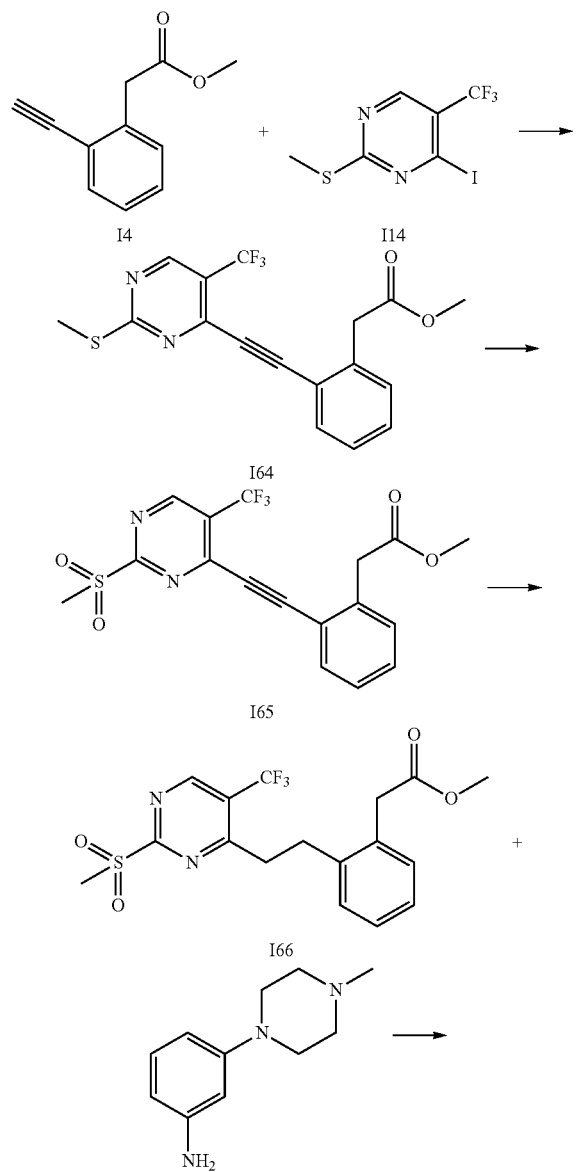

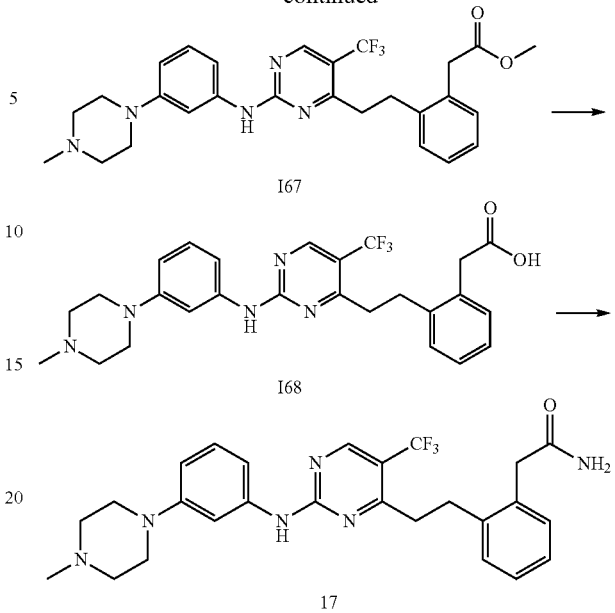

(a) Methyl 2-(2-((2-(methylthio)-5-(trifluoromethyl)pyrimidin-4-yl)ethynyl)phenyl)acetate (I64)

4-Iodo-2-(methylthio)-5-(trifluoromethyl)pyrimidine (I14) (2.00 g, 6.24 mmol), $PdCl_2(PPh_3)_2$ (438 mg, 625 μmol), CuI (119 mg, 625 μmol) and triphenylphosphine (164 mg, 625 μmol) were placed into an oven dried microwave reaction vial under nitrogen. Methyl 2-(2-ethynylphenyl)acetate (I4) (1.31 g, 7.49 mmol), THF (20 mL) and TEA (10 mL) were added and the resulting mixture was stirred at 100° C. under microwave irradiation for 10 minutes. The volatiles were evaporated under reduced pressure then the residue was adsorbed onto silica from DCM. The pre-adsorbed material was chromatographed on silica gel (0-25% ethyl acetate/petroleum benzine 40-60° C.) to give the title compound (I64) (1.571 g, 69%) as an orange solid; $^1$H NMR (400 MHz, $CDCl_3$) δ 8.71 (d, J=0.8 Hz, 1H), 7.68 (dd, J=7.7, 1.1 Hz, 1H), 7.50-7.29 (m, 3H), 3.93 (s, 2H), 3.71 (d, J=3.4 Hz, 3H), 2.62 (d, J=3.4 Hz, 3H).

(b) Methyl 2-(2-((2-(methylsulfonyl)-5-(trifluoromethyl)pyrimidin-4-yl)ethynyl)phenyl)acetate (I65)

Methyl 2-(2-((2-(methylthio)-5-(trifluoromethyl)pyrimidin-4-yl)ethynyl)phenyl)acetate (I64) (3.14 g, 8.57 mmol) was dissolved in DCM (150 mL) and the resulting solution cooled to 0° C. mCPBA (70%; 4.65 g, 18.9 mmol) was added then the reaction mixture was allowed to warm to room temperature, at which, stirring was continued overnight. The crude mixture was washed with 10% $NaHCO_3$ (200 mL) and the layers were separated. The organics were dried ($MgSO_4$) then evaporated under reduced pressure to give a light yellow solid. The solid was adsorbed onto silica then chromatographed on silica gel (0-50% ethyl acetate/petroleum benzine 40-60° C.) to give the title compound (I65) (2.876 g, 84%) as a yellow solid; $^1$H NMR (400 MHz, $CDCl_3$) δ 9.13 (d, J=0.7 Hz, 1H), 7.73 (dd, J=7.6, 0.9 Hz, 1H), 7.54-7.46 (m, 1H), 7.44-7.32 (m, 2H), 3.94 (s, 2H), 3.77-3.67 (m, 3H), 3.43 (s, 3H). LCMS Method C: rt 5.90 min; m/z 421.0 (M+Na), 399.1 (M+1), 367.0 (M-OMe), 339.1 (M-COOMe).

(c) Methyl 2-(2-(2-(2-(methylsulfonyl)-5-(trifluoromethyl)pyrimidin-4-yl)ethyl)phenyl)acetate (I66)

Methyl 2-(2-((2-(methylsulfonyl)-5-(trifluoromethyl)pyrimidin-4-yl)ethynyl)phenyl)acetate (I65) (1.50 g, 3.76 mmol) was taken up in DMF (30 mL) then 10% Pd/C (750 mg) was added. The resulting suspension was stirred under H$_2$ (1 atm) for 16 hours at room temperature. The crude reaction mixture was filtered through Celite, washing with MeOH. The filtrate was evaporated under reduced pressure to give a yellow liquid which was adsorbing onto silica. The silica adsorbed material was chromatographed on silica gel (0-100% ethyl acetate/petroleum benzine 40-60° C.) to give the title compound (I66) (1.38 g, 91%) as a yellow solid; $^1$H NMR (400 MHz, CDCl$_3$) δ 9.07 (d, J=0.7 Hz, 1H), 7.30-7.12 (m, 4H), 3.72 (s, 2H), 3.68 (s, 3H), 3.41-3.35 (m, 2H), 3.35 (s, 3H), 3.20 (dd, J=9.6, 6.3 Hz, 2H). LCMS Method C: rt 5.92 min; m/z 425.1 (M+Na), 403.1 (M+1), 401.1 (M−1), 371.1 (M-OMe), 343.1 (M-COOMe).

(d) Methyl 2-(2-(2-(2-((3-(4-methylpiperazin-1-yl)phenyl)amino)-5-(trifluoromethyl)pyrimidin-4-yl)ethyl)phenyl)acetate (I67)

3-(4-Methylpiperizin-1-nyl)aniline (36.0 mg, 186 µmol) was dissolved in trifluoroethanol (1 mL), then methyl 2-(2-(2-(2-(methylsulfonyl)-5-(trifluoromethyl)pyrimidin-4-yl)ethyl)phenyl)acetate (I66) (50 mg, 124 µmol) was added followed by trifluoroacetic acid (48 µL). The resulting mixture was stirred at 100° C. under microwave irradiation for 10 minutes. The resulting mixture was adsorbed onto silica then chromatographed on silica gel (0-10% MeOH/DCM) to give the title compound (I67) as a yellow liquid (69 mg). LCMS Method C: rt 5.10 min; m/z 514.3 (M+1). This procedure was repeated and the reaction products combined for progression into the following synthetic step.

(e) 2-(2-(2-(2-((3-(4-Methylpiperazin-1-yl)phenyl)amino)-5-(trifluoromethyl)pyrimidin-4-yl)ethyl)phenyl)acetic acid (I68)

Methyl 2-(2-(2-(2-((3-(4-methylpiperazin-1-yl)phenyl)amino)-5-(trifluoromethyl)pyrimidin-4-yl)ethyl)phenyl)acetate (I67) (150 mg, 292 µmol) was dissolved in a THF (10 mL), then LiOH.H$_2$O (36.7 mg, 876 µmol) was added. Water (2 mL) then MeOH (1 mL) was added. The resulting mixture was stirred at room temperature for 16 hours then the volatiles were removed by evaporation under reduced pressure. The residue was dissolved in MeOH (3 mL) then acidified with concentrated HCl to pH 2-3. The volatiles were evaporated under reduced pressure to give an orange residue. The residue was chromatographed on silica gel (0-20% MeOH/DCM) to give the title compound (I68) (120 mg, 82%) as a yellow crystalline solid; $^1$H NMR (400 MHz, d$_6$-DMSO) δ 11.04 (bs, 1H), 10.12 (s, 1H), 8.68 (s, 1H), 7.44 (m, 1H), 7.35 (m, 1H), 7.24-7.18 (m, 5H), 6.72 (m, 1H), 3.77-3.74 (m, partially obscured by residual water signal), 3.44 (m, 3H), 3.17-3.03 (m, 8H), 2.78 (s, 3H). LCMS Method C: rt 4.92 min; m/z 500.3 (M+1), 498.2 (M−1), 454.3 (M-COOH).

(f) 2-(2-(2-(2-((3-(4-Methylpiperazin-1-yl)phenyl)amino)-5-(trifluoromethyl)pyrimidin-4-yl)ethyl)phenyl)acetamide (17)

2-(2-(2-(2-((3-(4-Methylpiperazin-1-yl)phenyl)amino)-5-(trifluoromethyl)pyrimidin-4-yl)ethyl)phenyl)acetic acid (I68) (75.0 mg, 169 µmol) was dissolved in DMF (1 mL) then HATU (129 mg, 339 µmol), DIPEA (57 uL, 339 µmol) and ammonium chloride (181 mg, 3.39 mmol) were added. The resulting mixture was stirred at room temperature overnight then the volatiles were evaporated under reduced pressure. The residue was diluted with ethyl acetate and washed with 10% NaHCO$_3$, the layers were separated and the organic layer was dried (MgSO$_4$) then evaporated under reduced pressure to give a cream solid. The cream solid was adsorbed onto silica and chromatographed on silica gel (0-10% MeOH/DCM) to give the title compound (17) (23.3 mg, 28%) as a cream solid; $^1$H NMR (400 MHz, CD$_3$CN) δ 8.57 (s, 1H), 8.34 (s, 1H), 7.58 (s, 1H), 7.30-7.16 (m, 5H), 7.09 (d, J=8.0 Hz, 1H), 6.71 (dd, J=8.2, 1.9 Hz, 1H), 3.61 (s, 2H), 3.27 (t, J=4.9 Hz, 4H), 3.19-3.03 (m, 4H), 2.92 (bs, 4H), 2.91 (s, 3H). LCMS Method C: rt 4.43 min; m/z 499.7.

Example 18

N-Methyl-2-(2-(2-(2-((3-(4-methylpiperazin-1-yl)phenyl)amino)-5-(trifluoromethyl)pyrimidin-4-yl)ethyl)phenyl)acetamide (18)

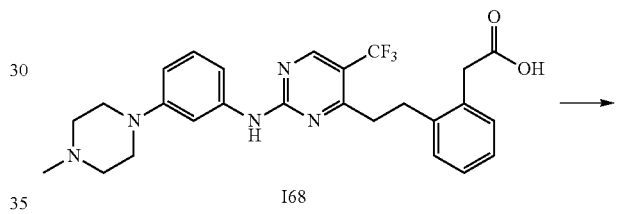

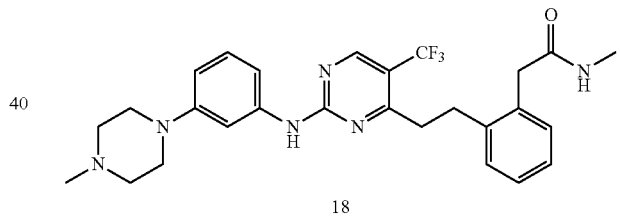

2-(2-(2-(2-((3-(4-Methylpiperazin-1-yl)phenyl)amino)-5-(trifluoromethyl)pyrimidin-4-yl)ethyl)phenyl)acetic acid (I68) (75.0 mg, 169 µmol) was dissolved in DMF (1 mL) then HATU (129 mg, 339 µmol), DIPEA (57 µL, 339 µmol) and methylamine (8.0 M in ethanol; 200 µL) were added. The resulting mixture was stirred at room temperature overnight then the volatiles were evaporated under reduced pressure. The residue was diluted with ethyl acetate and washed with 10% NaHCO$_3$, the layers were separated and the organic layer was dried (MgSO$_4$) then evaporated under reduced pressure to give a cream solid. The cream solid was adsorbed onto silica and chromatographed on silica gel (0-10% MeOH/DCM) to give the title compound (18) (9.0 mg, 10%) as a solid; $^1$H NMR (400 MHz, CD$_3$CN) δ 8.56 (d, J=0.6 Hz, 1H), 8.36-8.28 (m, 1H), 7.39 (s, 1H), 7.20 (ddd, J=5.6, 4.4, 1.9 Hz, 6H), 6.71-6.65 (m, 1H), 6.33-6.23 (m, 1H), 3.56 (s, 2H), 3.22-3.15 (m, 4H), 3.10 (s, 2H), 3.07 (s, 2H), 2.60 (d, J=4.7 Hz, 3H), 2.49-2.43 (m, 4H). LCMS Method C: rt 4.86 min; m/z 513.3.

Example 19

2-Methyl-5-(2-(2-((4-(piperazin-1-yl)phenyl)amino)-5-(trifluoromethyl)pyrimidin-4-yl)ethyl)benzamide (19)

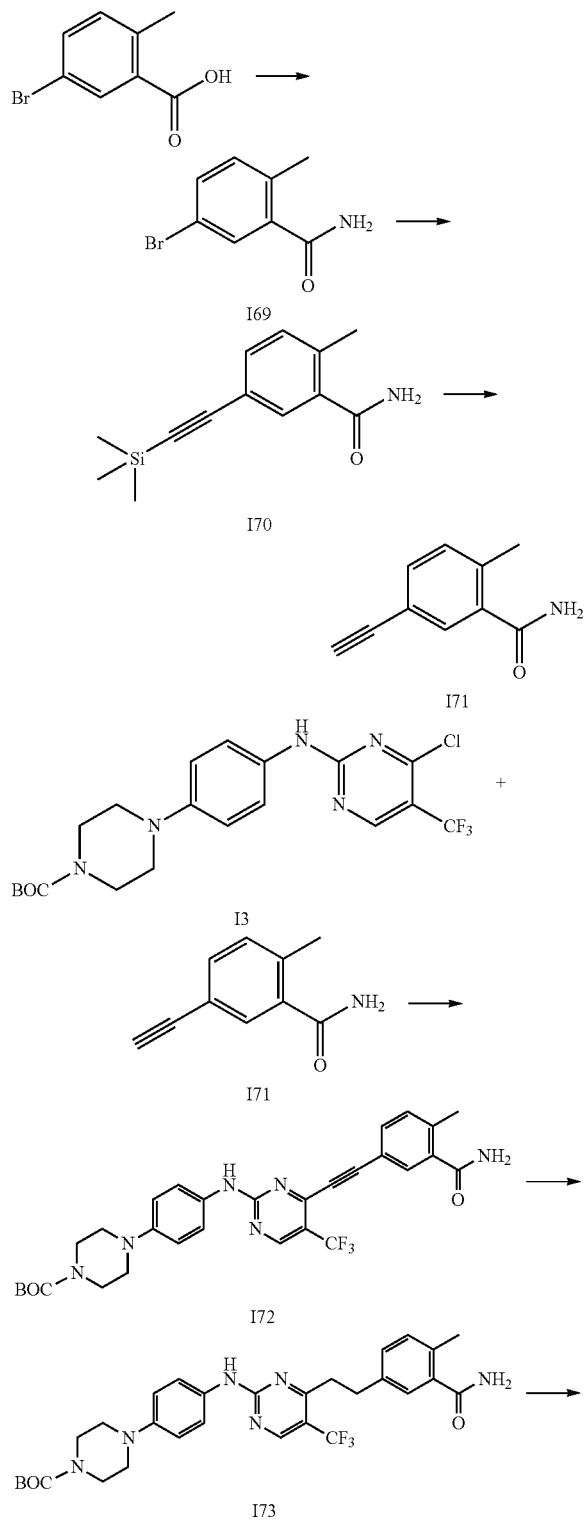

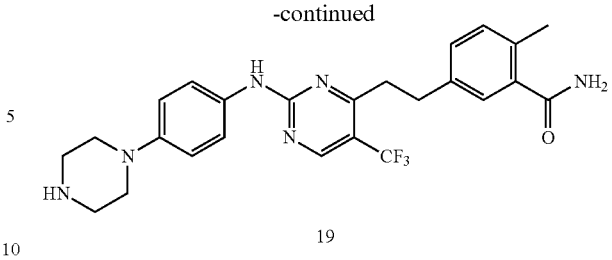

(a) 5-Bromo-2-methylbenzamide (I69)

To a mixture of 5-bromo-2-methylbenzoic acid (0.538 g, 2.50 mmol) and HATU (1.289 g, 3.390 mmol) in DMF (8 mL) was added DIPEA (0.800 mL, 4.59 mmol). The mixture was stirred for 10 minutes before addition of NH$_4$OH (0.50 mL) and then left stirring for 16 hours at room temperature. The mixture was poured in to water and cooled at 0° C. for 20 minutes before collecting the resulting precipitate via vacuum filtration to give the title compound (I69) (0.292 g, 55%); $^1$H NMR (400 MHz, CDCl$_3$) δ 7.58 (d, J=2.1 Hz, 1H), 7.45 (dd, J=8.2, 2.1 Hz, 1H), 7.12 (d, J=8.2 Hz, 1H), 5.68 (bs, 2H), 2.44 (s, 3H). LCMS Method C: rt 4.89 min; m/z 214, 216 [M+H]$^+$.

(b) 2-Methyl-5-((trimethylsilyl)ethynyl)benzamide (I70)

To a mixture of 5-bromo-2-methylbenzamide (I69) (0.292 g, 1.36 mmol), PdCl$_2$(PPh$_3$)$_2$ (0.049 g, 0.070 mmol), triphenylphosphine (0.054 g, 0.21 mmol) and copper iodide (0.036 g, 0.19 mmol) in DMF (3 mL) was added triethylamine (0.570 mL, 4.09 mmol) and trimethylsilylacetylene (0.210 mL, 1.49 mmol) and the resulting mixture heated under microwave irradiation at 120° C. for 25 minutes. The resulting mixture was concentrated under reduced pressure and purified using silica gel column chromatography (0-20% EtOAc/petroleum benzine 40-60° C.) to give the title compound (I70) (0.190 g, 60%); $^1$H NMR (400 MHz, d$_6$-DMSO) δ 7.80 (s, 1H), 7.40 (m, 3H), 7.24 (d, J=7.9 Hz, 1H), 2.36 (s, 3H), 0.22 (s, 9H).

(c) 5-Ethynyl-2-methylbenzamide (I71)

To a solution of 2-methyl-5-((trimethylsilyl)ethynyl)benzamide (I70) (0.190 g, 0.819 mmol) in THF (4 mL) at 0° C. was added 1.0 M solution TBAF in THF (0.5 mL). The mixture was then stirred under N$_2$ at 0° C. for 10 minutes and then at room temperature for 3 hours. The resulting mixture was concentrated under reduced pressure then diluted with water. The resulting precipitate was collected by vacuum filtration to give the title compound (I71) (0.087 g, 67%); $^1$H NMR (400 MHz, d$_6$-DMSO) δ 7.80 (s, 1H), 7.41 (m, 3H), 7.25 (d, J=7.7 Hz, 1H), 4.17 (s, 1H), 2.36 (s, 3H).

(d) tert-Butyl 4-(4-((4-((3-carbamoyl-4-methylphenyl)ethynyl)-5-(trifluoromethyl)pyrimidin-2-yl)amino)phenyl)piperazine-1-carboxylate (I72)

To a mixture of 5-ethynyl-2-methylbenzamide (I71) (0.041 g, 0.25 mmol), tert-butyl 4-(4-((4-chloro-5-(trifluoromethyl)

pyrimidin-2-yl)amino)phenyl)piperazine-1-carboxylate (I3) (0.105 g, 0.230 mmol), PdCl$_2$(PPh$_3$)$_2$ (0.011 g, 0.016 mmol), triphenylphosphine (0.010 g, 0.038 mmol) and copper(I) iodide (0.010 g, 0.53 mmol) in DMF (2 mL) was added triethylamine (0.091 mL, 0.65 mmol). The mixture was then heated under microwave irradiation at 120° C. for 30 minutes. The resulting mixture was concentrated under reduced pressure then purified using silica gel column chromatography (0-100% EtOAc/petroleum benzine 40-60° C.) to give title compound (I72) (0.092 g, 69%); $^1$H NMR (400 MHz, d$_6$-DMSO) δ 10.24 (s, 1H), 8.75 (s, 1H), 8.31 (s, 1H), 7.90 (s, 1H), 7.58 (m, 4H), 7.39 (m, 1H), 6.96 (d, J=9.0 Hz, 2H), 3.46 (dd, J=6.3, 3.3 Hz, 4H), 3.06 (m, 4H), 2.42 (s, 3H), 1.42 (s, 9H). LCMS Method C: rt 6.22 min; m/z 581.2 [M+H]$^+$.

(e) tert-Butyl 4-(4-((4-(3-carbamoyl-4-methylphenethyl)-5-(trifluoromethyl)pyrimidin-2-yl)amino)phenyl)piperazine-1-carboxylate (I73)

A mixture of tert-butyl 4-(4-((4-((3-carbamoyl-4-methylphenyl)ethynyl)-5-(trifluoromethyl)pyrimidin-2-yl)amino)phenyl)piperazine-1-carboxylate (I72) (0.092 g, 0.16 mmol) and 10% Pd/C (0.116 g) in DMF (5 mL) was stirred over night under a H$_2$ atmosphere. The mixture was filtered through Celite then concentrated under reduced pressure. The residue was then purified using silica gel column chromatography (0-100% EtOAc/petroleum benzine 40-60° C.) and the product triturated with methanol. The resulting precipitate was collected by vacuum filtration to give the title compound (I73) (29.5 mg, 32%); $^1$H NMR (400 MHz, d$_6$-DMSO) δ 10.00 (s, 1H), 8.61 (s, 1H), 7.66 (s, 1H), 7.55 (d, J=9.0 Hz, 2H), 7.33 (s, 1H), 7.25 (s, 1H), 7.16 (m, 2H), 6.94 (d, J=9.1 Hz, 2H), 3.46 (m, 4H), 3.04 (m, 8H), 2.32 (s, 3H), 1.42 (s, 9H). LCMS Method C: rt 6.18 min; m/z 585.3 [M+H]$^+$.

(f) 2-Methyl-5-(2-(2-((4-(piperazin-1-yl)phenyl)amino)-5-(trifluoromethyl)pyrimidin-4-yl)ethyl)benzamide (19)

To tert-butyl 4-(4-((4-(3-carbamoyl-4-methylphenethyl)-5-(trifluoromethyl)pyrimidin-2-yl)amino)phenyl)piperazine-1-carboxylate (I73) (0.029 g, 0.054 mmol) in DCM (2 mL) was added TFA (0.100 mL, 1.36 mmol) and the mixture stirred overnight (16 hours) at room temperature. The resulting mixture was then concentrated under reduced pressure and the residue taken up in EtOAc (10 mL). The resulting organic suspension was washed with 10% aqueous NaOH (10 mL) and the aqueous layer extracted with EtOAc (2×10 mL). The combined organics were washed with water (15 mL) then concentrated under reduced pressure. The residue was taken up in DCM (4 mL) and TFA (0.200 mL) and stirred overnight (16 hours). The resulting mixture was concentrated under reduced pressure then diluted with EtOAc (15 mL). The resulting solution was washed with 10% aqueous NaOH (15 mL) then the aqueous layer was extracted with EtOAc (15 mL). The combined organic extracts were washed with water (20 mL) then dried using a phase separation cartridge before concentrating under reduced pressure to give the title compound (19) (5.1 mg, 21%); $^1$H NMR (400 MHz, d$_6$-DMSO) δ 9.96 (s, 1H), 8.60 (s, 1H), 7.67 (s, 1H), 7.53 (d, J=9.0 Hz, 2H), 7.33 (s, 1H), 7.25 (s, 1H), 7.16 (m, 2H), 6.90 (d, J=9.1 Hz, 2H), 3.01 (m, 8H), 2.83 (m, 4H), 2.32 (s, 3H). LCMS Method C: rt 4.76 min; m/z 485.1 [M+H]$^+$.

Example 20

2-(2-(2-(2-((4-(4-Aminopiperidin-1-yl)phenyl)amino)-5-(trifluoromethyl)pyrimidin-4-yl)ethyl)phenyl)acetamide (20)

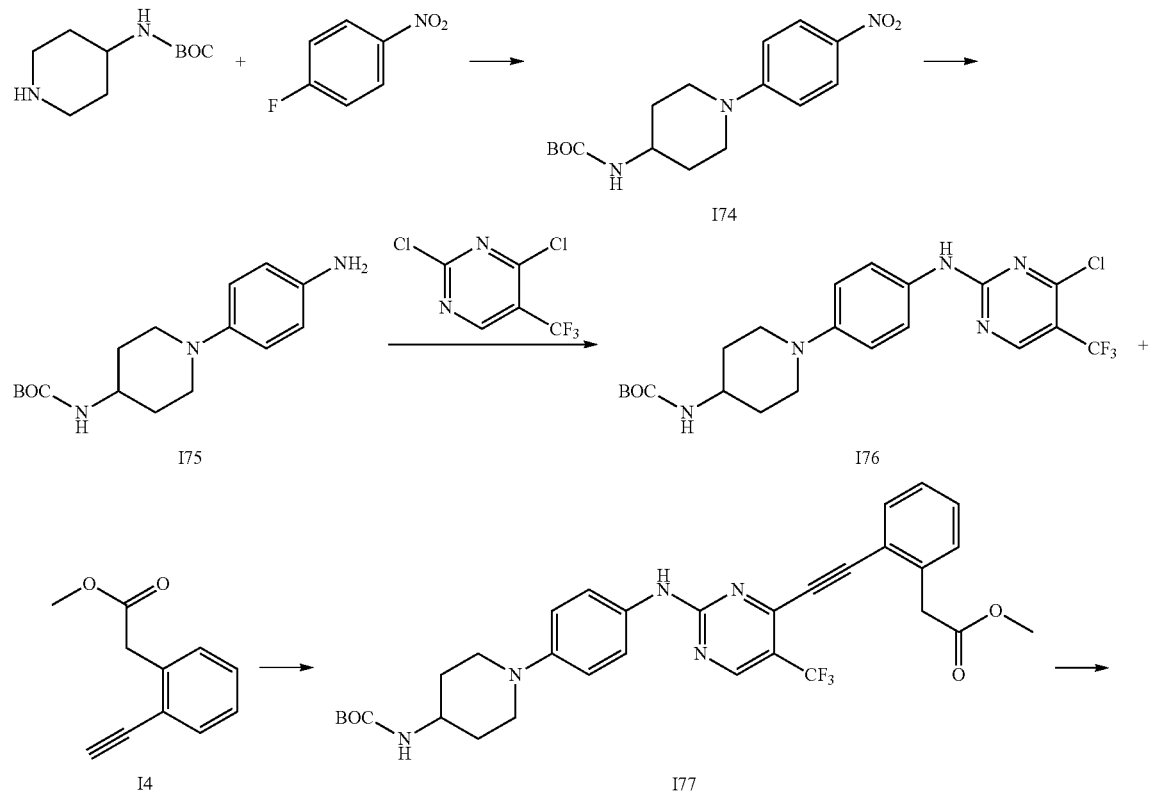

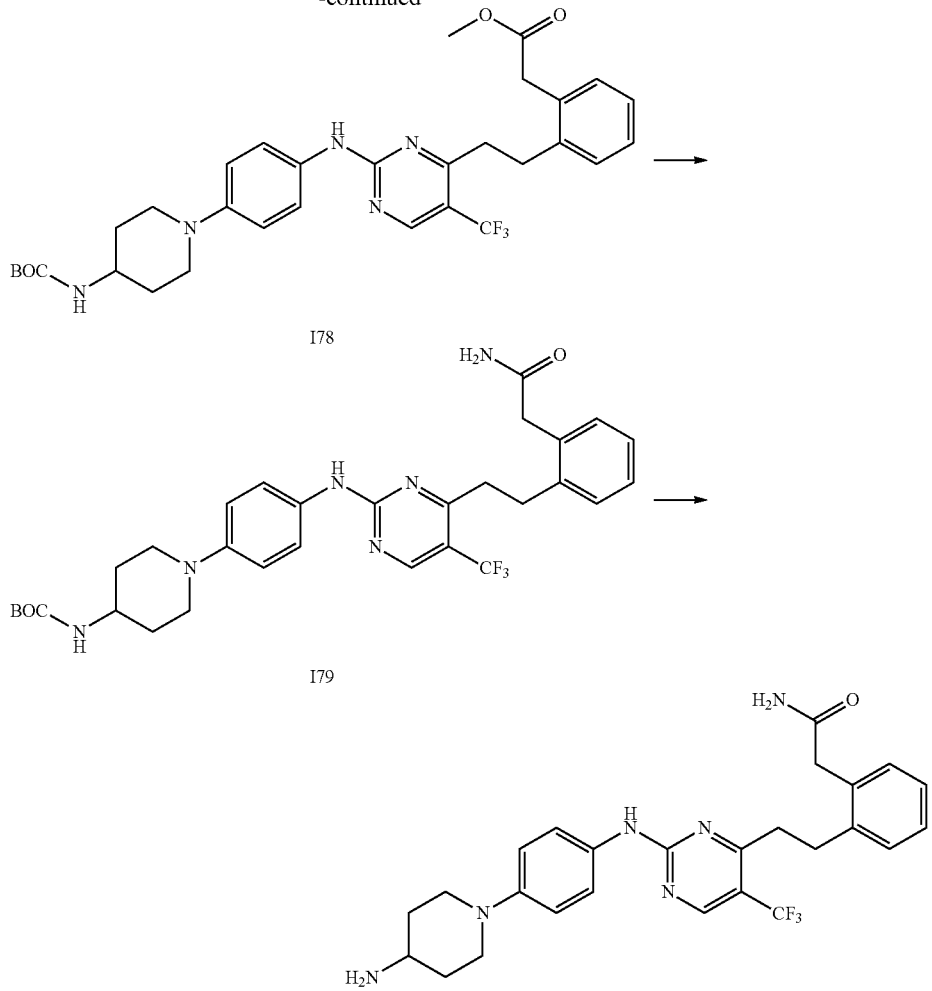

(a) tert-Butyl(1-(4-nitrophenyl)piperidin-4-yl)carbamate (I74)

tert-Butyl piperidin-4-ylcarbamate (1.200 g, 5.992 mmol) and 4-fluoronitrobenzene (0.705 g, 4.99 mmol) were placed in a 30 mL microwave vial then acetonitrile (20 mL) followed by diisopropylethylamine (1.778 mL, 9.986 mmol) were added. The reaction was heated under microwave irradiation at 150° C. for 15 minutes. The reaction mixture was diluted with EtOAc (200 mL) and 2 M aq. HCl (150 mL), the layers were separated and the aqueous layer was extracted with EtOAc (2×100 mL), the organics were combined and washed with brine (150 mL), dried (MgSO$_4$), filtered and concentrated in vacuo to give the title compound (I74) (1.040 g, 65%) as a yellow solid; $^1$H NMR (400 MHz, d$_6$-DMSO) 8.06-7.99 (m, 2H), 7.03-6.97 (m, 2H), 6.88 (d, J=7.5 Hz, 1H), 4.01-3.93 (m, 2H), 3.62-3.47 (m, 1H), 3.13-3.02 (m, 2H), 1.85-1.74 (m, 2H), 1.44-1.30 (m, 11H).

(b) tert-Butyl(1-(4-aminophenyl)piperidin-4-yl)carbamate (I75)

tert-Butyl(1-(4-nitrophenyl)piperidin-4-yl)carbamate (I74) (1.038 g, 3.230 mmol) was dissolved in dry DMF (15 mL), EtOAc (15 mL) and absolute EtOH (15 mL) under an atmosphere of nitrogen. 10% Pd/C (0.200 g) in EtOAc (5 mL) was added to the solution and the atmosphere was changed to hydrogen gas (balloon). The reaction was sealed with balloon and stirred at room temperature for 18 hours. The catalyst was removed by filtration through celite, which was washed with EtOAc (5×10 mL). The solvent was removed in vacuo to give a pink solid which was purified by silica gel chromatography using a gradient of 0-80% ethyl acetate in petroleum benzine 40-60° C. to give the title compound (I75) (0.730 g, 78%) as a purple-brown solid; $^1$H NMR (400 MHz, CDCl$_3$) δ 6.81 (d, J=8.6 Hz, 2H), 6.64 (d, J=8.7 Hz, 2H), 4.55-4.41 (m, 1H), 3.64-3.32 (m, 5H), 2.72 (t, J=11.0 Hz, 2H), 2.08-1.98 (m, 2H), 1.56 (ddd, J=23.7, 11.3, 3.9 Hz, 2H), 1.45 (s, 9H).). LCMS Method C: rt 0.38 min; m/z 292.0 [M+H]$^+$.

(c) tert-Butyl(1-(4-((4-chloro-5-(trifluoromethyl)pyrimidin-2-yl)amino)phenyl)piperidin-4-yl)carbamate (I76)

2,4-Dichloro-5-(trifluoromethyl)pyrimidine (0.551 g, 2.54 mmol) was stirred in a 1:1 t-BuOH:1,2-dichloroethane mixture (30 mL) at 0° C. A 1.0 M ZnCl$_2$ solution in diethyl ether (2.903 mL, 2.903 mmol) was added cautiously over 10 minutes, after addition the reaction was left stirring at 0° C. for 30 minutes. A solution of tert-butyl(1-(4-aminophenyl)piperidin-4-yl)carbamate (I75) (0.705 g, 2.42 mmol) in 1:1 t-BuOH:1,2-dichloroethane (15 mL) was added drop-wise over 15 minutes at 0° C., a solution of NEt$_3$ (0.405 mL, 2.903 mmol) in 1:1 t-BuOH:1,2-dichloroethane (15 mL) was added drop-wise over 15 minutes and the reaction was allowed to warm to room temperature and was stirred for 18 hours. The organic solvents were evaporated in vacuo and the crude oily solid was suspended in water (200 mL), the suspension was sonicated for 30 minutes and the product was separated by filtration, the solid was washed with water (10×20 mL) and dried under a high vacuum. The material was further purified by silica gel chromatography using a gradient of 0-50% ethyl acetate in petroleum benzine 40-60° C. to give the title compound (I76) (0.730 g, 64%) as a yellow solid; $^1$H NMR (400 MHz, d$_6$-DMSO) δ 10.41 (s, 1H), 8.71 (s, 1H), 7.46 (d, J=7.7 Hz, 2H), 6.92 (d, J=8.9 Hz, 2H), 6.84 (d, J=7.1 Hz, 1H), 3.60 (d, J=12.4 Hz, 2H), 2.69 (t, J=10.9 Hz, 2H), 1.78 (d, J=10.9 Hz, 2H), 1.54-1.34 (m, 11H). LCMS Method C: rt 6.36 min; m/z 474.1 [M+H]$^+$.

(d) Methyl 2-(2-((2-((4-(4-((tert-butoxycarbonyl)amino)piperidin-1-yl)phenyl)amino)-5-(trifluoromethyl)pyrimidin-4-yl)ethynyl)phenyl)acetate (I77)

A suspension of tert-butyl(1-(4-((4-chloro-5-(trifluoromethyl)pyrimidin-2-yl)amino)phenyl)piperidin-4-yl)carbamate (I76) (550 mg, 1.17 mmol), CuI (15 mg, 0.12 mmol), triphenylphosphine (31 mg, 0.117 mmol) and triethylamine (487 μL, 3.50 mmol) in DMF (6 mL) was sonicated for 5 minutes in a 10 mL microwave vial, to this PdCl$_2$(PPh$_3$)$_2$ (54.0 mg, 0.077 mmol) and methyl 2-(2-ethynylphenyl)acetate (I4) (305 mg, 1.75 mmol) were added and the reaction heated to 120° C. for 20 minutes under microwave irradiation. Upon cooling the reaction mixture was chromatographed on silica gel using gradient elution (0-100% ethyl acetate in petroleum benzine 40-60° C.) to yield a mixture of the title compound (I77) and homo-coupled acetylene which was used without further purification.

(e) Methyl 2-(2-(2-(2-((4-(4-((tert-butoxycarbonyl)amino)piperidin-1-yl)phenyl)amino)-5-(trifluoromethyl)pyrimidin-4-yl)ethyl)phenyl)acetate (I78)

To a solution of crude methyl 2-(2-((2-((4-(4-((tert-butoxycarbonyl)amino)piperidin-1-yl)phenyl)amino)-5-(trifluoromethyl)pyrimidin-4-yl)ethynyl)phenyl)acetate (I77) in DMF (10 mL) and triethylamine (1 mL) was added 20% Pd(OH)$_2$ (0.92 g) and the resulting suspension was stirred at room temperature overnight under an atmosphere of hydrogen. The reaction mixture was filtered through celite and the filter cake washed with EtOAc (3×75 mL). The combined filtrates were evaporated to dryness to give a brown solid, which was suspended in MeOH (25 mL) and then sonicated. The resulting suspension was filtered to give the title compound (I78) (211 mg, 29%) as a tan solid; $^1$H NMR (400 MHz, d$_6$-DMSO) δ 9.97 (s, 1H), 8.60 (s, 1H), 7.55 (d, J=9.0 Hz, 2H), 7.29-7.15 (m, 4H), 6.96-6.78 (m, 3H), 3.76 (s, 2H), 3.64-3.49 (m, 5H), 3.38 (s, 2H), 3.11-3.00 (m, 2H), 3.00-2.91 (m, 2H), 2.68 (t, J=12.0 Hz, 2H), 1.80 (d, J=10.7 Hz, 2H), 1.48 (ddd, J=15.0, 12.2, 3.5 Hz, 2H), 1.39 (s, 9H). LCMS Method C: rt 5.87 min; m/z 614 [M+H]$^+$.

(f) tert-Butyl(1-(4-((4-(2-(2-amino-2-oxoethyl)phenethyl)-5-(trifluoromethyl)pyrimidin-2-yl)amino)phenyl)piperidin-4-yl)carbamate (I79)

Lithium hydroxide mono hydrate (43.0 mg, 1.03 mmol) was added to a suspension of methyl 2-(2-(2-(2-((4-(4-((tert-butoxycarbonyl)amino)piperidin-1-yl)phenyl)amino)-5-(trifluoromethyl)pyrimidin-4-yl)ethyl)phenyl)acetate (I78) (211 mg, 0.344 mmol) in THF (10 mL), MeOH (1.0 mL) and water (1.5 mL) and the resulting mixture was stirred at room temperature for 16 hours. The organics were removed in vacuo then 2 M aqueous NaOH solution (100 mL) was added. The resulting solution was extracted with EtOAc (2×100 mL), then the combined organic extracts were dried (MgSO$_4$) and the solvent removed in vacuo to yield a white solid. The solid was dissolved in dry THF (10 mL) and dry DMF (2 mL) under an atmosphere of nitrogen. To this solution were added 1-hydroxybenzotriazole (72 mg, 0.53 mmol), EDCl (101 g, 0.529 mmol) and N,N-diisopropylethylamine (246 μL, 1.41 mmol) and the resulting mixture was stirred at room temperature for 10 minutes. Ammonium carbonate (203 mg, 2.12 mmol) was added in one portion and the reaction was stirred at room temperature for 3 days. The volatiles were removed in vacuo and the residue was taken up in EtOAc (100 mL) and saturated aqueous NaHCO$_3$ (100 mL). The layers were separated and the aqueous layer was extracted with EtOAc (70 mL). The combined organic layers were washed with water (2×100 mL), brine (50 mL), dried (MgSO$_4$) and concentrated in vacuo to give a yellow solid which was dissolved in a small amount of acetone and precipitated with petroleum benzine 40-60° C. to yield the title compound (I79) (138 mg, 65%) as a yellow solid; $^1$H NMR (400 MHz, d$_6$-DMSO) δ 9.97 (s, 1H), 8.60 (s, 1H), 7.56 (d, J=8.9 Hz, 2H), 7.44 (s, 1H), 7.27-7.12 (m, 4H), 6.96-6.81 (m, 4H), 3.58 (d, J=12.7 Hz, 2H), 3.50 (s, 2H), 3.15-2.93 (m, J=15.2, 6.3 Hz, 4H), 2.67 (t, J=12.0 Hz, 2H), 1.79 (d, J=11.4 Hz, 2H), 1.55-1.42 (m, 2H), 1.39 (s, 9H). LCMS Method C: rt 5.30 min; m/z 599 [M+H]$^+$.

(g) 2-(2-(2-(2-((4-(4-Aminopiperidin-1-yl)phenyl)amino)-5-(trifluoromethyl)pyrimidin-4-yl)ethyl)phenyl)acetamide (20)

tert-Butyl(1-(4-((4-(2-(2-amino-2-oxoethyl)phenethyl)-5-(trifluoromethyl)pyrimidin-2-yl)amino)phenyl)piperidin-4-yl)carbamate (I79) (138 mg, 0.231 mmol) was dissolved in dry dichloromethane (10 mL) under an atmosphere of nitrogen. Trifluoroacetic acid (1.0 mL, 13 mmol) was added to the solution and the reaction was stirred at room temperature overnight. The volatiles were removed in vacuo, EtOAc (50 mL) and sat. aq. NaHCO$_3$ (50 mL) were added to the residue and the layers were separated.

The aqueous layer was extracted with EtOAc (50 mL), the combined organics were washed with water (50 mL), brine (50 mL), dried (MgSO$_4$) and concentrated in vacuo to give a yellow solid which was taken up in acetone (~2 mL) and precipitated with petroleum benzine 40-60° C. to yield the title compound (20) (47 mg, 41%) as a white solid; $^1$H NMR (400 MHz, d$_6$-DMSO) δ 9.96 (d, J=6.3 Hz, 1H), 8.60 (d, J=1.4 Hz, 1H), 7.56 (t, J=7.8 Hz, 2H), 7.44 (s, 1H) 7.32-7.10 (m, 4H), 7.03-6.84 (m, 3H), 3.70-3.53 (m, 2H), 3.50 (s, 2H), 3.18-2.91 (m, 4H), 2.85-2.60 (m, J=34.4, 8.4 Hz, 3H), 1.84-

1.70 (m, 2H), 1.69-1.54 (m, J=15.3, 6.6 Hz, 2H). LCMS Method C: rt 4.64 min; m/z 499 [M+H]⁺.

Example 21

2-(2-(2-(2-((1,2,3,4-Tetrahydroisoquinolin-6-yl) amino)-5-(trifluoromethyl)pyrimidin-4-yl)ethyl)phenyl)acetamide (21)

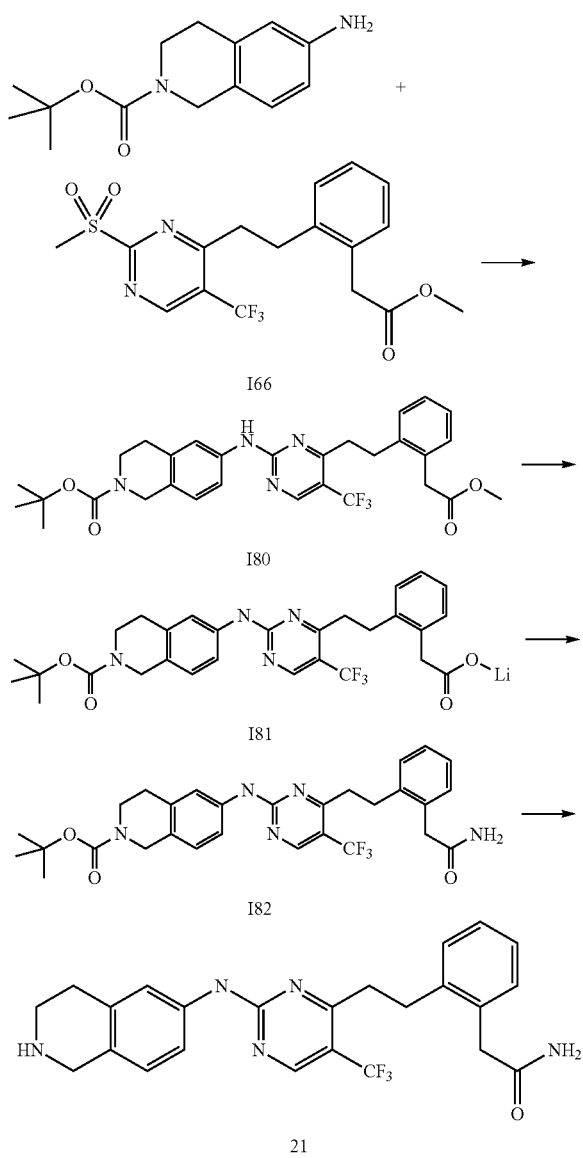

(a) tert-Butyl 6-((4-(2-(2-methoxy-2-oxoethyl)phenethyl)-5-(trifluoromethyl)pyrimidin-2-yl)amino)-3,4-dihydroisoquinoline-2(1H)-carboxylate (I80)

tert-Butyl 6-amino-3,4-dihydroisoquinoline-2(1H)-carboxylate (0.500 g, 2.01 mmol), methyl 2-(2-(2-(2-(methylsulfonyl)-5-(trifluoromethyl)pyrimidin-4-yl)ethyl)phenyl) acetate (I66) (0.675 g, 1.68 mmol), trifluoroethanol (3 mL), and TFA (0.3 mL) were loaded into a microwave tube, sonicated for two minutes, then heated under microwave irradiation at 100° C. for 20 minutes. The cooled mixture was concentrated, co-evaporated with toluene (3×20 mL) and loaded onto a 10 g SCX cartridge in methanol. The cartridge was eluted with methanol (200 mL), then with 1% methanolic methylamine (200 mL). The methanolic methylamine eluent was concentrated to give a brown oil (0.850 g). The oil was dissolved in DCM (5 mL), and Boc anhydride (549 mg, 2.52 mmol) was added. The resulting mixture was stirred under an oil bubbler for 18 hours, then diluted with DCM (50 mL) and washed with water (50 mL). The aqueous layer was extracted with DCM (2×50 mL), and the combined DCM phases dried (phase separation filter) and evaporated. Chromatography (Isolera, 40 g silica cartridge, 0-50% ethyl acetate/petroleum benzine 40-60° C.) gave the title compound (I80) (520 mg, 54%) as a yellow syrup; ¹H NMR (400 MHz, CDCl₃) δ 8.54 (s, 1H), 7.45 (s, 2H), 7.38 (s, 1H), 7.28-7.18 (m, overlaps with CDCl₃), 7.10 (d, J=8.5 Hz, 1H), 4.56 (s, 2H), 3.75 (s, 2H), 3.70-3.62 (m, 5H), 3.17-3.03 (m, 4H), 2.85 (t, J=5.6 Hz, 2H), 1.50 (s, 9H). LCMS Method C: rt 6.93 min; m/z 571.1 [M+H], m/z 515.0 [M+tBu+2H]⁺.

(b) Lithium 2-(2-(2-(2-((2-(tert-butoxycarbonyl)-1,2,3,4-tetrahydroisoquinolin-6-yl)amino)-5-(trifluoromethyl)pyrimidin-4-yl)ethyl)phenyl)acetate (I81)

tert-Butyl 6-((4-(2-(2-methoxy-2-oxoethyl)phenethyl)-5-(trifluoromethyl)pyrimidin-2-yl)amino)-3,4-dihydroisoquinoline-2(1H)-carboxylate (I80) (520 mg, 0.91 mmol) was dissolved in THF (20 mL) and a solution of lithium hydroxide hydrate (76 mg. 1.8 mmol) in water (5 mL) was added. After 18 hours the THF was removed under reduced pressure, the mixture was diluted with water (10 mL) and extracted with ethyl acetate (3×50 mL). The combined ethyl acetate phases were washed with brine, dried (sodium sulfate) and evaporated to give the title compound (I81) (414 mg, 81% yield) as a yellow solid; ¹H NMR (400 MHz, d₆-DMSO) δ 10.36 (s, 1H), 8.65 (s, 1H), 7.64 (s, 1H), 7.59 (d, J=8.4 Hz, 1H), 7.20-7.02 (m, 5H), 4.45 (s, 2H), 3.54 (t, J=5.8 Hz, 2H), 3.17 (s, 2H), 3.14-2.98 (m, 4H), 2.76 (t, J=5.7 Hz, 2H), 1.43 (s, 9H). LCMS Method C: rt 6.51 min; m/z 557.1 [M-Li+2H]⁺, 501.1 [M-tBu-Li+3H]⁺, 457.1 [M-Li-Boc+3H]⁺; m/z 555.1 [M-Li]⁻.

(c) tert-Butyl 6-((4-(2-(2-amino-2-oxoethyl)phenethyl)-5-(trifluoromethyl)pyrimidin-2-yl)amino)-3,4-dihydroisoquinoline-2(1H)-carboxylate (I82)

Lithium 2-(2-(2-(2-((2-(tert-butoxycarbonyl)-1,2,3,4-tetrahydroisoquinolin-6-yl)amino)-5-(trifluoromethyl)pyrimidin-4-yl)ethyl)phenyl)acetate (I81) (205 mg, 0.37 mmol) was dissolved in DMF (3 mL) and HATU (154 mg, 0.41 mmol) was added. After stirring for 3 minutes, ammonium carbonate (212 mg, 2.20 mmol) and DIPEA (0.26 mL, 1.5 mmol) were added and the mixture was stirred at room temperature for 18 hours. The resulting mixture was added to water (50 mL) and saturated sodium bicarbonate (10 mL) then extracted with ethyl acetate (3×50 mL). The organic extracts were washed with brine (2×50 mL), dried (sodium sulphate) and evaporated to dryness. The residue was chromatographed (12 g silica cartridge, 0-100% ethyl acetate/petroleum benzine 40-60° C.) and the product triturated with diethyl ether to give the title compound (I82) (138 mg, 67%) as an off-white foam; ¹H NMR (400 MHz, CDCl₃) δ 8.53 (s, 1H), 7.57 (s, 1H), 7.43 (d, J=8.9 Hz, 2H), 7.29-7.26 (m, overlaps with CHCl₃), 7.10 (d, J=8.4 Hz, 1H), 5.36 (d, J=14.4 Hz, 2H), 4.55 (s, 2H), 3.73 (s, 2H), 3.65 (s, 2H), 3.15-3.04 (m, 4H), 2.85 (t, J=5.8 Hz, 2H), 1.50 (s, 9H). LCMS Method C: rt 6.36 min; m/z 556.1 [M+H]⁺, 500.0 [M-tBu+2H]⁺, 456.1 [M-Boc+2H]⁺; m/z 554.2 [M-H]⁻.

(d) 2-(2-(2-(2-((1,2,3,4-Tetrahydroisoquinolin-6-yl)amino)-5-(trifluoromethyl)pyrimidin-4-yl)ethyl)phenyl)acetamide (21)

tert-Butyl 6-((4-(2-(2-amino-2-oxoethyl)phenethyl)-5-(trifluoromethyl)pyrimidin-2-yl)amino)-3,4-dihydroisoquinoline-2(1H)-carboxylate (I82) (136 mg, 0.245 mmol), DCM (10 mL) and TFA (1 mL) were stirred together at room temperature. After three hours the solution was concentrated and the residue treated with 1M sodium hydroxide (25 mL). The resulting suspension was extracted with ethyl acetate (3×50 mL) and the combined organic extracts washed with brine (100 mL), dried and evaporated to give the title compound (21) (81.6 mg, 74% yield) as a white solid; ¹H NMR (400 MHz, d₆-DMSO) δ 10.06 (s, 1H), 8.65 (s, 1H), 7.51 (s, 1H), 7.48 (dd, J=8.3, 2.1 Hz, 1H), 7.42 (s, 1H), 7.26-7.21 (m, 1H), 7.19-7.13 (m, 3H), 6.96 (d, J=8.3 Hz, 1H), 6.90 (s, 1H), 3.81 (s, 2H), 3.49 (s, 2H), 3.17 (d, J=3.1 Hz, 1H), 3.14-3.06 (m, 2H), 3.05-2.97 (m, 2H), 2.94 (t, J=5.9 Hz, 2H), 2.67 (t, J=5.6 Hz, 2H). LCMS Method C: rt: 4.76 min; m/z 456.1 [M+H]+; m/z 454.1 [M-H]⁻.

Example 22

2-(2-(2-(2-((4-(Morpholin-2-yl)phenyl)amino)-5-(trifluoromethyl)pyrimidin-4-yl)ethyl)phenyl)acetamide (22)

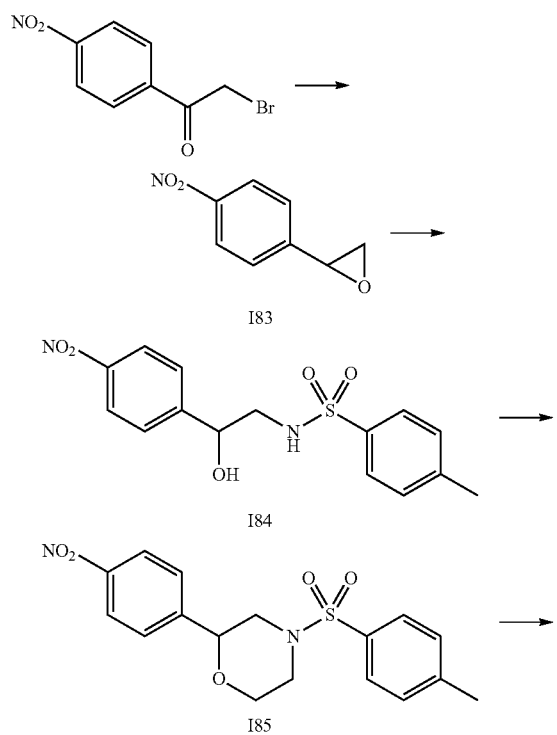

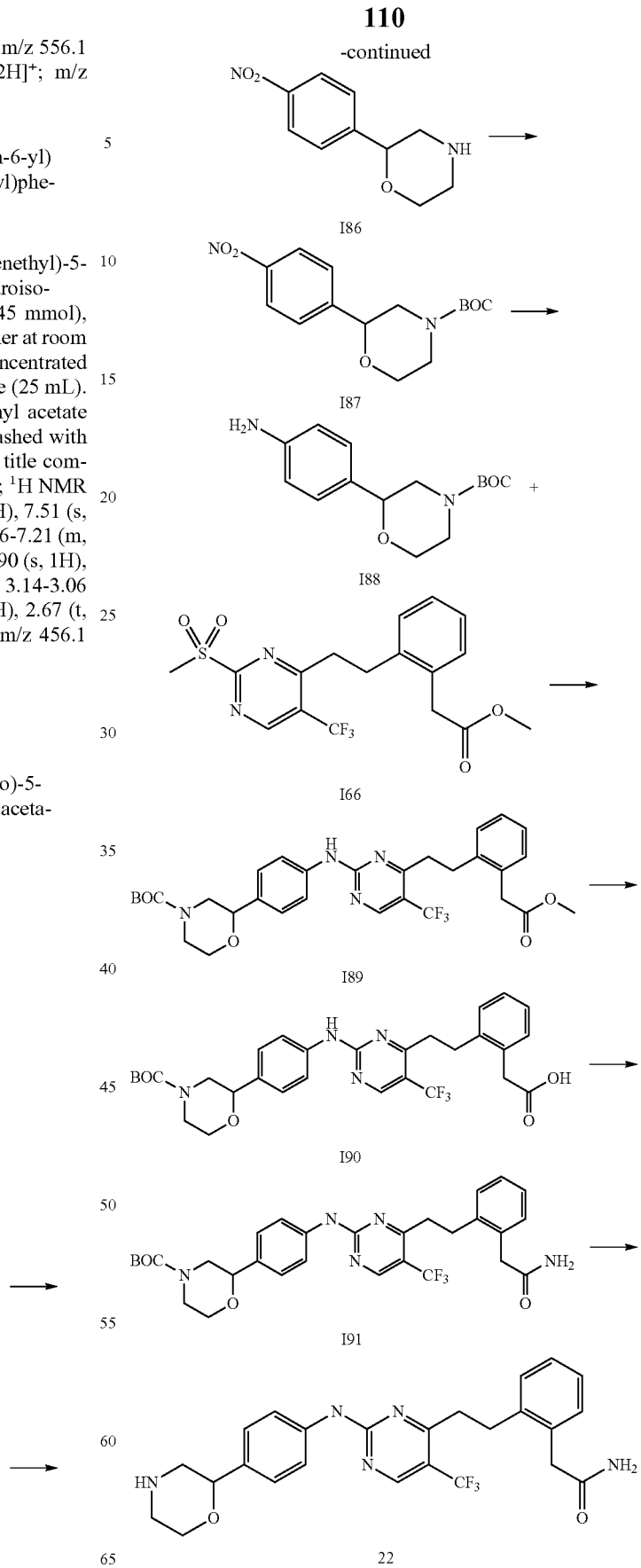

(a) 2-(4-Nitrophenyl)oxirane (I83)

2-Bromo-1-(4-nitrophenyl)ethanone (1.9 g, 7.9 mmol) was stirred in methanol (30 mL) and the suspension cooled in an ice bath. Sodium borohydride (0.33 g, 8.7 mmol) was added in one portion and after five minutes the ice bath was removed and the mixture stirred at room temperature. After three hours potassium carbonate (1.1 g, 7.9 mmol) was added, and the mixture stirred at room temperature for a further 16 hours. The methanol was evaporated, water (50 mL) was added, and the mixture extracted with DCM (3×100 mL). The combined DCM phases were washed with brine, dried (sodium sulfate) and evaporated to give the title compound (I83) (1.296 g, 99% yield) as a yellow solid; $^1$H NMR (400 MHz, CDCl$_3$) δ 8.25-8.18 (m, 2H), 7.50-7.41 (m, 2H), 3.96 (dd, J=4.1, 2.5 Hz, 1H), 3.23 (dd, J=5.5, 4.1 Hz, 1H), 2.78 (dd, J=5.5, 2.5 Hz, 1H). LCMS Method C: rt 5.42 min.

(b) N-(2-Hydroxy-2-(4-nitrophenyl)ethyl)-4-methylbenzenesulfonamide (I84)

Tosylamide (0.69 g, 4.0 mmol), 2-(4-nitrophenyl)oxirane (I83) (0.33 g, 2.0 mmol), benzyltriethylammonium chloride (46 mg, 0.20 mmol) and potassium carbonate (28 mg, 0.20 mmol) were suspended in dioxane (1.0 mL) and the resulting mixture was stirred at 90° C. After four hours the mixture was cooled to room temperature and poured into DCM (15 mL). The resulting mixture was filtered and evaporated. The residue was chromatographed (Isolera, 40 g silica cartridge, 0-100% ethyl acetate/petroleum benzine 40-60° C.) to give the title compound (I84) as an orange solid (363 mg, 38% yield); $^1$H NMR (400 MHz, d$_6$-DMSO) δ 8.19-8.13 (m, 2H), 7.64-7.59 (m, 2H), 7.57-7.52 (m, 2H), 7.34 (d, J=7.9 Hz, 2H), 7.27 (s, 1H), 5.82 (d, J=4.5 Hz, 1H), 4.71 (dd, J=10.7, 6.0 Hz, 1H), 2.92 (td, J=6.2, 1.7 Hz, 2H), 2.36 (s, 3H). LCMS Method C: rt 5.55 min, m/z 335.0 [M−H]$^-$.

(c) 2-(4-Nitrophenyl)-4-tosylmorpholine (I85)

N-(2-Hydroxy-2-(4-nitrophenyl)ethyl)-4-methylbenzenesulfonamide (I84) (0.610 g, 1.34 mmol) was sonicated in DCM (20 mL) for five minutes and cooled to 0° C. under nitrogen. A 60% dispersion of NaH (0.220 g, 5.44 mmol) was added and the mixture stirred for five minutes before (2-bromoethyl)diphenylsulfonium trifluoromethanesulfonate (1.21 g, 2.72 mmol) was added. The mixture was stirred for 17 hours, allowing the cooling bath to come to room temperature over this time. Ethyl acetate (200 mL), saturated ammonium chloride (80 mL) and water (20 mL) were added and the layers separated. The aqueous phase was extracted with ethyl acetate (2×100 mL) and the combined ethyl acetate phases were washed with brine, dried (sodium sulfate) and evaporated. The residue was chromatographed (Isolera, 40 g silica cartridge, 0-40% ethyl acetate/petroleum benzine 40-60° C.) to give the title compound (I85) (433 mg, 88%) as a white solid; $^1$H NMR (400 MHz, CDCl$_3$) b 8.22-8.18 (m, 2H), 7.63-7.59 (m, 2H), 7.52-7.48 (m, 2H), 7.33 (dd, J=8.5, 0.6 Hz, 2H), 4.71 (dd, J=10.2, 2.6 Hz, 1H), 4.10 (ddd, J=11.6, 3.4, 1.4 Hz, 1H), 3.87 (td, J=11.6, 2.7 Hz, 1H), 3.82-3.77 (m, 1H), 3.65 (ddt, J=11.6, 2.8, 1.6 Hz, 1H), 2.51 (td, J=11.6, 3.4 Hz, 1H), 2.43 (s, 3H), 2.18 (dd, J=11.5, 10.3 Hz, 1H). LCMS Method C: rt 6.20 min; m/z 363.0 [M+H]$^+$.

(d) 2-(4-Nitrophenyl)morpholine (I86)

A mixture of 2-(4-Nitrophenyl)-4-tosylmorpholine (I85) (430 mg, 1.19 mmol), phenol (670 mg, 7.12 mmol) and 33% HBr/AcOH (2.2 mL) was heated in a sealed tube (microwave tube, conventional heating) at 75° C. for twenty hours. The cooled mixture was concentrated and the residue loaded onto a 10 g SCX cartridge in methanol. The cartridge was washed with methanol (200 mL), then eluted with 1% methanolic methylamine (100 mL). The methylamine eluent was evaporated to give the title compound (I86) (204 mg, 83%) as a yellow oil; $^1$H NMR (400 MHz, CDCl$_3$) δ 8.27-8.18 (m, 2H), 7.57-7.51 (m, 2H), 4.63 (dd, J=10.3, 2.5 Hz, 1H), 4.13-4.04 (m, 1H), 3.82 (td, J=11.3, 3.1 Hz, 1H), 3.13 (dd, J=12.3, 2.5 Hz, 1H), 3.06-2.92 (m, 2H), 2.74 (dd, J=12.3, 10.3 Hz, 1H). LCMS Method C: rt 1.49, 1.58 min; m/z 209.1 [M+H]$^+$.

(e) tert-Butyl 2-(4-nitrophenyl)morpholine-4-carboxylate (I87)

2-(4-Nitrophenyl)morpholine (I86) (200 mg, 0.961 mmol) was dissolved in DCM (5 mL) then DMAP (12 mg, 10 mol %) and Boc anhydride (0.265 mL, 1.15 mmol) were added. After one hour the mixture was diluted with DCM (20 mL), and washed with water (20 mL). The aqueous phase was extracted with DCM (2×20 mL), and the combined DCM extracts were dried (hydrophobic frit) and evaporated. The residue was chromatographed (12 g silica cartridge, 0-40% ethyl acetate/petroleum benzine 40-60° C.) to give the title compound (I87) (0.230 g, 78%) as a white solid; $^1$H NMR (400 MHz, CDCl$_3$) δ 8.26-8.19 (m, 2H), 7.60-7.53 (m, 2H), 4.53 (dd, J=10.5, 2.6 Hz, 1H), 4.17 (br s, 1H), 4.05 (dd, J=11.5, 2.4 Hz, 1H), 3.97 (br s, 1H), 3.70 (td, J=11.7, 2.8 Hz, 1H), 3.06 (t, J=11.2 Hz, 1H), 2.84-2.67 (m, 1H), 1.49 (s, 9H). LCMS Method C: rt 6.23 min; m/z 209.1 [M−Boc+2H]$^+$.

(f) tert-Butyl 2-(4-aminophenyl)morpholine-4-carboxylate (I88)

tert-Butyl 2-(4-nitrophenyl)morpholine-4-carboxylate (I87) (100 mg, 0.324 mmol), activated charcoal (20 mg), iron(III) chloride hexahydrate (9 mg, 10 mol %), methanol (1 mL) and hydrazine hydrate (162 mg, 1.62 mmol @50%) were refluxed together for five hours. The mixture was filtered through cotton, and the cotton washed with DCM (5 mL). The filtrate was evaporated, and redissolved in 95% ethanol (3 mL) and ethyl acetate (2 mL). A solution of ammonium chloride (173 mg. 3.24 mmol) in water (1 mL) was added, followed by indium powder (153 mg, 1.30 mmol). The mixture was refluxed for four hours then filtered. The collected solids were washed with DCM (20 mL) and the combined filtrates then diluted with water (10 mL) and saturated sodium bicarbonate (10 mL). The aqueous phase was washed with DCM (2×25 mL), the combined DCM extracts dried (phase separation filter) and evaporated. The residue was dissolved in 95% ethanol (3 mL), and treated at reflux with further indium powder (153 mg, 1.30 mmol) and ammonium chloride (173 mg. 3.24 mmol) in water (1 mL). After three hours the mixture was diluted with water (10 mL) and filtered. The collected solids were washed sequentially with ethyl acetate (25 mL) and saturated sodium bicarbonate (10 mL). The filtrate aqueous phase was separated, and washed with ethyl acetate (2×25 mL). The combined organic extracts were washed with brine (50 mL), dried and evaporated. The residue was chromatographed (12 g silica cartridge, 0-100% ethyl acetate/petroleum benzine 40-60° C.) to give the title compound (I88) (51.4 mg, 57% yield) as a yellow oil; $^1$H NMR (400 MHz, CDCl$_3$) δ 7.19-7.12 (m, 2H), 6.71-6.63 (m, 2H), 4.33-4.25 (m, 1H), 4.03-3.85 (m, 3H), 3.73-3.60 (m, 3H), 3.02 (s, 1H), 2.84 (s, 1H). LCMS Method C: rt: 4.72 min; m/z 179.1 [M−Boc+2H]$^+$.

(g) tert-Butyl 2-(4-((4-(2-(2-methoxy-2-oxoethyl) phenethyl)-5-(trifluoromethyl)pyrimidin-2-yl)amino) phenyl)morpholine-4-carboxylate (I89)

tert-Butyl 2-(4-aminophenyl)morpholine-4-carboxylate (I88) (50 mg, 0.18 mmol) and methyl 2-(2-(2-(2-(methylsulfonyl)-5-(trifluoromethyl)pyrimidin-4-yl)ethyl)phenyl)acetate (I67) (72 mg, 0.18 mmol) were heated in trifluoroethanol (1.2 mL) and TFA (0.12 mL) under microwave irradiation (100° C./20 minutes). The mixture was concentrated, evaporated from toluene and loaded onto a 5 g SCX cartridge in methanol (1 mL). The cartridge was washed with methanol (50 mL), and then eluted with 1% methylamine/methanol (50 mL). The basic eluent was concentrated, and taken up in dichloromethane (5 mL). Boc anhydride (0.062 mL, 0.27 mmol) was added, and the mixture stirred at room temperature for 18 hours.

The mixture was evaporated onto silica gel, and chromatographed (12 g silica cartridge, 0-60% ethyl acetate/petroleum benzine 40-60° C.) to give the title compound (I89) (46 mg, 42% yield) as a pale yellow oil; $^1$H NMR (400 MHz, CDCl$_3$) b 8.55 (s, 1H), 7.64 (d, J=8.6 Hz, 2H), 7.47 (s, 1H), 7.37 (d, J=8.5 Hz, 2H), 7.29-7.18 (m, overlaps with CHCl$_3$), 4.41 (d, J=8.4 Hz, 1H), 4.08 (m, 3H), 3.76 (s, 2H), 3.73-3.64 (m, 4H), 3.16-2.98 (m, 5H), 2.85 (s, 1H), 1.51-1.47 (m, 9H). LCMS Method C: rt 6.88 min; m/z 601.1 [M+H]$^+$, 545.1 [M-tBu+2H]$^+$.

(h) 2-(2-(2-(2-((4-(4-(tert-Butoxycarbonyl)morpholin-2-yl)phenyl)amino)-5-(trifluoromethyl)pyrimidin-4-yl)ethyl)phenyl)acetic acid (I90)

tert-Butyl 2-(4-((4-(2-(2-methoxy-2-oxoethyl)phenethyl)-5-(trifluoromethyl)pyrimidin-2-yl)amino)phenyl)morpholine-4-carboxylate (I89) (46 mg, 0.077 mmol) was dissolved in THF (2 mL), and lithium hydroxide hydrate (6.0 mg, 0.15 mmol) in water (0.5 mL) was added. After 18 hours the mixture was concentrated, diluted with water (5 mL) and the pH adjusted to 3 with 6 M HCl. The mixture was extracted with ethyl acetate (3×10 mL), and the combined organic extracts washed with brine (20 mL), dried over sodium sulfate and evaporated to give the title compound (I90) (39 mg, 85% yield) as a pale yellow syrup; $^1$H NMR (400 MHz, CDCl$_3$) δ 8.52 (s, 1H), 7.54 (d, J=8.4 Hz, 2H), 7.35-7.27 (m, 4H), 4.38 (d, J=10.1 Hz, 1H), 4.07-3.80 (m, 5H), 3.67 (td, J=11.7, 2.7 Hz, 1H), 3.06 (s, 4H), 2.84 (s, 2H), 1.47 (s, 9H). LCMS Method C: rt 6.49 min; m/z 587.1 [M+H]$^+$, 531.0 [M-tBu+2H]$^+$, 487.1 [M-Boc+2H]+; m/z 585.2 [M–H]$^-$.

(i) tert-Butyl 2-(4-((4-(2-(2-amino-2-oxoethyl)phenethyl)-5-(trifluoromethyl)pyrimidin-2-yl)amino)phenyl)morpholine-4-carboxylate (I91)

2-(2-(2-(2-((4-(4-(tert-Butoxycarbonyl)morpholin-2-yl)phenyl)amino)-5-(trifluoromethyl)pyrimidin-4-yl)ethyl) phenyl)acetic acid (I90) (39 mg, 0.066 mmol) was dissolved in DMF (3 mL) and ammonium carbonate (38 mg, 0.40 mmol), HATU (28 mg, 0.073 mmol) and DIPEA (0.046 mL, 0.27 mmol) were added. The yellow mixture was stirred at room temperature for 18 hours then added to water (30 mL) and brine (10 mL). The mixture was extracted with ethyl acetate (3×30 mL), and the combined ethyl acetate phases washed with brine (50 mL), dried over sodium sulfate and evaporated. The residue was chromotographed (4 g deactivated* silica cartridge, 0-100% 1% isopropylamine in ethyl acetate/petroleum benzine 40-60° C.) to give the title compound (I91) (23.3 mg, 60% yield) as a colourless glass; $^1$H NMR (400 MHz, CDCl$_3$) δ 8.53 (s, 1H), 7.78 (s, 1H), 7.61 (d, J=8.4 Hz, 2H), 7.37 (d, J=8.5 Hz, 2H), 7.31-7.19 (m, 5H, overlaps with CHCl$_3$), 5.58 (s, 1H), 5.42 (s, 1H), 4.40 (d, J=8.5 Hz, 1H), 4.08-3.84 (m, 3H), 3.74-3.63 (m, 3H), 3.16-3.00 (m, 5H), 2.85 (s, 1H), 1.48 (s, 9H). LCMS Method C: rt 6.29 min; m/z 586.1 [M+H]$^+$, 530.1 [M-tBu+2H]$^+$, 608.1 [M+Na]+; m/z 584.1 [M–H]$^-$.

* cartridge deactivated by treating with 3 volumes of 1% isopropylamine in ethyl acetate followed by rinsing with a 3 volume gradient of 100-0% of 1% isopropylamine in ethyl acetate/petroleum benzine 40-60° C.

(j) 2-(2-(2-(2-((4-(morpholin-2-yl)phenyl)amino)-5-(trifluoromethyl)pyrimidin-4-yl)ethyl)phenyl)acetamide (22)

tert-Butyl 2-(4-((4-(2-(2-amino-2-oxoethyl)phenethyl)-5-(trifluoromethyl)pyrimidin-2-yl)amino)phenyl)morpholine-4-carboxylate (I91) (23 mg, 0.039 mmol) was stirred with DCM (3 mL) and TFA (0.3 mL). After 18 hours the mixture was concentrated and the residue suspended in 10% aqueous NaOH (1 mL) and brine (1 mL). The mixture was extracted with ethyl acetate (5×3 mL), and the combined ethyl acetate phases washed with brine (20 mL), dried over sodium sulfate and evaporated to give the title compound (22) (17 mg, 89%) as a white solid; $^1$H NMR (400 MHz, d$_6$-DMSO) δ 10.19 (s, 1H), 8.67 (s, 1H), 7.74-7.67 (m, 2H), 7.42 (s, 1H), 7.27 (d, J=8.6 Hz, 2H), 7.25-7.21 (m, 1H), 7.19-7.14 (m, 3H), 6.91 (s, 1H), 4.32 (dd, J=10.1, 2.1 Hz, 1H), 3.86 (d, J=10.9 Hz, 1H), 3.58 (dt, J=11.2, 7.2 Hz, 1H), 3.50 (s, 2H), 3.15-2.98 (m, 4H), 2.89 (dd, J=12.3, 2.2 Hz, 1H), 2.72 (d, J=5.2 Hz, 2H). LCMS Method C: rt 4.75 min; m/z 486.1 [M+H]$^+$, 508.0 [M+Na]+; m/z 484.1 [M–H]$^-$.

Example 23

2-(2-(2-(2-((4-(1-Acetylpiperidin-4-yl)phenyl) amino)-5-(trifluoromethyl)pyrimidin-4-yl)ethyl)phenyl)acetamide

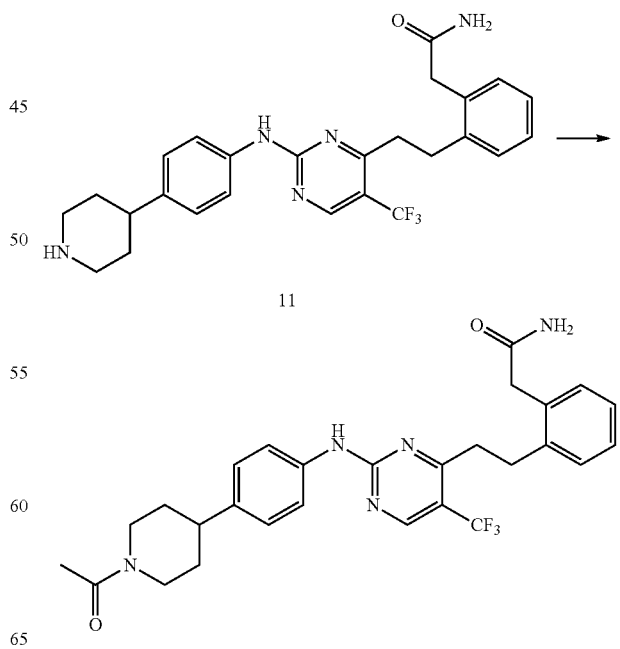

Triethylamine (34.6 μL, 0.248 mmol) and acetic anhydride (23.4 μL, 0.248 mmol) were added to a solution of the 2-(2-(2-(2-((4-(piperidin-4-yl)phenyl)amino)-5-(trifluoromethyl)pyrimidin-4-yl)ethyl)phenyl)acetamide (I1) (30 mg, 0.062 mmol) in DMF (10 mL). The reaction mixture was stirred at room temperature for 20 hours. The volatiles were removed in vacuo and the residue was diluted with EtOAc (20 mL) and sat. aq. NaHCO$_3$ (20 mL). The layers were separated and the aqueous layer was extracted with EtOAc (2×20 mL). The combined organic layers were washed with water (20 mL), brine (20 mL) and dried over Na$_2$SO$_4$. The solution was filtered and concentrated in vacuo to give a white solid which was suspended in DCM (ca 2 mL) and cyclohexane (ca 10 mL). The suspension was filtered to give the title compound (23) (24 mg, 72%) as an off-white solid; $^1$H NMR (400 MHz, d$_6$-DMSO) δ 10.14 (s, 1H), 8.66 (s, 1H), 7.71-7.63 (m, 2H), 7.42 (s, 1H), 7.27-7.12 (m, 6H), 6.91 (s, 1H), 4.57-4.48 (m, 1H), 3.93-3.90 (m, 1H), 3.50 (s, 2H), 3.16-3.06 (m, 3H), 3.06-2.97 (m, 2H), 2.77-2.65 (m, 1H), 2.62-2.51 (m, peak obscured by solvent), 2.03 (s, 3H), 1.81-1.74 (m, 2H), 1.57 (qd, J=12.6, 4.2 Hz, 1H), 1.49-1.35 (m, 1H); LCMS Method C: rt 5.89 min; m/z 526 [M+H]$^+$.

Example 24

2-(2-(2-(2-((4-(4-(Dimethylamino)piperidin-1-yl)phenyl)amino)-5-(trifluoromethyl)pyrimidin-4-yl)ethyl)phenyl)acetamide (24)

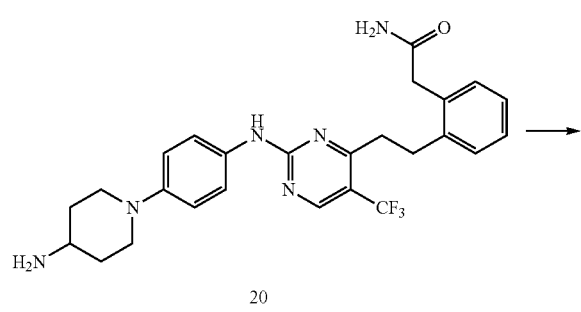

20

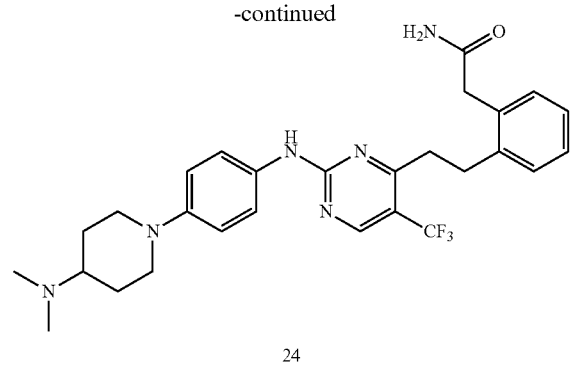

24

To a suspension of 2-(2-(2-(2-((4-(4-aminopiperidin-1-yl)phenyl)amino)-5-(trifluoromethyl)pyrimidin-4-yl)ethyl)phenyl)acetamide (20) (30 mg, 0.060 mmol) in anhydrous methanol (2 mL) was added a 37% aq. solution of formaldehyde (7 μL, 0.06 mmol) and sodium triacetoxyborohydride (0.038 g, 0.18 mmol) under an atmosphere of nitrogen. The resulting suspension was stirred at room temperature for 2.5 hours. The volatiles were removed in vacuo and the residue partitioned between in EtOAc (50 mL) and water (50 mL). The organic layer was separated, dried (MgSO$_4$) and the solvent removed in vacuo to yield a crude yellow oil. The crude oil was chromatographed on silica gel (Biotage Isolera: 0-100% MeOH in EtOAc) to yield the title compound (24) (11 mg, 35%) as a yellow solid; $^1$H NMR (400 MHz, d$_4$-MeOD) δ 8.51 (s, 1H), 7.57-7.51 (m, 2H), 7.31-7.18 (m, 4H), 7.04-6.99 (m, 2H), 3.76-3.67 (m, 4H), 3.20-3.13 (m, 2H), 3.09-3.03 (m, J=9.9, 5.5 Hz, 2H), 2.76-2.64 (m, 2H), 2.34 (s, 7H), 2.01 (d, J=12.7 Hz, 2H), 1.66 (qd, J=12.4, 3.9 Hz, 2H). LCMS Method C: rt 4.77 min; m/z=527 [M+1]$^+$.

Example 25

2-(2-(2-(2-((4-(Piperazin-1-ylmethyl)phenyl)amino)-5-(trifluoromethyl)pyrimidin-4-yl)ethyl)phenyl)acetamide (25)

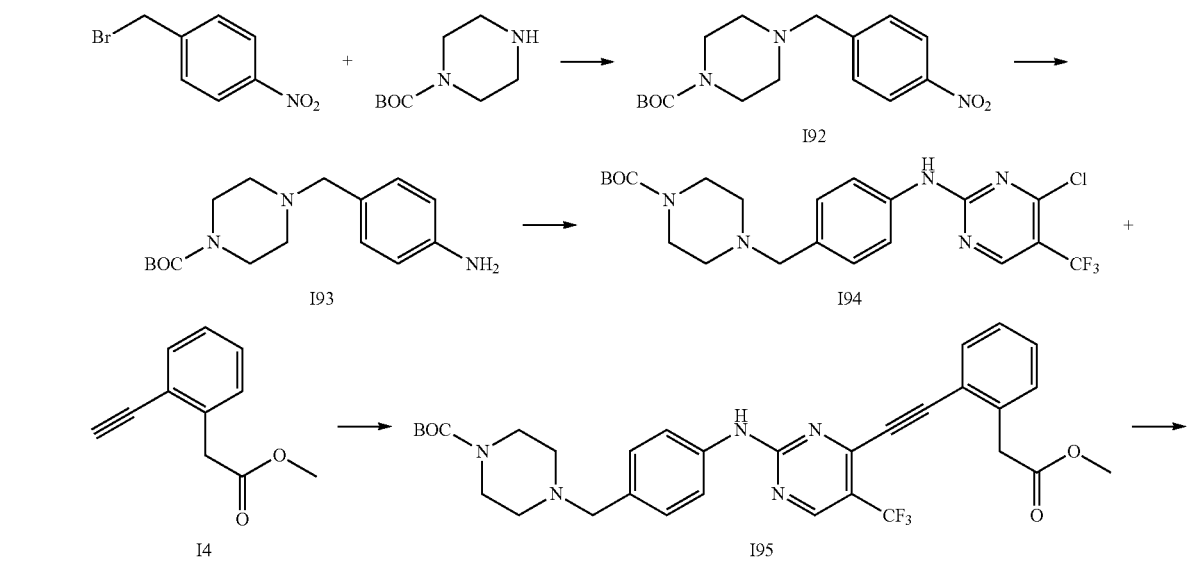

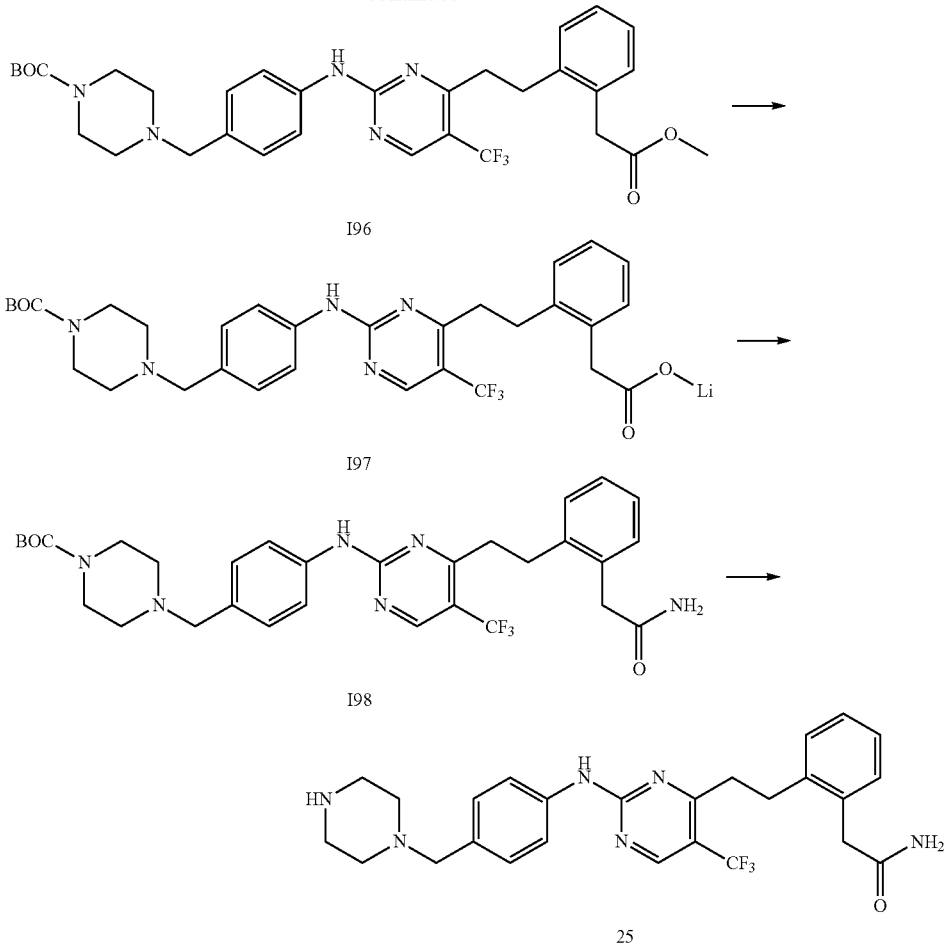

(a) tert-Butyl 4-(4-nitrobenzyl)piperazine-1-carboxylate (I92)

1-(Bromomethyl)-4-nitrobenzene (1.08 g, 5.00 mmol) was added to a vigorously stirred mixture of tert-butyl piperazine-1-carboxylate (1.02 g, 5.50 mmol) and sodium carbonate (0.583 g, 5.50 mmol) in DMF (5 mL) at room temperature and the resulting mixture stirred for two hours. Water (25 mL) was added, and the resulting suspension was allowed to stand for five minutes then filtered. The collected solid was washed with water (25 mL) and air-dried to give the title compound (I92) (1.523 g, 95% yield); $^1$H NMR (400 MHz, CDCl$_3$) δ 8.32-8.10 (m, 2H), 7.51 (d, J=8.8 Hz, 2H), 3.59 (s, 2H), 3.52-3.39 (m, 4H), 2.43-2.34 (m, 4H), 1.45 (s, 9H). LCMS Method C: rt 4.58 min, m/z 266.1 [M-tBu+2H]$^+$, 222.1 [M-Boc+2H]$^+$.

(b) tert-Butyl 4-(4-aminobenzyl)piperazine-1-carboxylate (I93)

tert-Butyl 4-(4-nitrobenzyl)piperazine-1-carboxylate (I92) (0.500 g, 1.56 mmol), ethyl acetate (100 mL) and 10% Pd/C (150 mg) were agitated under a hydrogen atmosphere at 50 psi. After two hours the mixture was filtered through celite and concentrated. The residue was chromatographed (12 g silica cartridge, 0-60% ethyl acetate/petroleum benzine 40-60° C.) to give the title compound (I93) (327 mg, 72% yield) as a white solid; $^1$H NMR (400 MHz, CDCl$_3$) δ 7.11-7.05 (m, 2H), 6.67-6.61 (m, 2H), 3.62 (s, 2H), 3.43-3.37 (m, 6H), 2.40-2.30 (m, 4H), 1.45 (s, 9H). LCMS Method C: rt 1.80 min; m/z 292.1 [M+H]$^+$.

(c) tert-Butyl 4-(4-((4-chloro-5-(trifluoromethyl) pyrimidin-2-yl)amino)benzyl)piperazine-1-carboxylate (I94)

2,4-Dichloro-5-(trifluoromethyl)pyrimidine (0.546 g, 2.52 mmol) in 1:1 dichloroethane: tert-butanol was cooled to 0° C. under nitrogen. A 1.0 M solution of zinc(II) chloride in diethyl ether (3.43 mL, 3.34 mmol) was added, and the mixture stirred for one hour at 0° C. tert-Butyl 4-(4-aminobenzyl)piperazine-1-carboxylate (I93) (0.667 g, 2.29 mmol) in 1:1 dichloroethane: tert-butanol (20 mL) was added dropwise over thirty minutes, followed by triethylamine (0.351 mL, 2.52 mmol) in 1:1 dichloroethane: tert-butanol (10 mL). The mixture was stirred overnight, allowing the ice bath to come to room temperature over this time. The mixture was concentrated onto silica gel and chromatographed (40 g silica cartridge, 0-100% ethyl acetate/petroleum benzine 40-60° C.) to give a residue which was triturated with petroleum benzine 40-60° C. to give the title compound (I94) (0.976 g, 90%) as an off white solid; $^1$H NMR (400 MHz, d$_4$-MeOD) δ 8.68 (d, J=0.6 Hz, 1H), 7.85 (d, J=8.6 Hz, 2H), 7.51 (d, J=8.6 Hz, 2H), 4.30 (s, 2H), 3.27-3.00 (br, overlaps with solvent), 1.47 (s, 9H). LCMS Method C: 5.08 min; m/z 472.1 [M+H]+; m/z 470.1 [M−H]$^-$.

(d) tert-Butyl 4-(4-((4-((2-(2-methoxy-2-oxoethyl) phenyl)ethynyl)-5-(trifluoromethyl)pyrimidin-2-yl) amino)benzyl)piperazine-1-carboxylate (I95)

tert-Butyl 4-(4-((4-chloro-5-(trifluoromethyl)pyrimidin-2-yl)amino)benzyl)piperazine-1-carboxylate (I94) (0.500 g, 1.06 mmol) and methyl 2-(2-ethynylphenyl)acetate (I4) (0.203 g, 1.17 mmol) were dissolved in DMF (10 mL) and bis(triphenylphosphine)palladium(II) chloride (37 mg, 5 mol %) was added. The mixture was degassed with nitrogen for ten minutes, then copper(I) iodide (10 mg, 5 mol %) and triethylamine (0.738 mL, 5.30 mmol) were added. The mixture was heated under microwave irradiation (100° C./20 minutes) then concentrated. Chromatography of the residue (12 g silica cartridge, 0-100% ethyl acetate/petroleum benzine 40-60° C.) gave the title compound (I95) (192 mg, 30% yield) as a brown oil; $^1$H NMR (400 MHz, CDCl$_3$) δ 8.63 (s, 1H), 7.68 (dd, J=7.6, 1.0 Hz, 1H), 7.59 (d, J=8.4 Hz, 2H), 7.50 (s, 1H), 7.42 (dd, J=7.5, 1.4 Hz, 1H), 7.38-7.29 (m, 4H), 3.95 (s, 2H), 3.70 (s, 3H), 3.50 (s, 2H), 3.45-3.40 (m, 4H), 2.43-2.35 (m, 4H), 1.45 (s, 9H). LCMS Method C: rt 5.30 min; m/z 610.1 [M+H]$^+$, m/z 608.2 [M−H]$^−$.

(e) tert-Butyl 4-(4-((4-(2-(2-methoxy-2-oxoethyl) phenethyl)-5-(trifluoromethyl)pyrimidin-2-yl)amino) benzyl)piperazine-1-carboxylate (I96)

tert-Butyl 4-(4-((4-((2-(2-methoxy-2-oxoethyl)phenyl) ethynyl)-5-(trifluoromethyl)pyrimidin-2-yl)amino)benzyl) piperazine-1-carboxylate (I95) (190 mg, 0.312 mmol) was stirred vigorously with 10% Pd/C (100 mg) in DMF (10 mL) under an atmosphere of hydrogen. After two the reaction was transferred to a Parr tube with the aid of ethyl acetate (10 mL) and the mixture was hydrogenated at 45 psi. After 18 hours Pearlman's catalyst (100 mg) and triethylamine (0.2 mL) were added, and the mixture agitated under hydrogen at 40 psi. After three hours the mixture was diluted with ethyl acetate (50 mL) and filtered through celite, washing the celite with ethyl acetate (2×25 mL). The filtrate was diluted with ethyl acetate (100 mL) and washed with 5% lithium chloride solution (3×100 mL). The organic phase was dried over sodium sulfate and evaporated to give the title compound (I96) (127 mg, 66% yield) as a yellow syrup; $^1$H NMR (400 MHz, CDCl$_3$) δ 8.54 (s, 1H), 7.63-7.56 (m, 2H), 7.46 (s, 1H), 7.31 (d, J=8.5 Hz, 2H), 7.26-7.17 (m, 4H), 3.75 (s, 2H), 3.68 (s, 3H), 3.50 (s, 2H), 3.46-3.40 (m, 4H), 3.17-3.05 (m, 4H), 2.45-2.34 (m, 4H), 1.45 (s, 9H). LCMS Method C: rt 5.63 min; m/z 614.2 [M+H]+; m/z 612.1 [M−H]$^−$.

(f) Lithium 2-(2-(2-(2-((4-((4-(tert-butoxycarbonyl) piperazin-1-yl)methyl)phenyl)amino)-5-(trifluoromethyl)pyrimidin-4-yl)ethyl)phenyl)acetate (I97)

tert-Butyl 4-(4-((4-(2-(2-methoxy-2-oxoethyl)phenethyl)-5-(trifluoromethyl)pyrimidin-2-yl)amino)benzyl)piperazine-1-carboxylate (I96) (120 mg, 0.196 mmol) was dissolved in THF (4 mL), and a solution of lithium hydroxide hydrate (25 mg, 0.59 mmol) in water (1 mL) was added. The mixture was stirred at room temperature for 18 hours then concentrated and the residue evaporated twice from toluene to give the title compound (I97) as a tan solid which was used without purification. LCMS Method C: rt 5.17 min; m/z 600.2 [M-Li+2H]+; 544.1 [M-tBu-Li+3H]$^+$; m/z 598.2 [M-Li]$^−$.

(g) tert-Butyl 4-(4-((4-(2-(2-amino-2-oxoethyl)phenethyl)-5-(trifluoromethyl)pyrimidin-2-yl)amino)benzyl)piperazine-1-carboxylate (I98)

The crude lithium 2-(2-(2-(2-((4-((4-(tert-butoxycarbonyl)piperazin-1-yl)methyl)phenyl)amino)-5-(trifluoromethyl)pyrimidin-4-yl)ethyl)phenyl)acetate (I97) was dissolved in DMF (2 mL) and ammonium chloride (210 mg, 3.92 mmol), HATU (149 mg, 0.392 mmol) and DIPEA (68.0 µL, 0.392 mmol) were added. The resulting mixture was stirred at room temperature for 18 hours, then concentrated. The residue was partitioned between saturated sodium bicarbonate (50 mL) and ethyl acetate (50 mL); the aqueous phase was extracted with further ethyl acetate (2×50 mL) and the combined ethyl acetate phases washed with brine (3×50 mL), dried over sodium sulfate and evaporated. The residue was chromatographed (4 g silica cartridge, 20-100% gradient of 1% isopropylamine in ethyl acetate/petroleum benzine 40-60° C., then 0-5% gradient methanol/1% isopropylamine in ethyl acetate) to give a residue which was chromatographed (12 g silica cartridge, 80-100% gradient of 1% isopropylamine in ethyl acetate/petroleum benzine 40-60° C.) to give the title compound (I98) (34 mg, 29% yield over two steps from ester) as a white foam; $^1$H NMR (400 MHz, CDCl$_3$) δ 8.54 (s, 1H), 7.62 (s, 1H), 7.57 (d, J=8.5 Hz, 2H), 7.31 (d, J=8.5 Hz, 2H), 7.29-7.20 (m, 8H), 5.38 (s, 2H), 3.73 (s, 2H), 3.49 (s, 2H), 3.46-3.39 (m, 4H), 3.16-3.04 (m, 4H), 2.44-2.34 (m, 4H), 1.45 (s, 9H). LCMS Method C: rt 5.08 min; m/z 599.1 [M+H]$^+$, 499.1 [M-Boc+2H]+; m/z 597.2 [M−H]$^−$.

(h) 2-(2-(2-(2-((4-(Piperazin-1-ylmethyl)phenyl) amino)-5-(trifluoromethyl)pyrimidin-4-yl)ethyl)phenyl)acetamide (25)

tert-Butyl 4-(4-((4-(2-(2-amino-2-oxoethyl)phenethyl)-5-(trifluoromethyl)pyrimidin-2-yl)amino)benzyl)piperazine-1-carboxylate (I98) (34 mg, 0.057 mmol) was dissolved in DCM (4 mL) and TFA (0.4 mL) was added. The resulting mixture was stirred for 16 hours at room temperature then concentrated under reduced pressure. The residue was suspended in 10% aqueous NaOH (2 mL) and brine (3 mL) then extracted with ethyl acetate (4×5 mL). The combined organic phases were washed with brine, dried (sodium sulphate) and evaporated to dryness. The residue was triturated with diethyl ether to give the title compound (25) (27.5 mg, 98%) as a yellow solid; $^1$H NMR (400 MHz, d$_6$-DMSO) δ 10.17 (s, 1H), 8.66 (s, 1H), 7.72-7.66 (m, 2H), 7.26-7.20 (m, 3H), 7.20-7.13 (m, 3H), 6.90 (s, 1H), 3.49 (s, 2H), 3.37 (s, 2H), 3.14-2.98 (m, 4H), 2.67 (t, J=4.7 Hz, 4H), 2.26 (s, 4H). LCMS Method C: rt 4.52 min; m/z 499.1 [M+H]+; m/z 497.1 [M−H]$^−$.

Example 26
2-(3-(2-(2-((4-(Piperidin-4-yl)phenyl)amino)-5-(trifluoromethyl)pyrimidin-4-yl)ethyl)pyrazin-2-yl)acetamide (26)
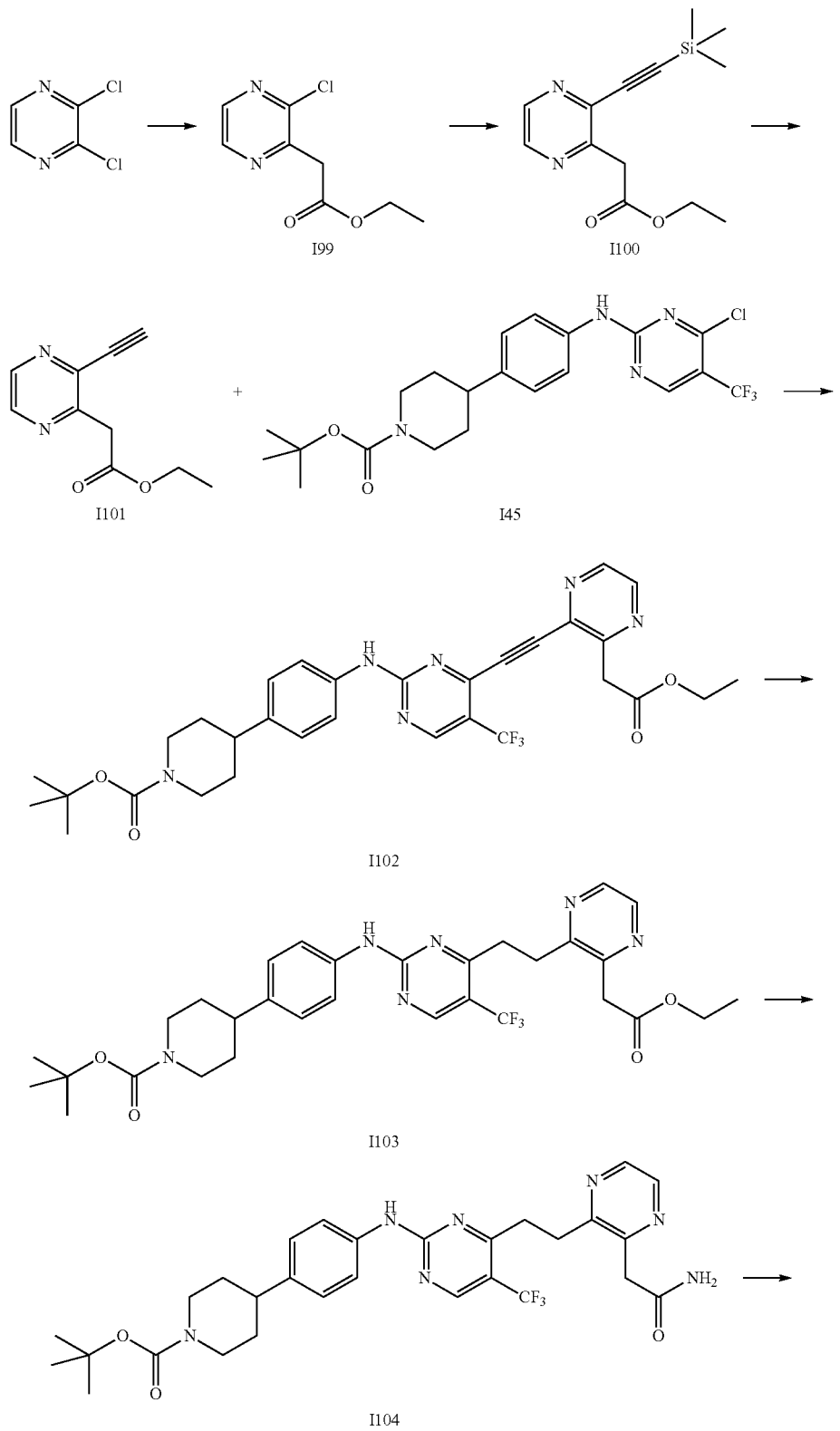

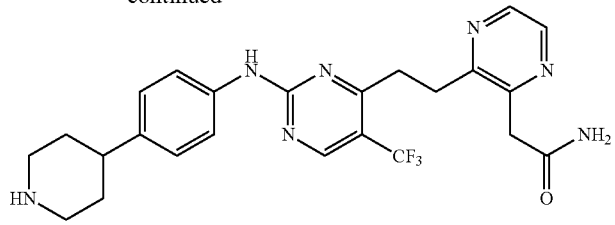

26

(a) Ethyl 2-(3-chloropyrazin-2-yl)acetate (I99)

To a 1.0 M solution of LiHMDS in toluene (14.8 mL, 14.8 mmol) under nitrogen at 0° C. was added 2,3-dichloropyrazine (0.699 mL, 6.71 mmol) and ethyl acetate (0.725 mL, 7.38 mmol). The mixture was stirred overnight for 18 hours, allowing the ice bath to warm to room temperature. The mixture was poured into saturated ammonium chloride (100 mL), and extracted with diethyl ether (3×100 mL). The combined ether extracts were washed with brine, dried (sodium sulphate) and evaporated. The residue was chromatographed (40 g silica cartridge, 0-25% ethyl acetate/petroleum benzine 40-60° C.) to give the title compound (I99) (0.414 g, 31% yield) as a pale yellow oil; $^1$H NMR (400 MHz, CDCl$_3$) δ 8.46 (d, J=2.5 Hz, 1H), 8.31 (d, J=2.5 Hz, 1H), 4.22 (q, J=7.1 Hz, 2H), 4.03 (s, 2H), 1.27 (t, J=7.1 Hz, 3H). LCMS Method C: rt 5.16 min.

(b) Ethyl 2-(3-((trimethylsilyl)ethynyl)pyrazin-2-yl)acetate (I100)

A mixture of the ethyl 2-(3-chloropyrazin-2-yl)acetate (I99) (0.410 g, 2.04 mmol), DMF (6 mL), triethylamine (2 mL), bis(triphenylphosphine)palladium(II) chloride (72 mg, 5 mol %) and copper(I) iodide (19 mg, 5 mol %) in a Schlenk tube was degassed with three vacuum/nitrogen cycles, then trimethylsilylacetylene (0.866 mL, 6.13 mmol) was added under nitrogen. The tube was flushed with nitrogen, sealed and heated to 90° C. After 18 hours the mixture was cooled and poured into water (50 mL). Saturated ammonium chloride (50 mL) was added, and the mixture was extracted with diethyl ether (3×100 mL). The combined ether phases were washed with brine, dried (sodium sulphate) and evaporated. The residue was chromatographed (40 g silica cartridge, 0-30% ethyl acetate/petroleum benzine 40-60° C.) to give the title compound (I100) (0.386 g, 72% yield) as a yellow oil; $^1$H NMR (400 MHz, CDCl$_3$) δ 8.47-8.41 (m, 2H), 4.20 (q, J=7.1 Hz, 2H), 4.05 (s, 2H), 1.26 (t, J=7.1 Hz), 0.28 (s, 9H). LCMS Method C: rt 6.20 min; m/z 263.1 [M+H]$^+$.

(c) Ethyl 2-(3-ethynylpyrazin-2-yl)acetate (I101)

Ethyl 2-(3-((trimethylsilyl)ethynyl)pyrazin-2-yl)acetate (I100) (0.386 g, 1.47 mmol) in THF (15 mL) was cooled to 0° C. and a 1.0 M solution of TBAF in THF (1.84 mL, 1.84 mmol) was added. The mixture was stirred for two minutes then poured into water (150 mL). The resulting mixture was extracted with diethyl ether (2×150 mL) and the combined ether phases washed with brine, dried (sodium sulphate) and evaporated to give the title compound (I101) (0.209 g, 75% yield) as a yellow-brown oil; $^1$H NMR (400 MHz, CDCl$_3$) δ 8.50-8.47 (m, 2H), 4.21 (q, J=7.1 Hz, 2H), 4.08 (s, 2H), 3.49 (s, 1H), 1.26 (t, J=7.1 Hz, 3H). LCMS Method C: rt 4.88 min; m/z 191.1 [M+H]$^+$.

(d) tert-Butyl 4-(4-((4-((3-(2-ethoxy-2-oxoethyl)pyrazin-2-yl)ethynyl)-5-(trifluoromethyl)pyrimidin-2-yl)amino)phenyl)piperidine-1-carboxylate (I102)

tert-Butyl 4-(4-((4-chloro-5-(trifluoromethyl)pyrimidin-2-yl)amino)phenyl)piperidine-1-carboxylate (I43) (140 mg, 0.306 mmol), ethyl 2-(3-ethynylpyrazin-2-yl)acetate (I101) (64 mg, 0.34 mmol), bis(triphenylphosphine)palladium(II) chloride (11 mg, 5 mol %) and DMF (2 mL) were loaded into a microwave tube and degassed with a nitrogen for ten minutes. Copper(I) iodide (3 mg, 5 mol %) and triethylamine (0.192 mL, 1.38 mmol) were added under nitrogen and the resulting mixture heated under microwave irradiation (120° C./15 minutes). The cooled mixture was concentrated, and the residue evaporated onto silica gel. Chromatography (12 g silica cartridge, 0-100% ethyl acetate/petroleum benzine 40-60° C.) gave the title compound (I102) (95.5 mg, 52% yield) as a yellow solid; $^1$H NMR (400 MHz, d$_6$-DMSO) δ 10.47 (s, 1H), 8.87 (d, J=0.5 Hz, 1H), 8.76-8.71 (m, 2H), 7.63 (d, J=8.6 Hz, 2H), 7.23 (d, J=8.6 Hz, 2H), 4.15-3.99 (m, 6H), 2.80 (s, 2H), 2.70-2.63 (m, 1H), 1.80-1.70 (m, 2H), 1.55-1.44 (m, 2H), 1.42 (s, 9H), 1.14 (t, J=7.1 Hz, 3H). LCMS Method C: rt 6.73 min; m/z 633.1 [M+Na]$^+$, 555.0 [M-tBu+2H]$^+$, 511.1 [M-Boc+2H]+; m/z 609.1 [M−H]$^-$.

(e) tert-Butyl 4-(4-((4-(2-(3-(2-ethoxy-2-oxoethyl)pyrazin-2-yl)ethyl)-5-(trifluoromethyl)pyrimidin-2-yl)amino)phenyl)piperidine-1-carboxylate (I103)

tert-Butyl 4-(4-((4-((3-(2-ethoxy-2-oxoethyl)pyrazin-2-yl)ethynyl)-5-(trifluoromethyl)pyrimidin-2-yl)amino)phenyl)piperidine-1-carboxylate (I102) (187 mg, 0.306 mmol) was dissolved in DMF (20 mL), triethylamine (0.1 mL) and a slurry of 10% Pd/C (0.100 g) in DMF (2 mL) was added. The mixture was purged with 3× vacuum/hydrogen cycles, and then stirred vigorously under a hydrogen atmosphere. After 17 hours the mixture was filtered through celite, and the celite washed with ethyl acetate (200 mL). The combined filtrates were washed with 1:1 water: saturated brine (4×100 mL), dried (sodium sulphate) and evaporated to give the title compound (I103) (142 mg, 76%) as a yellow oil; $^1$H NMR (400 MHz, d$_4$-MeOD) δ 8.51 (d, J=0.6 Hz, 1H), 8.42 (d, J=2.6 Hz, 1H), 8.34 (d, J=2.6 Hz, 1H), 7.48 (d, J=8.3 Hz, 2H), 7.20-7.13 (m, 2H), 4.21 (dd, J=11.4, 1.8 Hz, 2H), 4.15 (q, J=7.1 Hz, 2H), 3.97 (s, 2H), 3.37 (s, 4H), 2.87 (br s), 2.70 (tt, J=11.9, 3.3 Hz, 1H), 1.83 (d, J=12.4 Hz, 2H), 1.59 (ddd, J=25.6, 12.9, 4.4 Hz, 2H), 1.48 (s, 9H), 1.21 (t, J=7.1 Hz, 3H). LCMS Method C: rt 6.76 min; m/z 615.1 [M+H]$^+$, 559.1 [M-tBu+2H]$^+$, 515.1 [M-Boc+2H]$^+$.

(f) tert-Butyl 4-(4-((4-(2-(3-(2-amino-2-oxoethyl)
pyrazin-2-yl)ethyl)-5-(trifluoromethyl)pyrimidin-2-
yl)amino)phenyl)piperidine-1-carboxylate (I104)

tert-Butyl 4-(4-((4-(2-(3-(2-ethoxy-2-oxoethyl)pyrazin-2-yl)ethyl)-5-(trifluoromethyl)pyrimidin-2-yl)amino)phenyl) piperidine-1-carboxylate (I103) (142 mg, 0.231 mmol) was dissolved in THF (10 mL) and methanol (5 mL) then a solution of lithium hydroxide monohydrate (48.0 mg, 1.16 mmol) in water (2.5 mL) was added. The mixture was stirred at room temperature for 17 hours, and then concentrated. The residue was evaporated twice from toluene then dissolved in DMF (20 mL) and ammonium chloride (62 mg, 1.2 mmol), HOBt (47 mg, 0.35 mmol), PyBOP (181 mg, 0.347 mmol) and DIPEA (0.161 mL, 0.924 mmol) were added. After two hours the mixture was quenched with water (1 mL), concentrated and the residue partitioned between 1:3 saturated brine:water (30 mL) and ethyl acetate (20 mL). The aqueous phase was washed with ethyl acetate (3×20 mL) then the combined ethyl acetate phases were washed with brine (50 mL), dried (sodium sulfate) and evaporated. The residue was chromatographed (12 g silica cartridge, 20-100% ethyl acetate/petroleum benzine 40-60° C. then 100% ethyl acetate for 10 column volumes) to give the title compound (I104) (66.2 mg, 49% yield) as a colourless syrup; $^1$H NMR (400 MHz, d$_4$-MeOD) δ 8.40 (d, J=0.6 Hz, 1H), 8.29 (d, J=2.6 Hz, 1H), 8.24 (d, J=2.5 Hz, 1H), 7.40 (d, J=8.3 Hz, 2H), 7.09-7.01 (m, 2H), 4.10 (d, J=13.3 Hz, 2H), 3.81-3.75 (m, 2H), 3.34-3.23 (m, 4H), 2.76 (br s), 2.58 (tt, J=12.0, 3.4 Hz, 1H), 1.71 (d, J=12.2 Hz, 2H), 1.47 (ddd, J=25.5, 12.8, 4.3 Hz, 2H), 1.38 (s, 9H). LCMS Method C: 6.17 min; m/z 586.1 [M+H]$^+$, 530.1 [M-tBu+2H]$^+$, 486.1 [M-Boc+2H]$^+$; m/z 584.2 [M-H]$^-$.

(g) 2-(3-(2-(2-((4-(Piperidin-4-yl)phenyl)amino)-5-(trifluoromethyl)pyrimidin-4-yl)ethyl)pyrazin-2-yl) acetamide (26)

tert-Butyl 4-(4-((4-(2-(3-(2-amino-2-oxoethyl)pyrazin-2-yl)ethyl)-5-(trifluoromethyl)pyrimidin-2-yl)amino)phenyl) piperidine-1-carboxylate (I104) (66 mg, 0.11 mmol), DCM (20 mL) and TFA (2 mL) were stirred at room temperature for 17 hours, then concentrated. The residue was suspended in 10% NaOH (10 mL) and brine (10 mL), and the mixture extracted with ethyl acetate (4×20 mL). The combined ethyl acetate phases were washed with brine, dried (sodium sulphate) and evaporated to give the title compound (26) (47 mg, 85% yield) as a yellow solid; $^1$H NMR (400 MHz, d$_6$-DMSO) δ 10.05 (s, 1H), 8.64 (s, 1H), 8.42 (d, J=2.5 Hz, 1H), 8.39 (d, J=2.5 Hz, 1H), 7.61 (s, 1H), 7.54 (d, J=6.7 Hz, 2H), 7.14 (d, J=8.4 Hz, 2H), 7.08 (s, 1H), 3.78 (s, 2H), 3.07-2.97 (m, 2H), 2.63-2.53 (m, overlaps with solvent), 1.67 (d, J=12.1 Hz, 2H), 1.55-1.43 (m, 2H), 1.23 (s, 1H). LCMS Method C: rt 4.36 min; m/z 486.1 [M+H]+; m/z 484.1 [M-H]$^-$.

Example 27

2-(3-(2-(2-((4-(1-Methylpiperidin-4-yl)phenyl) amino)-5-(trifluoromethyl)pyrimidin-4-yl)ethyl) pyrazin-2-yl)acetamide (27)

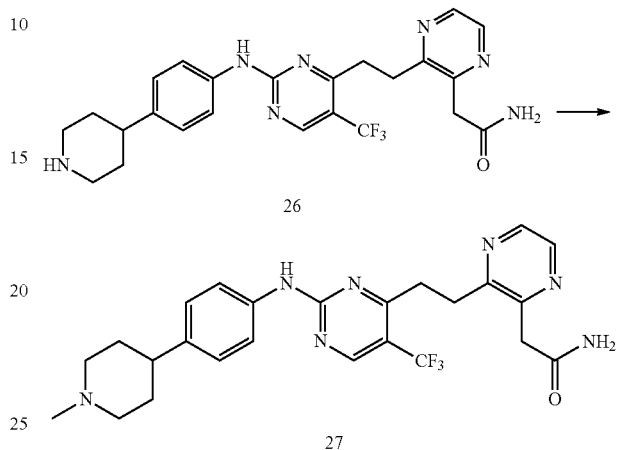

2-(3-(2-(2-((4-(Piperidin-4-yl)phenyl)amino)-5-(trifluoromethyl)pyrimidin-4-yl)ethyl)pyrazin-2-yl)acetamide (26) (42 mg, 0.087 mmol) was dissolved in methanol (4 mL) and 37% formaldehyde (26 μL, 0.35 mmol) was added. After five minutes sodium tri(acetoxy)borohydride (92 mg, 0.44 mmol) was added and the mixture stirred for three hours. The solution was concentrated, and the residue suspended in 10% sodium hydroxide (1 mL). After five minutes brine (2 mL) was added, and the mixture extracted with ethyl acetate (5×3 mL). The combined ethyl acetate phases were washed with brine, dried (sodium sulphate) and evaporated to give the title compound (27) (34 mg, 77% yield) as an off-white solid; $^1$H NMR (400 MHz, d$_6$-DMSO) δ 10.07 (s, 1H), 8.64 (s, 1H), 8.42 (d, J=2.6 Hz, 1H), 8.38 (d, J=2.6 Hz, 1H), 7.61 (s, 1H), 7.55 (d, J=7.3 Hz, 2H), 7.15 (d, J=8.5 Hz, 2H), 7.08 (s, 1H), 4.09 (d, J=4.7 Hz, 1H), 3.77 (s, 2H), 3.17 (d, J=4.3 Hz, 2H), 3.05-2.92 (m, 2H), 2.33 (s, 3H), 2.20 (s, 2H), 1.82-1.61 (m, 4H). LCMS Method C: rt 4.53 min; m/z 500.1 [M+H]+; m/z 498.2 [M-H]$^-$.

Example 28

2-(2-(2-(2-((2-Methyl-1,2,3,4-tetrahydroisoquinolin-6-yl)amino)-5-(trifluoromethyl)pyrimidin-4-yl)ethyl) phenyl)acetamide (28)

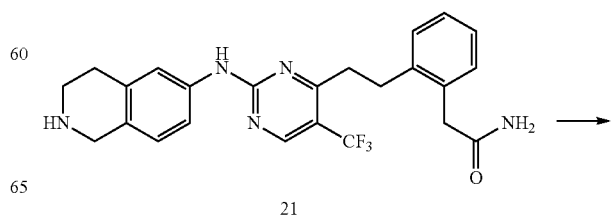

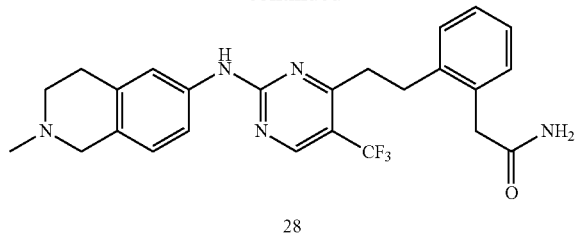

28

2-(2-(2-(2-((1,2,3,4-tetrahydroisoquinolin-6-yl)amino)-5-(trifluoromethyl)pyrimidin-4-yl)ethyl)phenyl)acetamide (21) (25 mg, 0.055 mmol) was suspended in methanol (2 mL) and 37% aqueous formaldehyde (0.016 mL, 0.22 mmol) was added. The mixture was stirred for five minutes then sodium tri(acetoxy)borohydride (58 mg, 0.27 mmol) was added. After stirring for 2 hours at room temperature the mixture was concentrated and the residue treated with 10% aqueous NaOH (1 mL) for five minutes. Brine (2 mL) was added, and the mixture was extracted with ethyl acetate (5×5 mL). The combined ethyl acetate extracts were washed with brine, dried (sodium sulphate) and evaporated to give the title compound (28) (22.8 mg, 88% yield) as an off-white solid; $^1$H NMR (400 MHz, d$_4$-MeOD) δ 8.54 (d, J=0.5 Hz, 1H), 7.52 (d, J=1.9 Hz, 1H), 7.47 (dd, J=8.3, 2.2 Hz, 1H), 7.28-7.16 (m, 4H), 7.04 (d, J=8.3 Hz, 1H), 3.66 (s, 2H), 3.60 (s, 2H), 3.21-3.11 (m, 2H), 3.11-3.02 (m, 2H), 2.96 (t, J=6.0 Hz, 2H), 2.76 (t, J=6.1 Hz, 2H), 2.46 (s, 3H). LCMS Method C: rt 4.78 min; m/z 470.1 [M+H]+; m/z 468.1 [M–H]−.

Example 29

2-(4-(2-(2-((4-(Piperidin-4-yl)phenyl)amino)-5-(trifluoromethyl)pyrimidin-4-yl)ethyl)pyrimidin-5-yl)acetamide (29)

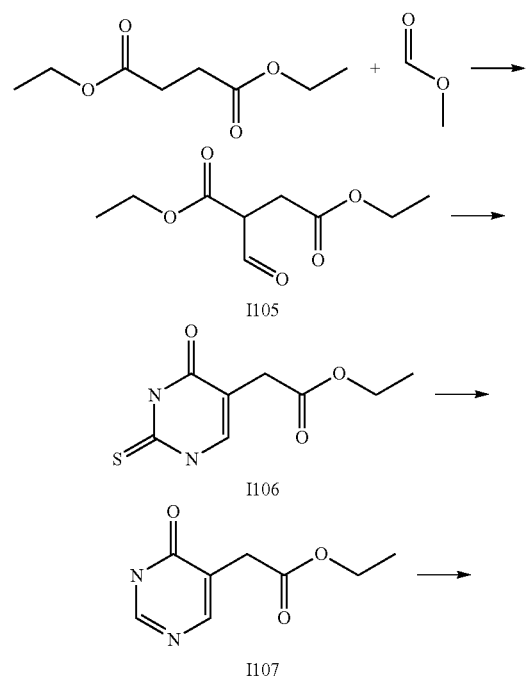

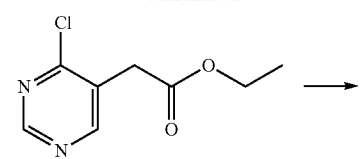

I108

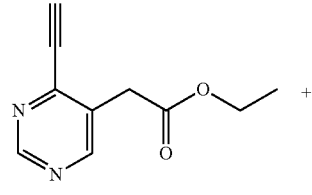

I110

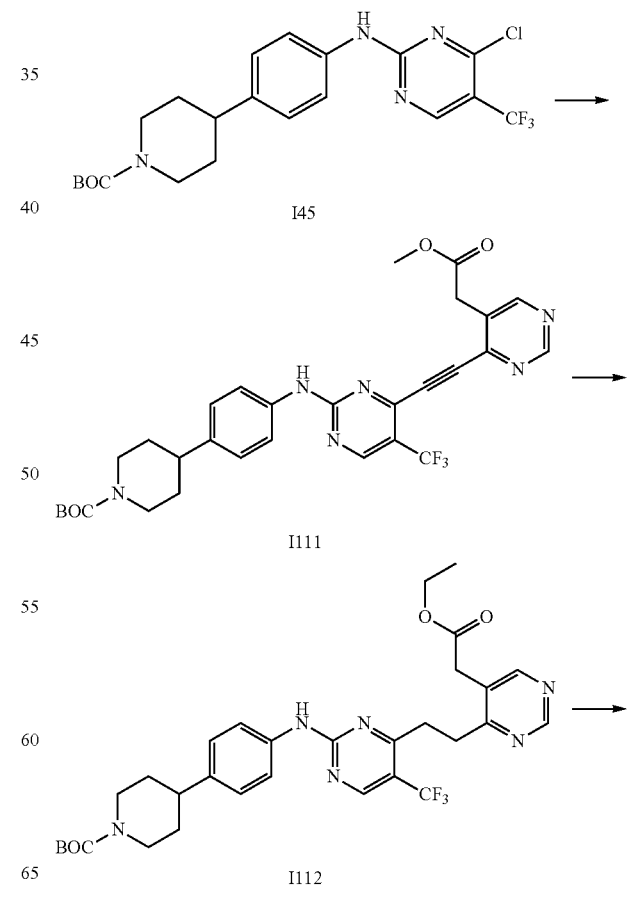

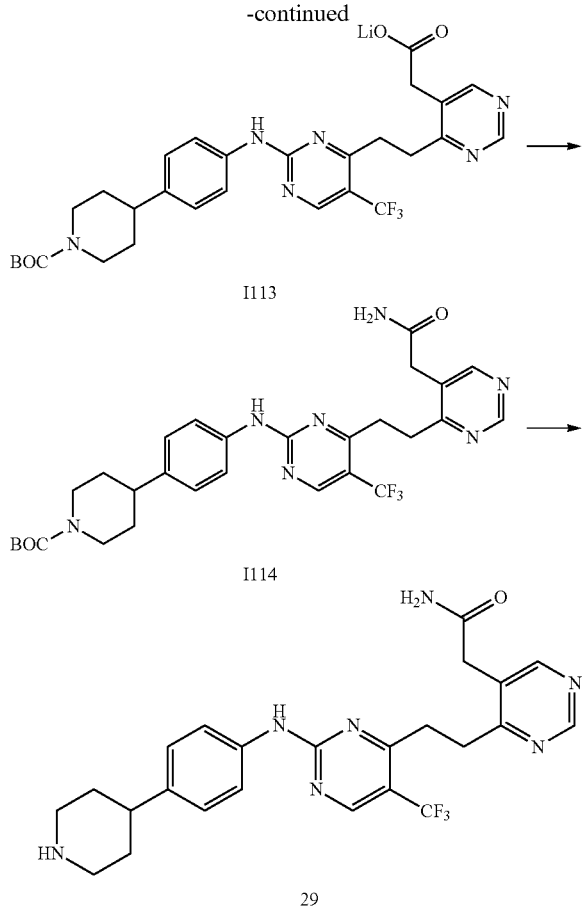

(a) Diethyl 2-formylsuccinate (I105)

A mixture of diethyl succinate (26.1 g, 25.0 mL, 0.150 mol) and ethyl formate (11.1 g, 12.1 mL, 0.150 mol) was added drop wise over 1.5 hours to a stirred suspension of sodium (3.40 g, 0.150 mol) in diethyl ether (120 mL) at 0° C. under nitrogen. On completion of addition, stirring was continued at room temperature for 17 hours. Water (120 mL) was cautiously added to the resulting suspension and stirring continued until all the solids were dissolved. The layers were separated and the aqueous layer was washed with diethyl ether (100 mL). The aqueous layer was then acidified to pH 5 using 11 N HCl and extracted with diethyl ether (3×100 mL), the ethereal extracts of the acidified layer were combined, dried (Na$_2$SO$_4$) then evaporated to dryness under reduced pressure to give the title compound (I105) (16.5 g) as a yellow mobile liquid. The crude product was not purified further and was used directly in the following step.

(b) Ethyl 2-(4-oxo-2-thioxo-1,2,3,4-tetrahydropyrimidin-5-yl)acetate (I106)

Sodium ethoxide (6.105 g, 89.71 mmol) was added to absolute ethanol (150 mL) under an atmosphere of nitrogen followed by diethyl-2-formylsuccinate (I105) (crude, 16.5 g) in absolute ethanol (30 mL) and thiourea (6.829 g, 89.71 mmol). The reaction mixture was heated at reflux for 1 hour then cooled to room temperature at which stirring was continued for 16 hours. The volatiles were evaporated under reduced pressure to give a brown oily solid. Cold aqueous acetic acid solution (15%; 120 mL) was added and the resulting mixture was sonicated and then stirred at 0° C. until all the residue was in suspension. The resulting precipitate was collected by filtration. The filter cake was washed with water (100 mL) and dried to give the title compound (I106) (6.31 g, 19% yield over 2 steps) as an off-white solid; $^1$H NMR (400 MHz, d$_6$-DMSO) δ 7.44 (s, 1H), 4.05 (q, J=7.1 Hz, 2H), 3.28 (s, 2H), 1.17 (t, J=7.1 Hz, 3H). LCMS Method C: rt 2.92 min; m/z 213.0 [M−H]$^−$.

(c) Ethyl 2-(6-oxo-1,6-dihydropyrimidin-5-yl)acetate (I107)

A Raney nickel suspension in water (Aldrich; 25 mL) was added to a stirred suspension of ethyl 2-(4-oxo-2-thioxo-1,2,3,4-tetrahydropyrimidin-5-yl)acetate (I106) (3.0 g, 14 mmol) in water (200 mL) at room temperature. The resulting suspension was heated at reflux for 20 hours and then stirred at room temperature for another 70 hours. The mixture was filtered through a thin pad of celite, the filter cake was washed with hot water (200 mL) and the combined filtrates were evaporated under reduced pressure to give a pale blue solid (~1.8 g). Dichloromethane (250 mL) was added and the resulting suspension was sonicated in an ultrasound bath until a fine suspended solid was obtained. The fine suspension was heated at reflux with vigorous stirring for 1 hour then filtered hot through a pad of celite, washing the filter cake with hot dichloromethane (200 mL). The filtrates were combined and evaporated to dryness under reduced pressure to give the title compound (I107) (1.01 g, 40% yield) as a white fluffy solid; $^1$H NMR (400 MHz, CDCl$_3$) δ 8.12 (s, 1H), 8.00-7.97 (m, 1H), 4.19 (q, J=7.1 Hz, 2H), 3.49 (s, 2H), 1.28 (t, J=7.1 Hz, 3H). LCMS Method C: rt 2.05 min; m/z 183.1 [M+H]$^+$.

(d) Ethyl 2-(4-chloropyrimidin-5-yl)acetate (I108)

To ethyl 2-(6-oxo-1,6-dihydropyrimidin-5-yl)acetate (I107) (0.868 g, 4.77 mmol) was added POCl$_3$ (6 mL) under an atmosphere of nitrogen and the resulting mixture was heated to reflux for 5 minutes and then cooled to room temperature. The reaction was slowly added to water (300 mL), the aqueous solution was extracted with DCM (3×100 mL), the combined organics were washed with brine (100 mL), dried (MgSO$_4$), filtered and concentrated in vacuo to give the title compound (I108) (0.885 g, 93% yield) as a pale yellow oil; $^1$H NMR (400 MHz, CDCl$_3$) δ 8.93 (s, 1H), 8.61 (s, 1H), 4.21 (q, J=7.1 Hz, 2H), 3.76 (s, 2H), 1.28 (t, J=7.1 Hz, 3H). LCMS Method C: rt 5.09 min; m/z 201.1, 203.1 [M+H]$^+$.

(e) Ethyl 2-(4-((triethylsilyl)ethynyl)pyrimidin-5-yl)acetate (I109)

To a nitrogen de-gassed solution of ethyl 2-(4-chloropyrimidin-5-yl)acetate (I108) (0.823 g, 4.10 mmol) in dry DMF (15 mL) were added triethylamine (1.715 mL, 12.31 mmol) followed by triphenylphosphine (0.124 g, 0.473 mmol), trans-dichlorobis(triphenyl-phosphine)palladium(II) (0.144 g, 0.205 mmol), Cu(I)I (0.078 g, 0.410 mmol) and finally (triethylsilyl)acetylene (1.470 mL, 8.204 mmol). The reaction mixture was then heated under microwave irradiation at 120° C. for 25 minutes, concentrated in vacuo and purified by silica gel chromatography (Isolera Biotage, 40 g Si cartridge, 0-30% EtOAc in petroleum benzine 40-60° C.) to give the title compound (I109) (1.176 g, 94% yield) as a yellow-orange oil; $^1$H NMR (400 MHz, CDCl$_3$) δ 9.08 (s, 1H), 8.68 (s, 1H), 4.18 (q, J=7.1 Hz, 2H), 3.80 (s, 2H), 1.26 (t, J=7.1 Hz, 3H), 1.10-1.01 (m, 9H), 0.77-0.67 (m, 6H) LCMS Method C: rt 6.64 min; m/z 305.1 [M+H]$^+$.

(f) Ethyl 2-(4-ethynylpyrimidin-5-yl)acetate (I110)

To a solution of ethyl 2-(4-((triethylsilyl)ethynyl)pyrimidin-5-yl)acetate (I109) (1.174 g, 3.856 mmol) in dry THF (40 mL) under an atmosphere of nitrogen was added acetic acid (0.243 mL, 4.24 mmol) followed by TBAF (1.0 M in THF, 4.049 mL, 4.049 mmol) dropwise at 0° C. The reaction was stirred at this temperature for 5 minutes and was then poured into sat. aq. NaHCO$_3$ (100 mL) and DCM (100 mL). The layers were separated and the aqueous layer was extracted with DCM (2×100 mL). The combined organics were washed with water (100 mL), brine (100 mL), dried (MgSO$_4$), filtered and concentrated in vacuo to give a brown oil. The crude material was purified by silica gel chromatography (Isolera Biotage, 40 g Si Cartridge, 0-60% EtOAc in petroleum benzine 40-60° C.) to give the title compound (I110) (0.397 g, 54% yield) as a brown oil; $^1$H NMR (400 MHz, CDCl$_3$) δ 9.11 (s, 1H), 8.72 (s, 1H), 4.20 (q, J=7.1 Hz, 2H), 3.81 (s, 2H), 3.56 (s, 1H), 1.27 (t, J=7.1 Hz, 3H). LCMS Method C: rt 4.78 min; m/z 191.1 [M+H]$^+$.

(g) tert-Butyl 4-(4-((4-((5-(2-ethoxy-2-oxoethyl) pyrimidin-4-yl)ethynyl)-5-(trifluoromethyl)pyrimidin-2-yl)amino)phenyl)piperidine-1-carboxylate (I111)

To a nitrogen de-gassed solution of ethyl 2-(4-ethynylpyrimidin-5-yl)acetate (I110) (0.146 g, 0.766 mmol) and tert-butyl 4-(4-((4-chloro-5-(trifluoromethyl)pyrimidin-2-yl) amino)phenyl)piperidine-1-carboxylate (I45) (0.250 g, 0.547 mmol) in dry DMF (15 mL) were added triethylamine (0.305 mL, 2.19 mmol), tri-tert-butylphosphonium tetrafluoroborate (0.016 g, 0.055 mmol), trans-dichlorobis(triphenylphosphine)palladium(II) (0.019 g, 0.027 mmol) and Cu(I)I (0.010 g, 0.055 mmol). The reaction mixture was heated under microwave irradiation at 120° C. for 20 minutes and then concentrated in vacuo to give a brown gum. The crude material was purified by silica gel chromatography (Isolera Biotage, 40 g Si cartridge, 0-70% EtOAc in petroleum benzine 40-60° C.) to give the title compound (I111) (0.093 g, 27% yield) as a yellow solid; $^1$H NMR (400 MHz, d$_6$-DMSO) δ 10.50 (s, 1H), 9.23 (s, 1H), 8.97 (s, 1H), 8.88 (s, 1H), 7.63 (d, J=8.6 Hz, 2H), 7.23 (d, J=8.6 Hz, 2H), 4.14-4.04 (m, 4H), 3.96 (s, 2H), 2.81 (br s, 2H), 2.70-2.61 (m, 1H), 1.75 (d, J=11.9 Hz, 2H), 1.53-1.37 (m, 11H), 1.14 (t, J=7.1 Hz, 3H). LCMS Method C: rt 6.64 min; m/z 609.2 [M−H]$^-$.

(h) tert-Butyl 4-(4-((4-(2-(5-(2-ethoxy-2-oxoethyl) pyrimidin-4-yl)ethyl)-5-(trifluoromethyl)pyrimidin-2-yl)amino)phenyl)piperidine-1-carboxylate (I112)

tert-Butyl 4-(4-((4-((5-(2-ethoxy-2-oxoethyl)pyrimidin-4-yl)ethynyl)-5-(trifluoromethyl)pyrimidin-2-yl)amino) phenyl)piperidine-1-carboxylate (I111) (0.108 g, 0.177 mmol) was dissolved in dry DMF (10 mL) under an atmosphere of nitrogen. Pd/C (10 wt. %; 0.040 g) in EtOAc (2 mL) was added to the solution and the atmosphere was changed to hydrogen gas (balloon). The reaction was sealed with balloon and stirred at room temperature for 22 hours. The catalyst was removed by filtration through Celite, which was washed with EtOAc (5×20 mL). The solvent was removed in vacuo to give a greyish semi-solid which was purified by silica gel chromatography (Isolera Biotage, 12 g Si Cartridge, 0-70% EtOAc in petroleum benzine 40-60° C.) to give the title compound (I112) (0.096 g, 88% yield) as a pale yellow foam; $^1$H NMR (400 MHz, d$_6$-DMSO) δ 10.06 (s, 1H), 9.00 (s, 1H), 8.64 (s, 1H), 8.59 (s, 1H), 7.56 (d, J=8.4 Hz, 2H), 7.16 (d, J=8.6 Hz, 2H), 4.11-4.04 (m, 4H), 3.83 (s, 2H), 3.28-3.21 (m, 4H), 2.79 (brs, 2H), 2.68-2.58 (m, 1H), 1.74 (d, J=13.1 Hz, 2H), 1.52-1.38 (m, 11H), 1.14 (t, J=7.1 Hz, 3H). LCMS Method C: rt 6.65 min; m/z 615.1 [M+H]$^+$.

(i) Lithium 2-(4-(2-(2-((4-(1-(tert-butoxycarbonyl) piperidin-4-yl)phenyl)amino)-5-(trifluoromethyl) pyrimidin-4-yl)ethyl)pyrimidin-5-yl)acetate (I113)

LiOH.H$_2$O (0.020 g, 0.468 mmol) was added to a solution of tert-butyl 4-(4-((4-(2-(5-(2-ethoxy-2-oxoethyl)pyrimidin-4-yl)ethyl)-5-(trifluoromethyl)pyrimidin-2-yl)amino)phenyl) piperidine-1-carboxylate (I112) (0.096 g, 0.156 mmol) in THF (7 mL), water (1.5 mL) and methanol (1 mL) and the resulting mixture was allowed to stir at room temperature for 18 hours. The volatiles were removed in vacuo and the residue was diluted with EtOAc (70 mL) and 2 M aqueous NaOH (80 mL). The layers were separated and the aqueous layer was extracted with EtOAc (2×70 mL), the combined organics were washed with brine (70 mL), dried (MgSO$_4$), filtered and concentrated under reduced pressure to give the title compound (I113) (0.096 g, quantitative) as a pale yellow solid. LCMS Method C: rt 6.19 min; m/z 587.1 [M+H]$^+$ (j) tert-Butyl 4-(4-((4-(2-(5-(2-amino-2-oxoethyl) pyrimidin-4-yl)ethyl)-5-(trifluoromethyl)pyrimidin-2-yl)amino)phenyl)piperidine-1-carboxylate (I114)

Lithium 2-(4-(2-(2-((4-(1-(tert-butoxycarbonyl)piperidin-4-yl)phenyl)amino)-5-(trifluoro-methyl)pyrimidin-4-yl) ethyl)pyrimidin-5-yl)acetate (I113) (0.092 g, 0.16 mmol) was dissolved in dry THF (7 mL) and dry DMF (1 mL) under an atmosphere of nitrogen. To the solution were added 1-hydroxybenzotriazole (0.023 g, 0.17 mmol) and EDCl (0.033 g, 0.17 mmol) and N,N-diisopropylethylamine (0.109 mL, 0.624 mmol) and the reaction mixture was stirred at room temperature for 10 minutes. Ammonium carbonate (0.075 g, 0.78 mmol) was added in one portion, and the reaction was stirred room temperature for 24 hours. More reagents were added, 1-hydroxybenzotriazole (0.011 g) and EDCl (0.016 g) and N,N-diisopropylethylamine (0.055 mL) and ammonium carbonate (0.035 g) and the reaction was stirred for another 20 hours at 35° C. The volatiles were removed in vacuo and the residual solution was diluted with EtOAc (70 mL) and sat. aq. NaHCO$_3$ (70 mL). The layers were separated and the aqueous layer was extracted with EtOAc (2×70 mL), the organic layers were combined and washed with water (100 mL), brine (100 mL), dried (MgSO$_4$), filtered and concentrated in vacuo to give an oily solid. The crude product was purified by silica gel chromatography (Isolera Biotage, 12 g Si Cartridge, 0-100% EtOAc in petroleum benzine 40-60° C., then 0-10% methanol in EtOAc) to give the title compound (I114) (0.076 g, 83% yield) as a pale yellow foam; $^1$H NMR (400 MHz, d$_6$-DMSO) δ 10.03 (s, 1H), 8.94 (s, 1H), 8.64 (s, 1H), 8.53 (s, 1H), 7.64 (br s, 1H), 7.55 (d, J=7.6 Hz, 2H), 7.16 (d, J=8.6 Hz, 2H), 7.11 (brs, 1H), 4.12-4.04 (m, 2H), 3.57 (s, 2H), 3.30-3.21 (m, 4H), 2.77 (br s, 2H), 2.68-2.58 (m, 1H), 1.74 (d, J=12.7 Hz, 2H), 1.53-1.37 (m, 11H). LCMS Method C: rt 6.12 min; m/z 586.1 [M+H]$^+$.

(k) 2-(4-(2-(2-((4-(Piperidin-4-yl)phenyl)amino)-5-(trifluoromethyl)pyrimidin-4-yl)ethyl)pyrimidin-5-yl)acetamide (29)

tert-Butyl 4-(4-((4-(2-(5-(2-amino-2-oxoethyl)pyrimidin-4-yl)ethyl)-5-(trifluoromethyl)pyrimidin-2-yl)amino)phenyl)piperidine-1-carboxylate (I114) (0.076 g, 0.13 mmol) was dissolved in DCM (5 mL) under an atmosphere of nitrogen. Trifluoroacetic acid (0.298 mL, 3.89 mmol) was added to the solution and the reaction was stirred at room temperature for 23 hours. Volatiles were removed in vacuo, EtOAc (70 mL) and 2 M aq. NaOH (70 mL) were added to the residue and the layers were separated. The aqueous layer was extracted with EtOAc (2×70 mL), the combined organics were washed with brine (2×50 mL), dried (MgSO$_4$), filtered and concentrated in vacuo to give a pale yellow gum. Methanol (~5 mL) and cyclohexane (~15 mL) were added to the product, some of the volatiles were removed in vacuo (~50%) which gave a yellow oil that separated from the solvent solution and was carefully transferred to a new flask with a pipette. The removed solution was concentrated in vacuo and then further dried under high-vacuum to give a pale yellow gum. Diethyl ether (5 mL) and methanol (1 mL) were added and the solution was concentrated in vacuo. The process was repeated twice with diethyl ether to give the title compound (29) (35 mg, 56% yield) as a pale yellow solid; $^1$H NMR (400 MHz, d$_4$-MeOD) δ 8.91 (s, 1H), 8.53-8.50 (m, 2H), 7.52 (d, J=8.2 Hz, 2H), 7.21-7.16 (m, 2H), 3.70 (s, 2H), 3.42-3.34 (m, 4H), 3.27-3.20 (m, 2H), 2.84 (td, J=12.5, 2.6 Hz, 2H), 2.70 (tt, J=12.2, 3.9 Hz, 1H), 1.89 (d, J=13.7 Hz, 2H), 1.72 (ddd, J=16.4, 12.9, 4.0 Hz, 2H). LCMS Method C: rt 4.46 min; m/z 486.1 [M+H]$^+$.

Example 30

2-(4-(2-(2-((4-(1-Methylpiperidin-4-yl)phenyl) amino)-5-(trifluoro-methyl)pyrimidin-4-yl)ethyl) pyrimidin-5-yl)acetamide (30)

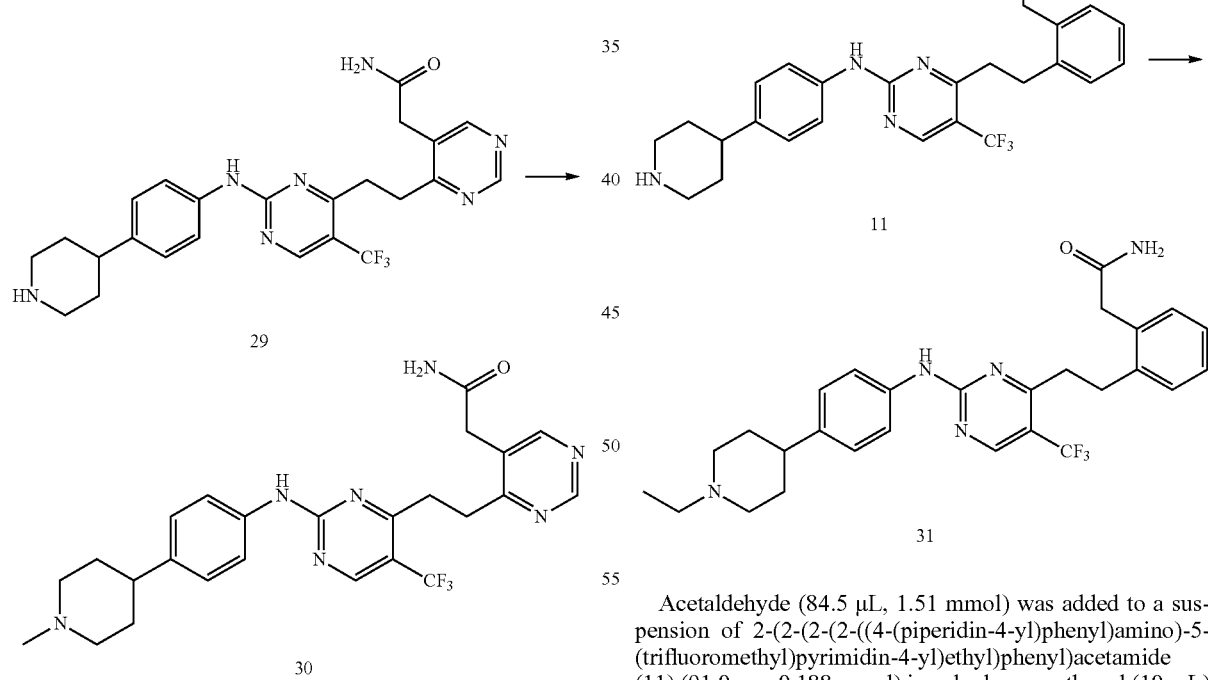

To a suspension of 2-(4-(2-(2-((4-(piperidin-4-yl)phenyl) amino)-5-(trifluoromethyl)pyrimidin-4-yl)ethyl)pyrimidin-5-yl)acetamide (29) (0.029 g, 0.060 mmol) in anhydrous methanol (2 mL) was added a 37% aq. solution of formaldehyde (0.018 mL, 0.24 mmol) under an atmosphere of nitrogen, followed by sodium triacetoxyborohydride (0.063 g, 0.30 mmol). The reaction was stirred at room temperature for 2.5 hours. The volatiles were removed in vacuo and the residue was diluted with EtOAc (50 mL) and sat. aq. NaHCO$_3$ (30 mL). The layers were separated and the aqueous layer was extracted with EtOAc (2×30 mL), the combined organic layers were washed with water (40 mL), brine (40 mL), dried (MgSO$_4$), filtered and concentrated in vacuo to give a solid which was taken up in DCM (~10 mL) and methanol (~1 mL) and concentrated in vacuo. The process was repeated with only DCM twice. The resulting off-white solid was suspended in DCM (5 mL) and cyclohexane was added (~10 mL). The suspension was sonicated and the product was collected by filtration. The solid was washed with petroleum benzine 40-60° C. (5×10 mL), air-dried and subsequently dried under high-vacuum to give the title compound (30) (0.017 g, 57% yield) as an off-white solid; $^1$H NMR (400 MHz, d$_6$-DMSO) δ 10.01 (s, 1H), 8.94 (s, 1H), 8.63 (s, 1H), 8.53 (s, 1H), 7.64 (s, 1H), 7.54 (d, J=8.0 Hz, 2H), 7.15 (d, J=8.5 Hz, 2H), 7.11 (s, 1H), 3.57 (s, 2H), 3.28-3.22 (m, 4H), 2.87 (d, J=11.2 Hz, 2H), 2.46-2.36 (m, 1H), 2.20 (s, 3H), 1.98 (t, J=10.6 Hz, 2H), 1.76-1.58 (m, 4H). LCMS Method C: rt 4.52 min; m/z 500.1 [M+H]$^+$.

Example 31

2-(2-(2-(2-((4-(1-Ethylpiperidin-4-yl)phenyl)amino)- 5-(trifluoromethyl)pyrimidin-4-yl)ethyl)phenyl)acetamide (31)

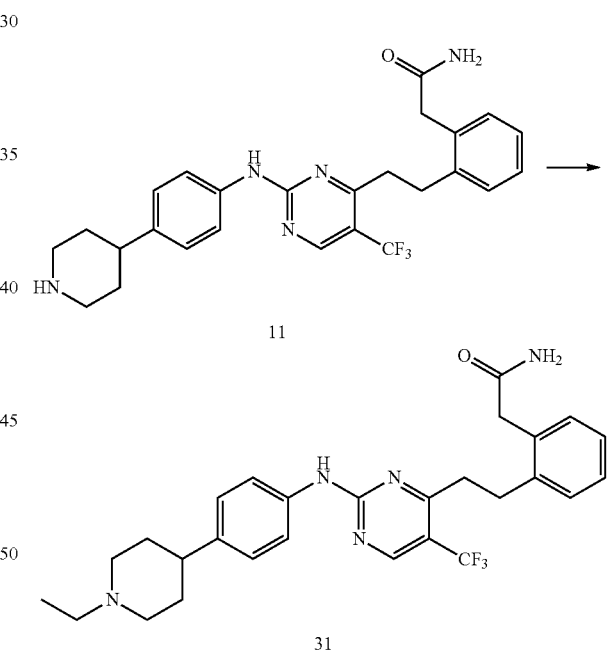

Acetaldehyde (84.5 µL, 1.51 mmol) was added to a suspension of 2-(2-(2-(2-((4-(piperidin-4-yl)phenyl)amino)-5-(trifluoromethyl)pyrimidin-4-yl)ethyl)phenyl)acetamide (11) (91.0 mg, 0.188 mmol) in anhydrous methanol (10 mL) under an atmosphere of nitrogen. Sodium triacetoxyborohydride (0.638 g, 3.01 mmol) was then added in one portion and the reaction was stirred at room temperature for 24 hours. The volatiles were removed in vacuo and the residue was diluted with EtOAc (35 mL) and sat. aq. NaHCO$_3$ (40 mL). The layers were separated and the aqueous layer was extracted with EtOAc (2×35 mL), the combined organic layers were washed with water (30 mL), brine (30 mL) and dried over Na₂SO₄. The solvent was removed under reduced pressure and the residue dissolved in DCM (5 mL) and MeOH (2 mL). Cyclohexane (20 mL) was added and the solvent removed in vacuo to afford a tan solid which was purified by column chromatography on silica gel (0-100% EtOAc in petroleum benzine 40-60° C.; then 0-75% MeOH in EtOAc) to yield a white solid. The solid was suspended in DCM (5 mL) and cyclohexane (20 mL) and filtered to afford the title compound (31) (40.7 mg, 42%) as an off-white solid; ¹H NMR (400 MHz, d₆-DMSO) δ 10.13 (s, 1H), 8.65 (s, 1H), 7.66 (d, J=8.6 Hz, 2H), 7.43 (s, 1H), 7.26-7.12 (m, 6H), 6.92 (s, 1H), 3.50 (s, 2H), 3.14-3.06 (m, 2H), 3.05-2.92 (m, 4H), 2.43 (tt, J=11.7, 3.7 Hz, 1H), 2.33 (q, J=7.2 Hz, 2H), 1.93 (td, J=11.5, 2.1 Hz, 2H), 1.73 (dd, J=11.8, 2.0 Hz, 2H), 1.62 (ddd, J=24.8, 12.4, 3.6 Hz, 2H), 1.01 (t, J=7.2 Hz, 3H); LCMS Method C: rt 4.90 min; m/z 512 [M+H]⁺.

Example 32

2-(2-(2-(2-((4-(Piperidin-4-yl)phenyl)amino)-5-(trifluoromethyl)pyrimidin-4-yl)ethyl)pyridin-3-yl)acetamide (32)

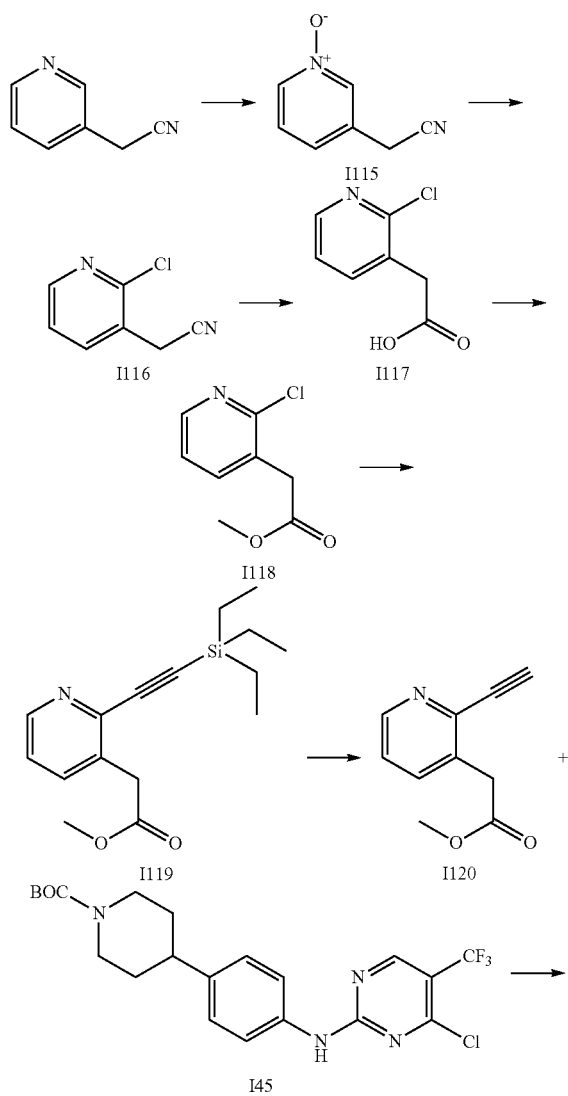

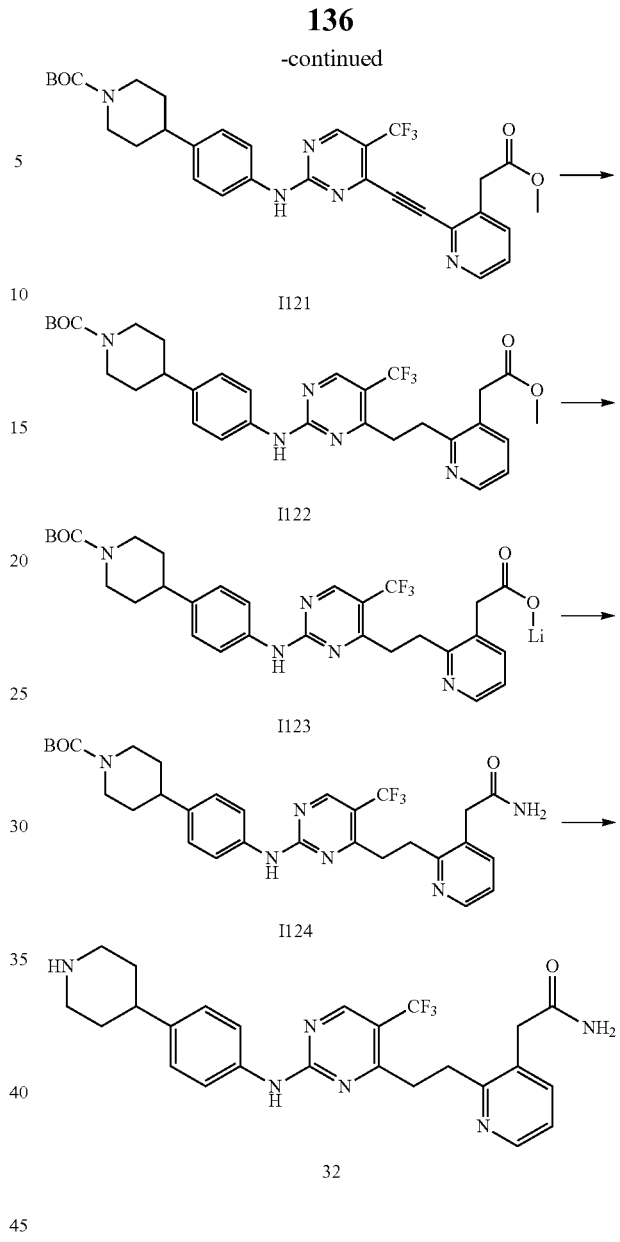

(a) (1-Oxypyridin-3-yl)acetonitrile (I115)

30% Hydrogen peroxide (12 mL) was added to a solution of 3-pyridylacetonitrile (7.50 g, 63.5 mmol) in acetic acid (40 mL) and the mixture heated at 95° C. for 20 hours. The reaction mixture was then cooled and stirred at room temperature for 72 hours. Water (35 mL) was then added and the solution concentrated under reduced pressure. Water (2×100 mL) was added to the residue and solution concentrated under reduced pressure. Residual water was removed azeotropically using toluene (2×100 mL) to yield the title compound (I115) (8.3 g, 97%) as a pale yellow solid which was used without further purification.

(b) (2-Chloropyridin-3-yl)acetonitrile (116)

(1-Oxypyridin-3-yl)acetonitrile (I115) (4.00 g, 29.8 mmol) was added slowly to a stirred solution of POCl₃ (50 mL). The mixture was heated to 80° C. in 5-7° C. increments every 10-15 minutes. The reaction was then heated at reflux for 3 hours. Excess POCl₃ was removed by distillation and the brown residue carefully poured on to cold water (200 mL). A saturated solution NaHCO$_3$ (300 mL) was then added carefully. Solid NaHCO$_3$ was added in portions to the aqueous mixture until the evolution of gas ceased. The aqueous layer was separated in to two portions (250 mL each) and each portion was extracted with EtOAc (3×100 mL). The combined organic layers were washed with brine (200 mL) and dried over Na$_2$SO$_4$. The solvent was removed and the residue purified by column chromatography on silica gel (0-100% EtOAc in petroleum benzine) to afford a mixture of two isomeric compounds. The mixture was re-purified by column chromatography on silica gel (0-40% diethyl ether in petroleum benzine 40-60° C.) to afford the title compound (I116) (0.932 g, 20%) as a white solid; $^1$H NMR (400 MHz, CDCl$_3$) δ 8.41 (dd, J=4.8, 1.8 Hz, 1H), 7.90 (ddt, J=7.6, 1.7, 0.7 Hz, 1H), 7.34 (dd, J=7.6, 4.8 Hz, 1H), 3.87 (s, 2H). LCMS Method C: rt 4.50 min; m/z 153 [M+H]$^+$.

(c) (2-Chloropyridin-3-yl)acetic acid (I117)

A solution of 15% w/w NaOH (15 mL) was added to (2-chloropyridin-3-yl)acetonitrile (I116) (0.932 g, 6.11 mmol). The mixture was heated at reflux for 35 minutes then cooled to room temperature. The mixture was further cooled to 0° C. and then acidified with conc. HCl (ca 5 mL) to pH 1. The suspension was left to stand for 1 hour in an ice bath. The precipitate was filtered and washed with cold propan-2-ol (3×15 mL) to yield the title compound (I117) (1.05 g, 100%) as an off-white solid; $^1$H NMR (400 MHz, d$_6$-DMSO) δ 12.63 (s, 1H), 8.32 (dd, J=4.8, 1.9 Hz, 1H), 7.86 (dd, J=7.5, 1.9 Hz, 1H), 7.41 (dd, J=7.5, 4.8 Hz, 1H), 3.75 (s, 2H). LCMS Method C: rt 4.06 min; m/z 172 [M+H]$^+$.

(d) Methyl 2-(2-chloropyridin-3-yl)acetate (I118)

Acetyl chloride (0.651 mL, 9.16 mmol) was added to a suspension of (2-chloropyridin-3-yl)acetic acid (I117) (1.048 g, 6.108 mmol) in MeOH (30 mL). The mixture was heated at reflux for 20 hours. The volatiles were removed in vacuo and the residue partitioned between DCM (100 mL) and sat. NaHCO$_3$ (100 mL). The layers were separated and the aqueous layer extracted with DCM (2×100 mL). The combined organic layers were washed with brine (100 mL), dried (Na$_2$SO$_4$) and the solvent removed under reduced pressure to yield an oil which was purified by column chromatography on silica gel (0-40% EtOAc in petroleum benzine 40-60° C.) to afford the title compound (I118) (0.863 g, 76%) as a pale yellow oil; $^1$H NMR (400 MHz, d$_6$-DMSO) δ 8.34 (dd, J=4.8, 1.9 Hz, 1H), 7.88 (dd, J=7.5, 1.9 Hz, 1H), 7.43 (dd, J=7.5, 4.8 Hz, 1H), 3.86 (s, 2H), 3.65 (s, 3H). LCMS Method C: rt 5.04 min; m/z 186 [M+H]$^+$.

(e) Methyl 2-(2-((triethylsilyl)ethynyl)pyridin-3-yl)acetate (I119)

A solution of triethylsilyl acetylene (0.579 mL, 3.23 mmol) in degassed DMF (3 mL) and triethylamine (0.901 mL, 6.47 mmol) were added to a mixture of methyl 2-(2-chloropyridin-3-yl)acetate (I118) (0.200 g, 1.08 mmol), Pd(PPh$_3$)$_2$Cl$_2$ (75.6 mg, 0.108 mmol), Cu(I)I (30.8 mg, 0.162 mmol) and triphenylphosphine (42.4 mg, 0.162 mmol) in degassed DMF (4 mL) and the resulting mixture was heated at 90° C. for 20 hours. The cooled mixture was diluted with EtOAc and passed through a plug of celite, washing with ethyl acetate (100 mL). Water (75 mL) was added to the filtrate and the layers separated. The aqueous layer was extracted with EtOAc (2×75 mL). The combined organic extracts were washed with brine (100 mL) and dried over Na$_2$SO$_4$. After filtration the solvent was removed under reduced pressure to give a dark brown residue. The residue was purified by column chromatography on silica gel (0-50% EtOAc in cyclohexane) to yield the title compound (I119) (0.353 g) as a brown oil which was used without further purification; $^1$H NMR (400 MHz, CDCl$_3$) δ 8.50 (dd, J=4.8, 1.6 Hz, 1H), 7.62 (dd, J=7.8, 1.6 Hz, 1H), 7.22 (dd, J=7.8, 4.8 Hz, 1H), 3.86 (s, 2H), 3.70 (s, 3H), 1.05 (t, J=7.9 Hz, 9H), 0.75-0.67 (m, 6H). LCMS Method C: rt 6.55 min; m/z 290 [M+H]$^+$.

(f) Methyl 2-(2-ethynylpyridin-3-yl)acetate (I120)

A solution of TBAF (1 M solution in THF; 0.207 mL, 0.207 mmol) was added to a solution of methyl 2-(2-((triethylsilyl)ethynyl)pyridin-3-yl)acetate (I119) (50.0 mg, 0.173 mmol) in THF (2 mL) at 0° C. The reaction was stirred for 2 minutes at 0° C. then diluted with saturated NaHCO$_3$ (20 mL). EtOAc (20 mL) was then added and the layers separated. The aqueous layer was extracted with EtOAc (2×20 mL) then the combined organic layers were washed with water 20 mL), brine (20 mL) and dried over Na$_2$SO$_4$. The solvent was removed in vacuo to yield a brown oily residue. The oil was purified using column chromatography on silica gel (0-55% EtOAc in cyclohexane) to afford the title compound (I120) (25.9 mg, 86%) as an orange oil; $^1$H NMR (400 MHz, CDCl$_3$) δ 8.52 (dd, J=4.8, 1.6 Hz, 1H), 7.65 (dd, J=7.9, 1.6 Hz, 1H), 7.29-7.24 (m, peak obscured by solvent), 3.87 (s, 2H), 3.72 (s, 3H), 3.35 (s, 1H). LCMS Method C: rt 4.74 min; m/z 176 [M+H]$^+$.

(g) tert-Butyl 4-(4-((4-((3-(2-methoxy-2-oxoethyl)pyridin-2-yl)ethynyl)-5-(trifluoromethyl)pyrimidin-2-yl)amino)phenyl)piperidine-1-carboxylate (I121)

A solution of methyl 2-(2-ethynylpyridin-3-yl)acetate (I120) (43.6 mg, 0.249 mmol) in dimethylformamide (2 mL) and triethylamine (107 µL, 0.765 mmol) were added to a mixture of tert-butyl 4-(4-((4-chloro-5-(trifluoromethyl)pyrimidin-2-yl)amino)phenyl)piperidine-1-carboxylate (I45) (87.4 mg, 0.191 mmol), Pd(PPh$_3$)$_2$Cl$_2$ (13 mg, 0.019 mmol), Cu(I)I (5.5 mg, 0.029 mmol) and triphenylphosphine (7.5 mg, 0.017 mmol) in dimethylformamide (2 mL). The reaction mixture was heated under microwave irradiation at 120° C. for 10 minutes. The cooled mixture was diluted with EtOAc and passed through a plug of celite, washing with ethyl acetate (100 mL). The solvent was removed under reduced pressure and the residue partitioned between EtOAc (70 mL) and water (50 mL). The layers separated and the aqueous layer extracted with EtOAc (2×50 mL). The combined organic extracts were washed with brine (70 mL) and dried over Na$_2$SO$_4$. After filtration the solvent was removed under reduced pressure to give a dark brown residue. The residue was purified by column chromatography on silica gel (0-40% EtOAc in petroleum benzine 40-60° C.) to yield the title compound (I121) (81.5 mg, 72%) as a brown viscous oil which was used without further purification.

(h) tert-Butyl 4-(4-((4-(2-(3-(2-methoxy-2-oxoethyl)pyridin-2-yl)ethyl)-5-(trifluoromethyl)pyrimidin-2-yl)amino)phenyl)piperidine-1-carboxylate (I122)

A solution of tert-butyl 4-(4-((4-((3-(2-methoxy-2-oxoethyl)pyridin-2-yl)ethynyl)-5-(trifluoromethyl)pyrimidin-2-yl)amino)phenyl)piperidine-1-carboxylate (I121) (81.5 mg, 0.137 mmol) in DMF (10 mL) was added to a solution of 10% Pd/C (170 mg) in DMF (7 mL). The reaction was stirred at room temperature for 24 hours under an atmosphere of hydrogen. The reaction was filtered through a pad of celite, washing with EtOAc (100 mL). The solvent was removed in vacuo to afford an oil which was purified on by column chromatography on silica gel (0-40% EtOAc in petroleum benzine 40-60° C.) to yield the title compound (I122) (61.4 mg, 75%) as a viscous oil; $^1$H NMR (400 MHz, CDCl$_3$) δ 8.51 (s, 1H), 8.46 (dd, J=4.8, 1.7 Hz, 1H), 7.56-7.50 (m, 3H), 7.49 (s, 1H), 7.19-7.14 (m, 2H), 7.12 (dd, J=7.7, 4.8 Hz, 1H), 4.23 (bs, 2H), 3.72 (s, 2H), 3.70 (s, 3H), 3.40-3.33 (m, 2H), 3.32-3.23 (m, 2H), 2.80 (t, J=12.1 Hz, 2H), 2.62 (tt, J=12.1, 3.5 Hz, 1H), 1.81 (d, J=12.9 Hz, 2H), 1.65-1.55 (m, 2H), 1.48 (s, 9H). LCMS Method C: rt 6.01 min; m/z 622 [M+Na]$^+$, 600 [M+H]$^+$, 544 [M-$^t$Butyl+2H]$^+$.

(i) Lithium 2-(2-(2-(2-((4-(1-(tert-butoxycarbonyl)piperidin-4-yl)phenyl)amino)-5-(trifluoromethyl)pyrimidin-4-yl)ethyl)pyridin-3-yl)acetate (I123)

LiOH.H$_2$O (19.1 mg, 0.455 mmol) was added to a solution of tert-butyl 4-(4-((4-(2-(3-(2-methoxy-2-oxoethyl)pyridin-2-yl)ethyl)-5-(trifluoromethyl)pyrimidin-2-yl)amino)phenyl)piperidine-1-carboxylate (I122) (90.9 mg, 0.152 mmol) in THF (7 mL), water (1.5 mL) and methanol (1 mL). The resulting mixture was allowed to stir at room temperature for 20 hours. The volatiles were removed in vacuo and the residue was diluted with EtOAc (50 mL) and sat. aq. NaHCO$_3$ (50 mL). The layers were separated and the aqueous layer was extracted with EtOAc (2×50 mL), the organic layers were combined, washed with brine (50 mL), dried over Na$_2$SO$_4$, filtered and concentrated under reduced pressure to give the title compound (I123) (81.3 mg, 91%) as a pale yellow viscous oil.

(j) tert-Butyl 4-(4-((4-(2-(3-(2-amino-2-oxoethyl)pyridin-2-yl)ethyl)-5-(trifluoromethyl)pyrimidin-2-yl)amino)phenyl)piperidine-1-carboxylate (I124)

1-Hydroxybenzotriazole (20.4 mg, 0.151 mmol), EDCl (29.0 mg, 0.151 mmol) and N,N-diisopropylethylamine (0.192 mL, 1.10 mmol) were added to a solution of lithium 2-(2-(2-(2-((4-(1-(tert-butoxycarbonyl)piperidin-4-yl)phenyl)amino)-5-(trifluoromethyl)pyrimidin-4-yl)ethyl)pyridin-3-yl)acetate (I123) (81.3 mg, 0.137 mmol) in dry THF (6 mL) and dry DMF (1 mL) under an atmosphere of nitrogen. Ammonium carbonate (106 mg, 1.10 mmol) was added in one portion to the stirred reaction mixture after 10 minutes. The reaction was left to stir at room temperature for 18 hours. The volatiles were removed in vacuo and the residue was diluted with EtOAc (50 mL) and washed with saturated NaHCO$_3$ (50 mL). The aqueous layer was extracted with EtOAc (2×50 mL). The combined organic layers were washed with brine (50 mL) and dried over Na$_2$SO$_4$. After filtration the solvent was removed in vacuo to afford a pale yellow oil. The crude material was purified by column chromatography on silica gel (0-100% EtOAc in petroleum benzine 40-60° C.) to afford the title compound (I124) (66.3 mg, 83%) as a white semi-solid; $^1$H NMR (400 MHz, CDCl$_3$) δ 8.50 (d, J=0.4 Hz, 1H), 8.49 (dd, J=4.8, 1.7 Hz, 1H), 7.62 (s, 1H), 7.54 (dd, J=7.7, 1.7 Hz, 1H), 7.51 (d, J=8.7 Hz, 2H), 7.19-7.13 (m, 3H), 5.40-5.35 (m, 2H), 4.23 (s, 2H), 3.68 (s, 2H), 3.41-3.35 (m, 2H), 3.32-3.24 (m, 2H), 2.80 (t, J=12.6 Hz, 2H), 2.63 (tt, J=12.0, 3.4 Hz, 1H), 1.81 (d, J=12.5 Hz, 2H), 1.65-1.57 (m, peaks obscured by solvent), 1.48 (s, 9H). LCMS Method C: rt 5.25 min; m/z 607 [M+Na]$^+$, 585 [M+H]$^+$, 529 [M-$^t$Butyl+2H]$^+$.

(k) 2-(2-(2-(2-((4-(Piperidin-4-yl)phenyl)amino)-5-(trifluoromethyl)pyrimidin-4-yl)ethyl)pyridin-3-yl)acetamide (32)

Trifluoroacetic acid (0.337 mL, 4.40 mmol) was added to a solution tert-butyl 4-(4-((4-(2-(3-(2-amino-2-oxoethyl)pyridin-2-yl)ethyl)-5-(trifluoromethyl)pyrimidin-2-yl)amino)phenyl)piperidine-1-carboxylate (I124) (64.3 mg, 0.110 mmol) in dry DCM (15 mL) under an atmosphere of nitrogen and the reaction was stirred at room temperature for 23 hours. The volatiles were removed in vacuo and the residue partitioned between EtOAc (40 mL) and 2 M NaOH (50 mL). The layers were separated and the aqueous layer was extracted with EtOAc (2×30 mL). The combined organic layers were washed with water (40 mL), brine (40 mL) and dried over Na$_2$SO$_4$. After filtration the solvent was removed under reduced pressure to give a yellow solid which was suspended in DCM (5 mL) and cyclohexane (15 mL). The precipitate was filtered to afford the title compound (32) (35.5 mg, 53%) as yellow solid; $^1$H NMR (400 MHz, d$_6$-DMSO) δ 10.05 (s, 1H), 8.64 (s, 1H), 8.36 (dd, J=4.8, 1.7 Hz, 1H), 7.62-7.55 (m, 3H), 7.53 (s, 1H), 7.18 (dd, J=7.6, 4.8 Hz, 1H), 7.15 (d, J=8.6 Hz, 2H), 7.00 (s, 1H), 3.53 (s, 2H), 3.24 (s, 4H), 3.02 (d, J=11.9 Hz, 2H), 2.61-2.52 (m, peaks obscured by solvent), 1.67 (d, J=11.3 Hz, 2H), 1.49 (qd, J=12.2, 3.8 Hz, 2H). LCMS Method C: rt 1.50, 1.59 min; m/z 485 [M+H]$^+$.

Example 33

2-(2-(2-(2-((4-(1-Methylpiperidin-4-yl)phenyl)amino)-5-(trifluoromethyl)pyrimidin-4-yl)ethyl)pyridin-3-yl)acetamide (33)

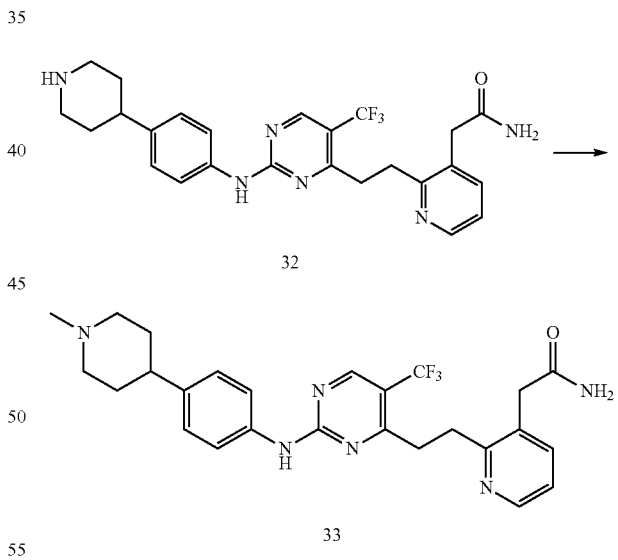

Formaldehyde (37 wt % in H$_2$O; 16.5 µL, 0.222 mmol) was added to a suspension of 2-(2-(2-(2-((4-(piperidin-4-yl)phenyl)amino)-5-(trifluoromethyl)pyrimidin-4-yl)ethyl)pyridin-3-yl)acetamide (32) (22 mg, 0.044 mmol) in anhydrous methanol (5 mL) under an atmosphere of nitrogen. Sodium triacetoxyborohydride (94.0 mg, 0.444 mmol) was then added in one portion and the reaction was stirred at room temperature for 2 hours. The volatiles were removed in vacuo and the residue was diluted with EtOAc (25 mL) and sat. aq. NaHCO$_3$ (25 mL). The layers were separated and the aqueous layer was extracted with EtOAc (2×25 mL), the combined organic layers were washed with water (25 mL), brine (25 mL) and dried over Na$_2$SO$_4$. The solvent was removed under reduced pressure to yield a white solid. The solid was suspended in DCM (5 mL) and cyclohexane (20 mL) and filtered to afford the title compound (33) (16 mg, 72%) as an off-white solid; $^1$H NMR (400 MHz, d$_6$-DMSO) δ 10.06 (s, 1H), 8.64 (s, 1H), 8.36 (dd, J=4.8, 1.7 Hz, 1H), 7.59 (dd, J=7.7, 1.2 Hz, 3H), 7.53 (s, 1H), 7.20-7.13 (m, 3H), 7.00 (s, 1H), 3.53 (s, 2H), 3.24 (s, 4H), 2.91 (d, J=10.6 Hz, 2H), 2.47-2.39 (m, 1H), 2.24 (s, 3H), 2.12-1.99 (m, 2H), 1.78-1.59 (m, 4H). LCMS Method C: rt 1.51, 1.579 min; m/z 499 [M+H]$^+$.

Example 34

2-(2-(2-((4-(1-Methylpiperidin-4-yl)phenyl)amino)-5-(trifluoromethyl)pyrimidin-4-yl)ethyl)isonicotinamide (34)

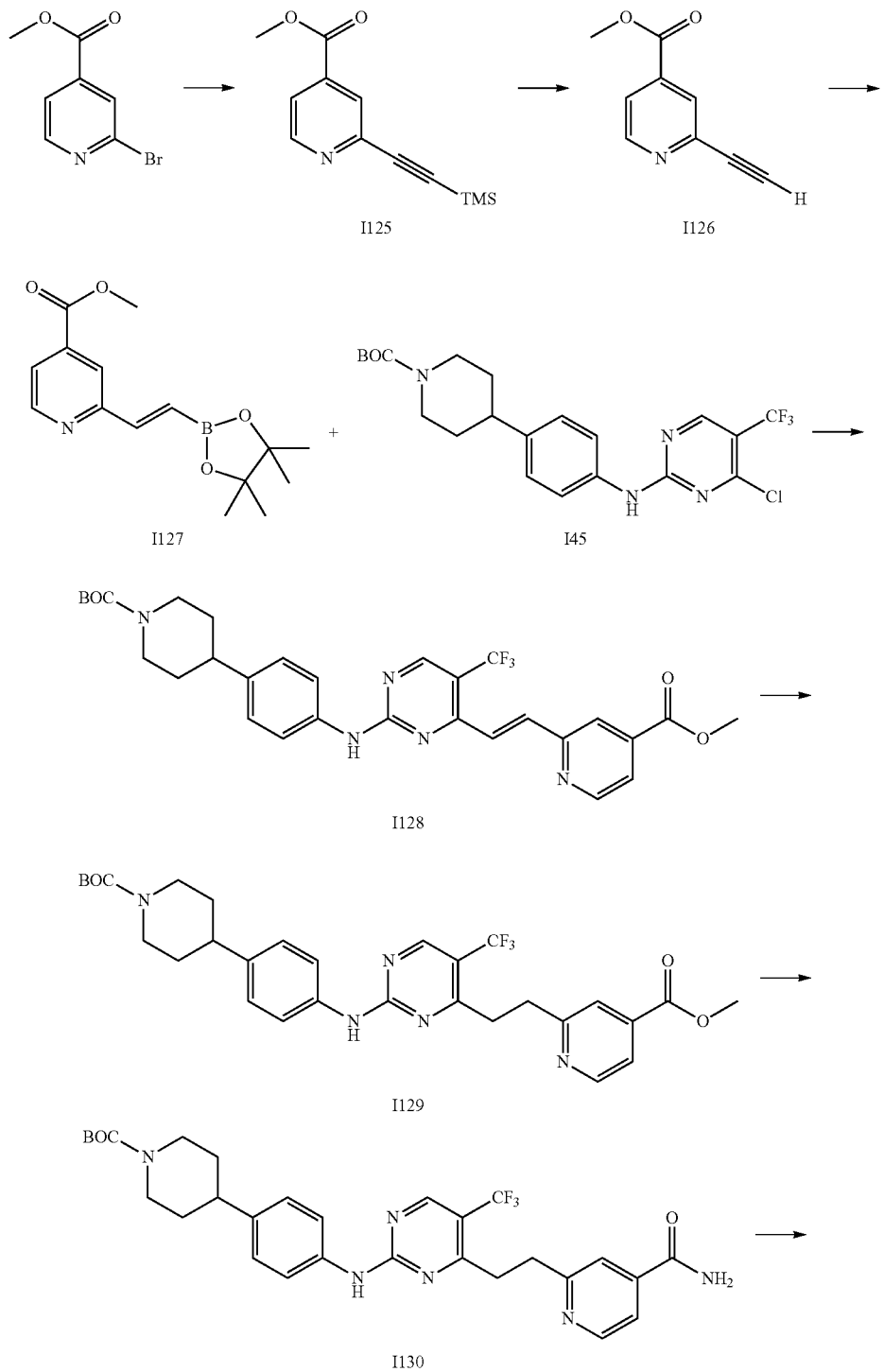

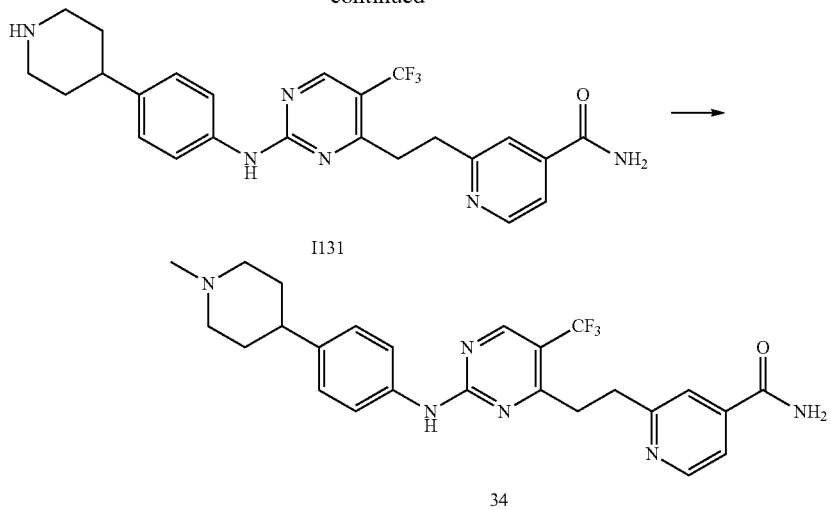

I131

(a) Methyl 2-((trimethylsilyl)ethynyl)isonicotinate (I125)

Methyl 2-bromonicotinate (1.00 g, 4.63 mmol), PdCl$_2$(PPh$_3$)$_2$ (162 mg, 0.231 mmol) triphenyl phosphine (60.7 mg, 0.231 mmol) and Cu(I)I (44.1 mg, 0.231 mmol) were placed into oven dried reaction flask under nitrogen then TMS-acetylene (785 µL, 5.55 mmol), dry, degassed THF (5 mL) and triethylamine (5 mL) were added. The resulting mixture was stirred at room temperature for 16 hours then evaporated under reduced pressure to give a black residue which was adsorbed onto silica gel. Chromatography (SiO$_2$, 0-20% ethyl acetate/petroleum benzine 40-60° C.) gave the title compound (I125) (708.6 mg, 66% yield) as a dark coloured liquid; $^1$H NMR (400 MHz, CDCl$_3$) δ 8.75-8.61 (m, 1H), 7.98 (dd, J=1.0, 0.4 Hz, 1H), 7.74 (dd, J=5.1, 1.6 Hz, 1H), 3.94 (s, 3H), 0.26 (s, 9H). LCMS Method C: rt 6.38 min; m/z 234.1 [M+1]$^+$.

(b) Methyl 2-ethynylisonicotinate (I126)

To a solution of methyl 2-((trimethylsilyl)ethynyl)isonicotinate (I125) (8.00 g, 34.2 mmol) in THF (150 mL) was added TBAF (1.0 M in THF) (51.4 mL, 51.4 mmol) at 0° C. The resulting solution was allowed to warm to room temperature at which stirring was continued for 1 hour. The reaction mixture was diluted with ethyl acetate (50 mL) and washed with 10% NaHCO$_3$ (50 mL). The organic layer was dried (MgSO$_4$) and evaporated under reduced pressure to give a dark brown/black residue. The residue was adsorbed onto silica gel and purified by chromatography (SiO$_2$, 0-20% ethyl acetate/petroleum benzine 40-60° C.) to give the title compound (I126) (4.5 g, 81%) as a yellow solid; $^1$H NMR (400 MHz, CDCl$_3$) δ 8.73 (dd, J=5.1, 0.9 Hz, 1H), 8.01 (dd, J=1.5, 0.9 Hz, 1H), 7.80 (dd, J=5.1, 1.6 Hz, 1H), 3.95 (s, 3H), 3.22 (s, 1H).

(c) (E)-Methyl 2-(2-(4,4,5,5-tetramethyl-1,3,2-dioxaborolan-2-yl)vinyl)isonicotinate (I127)

A solution of methyl 2-ethynylisonicotinate (I126) (100 mg, 0.621 mmol), Cu(I)Cl (1.84 mg, 0.0186 mmol), NaOtBu (3.6 mg, 0.037 mmol), bispinacolatodiboron (189 mg, 3.74 mmol), Xantphos (10.7 mg, 0.0937 mmol) and methanol (40 mg, 1.2 mmol) in THF (5 mL) was stirred at room temperature for 4 hours under nitrogen. The crude reaction mixture was adsorbed onto silica gel and solvents removed by evaporation under reduced pressure. Purification by chromatography (SiO$_2$, 0-20% ethyl acetate/petroleum benzine 40-60° C.) gave the title compound (I127) (141.3 mg, 79%) as a yellow liquid; $^1$H NMR (400 MHz, CDCl$_3$) δ 8.70 (dd, J=5.0, 0.6 Hz, 1H), 7.93-7.90 (m, 1H), 7.67 (dt, J=4.4, 2.2 Hz, 1H), 7.46 (d, J=18.3 Hz, 1H), 6.67 (d, J=18.3 Hz, 1H), 3.91 (s, 3H), 1.27 (s, 12H).

(d) (E)-Methyl 2-(2-(2-((4-(1-(tert-butoxycarbonyl)piperidin-4-yl)phenyl)amino)-5-(trifluoromethyl)pyrimidin-4-yl)vinyl)isonicotinate (I128)

An aqueous 2.0 M solution of Na$_2$CO$_3$ (0.3 mL) was added to a solution of tert-butyl 4-(4-((4-chloro-5-(trifluoromethyl)pyrimidin-2-yl)amino)phenyl)piperidine-1-carboxylate (I45) (100 mg, 0.103 mmol), (E)-methyl 2-(2-(4,4,5,5-tetramethyl-1,3,2-dioxaborolan-2-yl)vinyl)isonicotinate (I127) (76 mg, 0.26 mmol), Pd(PPh$_3$)$_4$ (75 mg, 0.66 mmol), LiCl (28 mg, 0.66 mmol) in 1,4-dioxane (5 mL) and the resulting mixture was stirred under nitrogen at 90° C. for 16 hours. The crude mixture was evaporated under reduced pressure and adsorbed onto silica gel. Chromatography (SiO$_2$, 0-50% ethyl acetate/petroleum benzine 40-60° C.) gave the title compound (I128) (110 mg, 86%) as a yellow solid; $^1$H NMR (400 MHz, CDCl$_3$) δ 8.84 (d, J=4.9 Hz, 1H), 8.64 (s, 1H), 8.14 (d, J=15.1 Hz, 1H), 8.02 (s, 1H), 7.88 (dd, J=15.1, 1.6 Hz, 1H), 7.80 (dd, J=4.9, 1.5 Hz, 1H), 7.60 (d, J=8.5 Hz, 2H), 7.36 (s, 1H), 7.25 (m, 1H), 4.33-4.19 (m, 2H), 4.00 (s, 3H), 2.82 (m, 2H), 2.67 (m, 1H), 1.85 (d, J=12.7 Hz, 2H), 1.64 (dd, J=12.5, 4.0 Hz, 2H), 1.59 (s, 9H). LCMS Method C: rt 6.93 min; m/z 584.21 [M+1]+, 582.1 [M−1]$^-$, 528.1 [M-tBu+2]+.

(e) Methyl 2-(2-(2-((4-(1-(tert-butoxycarbonyl)piperidin-4-yl)phenyl)amino)-5-(trifluoromethyl)pyrimidin-4-yl)ethyl)isonicotinate (I129)

A suspension of (E)-methyl 2-(2-(2-((4-(1-(tert-butoxycarbonyl)piperidin-4-yl)phenyl)amino)-5-(trifluoromethyl)pyrimidin-4-yl)vinyl)isonicotinate (I128) (110 mg, 0.188 mmol), and 10% Pd/C (20 mg) in MeOH (10 mL) was stirred under an atmosphere of hydrogen at atmospheric pressure for 16 hours. The resulting mixture was filtered and the filtrate evaporated under reduced pressure to give the title compound (I129) (70 mg, 63%) as a yellow liquid; $^1$H NMR (400 MHz, CDCl$_3$) δ 8.68 (dd, J=5.1, 0.7 Hz, 1H), 8.51 (s, 1H), 7.76 (s, 1H), 7.66 (dd, J=5.1, 1.5 Hz, 1H), 7.54-7.47 (m, 3H), 7.18 (t, J=5.5 Hz, 2H), 4.22 (s, 2H), 3.93 (d, J=3.9 Hz, 3H), 3.43-3.35 (m, 2H), 3.34-3.26 (m, 2H), 2.80 (t, J=12.1 Hz, 2H), 2.63 (d, J=3.5 Hz, 1H), 1.82 (d, J=12.3 Hz, 2H), 1.67-1.54 (m, 2H), 1.48 (d, J=7.1 Hz, 3H). LCMS Method C: rt 6.75 min; m/z 586.1 [M+1]+, 584.2 [M−1]−.

(f) tert-Butyl 4-(4-((4-(2-(4-carbamoylpyridin-2-yl)ethyl)-5-(trifluoromethyl)pyrimidin-2-yl)amino)phenyl)piperidine-1-carboxylate (I130)

A solution of methyl 2-(2-(2-((4-(1-(tert-butoxycarbonyl)piperidin-4-yl)phenyl)amino)-5-(trifluoromethyl)pyrimidin-4-yl)ethyl)isonicotinate (I129) (70.0 mg, 0.120 mmol), and LiOH.H$_2$O (15 mg, 0.36 mmol) in THF (5 mL), water (1 mL) and MeOH (0.5 mL) was stirred at room temperature for 4 hours. The volatiles were evaporated under reduced pressure to give a yellow solid which was dissolved in dry DMF (4 mL). HATU (133 mg, 0.350 mmol), DIPEA (60 μL, 0.034 mmol) and ammonium chloride (187 mg, 3.50 mmol) were added and the resulting mixture was stirred at room temperature overnight. The volatiles were evaporated under reduced pressure and the residue diluted with ethyl acetate. The resulting solution was washed with 10% aqueous NaHCO$_3$, then the organic layer was dried (MgSO$_4$) and volatiles removed by evaporation under reduced pressure. The residue was adsorbed onto silica gel and purified by chromatography (SiO$_2$, 0-100% ethyl acetate/petroleum benzine 40-60° C.) to give the title compound (I130) (50 mg, 50%) as a colourless solid; $^1$H NMR (400 MHz, CDCl$_3$) δ 8.67 (dd, J=5.1, 0.7 Hz, 1H), 8.51 (s, 1H), 7.60 (s, 1H), 7.55 (s, 1H), 7.53 (d, J=8.6 Hz, 2H), 7.44 (dd, J=5.1, 1.6 Hz, 1H), 7.18 (d, J=8.5 Hz, 2H), 6.37-6.20 (m, 1H), 6.18-5.96 (m, 1H), 4.22 (s, 2H), 3.34 (tt, J=10.4, 5.0 Hz, 4H), 2.63 (s, 1H), 1.81 (d, J=12.7 Hz, 2H), 1.73 (s, 2H), 1.60 (dd, J=12.7, 4.1 Hz, 2H), 1.48 (s, 9H). LCMS Method C: rt 6.04 min; m/z 571.2 [M+1C, 569.2 [M−1]−, 515.2 [M-t-Bu+2]+.

(g) 2-(2-(2-(2-((4-(Piperidin-4-yl)phenyl)amino)-5-(trifluoromethyl)pyrimidin-4-yl)ethyl)isonicotinamide (I131)

Trifluoroacetic acid (100 μL, 0.131 mmol) was added to a solution of tert-butyl 4-(4-((4-(2-(4-carbamoylpyridin-2-yl)ethyl)-5-(trifluoromethyl)pyrimidin-2-yl)amino)phenyl)piperidine-1-carboxylate (I130) (50 mg, 88 μmol) in DCM (4 mL) and the resulting mixture was stirred for 1 hour at room temperature. The volatiles were evaporated under reduced pressure and the residue purified by chromatography (SiO$_2$, 0-50% MeOH/DCM) to give the title compound (I131) (28 mg, 68%) as a colourless solid; $^1$H NMR (400 MHz, d$_4$-MeOD) δ 8.55 (d, J=5.2 Hz, 1H), 8.49 (s, 1H), 7.74 (s, 1H), 7.61 (dd, J=5.2, 1.3 Hz, 1H), 7.53 (d, J=8.3 Hz, 2H), 7.17 (d, J=8.5 Hz, 2H), 3.46 (d, J=12.7 Hz, 2H), 3.37 (t, J=7.0 Hz, 2H), 3.27 (dt, J=3.2, 1.6 Hz, 5H), 3.18-3.04 (m, 2H), 2.83 (ddd, J=12.1, 8.7, 3.6 Hz, 1H), 2.03 (d, J=13.8 Hz, 2H), 1.88 (ddd, J=16.7, 13.6, 3.8 Hz, 2H). LCMS Method C: rt 4.44 min; m/z 471.1 [M+1]+, 469.1 [M−1]−.

(h) 2-(2-(2-((4-(1-Methylpiperidin-4-yl)phenyl)amino)-5-(trifluoromethyl)pyrimidin-4-yl)ethyl)isonicotinamide (34)

Formaldehyde solution (37% aq; 24 μL, 0.30 mmol) was added to a solution of 2-(2-(2-((4-(Piperidin-4-yl)phenyl) amino)-5-(trifluoromethyl)pyrimidin-4-yl)ethyl)isonicotinamide (I131) (28 mg, 60 μmol) in dry MeOH (2 mL). Sodium triacetoxyborohydride (63 mg, 0.30 mmol) was added and the resulting mixture stirred at room temperature for 2 hours under nitrogen. Ethyl acetate was added and the resulting solution adsorbed onto silica gel. Chromatography (SiO$_2$, 0-50% MeOH/DCM) gave the title compound (34) (14 mg, 49%) as a colourless solid; $^1$H NMR (400 MHz, d$_4$-MeOD) δ 8.58 (d, J=4.9 Hz, 1H), 8.51 (s, 1H), 7.73 (s, 1H), 7.61 (dd, J=5.2, 1.6 Hz, 1H), 7.53 (d, J=8.5 Hz, 2H), 7.18 (d, J=8.6 Hz, 2H), 3.51-3.31 (m, 4H), 2.99 (d, J=11.7 Hz, 2H), 2.56-2.44 (m, 1H), 2.32 (s, 3H), 2.15 (d, J=2.8 Hz, 2H), 1.87-1.70 (m, 4H). LCMS Method C: rt 4.50 min; m/z 485.1 [M+1]+, 483.1 [M−1]−.

Example 35

2-(2-(2-(2-((4-(pyrrolidin-3-yl)phenyl)amino)-5-(trifluoromethyl)pyrimidin-4-yl)ethyl)phenyl)acetamide (35)

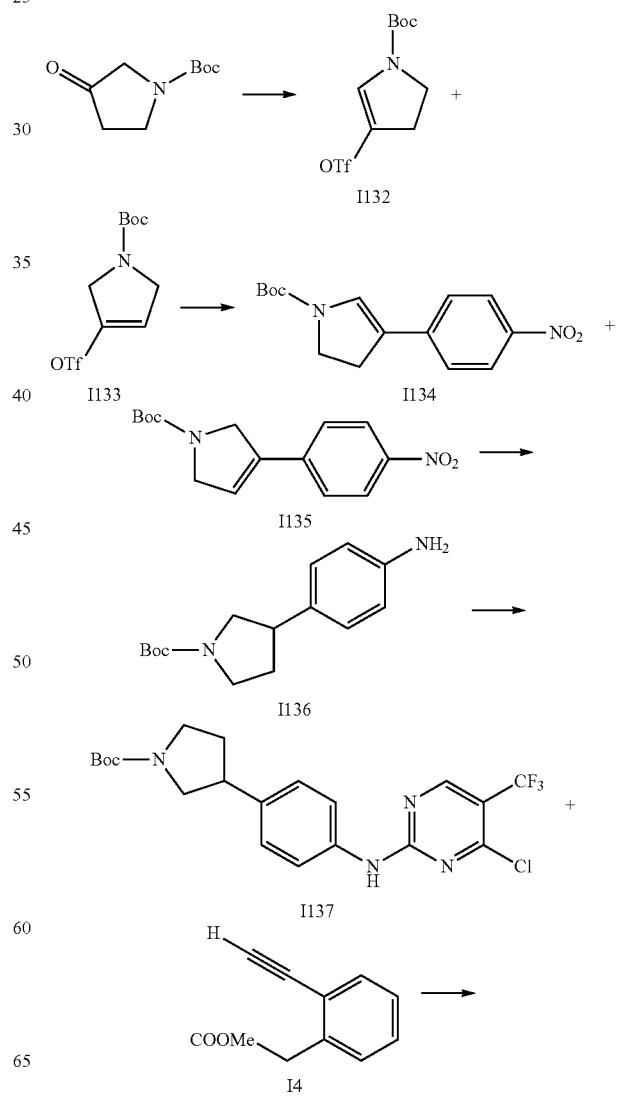

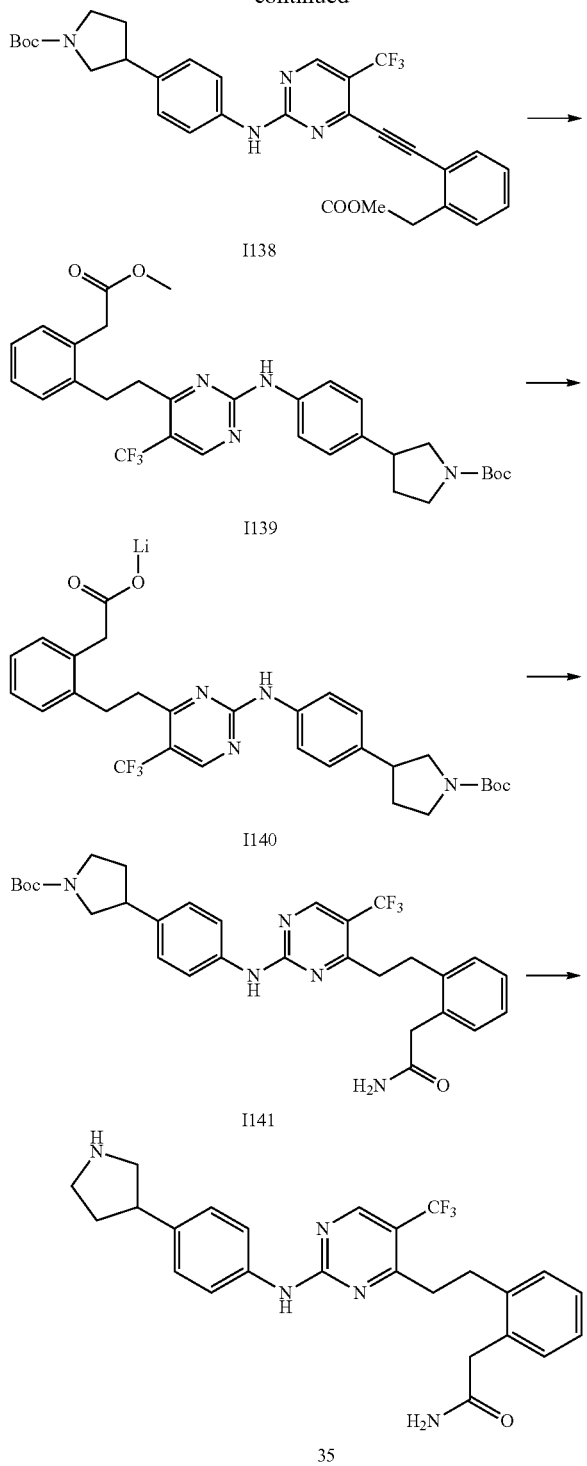

(a) tert-Butyl 4-(((trifluoromethyl)sulfonyl)oxy)-2,3-dihydro-H-pyrrole-1-carboxylate (I132 and I133)

To a stirred solution of sodium bis(trimethylsilyl)amide (1.01 g, 5.50 mmol) in THF (20 mL) was added dropwise a solution of tert-butyl 3-oxopyrrolidine-1-carboxylate (0.925 g, 5.00 mmol) in THF (7 mL) at –78° C. After being stirred for 15 minutes, N-phenyl-bis(trifluoromethanesulfonimide) (1.79 g, 5.00 mmol) in THF (12 mL) was added and the reaction mixture was stirred at –78° C. for an additional 3 hours, and then at room temperature for 1 hour. The reaction mixture was quenched with 10% aqueous NaHCO$_3$ and extracted with EtOAc. The organic layer was washed with brine, dried over MgSO$_4$, and concentrated in vacuo. The resulting residue was purified by column chromatography on silica gel (20-80% dichloromethane in petroleum benzine 40-60° C.) to give a mixture of the title compounds (I132 and I133) (1.44 g, 90%) as a pale yellow oil; $^1$H NMR (400 MHz, CDCl$_3$) δ 8.65 (s, 1H), 5.66 (d, J=17.5 Hz, 2H), 4.21-4.09 (m, 8H), 1.41 (s, 18H).

(b) tert-Butyl 4-(4-nitrophenyl)-2,3-dihydro-1H-pyrrole-1-carboxylate (I134 and I135)

A solution of 2 M aqueous Na$_2$CO$_3$ (5.70 mL, 9.09 mmol) was added to a degassed mixture of 4-nitrophenylboronic acid (0.909 g, 1.52 mmol, 1.2 eq), tert-butyl 4-(((trifluoromethyl)sulfonyl)oxy)-2,3-dihydro-1H-pyrrole-1-carboxylate (I34 and 135) (1.44 g, 4.54 mmol), LiCl (0.385 g, 9.08 mmol) and Pd(PPh$_3$)$_4$ (1.57 g, 1.36 mmol) in 1,4-dioxane (10 mL). The reaction mixture was stirred at 80-90° C. for 4 hours. The resulting mixture was dissolved in EtOAc (70 mL) and the organic layer was washed with H$_2$O (50 mL), brine (50 mL) and dried over Na$_2$SO$_4$ to yield a dark red oil. The oil was purified by column chromatography on silica gel (0-20% EtOAc in petroleum benzine 40-60° C.) to give a mixture of the title compounds (I134 and I135) (0.442 g, 34%) as a light yellow solid; $^1$H NMR (400 MHz, CDCl$_3$) δ 8.41-8.32 (m, 2H), 8.24-8.19 (m, 2H), 7.81-7.73 (m, 2H), 7.52 (dd, J=8.8, 2.4 Hz), 6.43-6.33 (m, 1H), 4.58-4.48 (m, 4H), 4.42-4.31 (m, 4H), 1.52 (s, 9H), 1.51 (s, 9H).

(c) tert-Butyl 3-(4-aminophenyl)pyrrolidine-1-carboxylate (I136)

A solution of tert-butyl 4-(4-nitrophenyl)-2,3-dihydro-1H-pyrrole-1-carboxylate (I134 and I135) (0.442 g, 1.52 mmol) in EtOH (10 mL) and DMF (10 mL) was added to a solution of 10% Pd/C (255 mg) in DMF (10 mL). The reaction was stirred at room temperature for 17 hours under an atmosphere of hydrogen. The reaction was filtered through a pad of celite and washed through with EtOAc (130 mL). The solvent was removed in vacuo to yield a brown oil which was purified by column chromatography on silica gel (0-50% EtOAc in petroleum benzine 40-60° C.) to give the title compound (I136) (0.307 g, 77%) as a brown oil; $^1$H NMR (400 MHz, CDCl$_3$) δ 7.02 (d, J=8.4 Hz, 2H), 6.64 (d, J=8.4 Hz, 2H), 3.85-3.49 (m, 4H), 3.43-3.29 (m, 1H), 3.29-3.15 (m, 2H), 2.18 (d, J=6.5 Hz, 1H), 1.97-1.85 (m, 1H), 1.47 (d, J=4.7 Hz, 9H). LCMS Method C: rt 4.88 min; m/z 163.2 [M-Boc+H]$^+$.

(d) tert-Butyl 3-(4-((4-chloro-5-(trifluoromethyl)pyrimidin-2-yl)amino)phenyl)pyrrolidine-1-carboxylate (I137)

Zinc chloride (1.0 M in Et$_2$O) (1.40 mL, 1.40 mmol) was added to a solution of 2,4-dichloro-5-(trifluoromethyl)pyrimidine (180 μL, 1.29 mmol) in 1:1 DCE/t-BuOH (10 mL) at 0° C. under a stream of nitrogen gas. The mixture was stirred for 1 hour at 0° C. and then tert-butyl 3-(4-aminophenyl)pyrrolidine-1-carboxylate (I136) (0.307 g, 1.17 mmol) in 1:1 DCE/tBuOH (10 mL) was added. A solution of NEt$_3$ (0.180 mL, 1.29 mmol, 1.1 eq) in 1:1 DCE/t-BuOH (5 mL) was next added dropwise at 0° C. The reaction mixture was vigorously stirred for a further 30 minutes at 0° C. after the final addition and then at room temperature for 16 hours. The solvent was removed in vacuo to afford a brown oily residue which was purified by column chromatography on silica gel (0-50% EtOAc in petroleum benzine 40-60° C.) to yield a pale yellow solid. The solid was suspended in MeOH (15 mL) and water (15 mL). The precipitate was filtered to afford the title compound (I137) (0.449 g, 87%) as a pale yellow solid; $^1$H NMR (400 MHz, CDCl$_3$)$^1$H NMR (400 MHz, CDCl$_3$) δ 8.56 (s, 1H), 7.53 (d, J=8.5 Hz, 2H), 7.40 (s, 1H), 7.26 (s, 2H), 3.92-3.73 (m, 1H), 3.69-3.51 (m, 1H), 3.48-3.22 (m, 3H), 2.26 (s, 1H), 2.03-1.90 (m, 1H), 1.48 (s, 9H). LCMS Method C: rt 6.68 min; m/z 443.0 [M+H]$^+$, 441.1 [M−H]$^−$.

(e) tert-Butyl 3-(4-((4-((2-(2-methoxy-2-oxoethyl)phenyl)ethynyl)-5-(trifluoromethyl)pyrimidin-2-yl)amino)phenyl)pyrrolidine-1-carboxylate (I138)

A solution of methyl 2-ethynylbenzoate (I4) (0.21 g, 1.2 mmol) in dimethylformamide (3 mL) and triethylamine (0.57 mL, 4.1 mmol) were added to a mixture of tert-butyl 3-(4-((4-chloro-5-(trifluoromethyl)pyrimidin-2-yl)amino)phenyl)pyrrolidine-1-carboxylate (I137) (0.45 g, 1.0 mmol, 1 eq), Pd(PPh$_3$)$_2$Cl$_2$ (71 mg, 0.10 mmol), Cu(I)I (30 mg, 0.15 mmol) and triphenylphosphine (40 mg, 0.15 mmol, 0.15) in dimethylformamide (4 mL). The reaction mixture was heated under microwave irradiation at 120° C. for 15 minutes. The reaction was cooled and the mixture diluted with EtOAc and passed through a plug of celite and washed through with EtOAc (60 mL). Water (50 mL) was added and the layers separated. The aqueous layer was extracted with EtOAc (2×50 mL). The combined organic extracts were washed with water (50 mL) and brine (50 mL) and dried over Na$_2$SO$_4$. After filtration the solvent was removed in vacuo to give a dark brown residue. The residue was purified by column chromatography on silica gel (0-20 then 20-50% EtOAc in in petroleum benzine 40-60° C.) to give the title compound (I138) (0.53 g, 90%) as an orange oil; $^1$H NMR (400 MHz, CDCl$_3$) δ 8.62 (s, 1H), 7.68 (dd, J=7.7, 1.0 Hz, 1H), 7.58 (d, J=8.4 Hz, 2H), 7.47-7.41 (m, 2H), 7.39-7.30 (m, 4H), 7.24 (s, 1H), 3.96 (s, 2H), 3.87-3.75 (m, 1H), 3.70 (s, 3H), 3.68-3.52 (m, 1H), 3.48-3.22 (m, 3H), 2.30-2.21 (m, 1H), 2.02-1.94 (m, 1H), 1.49 (s, 9H). LCMS Method C: rt 6.82 min; m/z 581.1 [M+H]$^+$.

(f) tert-Butyl 3-(4-((4-(2-(2-methoxy-2-oxoethyl)phenethyl)-5-(trifluoromethyl)pyrimidin-2-yl)amino)phenyl)pyrrolidine-1-carboxylate (I139)

A solution of tert-butyl 3-(4-((4-((2-(2-methoxy-2-oxoethyl)phenyl)ethynyl)-5-(trifluoromethyl)pyrimidin-2-yl)amino)phenyl)pyrrolidine-1-carboxylate (I138) (0.527 g, 0.906 mmol) in EtOH (10 mL) was added to a solution of 10% Pd/C (0.500 g) in DMF (6 mL). The reaction was stirred at room temperature for 24 hours under an atmosphere of hydrogen. The reaction was filtered through a pad of celite and washed through with EtOAc (80 mL). The solvent was removed in vacuo to afford a yellow oil. This was taken up in DMF/EtOH (1:1, 10 mL) and a slurry of 10% Pd/C (0.500 g, 1 eq) in DMF was added. The reaction was stirred under an atmosphere of H$_2$ at room temperature for an additional 24 hours. The reaction was filtered through a pad of celite and washed through with EtOAc (80 mL). The solvent removed in vacuo to afford a yellow oil which was purified by column chromatography on silica gel (0-45% EtOAc in petroleum benzine 40-60° C.) to yield the title compound (I139) (0.126 g, 24%) as a brown oil; $^1$H NMR (400 MHz, CDCl$_3$) δ 8.54 (s, 1H), 7.58 (d, J=8.2 Hz, 2H), 7.39 (s, 1H), 7.30-7.17 (m, 6H), 3.91-3.72 (m, 2H), 3.75 (s, 2H), 3.68 (s, 3H), 3.66-3.52 (m, 1H), 3.47-3.21 (m, 3H), 3.17-3.04 (m, 4H), 2.23 (d, J=20.4 Hz, 1H), 1.97 (dd, J=21.1, 10.2 Hz, 1H), 1.48 (d, J=3.1 Hz, 9H). LCMS Method C: rt 6.91 min; m/z 585 [M+H]$^+$, 607 [M+Na]$^+$.

(g) Lithium 2-(2-(2-(2-((4-(1-(tert-butoxycarbonyl)pyrrolidin-3-yl)phenyl)amino)-5-(trifluoromethyl)pyrimidin-4-yl)ethyl)phenyl)acetate (I140)

LiOH.H$_2$O (0.015 g, 0.65 mmol, 3 eq) was added to a solution of tert-butyl 3-(4-((4-(2-(2-methoxy-2-oxoethyl)phenethyl)-5-(trifluoromethyl)pyrimidin-2-yl)amino)phenyl)pyrrolidine-1-carboxylate (I139) (0.13 g, 0.22 mmol) in THF (7 mL), water (1.5 mL) and methanol (1 mL) and the resulting mixture was allowed to stir at room temperature for 70 hours. The volatiles were removed in vacuo and the residue was diluted with EtOAc (50 mL) and saturated aqueous NaHCO$_3$ (50 mL). The layers were separated and the aqueous layer was extracted with EtOAc (2×50 mL). The combined organic layers were washed with brine (50 mL), dried over MgSO$_4$ and the solvent removed in vacuo to give the title compound (I140) (0.12 g, 99%) as a pale yellow oil; LCMS Method C: rt 6.56 min; m/z 571.1 [M-Li+2H]$^+$, 515.1 [M-Li-$^t$Butyl+2H]$^+$, 471.1 [M-Li-Boc+2H]$^+$, 569.2 [M-Li-H]$^−$.

(h) tert-Butyl 3-(4-((4-(2-(2-amino-2-oxoethyl)phenethyl)-5-(trifluoromethyl)pyrimidin-2-yl)amino)phenyl)pyrrolidine-1-carboxylate (I141)

1-Hydroxybenzotriazole (38.0 mg, 0.28 mmol), EDCl (50.0 mg, 0.32 mmol) and N,N-diisopropylethylamine (187 uL, 1.08 mmol) were added to a solution of lithium 2-(2-(2-(2-((4-(1-(tert-butoxycarbonyl)pyrrolidin-3-yl)phenyl)amino)-5-(trifluoromethyl)pyrimidin-4-yl)ethyl)phenyl)acetate (I140) (124 mg, 0.215 mmol) in dry THF (6 mL) and dry DMF (1 mL) under an atmosphere of nitrogen. Ammonium carbonate (101 mg, 1.08 mmol) was added in one portion to the stirred reaction mixture after 10 minutes and the reaction was stirred at room temperature for 23 hours. The volatiles were removed in vacuo and the residual solution was diluted with EtOAc (65 mL) and washed with saturated NaHCO$_3$ (65 mL). The aqueous layer was extracted with EtOAc (2×50 mL). The combined organic layers were washed with brine (50 mL) and dried over MgSO$_4$. The solvent was removed in vacuo to afford a pale yellow oil. The crude material was purified by column chromatography on silica gel (0-80% EtOAc in petroleum benzine 40-60° C.) to give the title compound (I141) (76 mg, 62%) as a white solid; $^1$H NMR (400 MHz, CDCl$_3$) δ 8.54 (s, 1H), 8.02 (s, 1H), 7.56 (d, J=7.4 Hz, 2H), 7.29-7.20 (m, 4H, obscured by solvent), 5.36 (d, J=21.2 Hz, 2H), 3.89-3.76 (m, 1H), 3.66-3.51 (m, 2H), 3.45-3.27 (m, 4H), 3.15-3.04 (m, 4H), 2.29-2.25 (m, 1H), 2.01-1.94 (m, 1H), 1.49 (s, 9H). LCMS Method C: rt 6.37 min; m/z 570.1 [M+H]$^+$, 568.2 [M−H]$^−$.

(i) 2-(2-(2-(2-((4-(Pyrrolidin-3-yl)phenyl)amino)-5-(trifluoromethyl)pyrimidin-4-yl)ethyl)phenyl)acetamide (35)

To a solution of tert-butyl 3-(4-((4-(2-(2-amino-2-oxoethyl)phenethyl)-5-(trifluoromethyl)pyrimidin-2-yl)amino)phenyl)pyrrolidine-1-carboxylate (I141) in DCM (20 mL) was added TFA (4.0 mL) and the reaction mixture was stirred at room temperature for 30 minutes. The solvent was removed in vacuo and the residue taken up in EtOAc (10 mL) and 2 M NaOH (10 mL). The organic layer was extracted with EtOAc (2×10 mL), and the combined layers washed with water (10 mL), brine (10 mL) and dried over MgSO$_4$. The solvent was removed in vacuo to give a yellow solid. The solid was suspended in cyclohexane and filtered to give a brown solid (42 mg). The product was purified further by RP-HPLC (Waters, 0-80% CH$_3$CN in H$_2$O over 20 minutes at a flow rate of 10 mL/min). Fractions containing product were basified (pH 10) with 2 M NaOH and extracted with EtOAc. The combined organic layers were washed with brine (10 mL), dried (MgSO$_4$) and the solvent removed in vacuo to give the title compound (35) (17 mg, 27%) as a brown oil; $^1$H-NMR (400 MHz, d$_4$-MeOD) δ 8.56 (d, J=0.6 Hz, 1H), 7.73-7.68 (m, 2H), 7.33-7.16 (m, 6H), 3.67 (s, 2H), 3.60-3.46 (m, 2H), 3.42-3.33 (m, 2H), 3.14 (m, 5H), 2.45 (dtd, J=10.1, 7.1, 3.4 Hz, 1H), 2.18-2.05 (m, 1H); LCMS Method C: rt 4.84 min; m/z 470.1 [M+H]$^+$.

Example 36

2-(2-(2-(2-((4-((4-Methylpiperazin-1-yl)methyl)phenyl)amino)-5-(trifluoromethyl)pyrimidin-4-yl)ethyl)phenyl)acetamide (36)

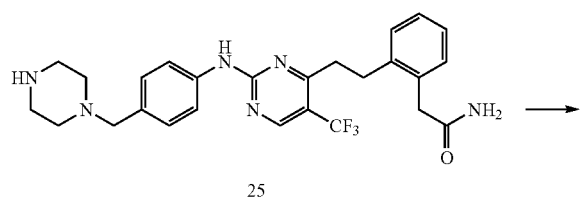

2-(2-(2-(2-((4-(Piperazin-1-ylmethyl)phenyl)amino)-5-(trifluoromethyl)pyrimidin-4-yl)ethyl)phenyl)acetamide (25) (11 mg, 0.022 mmol) was dissolved in methanol (1 mL). 37% Formaldehyde solution (7 μL) was added followed by sodium triacetoxyborohydride (24 mg, 0.11 mmol). The mixture was stirred vigorously at room temperature for two hours then concentrated. The residue was suspended in 10% sodium hydroxide (1 mL) and brine (2 mL) then extracted with ethyl acetate (5×2 mL). The combined ethyl acetate phases were washed with brine, dried over sodium sulfate, evaporated and the residue evaporated from DCM to give the title compound (36) (10.3 mg, 94% yield) as an off-white solid; $^1$H NMR (400 MHz, d$_4$-MeOD) δ 8.46 (d, J=0.5 Hz, 1H), 7.60-7.54 (m, 2H), 7.20 (d, J=8.6 Hz, 2H), 7.18-7.13 (m, 1H), 7.13-7.07 (m, 3H), 3.57 (s, 2H), 3.46 (s, 2H), 3.06 (qd, J=6.8, 3.1 Hz, 2H), 3.01-2.94 (m, 2H), 2.54 (s, 8H), 2.29 (s, 3H). LCMS Method C: 4.70 min; m/z 513.2 [M+H+]$^+$; m/z 511.0 [M−H]$^−$.

Example 37

3-(2-(2-((4-(Piperazin-1-ylmethyl)phenyl)amino)-5-(trifluoromethyl)pyrimidin-4-yl)ethyl)benzamide (37)

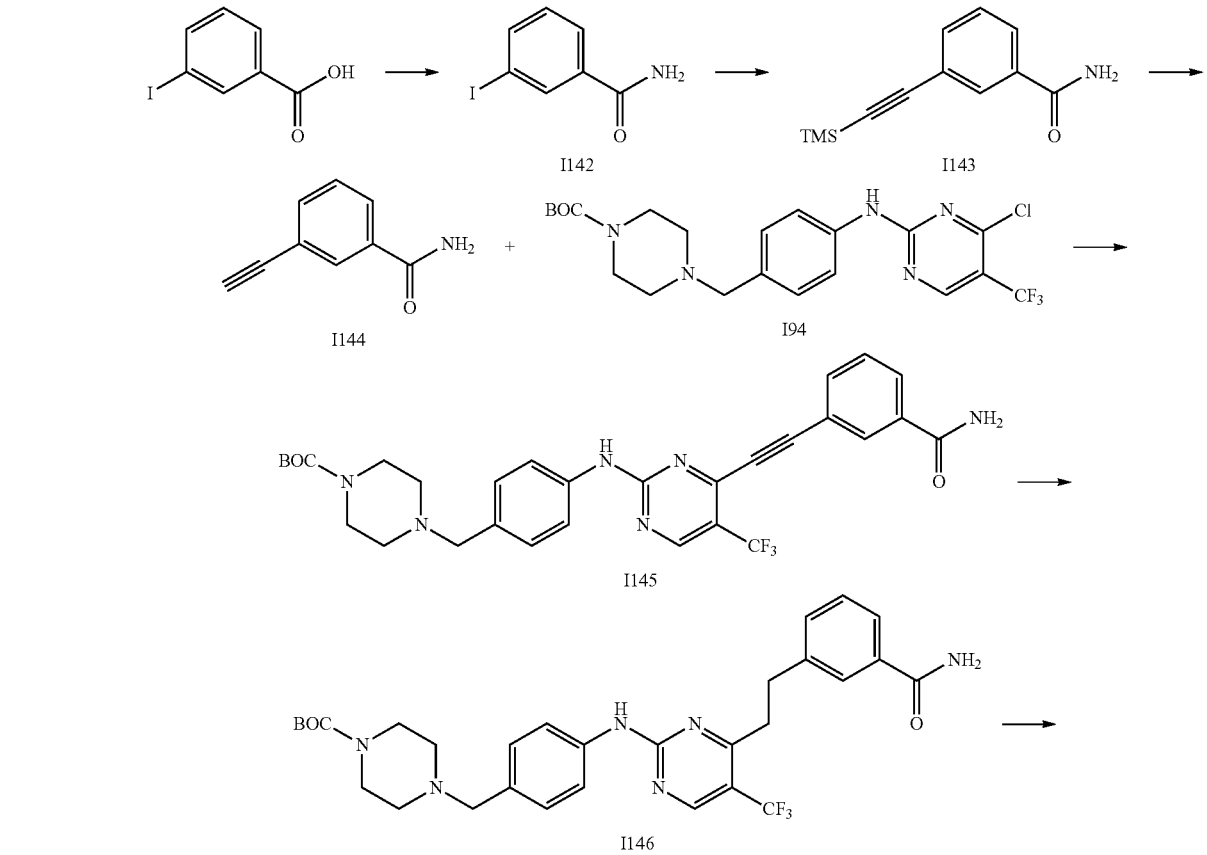

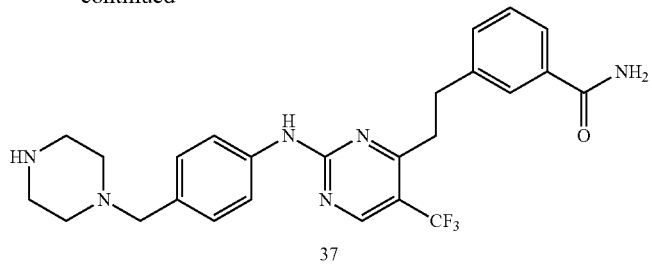

37

(a) 3-Iodobenzamide (I142)

3-Iodobenzoic acid (2.00 g, 8.06 mmol) was dissolved in THF (20 mL) then oxalyl chloride (1.4 mL, 16 mmol) and DMF (0.05 mL) were added and the resulting mixture stirred for 2 hours. The volatiles were evaporated under reduced pressure and the residue was dissolved in THF (20 mL) and concentrated aqueous ammonia (10 mL). After 60 minutes water (200 mL) was added and after a further 30 minutes the resulting precipitate was collected by filtration and air dried to give the title compound (I142) (1.97 g, 99% yield) as a white powder; $^1$H NMR (400 MHz, $d_4$-MeOH) δ 8.23 (t, J=1.8 Hz, 1H), 7.90 (ddd, J=7.9, 1.7, 1.0 Hz, 1H), 7.86 (ddd, J=7.8, 1.7, 1.0 Hz, 1H), 7.24 (t, J=7.8 Hz, 1H). LCMS Method C: rt 5.29 min, m/z 248.1 [M+H]$^+$.

(b) 3-((Trimethylsilyl)ethynyl)benzamide (I143)

3-Iodobenzamide (I142) (1.00 g, 4.05 mmol), bis(triphenylphosphine)palladium(II) chloride (0.142 g, 5 mol %), copper(I) iodide (0.077 g, 10 mol %), DMF (4 mL) and diisopropylamine (12 mL) were loaded into a microwave tube. The mixture was degassed for ten minutes with nitrogen, then trimethylsilylacetylene (0.69 mL, 4.9 mmol) was added and the resulting mixture heated under microwave irradiation at 120° C. for 15 minutes. The volatiles were evaporated under reduced pressure and the residue chromatographed (Biotage Isolera, 40 g silica cartridge, 0-100% ethyl acetate/petroleum benzine 40-60° C.) to give the title compound (I143) (0.569 g, 65% yield) as a brown solid; $^1$H NMR (400 MHz, CDCl$_3$) δ 7.88 (td, J=1.8, 0.5 Hz, 1H), 7.78 (ddd, J=7.8, 1.8, 1.2 Hz, 1H), 7.63-7.59 (m, 1H), 7.40 (td, J=7.8, 0.5 Hz, 1H), 6.05 (br s, 1H), 5.67 (br s, 1H), 0.26 (s, 9H). LCMS Method C: rt 5.94 min, m/z 218.2 [M+H]$^+$.

(c) 3-Ethynylbenzamide (I144)

3-((Trimethylsilyl)ethynyl)benzamide (I143) (0.565 g, 2.60 mmol) was dissolved in THF (33 mL), and 1 M TBAF in THF (3.25 mL, 3.25 mmol) was added. After two hours the reaction was poured into water (200 mL) and the resulting solution was extracted with diethyl ether (3×200 mL). The combined ether phases were washed with brine (200 mL), dried over sodium sulfate then evaporated to give the title compound (I144) (0.357 g, 95% yield) as a tan solid; $^1$H NMR (400 MHz, CDCl$_3$) δ 7.92 (t, J=1.5 Hz, 1H), 7.83-7.79 (m, 1H), 7.64 (dt, J=7.7, 1.4 Hz, 1H), 7.42 (td, J=7.8, 0.5 Hz, 1H), 6.07 (br s, 1H), 5.77 (br s, 1H), 3.13 (s, 1H). LCMS Method C: rt 4.74 min, m/z 146.2 [M+H]$^+$.

(d) tert-Butyl 4-(4-((4-((3-carbamoylphenyl)ethynyl)-5-(trifluoromethyl)pyrimidin-2-yl)amino)benzyl)piperazine-1-carboxylate (I145)

tert-Butyl 4-(4-((4-chloro-5-(trifluoromethyl)pyrimidin-2-yl)amino)benzyl)piperazine-1-carboxylate (I94) (0.30 g, 0.64 mmol), 3-ethynylbenzamide (I144) (102 mg, 0.70 mmol), copper(I) iodide (12 mg, 10 mol %), triphenylphosphine (17 mg, 10 mol %), bis(triphenylphosphine)palladium (II) chloride (22 mg, 5 mol %), DMF (3 mL) and triethylamine (0.443 mL, 3.18 mmol) were loaded into a microwave tube and degassed with nitrogen for five minutes. The resulting mixture was heated under microwave irradiation at 120° C. for 15 minutes then cooled to room temperature. The cooled mixture was added to 5% aqueous potassium carbonate (150 mL) and the resulting mixture extracted with ethyl acetate (3×150 mL). The combined ethyl acetate phases were washed with water (200 mL), brine (200 mL), dried then evaporated. The residue was chromatographed (Biotage Isolera: 12 g silica cartridge, 20-100% ethyl acetate/petroleum benzine 40-60° C. then 0-10% methanol/ethyl acetate) to give the title compound (I145) (107 mg, 29% yield) as a yellow solid; $^1$H NMR (400 MHz, $d_6$-DMSO) δ 10.46 (s, 1H), 8.84 (s, 1H), 8.17 (s, 1H), 8.09 (t, J=1.7 Hz, 1H), 8.04 (dt, J=7.9, 1.4 Hz, 1H), 7.77 (dt, J=7.8, 1.3 Hz, 1H), 7.71-7.66 (m, 2H), 7.66-7.52 (m), 7.27 (d, J=8.6 Hz, 2H), 3.44 (s, 2H), 2.33-2.26 (m, 4H), 1.38 (s, 9H). LCMS Method C: rt 5.06 min; m/z 581.1 [M+H]$^+$, 525.1 [M-tBu+2H]+; m/z 579.2 [M-H]$^-$.

(e) tert-Butyl 4-(4-((4-(3-carbamoylphenethyl)-5-(trifluoromethyl)pyrimidin-2-yl)amino)benzyl)piperazine-1-carboxylate (I146)

A suspension of tert-butyl 4-(4-((4-((3-carbamoylphenyl)ethynyl)-5-(trifluoromethyl)pyrimidin-2-yl)amino)benzyl)piperazine-1-carboxylate (I145) (105 mg, 0.18 mmol) and Pd/C (75 mg) was stirred in DMF (5 mL) and triethylamine (0.15 mL) at 30° C. under hydrogen for 18 hours. After filtration the volatiles were evaporated under reduced pressure and the residue chromatographed (Biotage Isolera: 4 g silica cartridge, 0-2% methanol/ethyl acetate) to give the title compound (I146) (66.6 mg, 63% yield) as a white solid; $^1$H NMR (400 MHz, $d_6$-DMSO) δ 10.20 (s, 1H), 8.67 (s, 1H), 7.93 (s, 1H), 7.79 (s, 1H), 7.74-7.50 (m, 8H), 7.40-7.35 (m, 2H), 7.33 (s, 1H), 7.24 (d, J=8.6 Hz, 2H), 3.43 (s, 2H), 3.17-3.04 (m, 4H), 2.36-2.23 (m, 4H), 1.38 (s, 9H). LCMS Method C: rt 5.05 min; m/z 585.2 [M+H]+; m/z 583.2 [M-H]$^-$.

(f) 3-(2-(2-((4-(Piperazin-1-ylmethyl)phenyl)amino)-5-(trifluoromethyl)pyrimidin-4-yl)ethyl)benzamide (37)

tert-Butyl 4-(4-((4-(3-carbamoylphenethyl)-5-(trifluoromethyl)pyrimidin-2-yl)amino)benzyl)piperazine-1-carboxylate (I146) (65 mg, 0.11 mmol) was dissolved in DCM (10 mL) then TFA (1 mL) was added and the resulting mixture stirred at room temperature for 18 hours. The volatiles were evaporated under reduced pressure and the residue partitioned between 10% sodium hydroxide (25 mL) and ethyl acetate (25 mL). The aqueous phase was extracted with ethyl acetate (3×25 mL) then the combined ethyl acetate phases washed with brine, dried over sodium sulfate and evaporated. The residue was washed with toluene (2×2 mL) and DCM (2×0.5 mL) to give the title compound (37) (22 mg, 40% yield) as a white solid; $^1$H NMR (400 MHz, d$_6$-DMSO) δ 10.19 (s, 1H), 8.66 (s, 1H), 7.94 (s, 1H), 7.78 (s, 1H), 7.74-7.64 (m, 3H), 7.40-7.35 (m, 2H), 7.35-7.29 (m, 1H), 7.23 (d, J=8.2 Hz, 2H), 3.38 (s, 2H), 3.17-3.02 (m, 4H), 2.75-2.61 (m, 4H), 2.29 (s, 4H). LCMS Method C: rt 4.52 min; m/z 485.1 [M+H]+; m/z 483.1 [M−H]−.

Example 38

2-(2-(2-(2-((4-(1-Ethylpiperidin-4-yl)phenyl)amino)-5-(trifluoromethyl)pyrimidin-4-yl)ethyl)pyridin-3-yl)acetamide (38)

A mixture of 2-(2-(2-(2-((4-(piperidin-4-yl)phenyl)amino)-5-(trifluoromethyl)pyrimidin-4-yl)ethyl)pyridin-3-yl)acetamide (32) (74 mg, 0.15 mmol), bromoethane (12 µL, 0.16 mmol) and potassium carbonate (63 mg, 0.46 mmol) in DMF (5 mL) was stirred for 48 h at room temperature under an inert atmosphere. The volatiles were removed under reduced pressure and the residue partitioned between ethyl acetate (20 mL) and saturated sodium hydrogen carbonate solution (20 mL). The aqueous layer was extracted with ethyl acetate (2×30 mL) and the combined organics were washed with brine then dried (MgSO$_4$). The solvent was removed under reduced pressure and the resulting solid was chromatographed (Biotage Isolera: C-18 reverse phase column, 0-100% MeCN in H$_2$O) to give the title compound (38) (22 mg, 28%) as an off-white solid; $^1$H NMR (400 MHz, d$_6$-DMSO) δ 10.07 (s, 1H), 8.65 (s, 1H), 8.37 (dd, J=4.8, 1.7 Hz, 1H), 7.65-7.57 (m, 3H), 7.55 (s, 1H), 7.26-7.13 (m, 3H), 7.02 (s, 1H), 3.54 (s, 2H), 3.25 (s, 4H), 2.98 (d, J=11.3 Hz, 2H), 2.48-2.30 (m, 3H), 1.95 (q, J=11.7, 11.3 Hz, 2H), 1.73 (d, J=10.5 Hz, 2H), 1.63 (qd, J=12.4, 3.6 Hz, 2H), 1.03 (t, J=7.2 Hz, 3H). LCMS Method C: rt 4.16 min; m/z 513 [M+H]+.

Example 39

2-(2-(2-(2-((4-(Piperidin-3-yl)phenyl)amino)-5-(trifluoromethyl)pyrimidin-4-yl)ethyl)pyridin-3-yl)acetamide (39)

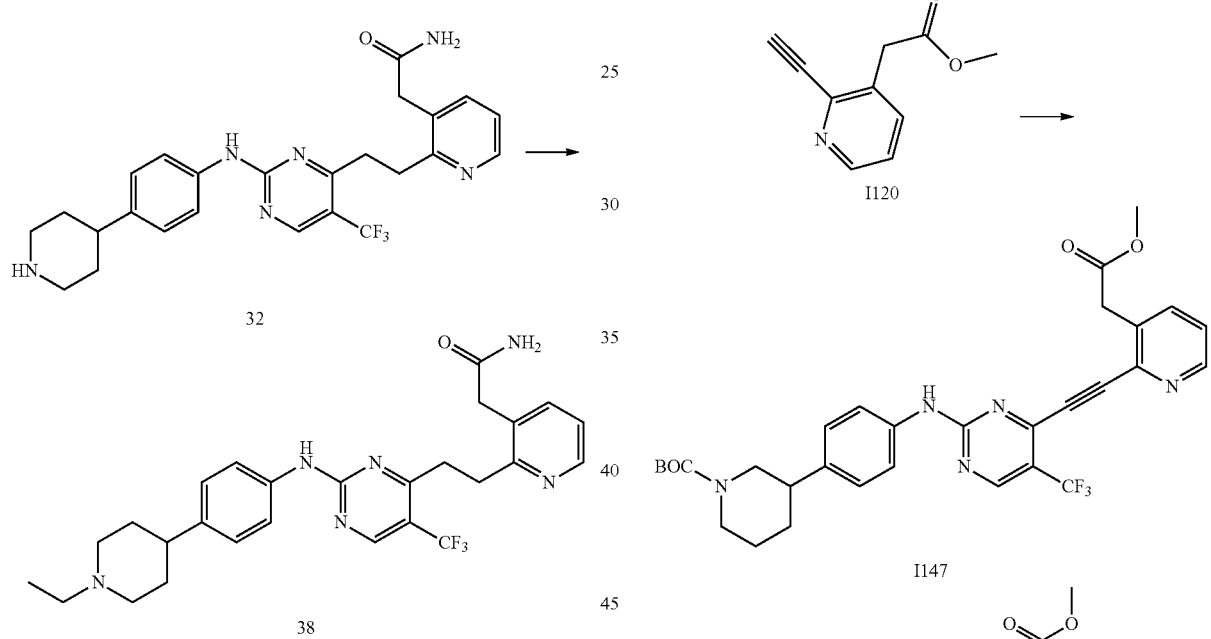

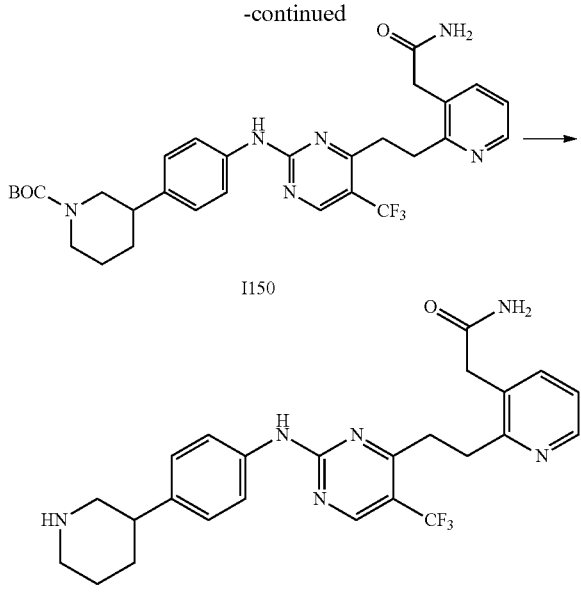

(a) tert-Butyl 3-(4-((4-((3-(2-methoxy-2-oxoethyl)pyridin-2-yl)ethynyl)-5-(trifluoromethyl)pyrimidin-2-yl)amino)phenyl)piperidine-1-carboxylate (I147)

A solution of methyl 2-(2-ethynylpyridin-3-yl)acetate (I120) (0.100 g, 0.571 mmol) in THF (1 mL) and triethylamine (0.199 mL, 1.43 mmol) was added to a mixture of tert-butyl 3-(4-((4-chloro-5-(trifluoromethyl)pyrimidin-2-yl)amino)phenyl)piperidine-1-carboxylate (I24) (0.217 g, 0.476 mmol), Pd(PPh$_3$)$_2$Cl$_2$ (0.033 g, 0.048 mmol), Cu(I)I (0.014 g, 0.071 mmol) and triphenylphosphine (0.019 g, 0.071 mmol) in dimethylformamide (3 mL). The resulting mixture was heated under microwave irradiation at 120° C. for 20 minutes then cooled, degassed for 10 minutes and heated under microwave irradiation at 120° C. for a further 20 minutes. The cooled mixture was diluted with ethyl acetate and the resulting solution passed through a plug of Celite, washing with ethyl acetate (250 mL). The volatiles were removed to give a brown solid which was chromatographed (Biotage Isolera: 25 g silica cartridge, 0-40% EtOAc in petroleum benzine 40-60° C.) to give the title compound (I147) (0.061 g, 22%); $^1$H NMR (400 MHz, CDCl$_3$) δ 8.63 (s, 1H), 8.62 (d, J=1.2 Hz, 1H), 7.72 (dd, J=7.9, 1.3 Hz, 1H), 7.57 (d, J=8.4 Hz, 2H), 7.54 (s, 1H), 7.35 (dd, J=7.9, 4.7 Hz, 1H), 7.23 (d, J=8.5 Hz, 1H), 4.30-4.06 (m) 3.95 (s, 2H), 3.71 (s, 3H), 2.84-2.58 (m, 3H), 2.06-1.98 (m), 1.70-1.66 (m, 2H), 1.69-1.51 (m, 2H), 1.47 (s, 9H).

(b) tert-Butyl 3-(4-((4-(2-(3-(2-methoxy-2-oxoethyl)pyridin-2-yl)ethyl)-5-(trifluoromethyl)pyrimidin-2-yl)amino)phenyl)piperidine-1-carboxylate (I148)

To a solution of tert-butyl 3-(4-((4-((3-(2-methoxy-2-oxoethyl)pyridin-2-yl)ethynyl)-5-(trifluoromethyl)pyrimidin-2-yl)amino)phenyl)piperidine-1-carboxylate (I147) (0.061 g, 0.10 mmol) in DMF (9 mL) and triethylamine (1 mL) was added a slurry of Pd/C (0.070 g) in DMF (3 mL). The resulting mixture was stirred under an atmosphere of hydrogen at room temperature for 16 hours. The crude reaction mixture was diluted with ethyl acetate then filtered through a pad of Celite. The Celite was washed with ethyl acetate and the filtrates combined. The solvent was removed in vacuo to give a brown oil which was taken up in DMF (9 mL) and triethylamine (1 mL). A slurry of Pd/C (0.070 g) in DMF (3 mL) was added and the resulting mixture was stirred under an atmosphere of hydrogen at room temperature for a further 19 hours. The crude reaction mixture was diluted with ethyl acetate then filtered through a pad of Celite. The Celite was washed with ethyl acetate and the filtrates combined. The solvent was removed in vacuo to give a brown oil which was chromatographed (Biotage Isolera: 25 g silica cartridge, 0-50% EtOAc in petroleum benzine 40-60° C.) to give the title compound (I148) (0.030 g, 49%) as a yellow oil; $^1$H NMR (400 MHz, CDCl$_3$) δ 8.50 (s, 1H), 8.46 (dd, J=4.8, 1.7 Hz, 1H), 7.61-7.46 (m, 4H, NH), 7.19 (d, J=8.6 Hz, 2H), 7.12 (dd, J=7.7, 4.8 Hz, 1H), 4.35-3.99 (m), 3.72 (s, 2H), 3.70 (s, 3H), 3.37 (J=7.4 Hz, 2H), 3.28 (t, J=6.9 Hz, 2H), 2.80-2.57 (m, 3H), 2.07-1.95 (m), 1.91-1.69 (m, 2H), 1.69-1.50 (m, 3H), 1.46 (s, 9H). LCMS Method C: rt=6.00 min, m/z 600.2 [M+H]$^+$.

(c) 2-(2-(2-(2-((4-(1-(tert-Butoxycarbonyl)piperidin-3-yl)phenyl)amino)-5-(trifluoromethyl)pyrimidin-4-yl)ethyl)pyridin-3-yl)acetic acid (I149)

To a solution of tert-butyl 3-(4-((4-(2-(3-(2-methoxy-2-oxoethyl)pyridin-2-yl)ethyl)-5-(trifluoromethyl)pyrimidin-2-yl)amino)phenyl)piperidine-1-carboxylate (I148) (0.030 g, 0.050 mmol) in THF (7 mL), water (1.5 mL) and MeOH (1 mL) was added lithium hydroxide monohydrate (0.020 g, 0.48 mmol). The reaction mixture was stirred at room temperature for 17 hours then the volatiles were removed in vacuo and the residue was partitioned between ethyl acetate (10 mL) and saturated aqueous sodium hydrogen carbonate (10 mL). The layers were separated and the aqueous layer was extracted with ethyl acetate (2×10 mL). The combined organic layers were washed with brine (10 mL), dried (MgSO$_4$) then the solvent removed in vacuo to give the title compound (I149) (0.029 g, 99%) as a white solid. LCMS Method C: rt 5.50 min, m/z=586.1 [M+H]$^+$, 584.2 [M−H]$^−$.

(d) tert-Butyl 3-(4-((4-(2-(3-(2-amino-2-oxoethyl)pyridin-2-yl)ethyl)-5-(trifluoromethyl)pyrimidin-2-yl)amino)phenyl)piperidine-1-carboxylate (I150)

1-Hydroxybenzotriazole (20 mg, 0.15 mmol), EDCl.HCl (32 mg, 0.17 mmol) and N,N-diisopropylethylamine (45 µL, 0.26 mmol) were added to a solution of 2-(2-(2-(2-((4-(1-(tert-butoxycarbonyl)piperidin-3-yl)phenyl)amino)-5-(trifluoromethyl)pyrimidin-4-yl)ethyl)pyridin-3-yl)acetic acid (I149) (29 mg, 0.051 mmol) in dry DMF (5 mL) under an atmosphere of nitrogen. Ammonium carbonate (50 mg, 0.52 mmol) was added in one portion after 10 minutes then stirring was continued at room temperature for 17 hours. Further portions of 1-hydroxybenzotriazole (20.0 mg, 0.15 mmol), EDCl.HCl (32 mg, 0.17 mmol) and N,N-diisopropylethylamine (45 µL, 0.26 mmol) were added, then ammonium carbonate (50 mg, 0.52 mmol) was added in one portion after 10 min. The resulting solution was stirred at 25° C. for 24 hours. The volatiles were removed in vacuo and the residue was partitioned between ethyl acetate (10 mL) and saturated sodium hydrogen carbonate (10 mL). The aqueous layer was extracted with ethyl acetate (2×10 mL) then the combined organic layers were washed with brine (10 mL), dried (MgSO$_4$) and evaporated to dryness. The residue was chromatographed (Biotage Isolera: 10 g silica cartridge, 0-100% EtOAc/petroleum benzine 40-60° C. then 10 g silica cartridge, 50-100% EtOAc/petroleum benzine 40-60° C.) to give the title compound (I150) (0.023 g, 77%) as a white solid; $^1$H NMR (400 MHz, CDCl$_3$) δ 8.49 (s, 1H), 8.46 (dd, J=4.8, 1.6 Hz, 1H), 7.77 (br s, 1H), 7.57-7.44 (m, 3H), 7.19 (d, J=8.5 Hz, 2H), 7.14 (dd, J=7.6, 4.8 Hz, 1H), 5.63 (d, J=22.0 Hz, 2H), 4.35-3.96 (m), 3.67 (s, 2H), 3.41-3.33 (m, 2H), 3.27 (t, J=6.9 Hz, 2H), 2.83-2.58 (m, 3H), 2.01-1.99 (m, 1H), 1.80-1.71 (m, 1H), 1.68 (s, 3H), 1.65-1.52 (m, 2H), 1.46 (s, 9H).

(e) 2-(2-(2-(2-((4-(Piperidin-3-yl)phenyl)amino)-5-(trifluoromethyl)pyrimidin-4-yl)ethyl)pyridin-3-yl)acetamide (39)

To a solution of tert-butyl 3-(4-((4-(2-(3-(2-amino-2-oxo-ethyl)pyridin-2-yl)ethyl)-5-(trifluoromethyl)pyrimidin-2-yl)amino)phenyl)piperidine-1-carboxylate (I150) (23 mg, 0.039 mmol) in DCM (7 mL) was added TFA (1 mL). The resulting solution was stirred at room temperature for 17 hours then the volatiles were removed in vacuo. The residue was partitioned between ethyl acetate (50 mL) and a 2.0 M solution of NaOH (50 mL) then the organic layer was washed with water (50 mL), brine (50 mL) and dried over MgSO$_4$ before being evaporated in vacuo to give the title compound (39) (18 mg, 94%) as a white solid; $^1$H NMR (400 MHz, d$_4$-MeOH) δ 8.52 (s, 1H), 8.37 (dd, J=4.9, 1.6 Hz, 1H), 7.67 (dd, J=7.7, 1.6 Hz, 1H), 7.61 (d, J=8.6 Hz, 2H), 7.27-7.17 (m, 3H), 3.68 (s, 2H), 3.39-3.32 (m, 2H), 3.27 (d, J=8.7 Hz, 2H), 3.21-3.14 (m, 2H), 2.82-2.70 (m, 3H), 2.07-1.94 (m, 1H), 1.94-1.83 (m, 1H), 1.80-1.64 (m, 2H). LCMS Method C: rt 4.12 min, m/z=485.1 [M+H]$^+$, 483.1 [M–H]$^−$.

Example 40

2-(2-(2-(2-((4-(1-Ethylpiperidin-3-yl)phenyl)amino)-5-(trifluoromethyl)pyrimidin-4-yl)ethyl)pyridin-3-yl)acetamide (40)

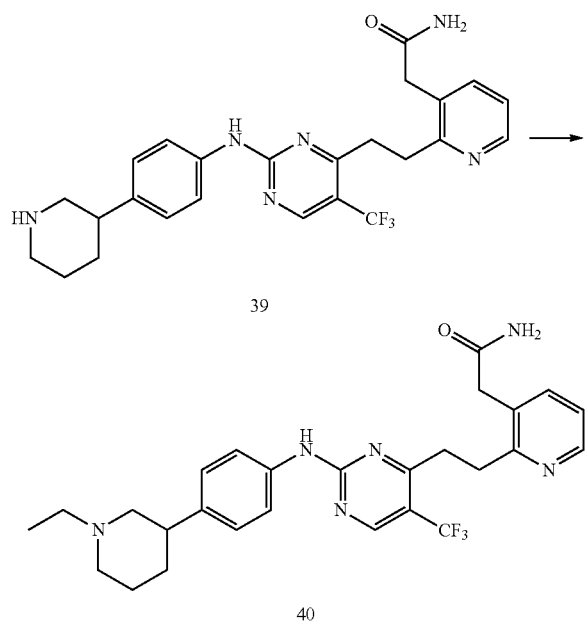

N,N-Diisopropylethylamine (18.0 μL, 0.103 mmol) was added to a solution of 2-(2-(2-(2-((4-(Piperidin-3-yl)phenyl)amino)-5-(trifluoromethyl)pyrimidin-4-yl)ethyl)pyridin-3-yl)acetamide (39) (17 mg, 0.034 mmol) in DMF (5 mL). The mixture was stirred for 5 min then bromoethane (4.0 μL, 0.051 mmol) was added and stirring was continued for 24 h at room temperature. A further portion of bromoethane (4.0 μL, 0.051 mmol) was added and the reaction mixture was stirred for an additional 16 hours at room temperature. The volatiles were evaporated in vacuo and the residue partitioned between ethyl acetate (10 mL) and saturated aqueous sodium hydrogen carbonate (10 mL). The layers were separated and the aqueous layer extracted with ethyl acetate (2×10 mL). The combined organic layers were washed with water (10 mL), brine (10 mL) and dried over Na$_2$SO$_4$. Filtration then removal of the solvent under reduced pressure afforded a beige solid which was purified by mass-directed preparative HPLC to afford the title compound (40) (6.2 mg, 36%) as a white solid; $^1$H NMR (400 MHz, d$_4$-MeOH) δ 8.54 (s, 1H), 8.38 (dd, J=4.8, 1.5 Hz, 1H), 7.69-7.66 (m, 3H), 7.28-7.19 (m, 3H), 3.68 (s, 2H), 3.59-3.46 (m, 2H), 3.38-3.22 (m, partially obscured by d$_4$-MeOH), 3.19-3.08 (m, 2H), 3.04-2.80 (m, 3H), 2.12-1.99 (m, 2H), 1.99-1.70 (m, 2H), 1.34 (t, J=7.3 Hz, 3H). LCMS Method C: rt=4.20 min, m/z=513.2 [M+H]$^+$, 511.2 [M–H]$^−$.

Biological Assays

The activity of compounds of the invention can be profiled using biochemical and cellular assays.

Primary potency at FAK can be assessed using an Alpha Screen™ technology biochemical assay.

The kinetics of this binding may be further studied using a surface plasmon resonance (SPR) technology assay using a Biacore™ S51 sensor to establish K$_a$, k$_d$ and consequently K$_D$. When off rates from the protein greatly exceed on rates, as may occur for highly potent compounds, K$_D$ gives an accurate measure of protein-ligand binding affinity.

The ability of compounds of the invention to inhibit FAK within cells can be assessed with an ELISA-type assay performed using a Meso Scale Discovery SECTOR Imager 6000 instrument. In this assay the ability of compounds of the invention to inhibit phosphorylation of Y397-FAK is determined.

The effect of compounds of the invention on inhibition of cellular proliferation resulting from non-FAK activity may be assessed using a 2D proliferation assay using a suitable cell line. This gives an indication of off-target activities and potential toxicity arising from them. Therefore, comparing inhibition of phosphorylation of Y397-FAK and 2D proliferation gives a measure of FAK specific mediated effects and also of potential toxicity resulting from off-target activity.

Primary potency at VEGFR3 can be assessed using an Alpha Screen™ technology biochemical assay.

The ability of compounds of the invention to inhibit VEGFR3 within cells can be assessed with an ELISA type assay.

FAK Biochemical Alpha Screen™ Assay

A biotin labeled peptide is used as substrate (amino acid sequence: Biotin-Glu-Gly-Pro-Trp-Leu-Glu-Glu-Glu-Glu-Glu-Ala-Tyr-Gly-Trp-Met-Asp-Phe-NH$_2$). FAK enzyme was expressed in insect cells as catalytic domain (amino acids 411-686) N-terminally tagged with six histidine amino acids and a Tobacco Etch Virus (TeV) cleavage sequence. After lysing the cells by sonication, the kinase was purified by Ni-Immobilised Metal Affinity Chromatography chromatography, TeV cleavage leaving a N-terminal glycine, and gel filtration. The 15 μl assay reactions are run in Greiner brand white 384-well low volume plates. All reactions contained 10 mM HEPES pH 7.4, 25 mM NaCl, 10 mM MgCl$_2$, 0.01% (v/v) Tween-20, 50 μM Na$_3$VO$_4$, 0.01% (w/v) albumin from chicken egg white, 111 nM peptide substrate, 80 μM ATP, and 4 ng/reaction FAK enzyme, with the enzyme being omitted from negative control reactions. Compounds were added in a volume of 100 nl from dilution series made up in DMSO, positive and negative control reactions receiving the same volume DMSO without compounds. The plates were sealed with adhesive seals and incubated for 90 minutes at 30° C. The reactions were stopped with the detection reagents added at the same time. Product formation was quantified as amplified luminescence between PerkinElmer AlphaScreen™ beads, using Streptavidin-coated donor and anti-phosphotyrosine (P-Tyr-100) acceptor beads. To each reaction, 5 µl containing 10 mM HEPES pH 7.4, 25 mM NaCl, 100 mM EDTA, 0.01% (v/v) Tween-20, and 6.25 µg/ml of each bead type were added. Plates were incubated for 6 hours before being read on a PerkinElmer EnVision™ plate reader in HTS Alphascreen™ mode. $IC_{50}$ values were obtained by calculating percent inhibition (%1) for each reaction relative to controls on the same plate (% I=(I−CN)/(CP−CN) where CN/CP are the averages of the negative/positive reactions, respectively), then fitting the %1 data vs. compound concentration [I] to % I=(A+((B−A)/(1+((C/[I])^D)))) where A is the lower asymptote, B is the upper asymptote, C is the $IC_{50}$ value, and D is the slope factor.

Results

| Compound | $IC_{50}$ (nM) |
|---|---|
| 1 | 2.1 |
| 2 | 2.5 |
| 3 | 1.9 |
| 4 | 1.5 |
| 5 | 2.4 |
| 6 | 4.2 |
| 7 | 9.6 |
| 8 | 6.1 |
| 9 | 7.0 |
| 10 | 2.9 |
| 11 | 3.0 |
| 12 | 6.3 |
| 13 | 0.60 |
| 14 | 21 |
| 15 | 18 |
| 16 | 2.0 |
| 17 | 3.4 |
| 18 | 13 |
| 19 | 7.7 |
| 20 | 0.81 |
| 21 | 2.4 |
| 22 | 2.8 |
| 23 | 0.39 |
| 24 | 0.77 |
| 25 | 3.0 |
| 26 | 20 |
| 27 | 7.2 |
| 28 | 0.30 |
| 29 | 11 |
| 30 | 11 |
| 31 | 3.6 |
| 32 | 3.5 |
| 33 | 6.2 |
| 34 | 5.7 |
| 35 | 7.7 |
| 36 | 2.3 |
| 37 | 15 |
| 38 | 23 |
| 39 | 14 |
| 40 | 51 |

FAK Biacore™ SPR Assay

Binding parameters of compounds were determined using a Biacore™ S51 sensor.

An anti-GST antibody was immobilized onto a CM5 chip by primary amine-coupling in accordance with the manufacturer's recommendations.

In running buffer (0.01 M HEPES pH 7.4, 0.15 M NaCl, 0.005% Surfactant P20, 10 mM $MgCl_2$, and 1% DMSO) N-terminally GST-fused purified FAK enzyme was captured on both spot 1 and 2. Spot 1 was subsequently blocked by loading with 30 nM PF-562,271 at the beginning of each cycle. Concentration series' of the test compounds were injected over the spots at 25° C. The specific binding was calculated as difference between spot 2 and 1 signals followed by solvent correction. Fitting to a one site binding model yielded the kinetic rate constants $k_d$ and $k_a$ and the equilibrium binding constant $K_D=k_d/k_a$.

For compounds with an expected $K_D$<5 nM N-terminally GST-fused purified FAK enzyme was captured on spot 2 of the anti-GST antibody coated chip only. After the injection cycle of a compound the chip surface was regenerated with 10 mM glycine-HCl, pH2.2 before capturing the enzyme again. The binding sensorgrams were analysed as described before.

Results

| Compound | $K_D$ (nM) |
|---|---|
| 1 | 0.49 |
| 2 | 1.5 |
| 3 | 0.91 |
| 4 | 0.73 |
| 5 | 0.57 |
| 6 | 6.3 |
| 7 | 2.3 |
| 8 | 1.0 |
| 9 | 7.0 |
| 10 | 0.96 |
| 11 | 0.61 |
| 12 | 0.92 |
| 13 | 0.47 |
| 14 | 6.1 |
| 15 | 5.0 |
| 16 | 1.3 |
| 17 | 3.5 |
| 18 | 13 |
| 19 | 7.8 |
| 20 | 0.63 |
| 21 | 0.44 |
| 22 | 0.99 |
| 23 | 1.3 |
| 24 | 0.77 |
| 25 | 1.1 |
| 26 | 14 |
| 27 | 16.6 |
| 28 | 0.94 |
| 29 | 12.1 |
| 30 | 5.7 |
| 31 | 1.0 |
| 32 | 2.5 |
| 33 | 5.6 |
| 34 | 5.0 |
| 35 | 1.6 |
| 36 | 0.48 |

P397Y-FAK Inhibition MSD Platform Cellular Biomarker Assay

Compounds of the invention may be tested for in vitro activity in the following assay: 96-well plates (cat#MA6000, Meso Scale Discovery) are coated with 30 µL/well of mouse monoclonal FAK antibody [63D5](cat#ab72140, Abcam) pre-diluted in PBS to a concentration of 1 mg/mL. The plates are sealed with adhesive film and incubated for 16 hours at 4° C. The antibody is then flicked out of the plates and 150 µL of 3% [w/v] Blocker A (cat#R93AA-1, Meso Scale Discovery) is added. The plates are resealed with adhesive film and incubated at room temperature on a shaker set at medium speed for 2 hours. The plates are then washed three times with a solution containing 50 mM Tris-HCl pH 7.5, 0.15M NaCl and 0.02% Tween-20, before cell lysate addition described below.

Cells are split 1:2 into T150 cell culture flasks 2 days prior to compound treatment. On the day prior to compound treatment, 200 μL media containing 20,000 cells is seeded into all wells of white, clear-bottom, TC treated, μclear, 96-well microtitre plates (cat#655098, Greiner Bio-One), and the plates are incubated at 37° C. and 5% $CO_2$ for 36 hours. 1 μL/well of compound is then added from dilution series prepared in DMSO. Negative control wells receive the same volume of DMSO without compounds, and positive control wells receive 2 μM of a control compound in the same volume of DMSO. Cells are treated for 1 hour at 37° C. and 5% $CO_2$. The media/compounds are then flicked off and 55 μL/well of ice-cold complete lysis buffer is added. Complete lysis buffer is prepared by adding 1 tablet PhosSTOP complete phosphatase inhibitor (cat#04906837001, Roche) and 1 tablet Complete, Mini, EDTA-free, protease inhibitor (cat#04693159001, Roche) per 10 mL of incomplete lysis buffer (150 mM NaCl, 20 mM Tris-HCl pH 7.5, 1 mM EDTA, 1 mM EGTA, 1% Triton-X 100). Plates are incubated on ice for 30 minutes, with 30 seconds high speed plate shaking every 5 minutes. 40 μL/well of cell lysate is transferred to the coated, blocked and washed 96-well microtitre plates described above. The 96-well plates are sealed with adhesive film and incubated for 16 hours at 4° C. The plates are then washed three times with a solution containing 50 mM Tris-HCl pH 7.5, 0.15M NaCl and 0.02% Tween-20 and tapped dry. 25 μL/well of detection solution (1% [w/v] Blocker A (cat#R93AA-1, Meso Scale Discovery) in 50 mM Tris-HCl pH 7.5, 0.15M NaCl and 0.02% Tween-20, with 1:600 rabbit polyclonal FAK phospho Y397 antibody (cat#ab39967, Abcam), 1:1000 anti-rabbit sulfo-tag antibody (cat#R32AB-1 Meso Scale Discovery) and 1:40 reconstituted Blocker D-M (cat#D609-0100, Rockland Immunochemicals for Research)) is added, and the plates resealed with adhesive film and incubated for 1 hour at room temperature on a plate shaker set to medium speed. Plates are then washed three times with a solution containing 50 mM Tris-HCl pH 7.5, 0.15M NaCl and 0.02% Tween-20 and tapped dry. 150 μL/well of Read Buffer T+Surfactant (cat#R92TC-1, Meso Scale Discovery) is then added, and pFAK-397 levels quantified using a Meso Scale Discovery SECTOR Imager 6000 instrument.

$IC_{50}$ values are determined by first calculating percent inhibition (%I) for each lysate relative to controls on the same plate (% I=(S−CP)/(CN−CP)) where S is the sample result, CN is the average result of DMSO only treated negative controls, and CP is the average result of 2 μM treated positive controls. % I is plotted against compound concentration [I] and the data fitted using the following equation, % I=(A+((B−A)/(1+((C/[I])^D)))), where A is the lower asymptote, B is the upper asymptote, C is the IC50 value, and D is the slope factor.

Results for MDA-231-LNA Cells

| Compound | $IC_{50}$ (nM) | % response of control at 2 μM |
|---|---|---|
| 1 | 59 | 114 |
| 2 | 58 | 96 |
| 3 | 27 | 99 |
| 4 | 140 | 105 |
| 5 | 70 | 109 |
| 6 | 440 | 108 |
| 7 | 260 | 114 |
| 8 | 124 | 105 |
| 9 | 214 | 105 |
| 10 | 37 | 109 |
| 11 | 116 | 112 |
| 12 | 522 | 106 |
| 13 | 26 | 111 |
| 14 | 572 | 71 |
| 16 | 36 | 111 |
| 17 | 60 | 89 |
| 18 | 880 | 98 |
| 20 | 13 | 111 |
| 21 | 1 | 87 |
| 22 | 23 | 91 |
| 23 | 8 | 120 |
| 24 | 12 | 107 |
| 25 | 25 | 85 |
| 27 | 341 | 107 |
| 28 | 7 | 86 |
| 30 | 281 | 119 |
| 31 | 39 | 139 |
| 33 | 24 | 84 |

2D Cellular Proliferation Assay

Cells are split 1:4 into T75 cell culture flasks two days prior to cell seeding. A variety of cancer cell lines can be utilized in this assay.

On the day of cell seeding 100 μL/well of media containing 1000-5000 cells are added to 96-well microtitre plates (Cat.#655 180, greiner bio-one) except wells G12 and H12 to which 100 μl of media is added. In a second plate, a single row of cells is seeded at the same concentration. This second plate is known as the t=0 plate and is used to calculate the relative cell number prior to addition of test agent. The plates containing cells are incubated for 24 hours at 37° C./5% $CO_2$. 0.5 μL/well of compound is then added from dilution series prepared in DMSO. A compound with known potency is included for each set of plates in order to assess assay performance. Negative control wells receive the same volume of DMSO without compounds.

Background signal is determined from wells containing media alone. The t=0 plate is read using addition of a resazurin-based reagent (see below) on the day that other plates have compound added to them. Plates containing cells to which compound has been added are then incubated for 3 days at 37° C. and 5% $CO_2$.

After 3 days of incubation, cell proliferation is quantified by addition of 20 μl/well of a resazurin-based reagent with a typical composition as follows: Resazurin, Sigma# R7017-1G, 0.015% w/v; methylene blue, Sigma#MB-1(25 g), 0.0025% w/v; potassium hexacyanoferrate (III), Sigma# P8131-100G, 0.033 w/v; potassium hexacyanoferrate (II) trihydrate, Sigma# P9387-100G, 0.042% w/v; in PBS buffer. Plates are incubated with resazurin-based reagent for 1-4 hours (37° C., 5% $CO_2$) prior to the determination of fluorescence at, or near ($579_{Ex}/584_{Em}$).

Percentage inhibition of proliferation (% I) for each treated well relative to controls on the same plate is calculated using the equation % I=(S−B)−($T_0$−B)/(CN−B)−($T_0$−B) where S is the sample result B is the background fluorescence, $T_0$ is the t=0 value and CN is the average result of DMSO only treated negative controls. For IC50 determination, % I is plotted against compound concentration [I] and the data fitted using the following equation, % I=(A+((B−A)/(1+((C/[I])^D)))), where A is the lower asymptote, B is the upper asymptote, C is the $IC_{50}$ value, and D is the slope factor.

Results for MDA-231-LNA Cells

| Compound | IC$_{50}$ (µM) |
| --- | --- |
| 1 | 1.15 |
| 2 | 3.21 |
| 3 | 1.63 |
| 4 | 1.73 |
| 5 | 1.54 |
| 6 | 3.91 |
| 7 | 1.73 |
| 8 | 1.16 |
| 9 | 3.58 |
| 10 | 1.43 |
| 11 | 2.25 |
| 12 | 1.70 |
| 13 | >1.0 |
| 14 | 4.49 |
| 15 | 2.37 |
| 16 | 2.00 |
| 17 | 3.51 |
| 18 | >5 |
| 19 | 1.49 |
| 20 | 1.46 |
| 21 | 0.80 |
| 22 | 1.07 |
| 23 | 4.82 |
| 24 | 1.70 |
| 25 | 2.89 |
| 26 | >5.5 |
| 27 | 2.81 |
| 28 | 1.35 |
| 29 | >5 |
| 30 | >5 |
| 31 | 4.10 |
| 32 | >5 |
| 33 | 1.52 |
| 34 | 7.85 |
| 35 | >10 |
| 36 | 5.62 |
| 37 | 2.79 |
| 38 | >10 |

VEGFR3 Biochemical Asay

Compounds of the invention may be tested for in vitro activity in the following assay: A biotin labeled peptide is used as substrate (amino acid sequence: Biotin-Glu-Gly-Pro-Trp-Leu-Glu-Glu-Glu-Glu-Glu-Ala-Tyr-Gly-Trp-Met-Asp-Phe-NH$_2$). VEGFR3 cytoplasmic domain (amino acids 798-1298) was purchased as N-terminal GST-fusion protein ("the enzyme"). The 15 µl assay reactions are run in Greiner brand white 384-well low volume plates. All reactions contained 10 mM HEPES pH 7.4, 10 mM MgCl$_2$, 0.01% (v/v) Tween-20, 50 µM Na$_3$VO$_4$, 0.01% (w/v) albumin from chicken egg white, 1 mM Dithiothreitol, 111 nM peptide substrate, 500 µM ATP, and 3.8 ng/reaction enzyme, with the enzyme being omitted from negative control reactions. Compounds were added in a volume of 100 nl from dilution series prepared in DMSO, positive and negative control reactions receiving the same volume DMSO without compound. The plates were sealed with adhesive seals and incubated for 90 minutes at 30 degree Celsius. The reactions were stopped with the detection reagents added at the same time as follows: Product formation was quantified as amplified luminescence between PerkinElmer AlphaScreen™ beads, using Streptavidin-coated donor and anti-phosphotyrosine (P-Tyr-100) acceptor beads. To each reaction, 5 µl containing 10 mM HEPES pH 7.4, 25 mM NaCl, 100 mM EDTA, 0.01% (v/v) Tween-20, and 6.25 µg/ml of each bead type were added. Plates were incubated for 6 hours before being read on a PerkinElmer EnVision™ plate reader in HTS Alphascreen™ mode. IC$_{50}$ values were obtained by calculating percent inhibition (% I) for each reaction relative to controls on the same plate (% I=(I−CN)/(CP−CN) where CN/CP are the averages of the negative/positive reactions, respectively), then fitting the %1 data vs. compound concentration [I] to % I=(A+((B−A)/(1+((C/[I])^D)))) where A is the lower asymptote, B is the upper asymptote, C is the IC$_{50}$ value, and D is the slope factor.

The above assay was also run in a slightly modified form in some cases (indicated below with *). In these cases, VEGFR3 cytoplasmic domain (amino acids 818-1177, lacking 949-1002 of UniProt accession number P35916) was expressed and purified as N-terminal Hexa-His-fusion protein ("the enzyme"), rather than using the N-terminal GST-fusion protein.

Results

| Compound | IC$_{50}$ (nM) |
| --- | --- |
| 1 | 10 |
| 2 | 120* |
| 3 | 1.1 |
| 4 | 4.0 |
| 5 | 12 |
| 6 | 52 |
| 7 | 48 |
| 8 | 4.8 |
| 9 | 2.5 |
| 10 | 4.0 |
| 11 | 2.5 |
| 12 | 12 |
| 13 | 70 |
| 14 | 101 |
| 15 | 37 |
| 16 | 11 |
| 17 | 31 |
| 18 | 664 |
| 19 | 37 |
| 20 | 5.0 |
| 21 | 25 |
| 22 | 15 |
| 23 | 12 |
| 24 | 3.9 |
| 25 | 14 |
| 26 | 51 |
| 27 | 30 |
| 28 | 10 |
| 29 | 68 |
| 30 | 7 |
| 31 | 12 |
| 32 | 5.1* |
| 33 | 16* |
| 34 | 184* |
| 35 | 53* |
| 36 | 16 |
| 37 | 254 |
| 38 | 23* |
| 39 | 23* |
| 40 | 46* |

Flt4 Phospho ELISA Assay

Compounds of the invention may be tested for in vitro activity in the following assay: Adult human dermal lymphatic microvascular endothelial cells (HMVEC-dLyAD) (Cat#CC-2810, Lonza) were seeded into clear-bottom, TC treated 12 well plates (Cat #665180, Greiner Bio-One) in Endogro MV complete (Cat#SCME004, Millipore) at 200,000 cells/well (volume 1 mL), and the plates incubated at 37° C. and 5% CO$_2$ for 6 hours. The media was replaced with Endogro Basal (Cat #SCME-BM, Millipore)+0.1% BSA (Cat#A8412, Sigma) and cells incubated for a further period (overnight at 37° C. and 5% CO$_2$).

96 well Maxisorp immuno plates (Cat #439454, Nunc) were coated with 100 µL of Total VEGFR2 capture antibody (Part #841888, Human Total VEGFR3/Flt4 ELISA Kit, Cat #DYC3491, R&D Systems), or Phospho VEGF R3 Capture antibody (Part #841885, Human Phospho VEGF R3/Flt4

ELISA Kit, Cat#DYC2724, R&D Systems). The plates were covered and incubated at room temperature overnight. The coating antibody was flicked out and the plates washed three times with Wash Buffer (Phosphate buffered saline (137 mM NaCl, 2.7 nM KCL, 8.1 nM $Na_2HPO_4$, 1.5 mL $KH_2PO_4$, pH7.2-7.4), 0.05% Tween 20). 300 µL of Blocking buffer (5% v/v Tween 20, 5% w/v sucrose in PBS) was then added to wells and plate incubated for 2 hours at room temperature. Blocking solution is flicked out and plates washed three times and tapped dry.

Compound dilution series were prepared in Endogro basal (Cat #SCME-BM, Millipore)+0.1% BSA (Cat#A8412, Sigma) with constant 0.1% DMSO concentration. 439 µL of sample or vehicle control was added to the cell monolayers. Cells are treated for 1 hour at 37° C. and 5% $CO_2$. 250 ng/mL Recombinant human VEGF-C(Cat #2179-VC, R & D Systems) added to wells and plates incubated for an additional 10 minutes at 37° C. and 5% $CO_2$.

The media and compounds were removed and the cell monolayer washed once in Dulbecco's Phosphate Buffered Saline (Cat #21600-044, Invitrogen). 130 µL of Lysis buffer added to wells and cell lysate harvested and transferred to tubes and stored on ice. Complete lysis buffer was prepared by adding 10 µL Protease Inhibitor Cocktail (Cat #P8340, Sigma-Aldrich), 10 µL PMSF (Phenylmethanesulfonyl fluoride, Cat #P7626, Sigma-Aldrich, prepared as 500 mM DMSO stock) per 1 mL of Phosphosafe™ Extraction Reagent (Cat #71296, Merck).

The harvested samples were then diluted 1:2 in IC Diluent #18 (5% Tween 20/PBS) and 100 µL transferred to the Total and Phospho VEGFR3 coated, blocked and washed 96 well plates and incubated for 2 hours at room temperature. The plates were then washed three times in wash buffer as described above and tapped dry. For detection of Total VEGFR3 100 µL of Detection antibody (Total VEGFR3 Detection Antibody Part#841888 in Total VEGFR3 kit) diluted in IC Diluent #1 (1% w/v BSA (Cat #A7906, Sigma-Aldrich)/PBS) was added to wells and the plate incubated for 2 hours at room temperature. The plate was then washed three times in wash buffer and tapped dry. 100 µL of streptavidin-HPR diluted in IC diluent #1 Streptavidin-HRP, Part #890803 in Total VEGFR3 kit) was added to wells and incubated at room temperature for 20 minutes followed by washing as described above. 100 µL Substrate solution (3,3',5,5'-Tetramethylbenzidine (TMB) Liquid Substrate System for ELISA, Cat #T0440, Sigma-Aldrich) was added and the plate incubated for 20 minutes in the dark at room temperature followed by the addition of 50 µL stop solution (2N $H_2SO_4$).

Total VEGFR3 levels were quantified using a Multiskan Ascent plate reader and Ascent software fitted with 450 nm filter.

For detection of Phospho VEGFR3, 100 µL of Detection antibody (Anti-Phospho-Tyrosine-HRP Detection Antibody, Part #841403 in Phospho VEGFR3 kit) was diluted in IC Diluent #1 (1% w/v BSA/PBS), added to the wells and the plate incubated for 2 hours at room temperature. The plate was then washed three times in wash buffer as described above and tapped dry. 100 µL Substrate solution (3,3',5,5'-Tetramethylbenzidine (TMB) Liquid Substrate System for ELISA, Cat #T0440, Sigma-Aldrich) was added and the plate incubated for 20 minutes in the dark at room temperature followed by the addition of 50 µL stop solution (2N $H_2SO_4$).

Phospho VEGFR3 levels were quantified using a Multiscan ascent plate reader and ascent software fitted with 450 nm filter.

$IC_{50}$ values are determined by first calculating the level of phospho VEGFR3 relative to Total VEGFR3 according to the following formula:

$$SRP = \frac{SP}{ST}$$

where SRP is the Sample Relative Phospho level, SP is Phospho VEGFR3 reading and ST is Total VEGFR3 reading.

Percent inhibition (% I) for each lysate relative to vehicle control (VEGF-C stimulated) is then calculated according to the following formula:

$$\% I = \frac{SRP \text{ Vehicle} - SRP \text{ Test}}{SRP \text{ Vehicle}} * 100$$

where SRP is the Sample Relative Phospho level as calculated above.

% I is plotted against compound concentration and data fitted using a Sigmoidal dose response curve (GraphPad Prism 4 for Windows) with the following equation (Y=Bottom+(Top-Bottom)/(1+10^(LogEC50−X))) where X is the logarithm of the concentration, Y is the response. Y starts at Bottom and goes to Top with a sigmoid shape.

Results

| Compound | $IC_{50}$ (nM) |
|---|---|
| 3 | 80 |
| 5 | 240 |
| 8 | 127 |
| 11 | 67 |
| 12 | 81 |
| 16 | 36 |
| 17 | 44 |
| 20 | 30 |
| 21 | 113 |
| 22 | 30 |
| 24 | 71 |
| 25 | 66 |
| 30 | 658 |
| 31 | 67 |
| 33 | 81 |
| 36 | 169 |

Combination Study—Survival Advantage in the MDA-231-LNA Orthotopic Xenograft Model $2 \times 10^6$ MDA-231-LNA cells in sterile PBS were injected into the mammary fat pad of female Balb/c SCID mice (6-8 weeks, n=10 per group). Once the tumours were palpable (day 14 post injection of cells) mice were treated once daily with vehicle; hydroxypropylmethylcellulose vehicle (HPMC-SV; 0.2 ml/dose), Avastin (12.5 mg/kg i.p. twice weekly), compound 16 p.o. 54 mg/kg BID or a combination of Avastin and compound 16 at the doses described above.

Compound 16 was formulated as the citrate salt in hydroxypropylmethylcellulose suspension vehicle (HPMC-SV) and delivered orally in 0.2 ml. Avastin (clinical formulation; Roche, Dee Why, New South Wales, Australia) was diluted in phosphate buffered saline and administered by intraperitoneal injection in 0.2 ml.

With the exception of three mice per group that were culled after 13 days of dosing for immunohistochemical analysis of tumour vascular density and mature macrophage infiltration, all other mice were killed by isoflurane anaesthesia and cervical dislocation when tumours reached 1500 $mm^3$. Mice harvested for tumour immunohistochemical analysis were not included in Kaplan-Meier analysis.

FIG. 1 shows the Kaplan-Meier survival curves (vehicle—black line; compound 16—dashed black line; Avastin—grey line; compound 16+Avastin—dashed grey line). All groups consist of 7 mice. * p=0.02 compared to Avastin alone by Log Rank (Mantel-Cox) test.

Figure 2A:
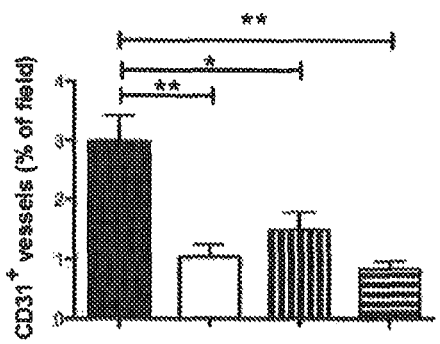
FIG. 2a shows quantitated CD31+ blood vessel staining and FIG. 2b shows F4/80+ mature macrophage staining of the tumours from FIG. 1
Figure 2B:
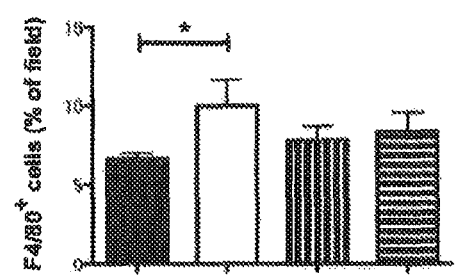

FIG. 2a shows quantitated CD31+ blood vessel staining and FIG. 2b shows F4/80+ mature macrophage staining in MDA-231-LNA primary tumours at day 13. (Vehicle-black bar; Avastin—white bar; compound 16—vertical striped bar; Avastin+ compound 16—horizontal striped bar). All bars represent the mean±S.E.M of n=7 mice per group. * p<0.05 and ** p<0.01 by one-way ANOVA.

These results show that compound 16 in combination with Avastin can increase survival time in the MDA-231-LNA orthotopic model of triple negative breast cancer (median survival time for Avastin=24 days vs 34 days for Avastin+ compound 16, p=0.02 by Log-Rank test). Consistent with ability of compound 16 to inhibit VEGFR3, single agent treatment with compound 16 caused a 50% decrease (p<0.05) in CD31+ vascular density in tumours after 13 days of dosing. Tumours from Avastin-treated mice displayed an increased level of F4/80+ macrophage infiltrates compared to vehicle. In contrast, tumours from mice treated with Avastin+ compound 16 did not contain significantly elevated levels of tumour-associated macrophages.

The invention claimed is:

1. A method of treating breast cancer comprising administering a therapeutically-effective amount of a compound of formula (I) in combination with a VEGF receptor tyrosine kinase inhibitor or a therapeutic antibody against vascular endothelial growth factors, wherein the compound of the formula (I) is:

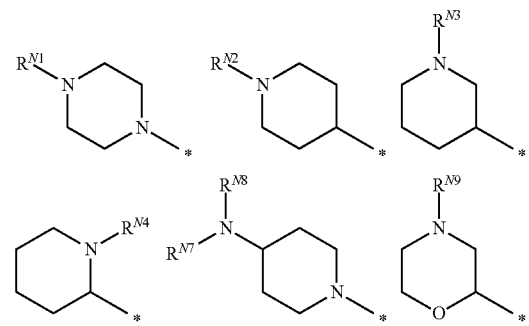

(I)

wherein:
$R^1$ is selected from: H and

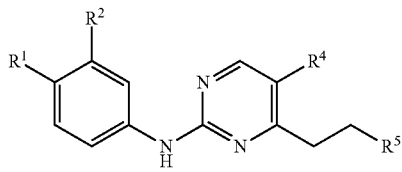

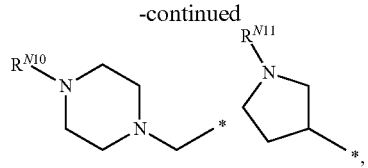

wherein:
$R^{N1}$ is selected from H, $C_{1-3}$ alkyl and $C(=O)Me$;
$R^{N2}$ is selected from H, $C_{1-3}$ alkyl and $C(=O)Me$;
$R^{N3}$ is selected from H, $C_{1-3}$ alkyl and $C(=O)Me$;
$R^{N4}$ is selected from H and $CH_3$,
$R^{N7}$ and $R^{N8}$ are independently selected from H and $CH_3$;
$R^{N9}$ is selected from H, $C_{1-3}$ alkyl and $C(=O)Me$;
$R^{N10}$ is selected from H, $C_{1-3}$ alkyl and $C(=O)Me$;
$R^{N11}$ is selected from H, $C_{1-3}$ alkyl and $C(=O)Me$;
$R^2$ is selected from H and

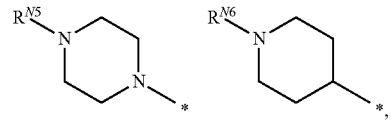

wherein:
$R^{N5}$ is selected from H, $C_{1-3}$ alkyl and $C(=O)Me$;
$R^{N6}$ is selected from H, $C_{1-3}$ alkyl and $C(=O)Me$;
and wherein only one of $R^1$ and $R^2$ is H;
or $R^1$ and $R^2$ together form the group —$CH_2$—N($R^{N12}$)—$C_2H_4$—, where $R^{N12}$ is selected from H, $C_{1-3}$ alkyl and $C(=O)Me$;
$R^4$ is selected from $CF_3$, halo, $CF_2H$ and CN; and
$R^5$ is selected from groups of the following formulae:

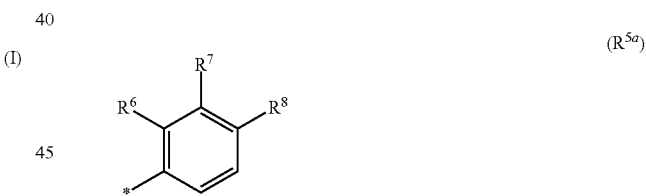

(R^{5a})

(R^{5b})

(R^{5c})

(R^{5d})

-continued

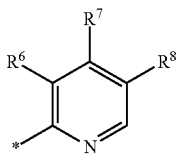

(R^{5e})

wherein:
$R^6$ is selected from H, $(CHR^{C1})_{n1}C(O)N(R^{N13})Z^1$ and $(CH_2)_{n2}C(O)OZ^2$; wherein:
n1 is 1;
$R^{C1}$ is H or Me;
$R^{N13}$ is H or $CH_3$;
$Z^1$ is H, $CH_3$ or $OCH_3$;
n2 is 1; and
$Z^2$ is $CH_3$;
and where only one of $(R^{N13})$ and $Z^1$ can be $CH_3$,
$R^7$, if present, is selected from H, and $(CH_2)_{m1}C(O)N(R^{M1})Y^1$, wherein:
m1 is 0 or 1;
$R^{M1}$ is H; and
$Y^1$ is H, Me or $OCH_3$;
and one of $R^6$ and $R^7$ is not H; and
$R^8$, if present, is H or, when $R^7$ is $C(=O)NH_2$, $R^8$ is selected from H and $C_{1-2}$ alkyl.

2. A method according to claim 1, wherein the compound of formula (I) is:

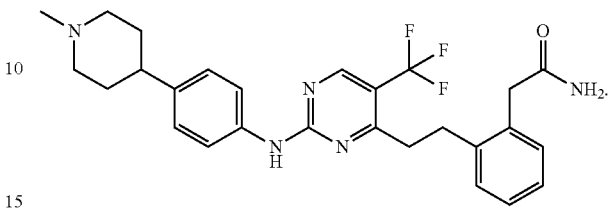

3. A method according to claim 1, wherein the VEGF receptor tyrosine kinase inhibitor or a therapeutic antibody against vascular endothelial growth factors is bevacizumab.

4. A method according to claim 2, wherein the VEGF receptor tyrosine kinase inhibitor or a therapeutic antibody against vascular endothelial growth factors is bevacizumab.

* * * * *